US012692478B2

(12) United States Patent
Parmar

(10) Patent No.: US 12,692,478 B2
(45) Date of Patent: Jul. 28, 2026

(54) POPULATIONS OF ENRICHED REGULATORY T CELLS AND METHODS FOR PRODUCING SAME

(71) Applicant: Cellenkos Inc., Houston, TX (US)

(72) Inventor: Simrit Parmar, Houston, TX (US)

(73) Assignee: Cellenkos, Inc., Houston, TX (US)

( * ) Notice: Subject to any disclaimer, the term of this patent is extended or adjusted under 35 U.S.C. 154(b) by 1035 days.

(21) Appl. No.: 17/704,623

(22) Filed: Mar. 25, 2022

(65) Prior Publication Data

US 2023/0066340 A1     Mar. 2, 2023

Related U.S. Application Data

(60) Provisional application No. 63/166,012, filed on Mar. 25, 2021.

(51) Int. Cl.
| | |
|---|---|
| *C12N 5/0783* | (2010.01) |
| *A61K 40/11* | (2025.01) |
| *A61K 40/22* | (2025.01) |
| *A61K 40/31* | (2025.01) |
| *A61K 40/41* | (2025.01) |
| *A61K 40/42* | (2025.01) |
| *A61K 40/46* | (2025.01) |
| *A61P 35/00* | (2006.01) |

(52) U.S. Cl.
CPC ............ *C12N 5/0636* (2013.01); *A61K 40/11* (2025.01); *A61K 40/22* (2025.01); *A61K 40/31* (2025.01); *A61K 40/416* (2025.01); *A61K 40/418* (2025.01); *A61K 40/4211* (2025.01); *A61K 40/46* (2025.01); *A61P 35/00* (2018.01); *C12N 5/0637* (2013.01); *A61K 2239/31* (2023.05); *A61K 2239/38* (2023.05); *A61K 2239/48* (2023.05); *C12N 2501/2302* (2013.01); *C12N 2501/599* (2013.01)

(58) Field of Classification Search
None
See application file for complete search history.

(56) References Cited

U.S. PATENT DOCUMENTS

| | | |
|---|---|---|
| 7,651,855 B2 | 1/2010 | Blazar et al. |
| 9,187,727 B2 | 11/2015 | Godfrey et al. |
| 10,006,901 B2 | 6/2018 | Schuler et al. |
| 2003/0049696 A1 | 3/2003 | Norment et al. |
| 2003/0119185 A1 | 6/2003 | Berenson et al. |
| 2004/0173778 A1 | 9/2004 | Roncarolo et al. |
| 2006/0121005 A1 | 6/2006 | Berenson et al. |
| 2011/0117069 A1 | 5/2011 | Ansorge et al. |
| 2015/0004176 A1 | 1/2015 | Garcia Santana |
| 2019/0119635 A1 | 4/2019 | Robbins et al. |
| 2021/0121500 A1 | 4/2021 | Parmar |
| 2022/0298477 A1 | 9/2022 | Parmar |

FOREIGN PATENT DOCUMENTS

| | | |
|---|---|---|
| CN | 102517253 B | 4/2014 |
| JP | 2016523102 A | 8/2016 |
| JP | 2018516988 A | 6/2018 |
| WO | WO2014/209855 A1 | 12/2014 |
| WO | WO-2016090250 A1 | 6/2016 |
| WO | WO2016/196774 A1 | 12/2016 |
| WO | WO-2017117112 A1 | 7/2017 |
| WO | WO2019/157158 A2 | 8/2019 |
| WO | WO-2021062221 A1 | 4/2021 |

OTHER PUBLICATIONS

Booth, N. J. et al., "Different proliferative potential and migratory characteristics of human CD4+ regulatory T cells that express either CD45RA or CD45RO," J Immunol, 184(8):4317-4326 (2010); https://doi.Org/10.4049/jimmunol.0903781.

Chakraborty, R. et al., Supplementary Appendix to "Robust and cost effective expansion of human regulatory T cells highly functional in a xenograft model of graft-versus-host disease," Cell Ther. Immunother., 98:533-537 (2013).

Kaur, I. et al., "Comparison of two methodologies for the enrichment of mononuclear cells from thawed cord blood products: The automated Sepax system versus the manual Ficoll method," Cytotherapy, 19:433-439 (2017).

MacDonald, K. N. et al., "Methods to manufacture regulatory T cells for cell therapy," Clinical and Experimental Immunology, 197:14-23 (2019).

Chakraborty, R. et al., "Robust and cost effective expansion of human regulatory T cells highly functional in a xenograft model of graft-versus-host disease," Cell Ther. Immunother., 98:533-537 (2013).

Rodriguez, L. et al., "Washing of cord blood grafts after thawing: high cell recovery using an automated and closed system," Vox Sanguinis, 87:165-172 (2004).

Anonymous: "A Clinical Trial of CK0801 (a New Drug) in Patients With Bone Marrow Failure Syndrome (BMF)," Dec. 12, 2018; retrieved from the Internet at https://clinical trials.gov/ct2/show/NCT03773393, 7 pages.

Anonymous: "Umbilical Cord Blood-derived CD4+/CD25+ T-regulatory Cells CK0801 (Code C158084)," NCI Thesaurus—National Cancer Institute, Oct. 26, 2020; retrieved from the Internet at https://ncit.nci.nih.gov/ncitbrowser/pages/concept_details.jsf?dictionary=NCI_Thesaurus&version=20.10d&code=C158084&ns=ncit&type=all&key=null&b=1&n=0&vse=null, 2 pages.

Bluestone, J. A. et al,. "Type 1 diabetes immunotherapy using polyclonal regulatory T cells," Sci Transl Med, Nov. 25, 2015;7(315):315ra189, 14 pages; doi: 10.1126/scitranslmed.aad4134.

(Continued)

*Primary Examiner* — Ruixiang Li

(74) *Attorney, Agent, or Firm* — Fenwick & West LLP; Matthew Pavao

(57) ABSTRACT

Provided herein are populations of enriched ex vivo expanded umbilical cord blood-derived regulatory T cells. Also provided are methods of making and using the same.

28 Claims, 84 Drawing Sheets

(56) References Cited

OTHER PUBLICATIONS

Brunstein, C. G. et al., "Infusion of ex vivo expanded T regulatory cells in adults transplanted with umbilical cord blood: safety profile and detection kinetics," Blood, 117(3):1061-1070 (2011).

Brunstein, C. G. et al., "Umbilical cord blood-derived T regulatory cells to prevent GVHD: kinetics, toxicity profile, and clinical effect," Blood, 127(8):1044-1051 (2016).

Burrell, B. E. et al., "Regulatory T Cell Induction, Migration, and Function in Transplantation," J Immunol, 189(10): 4705-4711 (2012); https://doi.org/10.4049/jimmunol.1202027.

Chen, Z. et al., "The Ubiquitin Ligase Stub1 Negatively Modulates Regulatory T Cell Suppressive Activity by Promoting Degradation of the Transcription Factor Foxp3," Immunity, 39:272-285 (2013).

Fan, H.et al. "Comparative study of regulatory T cells expanded ex vivo from cord blood and adult peripheral blood", Immunology. Jun. 2012; 136(2): 218-30.

Gladstone, D. E. et al., "Randomized, Multi-Center, Double-Blinded, Placebo Controlled Safety and Early Efficacy Trial of Cryopreserved Cord Blood Derived T-Regulatory Cell Infusions (CK0802) in the Treatment of COVID-19 Induced Ards. (Resolve Trial)," Blood, 138:828-830 (2021).

Gladstone, D. E. et al., "Regulatory T Cells for Treating Patients with COVID-19 and Acute Respiratory Distress Syndrome: Two Case Reports," Annals of Internal Medicine, 173(10):852-853 (2020).

Horne, E., "Cellenkos, Inc. Initiates Phase 1 Clinical Trial of CK0801 for Treatment of bone Marrow Failure Syndromes," Jun. 4, 2019; retrieved from the Internet at https://www.prnewswire.com/news-releases/cellenkos-inc-initiates- phase-1-clinical-trial-of-ck0801-for-treatment-of-bone-marrow-failure-syndromes-300861217.html, 3 pages.

Huang, M. et al., "Novel CD4+CD8+ Umbilical Cord Blood Regulatory T Cells," Blood, 134 (Supplement 1): 4446 (2019), 3 pages; http://doi.org/10.1182/blood-2019-131948.

International Search Report and Written Opinion mailed Jun. 24, 2022 for International Application No. PCT/US2022/021960, 18 pages.

International Search Report and Written Opinion mailed Jun. 27, 2022 for International Application No. PCT/US2022/021402, 19 pages.

International Search Report and Written Opinion mailed Nov. 27, 2020 for International Application No. PCT/US2020/052815, 19 pages.

Kadia, T. M. et al., "Adoptive Therapy with Allogeneic Cord Blood T Regulatory Cells Improves Transfusion Requirement in Bone Marrow Failure Syndromes," Blood, 138 (Supplement 1): 3875 (Nov. 2021), 4 pages; https://doi.org/10.1182/blood-2021-153864.

Kadia, T. M. et al., "Adoptive Therapy with Allogeneic Cord Blood T Regulatory Cells Show Safety and Early Clinical Signal in Primary Myelofibrosis," Blood, 136 (Supplement 1): 41 (2020), 5 pages; http://doi.org/10.1182/blood-2020-138585.

Kadia, T. M. et al., "Phase I Clinical Trial of CK0801 (cord blood regulatory T cells) in Patients with Bone Marrow Failure Syndrome (BMF) Including Aplastic Anemia, Myelodysplasia and Myelofibrosis," Blood, 134 (Supplement 1): 1221 (2019), 5 pages; http://doi.org/10.1182/blood-2019-127702.

Kean, L. S. et al., "Significant mobilization of both conventional and regulatory T cells with AMD3100," Blood, 118(25):6580-6590 (2011).

Kellner, J. N. et al., "Ex vivo generation of umbilical cord blood T regulatory cells expressing the homing markers CD62L and cutaneous lymphocyte antigen," Oncotarget, 9(72):33694-33701 (2018).

Kellner, J. N. et al., "Third party, umbilical cord blood derived regulatory T-cells for prevention of graft versus host disease in allogeneic hematopoietic stem cell transplantation: feasibility, safety and immune reconstitution," Oncotarget, 9(86):35611-35622 (2018).

Kotsianidis, I. et al., "Kinetics, function and bone marrow trafficking of CD4+ CD25+ FOXP3+ regulatory T cells in myelodysplastic syndromes (MDS)," Leukemia, 23:510-518 (2009).

Lyu, M.-A. et al., "Adoptive Cord Blood T Regulatory Cell Therapy Leads to Resolution of Inflammation and Decreased Proteinuria in Lupus Nephritis," Blood, 136 (Supplement 1): 5 (2020), 4 pages; http://doi.org/10.1182/blood-2020-140420.

Lyu, M.-A. et al., "Single Injection of Cord Blood Regulatory T Cells Can Delay the Manifestations of Systemic Lupus Erythematosus," Blood, 134 (Supplement 1): 1938 (2019), 3 pages; http://doi.org/10.1182/blood-2019-131436.

Ma, H. et al., "Adoptive Therapy with Cord Blood Regulatory T Cells Can Treat Graft Vs Host Disease," Blood, 134 (Supplement 1): 1940 (2019), 3 pages; http://doi.org/10.1182/blood-2019-129395.

Nishimoto, M. et al., "Adoptive Therapy with Cord Blood T Regulatory Cells Enhances Anti-Myeloma Efficacy of T Cell Based Immunotherapies," Blood, 136 (Supplement 1): 26 (2020), 4 pages; http://doi.org/10.1182/blood-2020-143142.

Nishimoto, M. et al., "Cord Blood Regulatory T Cells Do Not Impair Anti-Myeloma Effect of Conventional T Cells," Biology of Blood and Marrow Transplantation, vol. 26, Issue 3, Supplement, Mar. 2020, p. S225, 1 page.

Nishimoto, M. et al., "Cord Blood Regulatory T Cells Prevent Multiple Myeloma Progression by Suppressing Inflammation," Blood, 134 (Supplement): 3095 (2019), 4 pages; http://doi.org/10.1182/blood-2019-128418.

Ohkura, N. et al., "Development and Maintenance of Regulatory T cells," Immunity, 38:414-423 (2013).

Opstelten, R. et al., "GPA33: A Marker to Identify Stable Human Regulatory T Cells," J Immunol, 204:3139-3148 (2020).

Pace, L. et al., "IL-4 Modulation of CD4+ CD4+ T Regulatory Cell-Mediated Suppression," J Immunol, 174(12):7645-7653 (2005); https://doi.org/10.4049/jimmunol.174.12.7645.

Parmar, S. et al., "Third-party umbilical cord blood derived regulatory T cells prevent xenogenic graft-versus-host disease," Cytotherapy, 16:90-100 (2014).

Rubinstein, P. et al., "Processing and cryopreservation of placental/umbilical cord blood for unrelated bone marrow reconstitution," Proc. Natl. Acad. Sci. USA, 92:10119-10122 (1995).

Schmaler, M. et al., "IL-7R signaling in regulatory T cells maintains peripheral and allograft tolerance in mice," PNAS, 112(43):13330-13335 (2015).

Schneidawind, D. et al., "Regulatory T cells and natural killer T cells for modulation of GVHD following allogeneic hematopoietic cell transplantation," Blood, 122(18):3116-3121 (2013).

Seay, H. R. et al., "Expansion of Human Tregs from Cryopreserved Umbilical Cord Blood for GMP-Compliant Autologous Adoptive Cell Transfer Therapy," Molecular Therapy: Methods & Clinical Development, 4:178-191 (2017).

Song, M.-K. et al., "Understanding Splenomegaly in Myelofibrosis: Association with Molecular Pathogenesis," Int. J. Mol. Sci., 19:898 (2018), 11 pages; doi:10.3390/ijms19030898.

Tang, Q. & Bluestone, J. A., "Regulatory T-Cell Therapy in Transplantation: Moving to the Clinic," Cold Spring Harb Perspect Med 2013; 3:a0155, 16 pages; doi: 10.1101/cshperspect.a015552.

Tosiek, M. J. et al., "IL-15-dependent balance between Foxp3 and RORγt expression impacts inflammatory bowel disease," Nature Communications, 7:10888 (2016), 11 pages; doi:10.1038/ncomms10888.

Zeng, K. et al., "Allogeneic Cord Blood Regulatory T Cells Can Prevent Graft Vs. Host Disease and Preserve Graft Vs Leukemia Effect: Update on Phase I/II Clinical Trial," Blood, 134, (Supplement 1): 4547 (2019), 4 pages; http://doi.org/10.1182/blood-2019-127726.

Zeng, K. et al., "Combination of Cord Blood T Regulatory Cells with Ruxolitinib Decreases Side Effects and Improves Survival in Xenogenic Graft Vs. Host Disease," Blood, 136 (Supplement 1): 2 (2020), 3 pages; http://doi.org/10.1182/blood-2020-140417.

Zeng, K. et al., "Cord Blood T Regulatory Cells Can Dampen Cytokine Release Syndrome and Improve on Target Efficacy of CD19 CAR T Cells," Blood, 136 (Supplement 1): 15 (2020), 4 pages; http://doi.org/10.1182/blood-2020-138812.

Zhou, L. et al., "Bone Marrow is a Reservoir for CD4+ CD25+ Regulatory T Cells that Traffic through CXCL12/CXCR4 Signals," Cancer Research, 64:8451-8455 (2004).

Treanor, B., "B-cell receptor: from resting state to activate," Immunology, 136:21-27 (2012).

(56) References Cited

OTHER PUBLICATIONS

18th Congress of the European Hematology Association Stockholm, Swedfen, Jun. 13-16, 2013, vol. 98.

Fuhlbrigge et al. "Cutaneous lymphocyte antigen is a specialized form of PSGL-1 expressed on skin-homing T cells", Nature. Oct. 30, 1997;389(6654):978-81.

Lin, et al. "Regulatory T Cells d Accute Lung Injury: Cyutokines, Uncontrolled Inflammation, and Therapeutic Implications", Jul. 9, 2018, vol. 9, 10 pages.

Written Opinion and Search Report issued in Singapore Patent Application No. 11202202465V dated May 26, 2025, 11 pages.

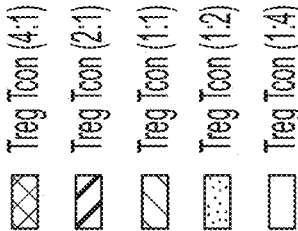
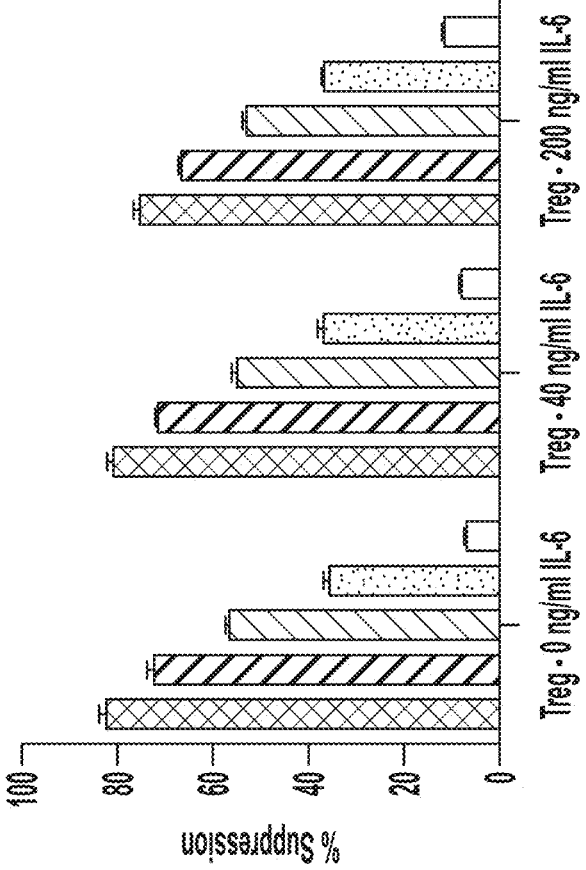
FIG. 4A

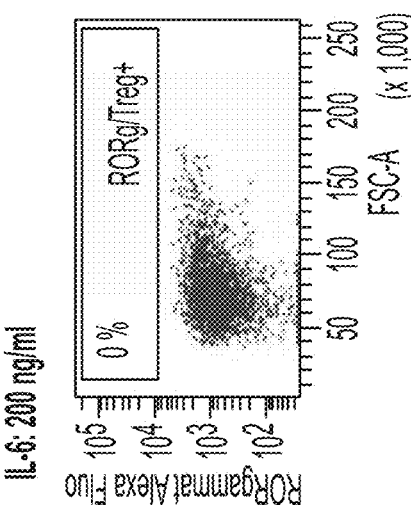
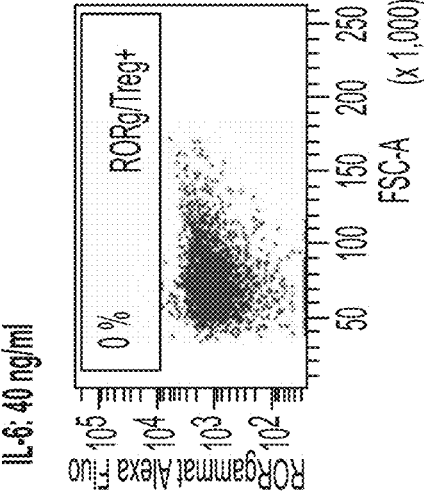
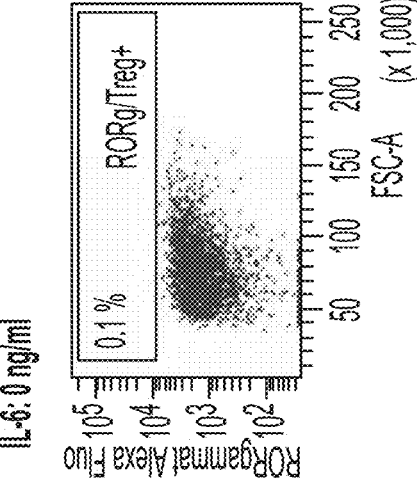
FIG. 4B

Treg
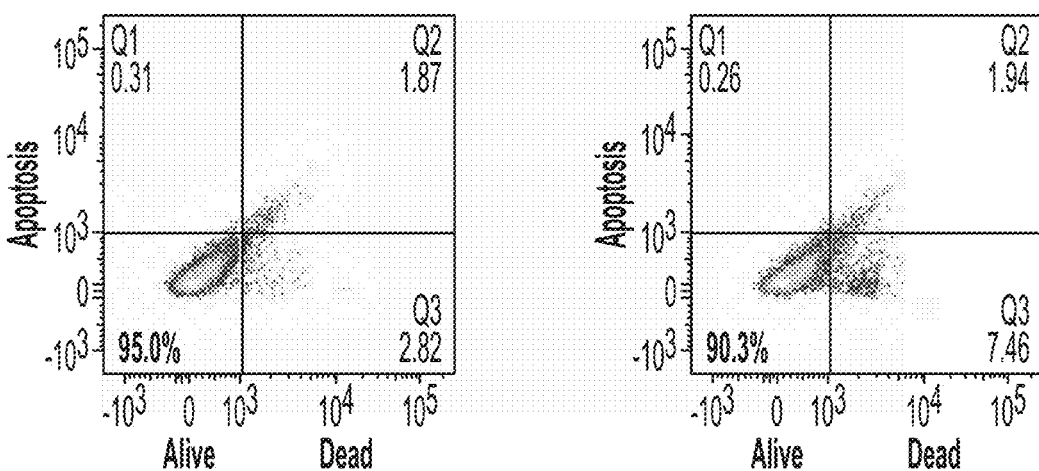
Tcon
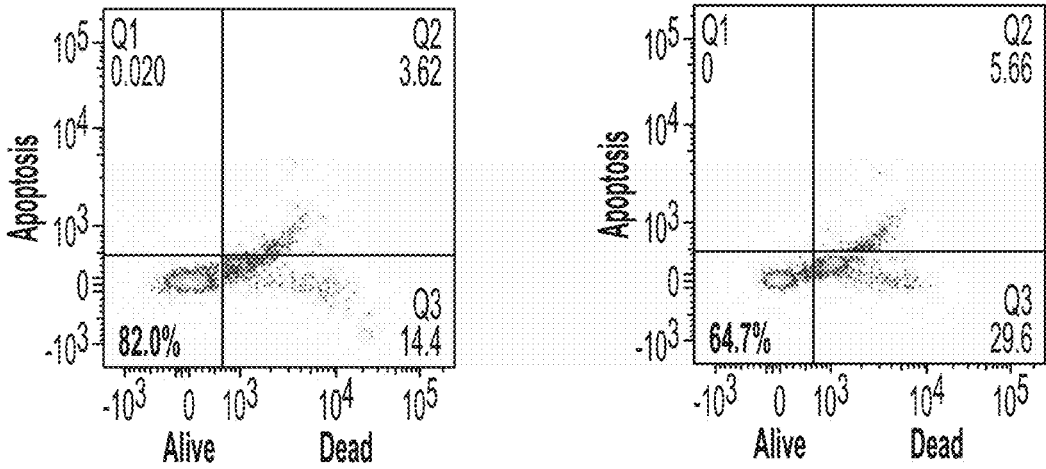
FIG. 7A

Kidney

| | CK0801 | CK0802 | CK0804 | CK0803 | CK0805 |
|---|---|---|---|---|---|
| HLA Matching | HLA match 3 out of 6 | N/A | N/A | N/A | N/A |
| Collection date | On or after 25 May 2005 | On or after 25 May 2005 | On or after 25 May 2005 | On or after 25 May 2005 | On or after 25 May 2005 |
| Total nucleated cell count | > 100 x 10⁷ $> 100 \times 10^7$ | $> 100 \times 10^7$ | $> 100 \times 10^7$ | $> 100 \times 10^7$ | $> 100 \times 10^7$ |
| CD34+ cell count | N/A | $> 5 \times 10^6$ | $> 5 \times 10^6$ | $> 5 \times 10^6$ | $> 5 \times 10^6$ |
| CBU Source | Public Cord Blood bank (CBB) qualified by NMDP, -or- CBB licensed, registered or accredited by AABB/FACT or appropriate governmental authority | Public Cord Blood bank (CBB) qualified by NMDP, -or- CBB licensed, registered or accredited by AABB/FACT or appropriate governmental authority | Public Cord Blood bank (CBB) qualified by NMDP, -or- CBB licensed, registered or accredited by AABB/FACT or appropriate governmental authority | Public Cord Blood bank (CBB) qualified by NMDP, -or- CBB licensed, registered or accredited by AABB/FACT or appropriate governmental authority | Public Cord Blood bank (CBB) qualified by NMDP, -or- CBB licensed, registered or accredited by AABB/FACT or appropriate governmental authority |
| CBU Testing | CLIA accredited laboratories | CLIA accredited laboratories | CLIA accredited laboratories | CLIA accredited laboratories | CLIA accredited laboratories |
| Storage | $\leq 150°C$ | $\leq 150°C$ | $\leq 150°C$ | $\leq 150°C$ | $\leq 150°C$ |
| Volume | $\leq 80$ mL | $\leq 80$ mL | $\leq 80$ mL | $\leq 80$ mL | $\leq 80$ mL |
| Pre-Freeze viability | > 85% | > 85% | > 85% | > 85% | > 85% |
| Sterility | No growth/ negative | No growth/ negative | No growth/ negative | No growth/ negative | No growth/ negative |
| RBC-status | Depleted | Depleted | Depleted | Depleted | Depleted |
| Plasma-Status | Depleted | Depleted | Depleted | Depleted | Depleted |

FIG. 29

| | CK0801 | CK0802, CK0803, CK0804, CK0805 |
|---|---|---|
| Donor mother anti-HIV-1,2 | Non-reactive/negative | Non-reactive/negative |
| Donor mother HIV p24 or NAT | Non-reactive/negative | Non-reactive/negative |
| Donor mother HBsAg | Non-reactive/negative | Non-reactive/negative |
| Donor mother anti-HTLV I/II | Non-reactive/negative | Non-reactive/negative |
| Donor mother anti-HBc | Non-reactive/negative | Non-reactive/negative |
| Donor mother HBV NAT | Non-reactive/negative | Non-reactive/negative |
| Donor mother anti-HCV | Non-reactive/negative | Non-reactive/negative |
| Donor mother HCV NAT | Non-reactive/negative | Non-reactive/negative |
| Donor mother Chagas | Non-reactive/negative | Non-reactive/negative |
| Donor mother WNV NAT | Non-reactive/negative | Non-reactive/negative |
| Donor mother anti-CMV | *As reported* | Non-reactive/negative |
| Donor mother syphilis | Non-reactive/negative | Non-reactive/negative |
| Donor mother CJD (Creutzfeldt-Jakob disease) | Non-reactive/negative | Non-reactive/negative |
| Donor mother Zika NAT | Non-reactive/negative | Non-reactive/negative |
| Donor mother Pre-eclampsia | Negative | Negative |
| High risk pregnancy | Negative | Negative |

FIG. 30

| Cohort | Diagnosis | Serious Adverse Events | Efficacy at Day 30 | Response Duration | Last Follow up |
|---|---|---|---|---|---|
| Dose level 1 = 1x10⁶ cells/kg | Primary Myelofibrosis | None | Decrease in JAK2 mutation | 9 mos | 11 mos |
| | Primary Myelofibrosis | None | Improvement in MPN Symptom Burden Score Improvement in bone marrow cellularity | 4 mos | 9 mos |
| | Aplastic Anemia | None | Blood and Platelet transfusion improvement Resolution of bone marrow dysplasia | 1.5 mos | 8 mos |
| Dose level 1 = 3x10⁶ cells/kg | Aplastic Anemia | None | Blood and Platelet transfusion improvement Resolution of bone marrow dysplasia | 1.5 mos | 5 mos |
| | Primary Myelofibrosis | None | Improvement in chronic pain | 1 mos | 4 mos |
| | Primary Myelofibrosis | None | Blood and Platelet transfusion improvement | 1 mos | 2 mos |

FIG. 43

|  | JAK2V617F (allele %) | WBC (k/ul) | Hb (g/dl) | Plt (k/ul) | Blast (%) | BM Cellularity (%) | Splenomegaly (cm) | hepatomegaly (cm) | Jakafi Dose (mg BID) |
|---|---|---|---|---|---|---|---|---|---|
| Baseline | 86 | 8.5 | 12.1 | 73 | 0 | 5-20 | 17 | 6 | 20 |
| 1 month | 50.75 | 9.7 | 12.7 | 72 | 1 | 20 | 17 | 6 | 20 |
| 4 month | 53.6 | 9.4 | 11 | 76 | 0 | 5-10 | 14 | 6 | 20 |

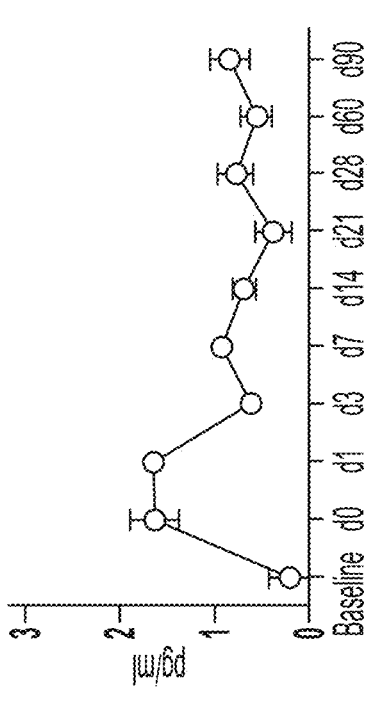
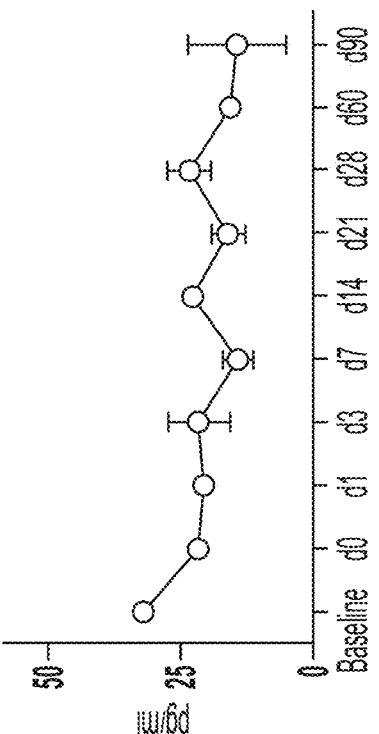
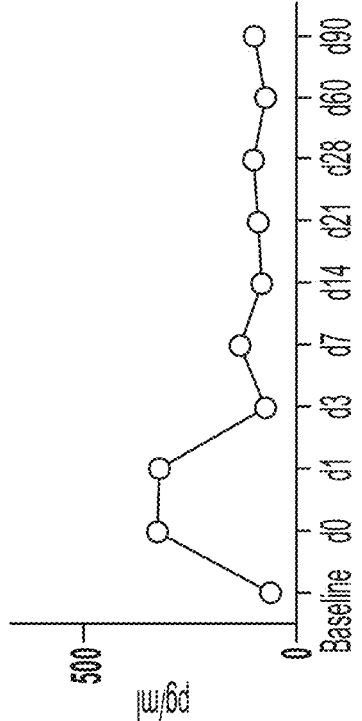
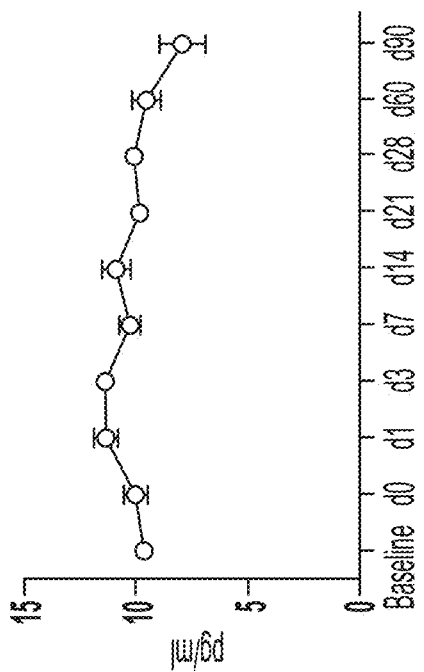
FIG. 47

| Comparisons | Observed value | p-value |
|---|---|---|
| Blank vs Mock | 0.00 | 1.00 |
| Blank vs Treg | 0.66 | 0.41 |
| Blank vs CART alone | 1.00 | 0.31 |
| Blank vs CART+Treg | 5.21 | 0.02 |
| Mock vs Treg | 0.66 | 0.41 |
| Mock vs CART alone | 1.00 | 0.31 |
| Mock vs CART+Treg | 5.21 | 0.02 |
| Treg vs CART alone | 2.00 | 0.15 |
| Treg vs CART+Treg | 4.00 | 0.04 |
| CART alone vs CART+Treg | 3.00 | 0.08 |

FIG. 60A

| CD19-CART cells (cell number/µl) | | | | |
|---|---|---|---|---|
| | Liver | BM | Spleen | PB |
| Blank | 0 | 0 | 0 | 0 |
| Mock | 0 | 0 | 0 | 0 |
| CART alone | 0 | 0 | 0 | 0 |
| CART+Treg | 23.8 | 37.6 | 6.4 | 20.1 |

FIG. 60B

| | D 0 | D + 9 | D + 27 | D + 28 | D + 29 | D + 17 | D + 18 | D + 19 | D + 20 | D + 21 | D + 22 | D + 23 | D + 24 | D + 25 | D + 25 | D + 27 | D + 28 | D + 29 | D + 30 | D + 31 | D + 32 | D + 32 | D + 33 | D + 34 | D + 35 | D + 36 | D + 37 | D + 38 | D + 39 | D + 40 | D + 41 | D + 42 | D + 43 | D + 44 | D + 45 |
|---|---|---|---|---|---|---|---|---|---|---|---|---|---|---|---|---|---|---|---|---|---|---|---|---|---|---|---|---|---|---|---|---|---|---|---|
| MM1S | x | | | | | | | | | | | | | | | | | | | | | | | | | | | | | | | | | | |
| PanT | | X | | | | | | | | | | | | | | | | | | | | | | | | | | | | | | | | | |
| BiTE | | | | | | | | | | | | | | | | X | X | X | X | X | X | X | X | X | X | X | X | X | X | X | X | X | X | X | X |
| Treg | | | | | | | | | | | | | | | | | | X | | | | | | | X | | | | | | | | | X | |

FIG. 61E

CXCR4 selection: Day 0 (double) enrichment

CXCR4 selection: Day 3 (sequential) enrichment

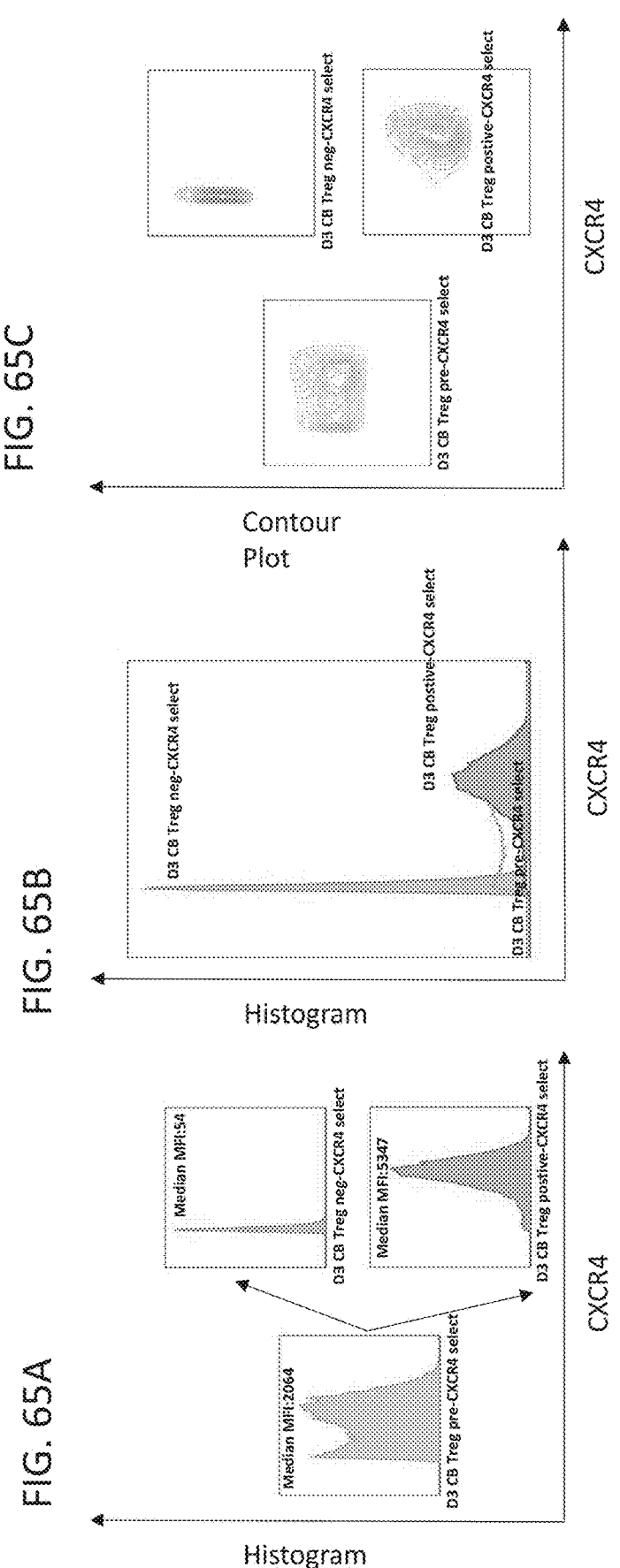

POPULATIONS OF ENRICHED REGULATORY T CELLS AND METHODS FOR PRODUCING SAME

CROSS-REFERENCE TO RELATED APPLICATIONS

This application claims the benefit of U.S. Provisional Patent Application No. 63/166,012, filed Mar. 25, 2021, which is incorporated by reference herein in its entirety for all purposes.

TECHNICAL FIELD

The present disclosure relates generally to the field of immune-regulatory T-cells (Treg) and methods of producing enriched populations of Tregs.

BACKGROUND

Dysregulation of the CXCL12/CXCR4 pathway leads to disorders such as primary myelofibrosis. There is a need for effective treatments for such disorders.

SUMMARY

Provided herein is a method for producing an expanded population of human T regulatory (Treg) cells enriched for CXCR4$^+$ Treg cells from a cryopreserved human umbilical cord blood unit, the method comprising: (a) thawing the cryopreserved human umbilical cord blood unit; (b) diluting and washing the thawed umbilical cord blood unit in a functionally closed system; (c) isolating Treg cells using a double selection method based on CD25$^+$ cell surface expression; (d) ex vivo expanding the isolated CD25$^+$ Treg cells in a culture medium, in a gas permeable cultureware, in the presence of: (1) an effective amount of interleukin-2 (IL-2); (2) a reagent that specifically binds to CD3 and CD28; and (3) anti-CXCR4 magnetic microbeads, for up to 10 days or up to 12 days, wherein the culture medium is replaced about every 48 hours, to produce a CXCR4-enriched culture of CD25$^+$ Treg cells; and (e) harvesting the activated CD25$^+$ CXCR4$^+$ cells from the culture medium to produce an expanded population of human Treg cells enriched for CXCR4$^+$ Treg cells.

In some embodiments, in step (d), (1) the ex vivo expansion is initiated at day 0; (2) the effective amount of IL-2 is added to the isolated CD25$^+$ Treg cells at day 0; and (3) the reagent that specifically binds to CD3 and CD28 is added to the isolated CD25$^+$ Treg cells at day 0.

In some embodiments, the reagent that specifically binds to CD3 and CD28 is removed from the culture medium before the anti-CXCR4 magnetic microbeads are added to the culture medium.

In some embodiments, in step (d), the anti-CXCR4 magnetic microbeads are added to the culture medium 3 or 4 days after the ex vivo expansion is initiated. In some embodiments, in step (d), the anti-CXCR4 magnetic microbeads are added to the culture medium for about 30 minutes before a double ferromagnetic column is used to isolate CXCR4$^+$ Treg cells. In some embodiments, the isolated CD25$^+$ Treg cells are enriched for CXCR4 on the third feed of ex vivo expansion.

In some embodiments, step (d) takes place over 4 or 5 days.

In some embodiments, the reagent that specifically binds to CD25 is an anti-CD25 antibody or an antigen-binding fragment thereof. In some embodiments, the reagent that specifically binds to CD25 is conjugated to a solid support. In some embodiments, the solid support is a magnetic microbead.

In some embodiments, the reagent that specifically binds to CD3 and CD28 comprises an anti-CD3 antibody or an antigen-binding fragment thereof and an anti-CD28 antibody or an antigen-binding fragment thereof. In some embodiments, the reagent that specifically binds to CD3 and CD28 comprises anti-CD3 coated beads and anti-CD28 coated beads.

In some embodiments, the effective amount of IL-2 is about 1000 IU/ml.

Provided herein is a method for producing an expanded population of human Treg cells enriched for CXCR4$^+$ Treg cells from a cryopreserved human umbilical cord blood unit, the method comprising: (a) thawing the cryopreserved human umbilical cord blood unit; (b) diluting and washing the thawed umbilical cord blood unit in a functionally closed system; (c) isolating Treg cells using a double selection method based on CD25$^+$ cell surface expression; (d) ex vivo expanding the isolated CD25$^+$ Treg cells in a culture medium, in a gas permeable cultureware, wherein the ex vivo expansion step comprises: (1) at day 0, adding anti-CD3 and anti-CD28 coated beads to the CD25$^+$ Treg cells in the culture medium; (2) at day 2, adding about 1000 IU/ml IL-2 to the culture medium; (3) at day 3 or 4, removing the anti-CD3 and anti-CD28 coated beads from the culture medium and adding anti-CXCR4 magnetic microbeads to the culture medium; and (4) at day 3 or 4, removing the anti-CXCR4 magnetic microbeads attached to CXCR4$^+$ Treg cells from the culture medium, and adding fresh anti-CD3 and anti-CD28 coated beads to the CXCR4$^+$ Treg cells, wherein the ex vivo expansion takes place for up to 10 days or up to 12 days, wherein the culture medium is replaced about every 48 hours, to produce a CXCR4-enriched culture of CD25$^+$ Treg cells; and (e) harvesting the activated CD25$^+$ CXCR4$^+$ cells from the culture medium to produce an expanded population of human Treg cells enriched for CXCR4$^+$ Treg cells.

In some embodiments, in step (d), IL-2 is added to the culture medium comprising isolated CD25$^+$ Treg cells about every 48 hours.

In some embodiments, the anti-CD3 coated beads and the anti-CD28 coated beads are at a 1:1 ratio. In some embodiments, the CD25$^+$ cells and the anti-CD3 and anti-CD28 coated beads are at a 1:1 ratio.

In some embodiments, in step (e), about $1 \times 10^6$ CD25$^+$ cells/ml are cultured.

In some embodiments, in step (e), the cells are initially cultured in gas-permeable cultureware that has a membrane surface area of 10 cm$^2$. In some embodiments, the culture is subsequently transferred to gas-permeable cultureware that has a membrane surface area of 100 cm$^2$. In some embodiments, in step (d), the culture is not rocked or agitated when the IL-2 is added.

In some embodiments, in step (a), the cryopreserved human umbilical cord blood unit is thawed in a single step in a water bath.

In some embodiments, step (b) does not comprise manual washing. In some embodiments, step (b) takes place in a solution comprising PBS, EDTA, and about 0.5% human serum albumin.

In some embodiments, a double ferromagnetic column method is used in step (c) to isolate CD25$^+$ Treg cells.

In some embodiments, the method further comprising cryopreserving the expanded population of human Treg cells enriched for CXCR4$^+$ Treg cells.

In some embodiments, the expanded population of human Treg cells enriched for CXCR4$^+$ Treg cells is: (i) ≥60% CD4$^+$CD25$^+$; (ii) ≥60% CD4$^+$CD25$^+$ CXCR4$^+$; and (iii) ≤10% CD4$^-$CD8$^+$, as measured by flow cytometry.

Provided herein is an expanded population of human Treg cells enriched for CXCR4$^+$ Treg cells produced by a method disclosed herein.

Provided herein is a method for treating or preventing a bone marrow failure syndrome in a subject, the method comprising administering to the subject an effective amount of the population of activated human Treg cells produced by a method disclosed herein or a population disclosed herein. In some embodiments, the bone marrow failure syndrome is aplastic anemia, primary myelofibrosis or myelodysplastic syndrome.

Provided herein is a method for treating or preventing primary myelofibrosis in a subject, the method comprising administering to the subject an effective amount of the population of activated human Treg cells produced by a method disclosed herein or a population disclosed herein, wherein a dose of 100 million Treg cells is administered to the subject on day 1 of a 28-day cycle for up to 6 cycles.

BRIEF DESCRIPTION OF THE DRAWINGS

FIG. 2A shows significant suppression of the proliferating conventional T cells when co-incubated with Tregs at different ratios. FIG. 2B shows significantly increased suppression capacity of the activated expanded cord blood Tregs harvested at day 14 when compared to freshly isolated cord blood Tregs at day 0 in HLA matched pair (p=0.03) and HLA mismatch pair (p=0.03, 2-sided t-test). (n=2)

FIG. 4A-FIG. 4D depict a series of graphs and plots showing that expanded activated Treg cells continue to remain suppressive, do not express RORγt and show reciprocal increase in IL-10 expression in response to stress. Cord blood Tregs were expanded in culture in the presence of IL-2 and CD3/CD28 co-expressing beads. Cells were also treated with 0 ng/ml, 40 ng/ml or 200 ng/ml IL-6. The cells were fed every 48 hours, and flow cytometry based analysis was performed for the intracellular staining of RORγt as well as the cytokine release assay for IL-10 and IL-17.

FIG. 5A: Positive control includes Tcon cells in presence of CD3/28 beads. FIG. 5B: Negative control—Tcon cells in absence of CD3/28 beads. FIG. 5C: Co-culture of fresh CB Treg cells suppresses Tcon cell proliferation. FIG. 5D: Co-culture of cryopreserved CB Treg cells suppresses Tcon cell proliferation.

FIG. 7A-FIG. 7B show that expanded cord blood Tregs remain suppressive in the presence of dexamethasone (referred to as "Dex" or "steroid"). "Tcon" refers to conventional T cells. "Treg" refers to regulatory T cells. Top left and bottom left panels are steroid (−). Top right and bottom right panels are with 100 μg/mL steroid.

FIG. 8A depicts CD25, CD8 and CD127 expression in cryopreserved Tregs upon thawing. FIG. 8B depicts that cryopreserved Tregs exhibit high expression of Helios and FoxP3. FIG. 8C depicts that cryopreserved Tregs suppress proliferating conventional T cells using CellTrace™ Violet Dye based suppression assay.

FIG. 9A is a graph depicting the effect of fresh activated Treg cells or cryopreserved (frozen) activated Treg cells on the GVHD score. FIG. 9B is a graph depicting the effect of fresh activated Treg cells or cryopreserved (frozen) activated Treg cells on the weight of mice. "CB" refers to umbilical cord blood. "PBMC" refers to peripheral blood mononuclear cells.

FIG. 10A depicts the GVHD Prophylaxis study design where the NSG mice undergo sublethal irradiation on day −1 followed by injection of cord blood (CB) Tregs—1×10$^7$ cells and injection of PBMC-1×10$^7$ cells on day 0. Subsequently, mice are followed every other day for measurement of weight and GVHD score. Peripheral blood and serum is drawn at baseline and at weekly intervals thereafter starting at day +7. FIG. 10B depicts the GVHD Treatment study design where the NSG mice undergo sublethal irradiation on day −1 and injection of PBMC-1×10$^7$ cells on day 0. Injection of CB Tregs—1×10$^7$ cells is administered on day +4, +11, +18 and +25. Subsequently, mice are followed every other day for measurement of weight, GVHD score and survival. Peripheral blood and serum is drawn at baseline and at weekly intervals thereafter starting at day +7. "PBMC" refers to peripheral blood mononuclear cells. "Frozen Tregs" refers to cryopreserved Tregs. "NSG" refers to non-SCID gamma null mouse.

FIG. 12A: IP-10; FIG. 12B: TNFα; FIG. 12C: GM-CSF; FIG. 12D: MIP-1β; FIG. 12E: FLT-3L; FIG. 12F: IFN-γ.

FIG. 21A is a line graph showing the effect on mouse weight over time. CB Treg recipients preserve weight whereas a decrease in the "myeloma alone" arm demonstrates weight loss beginning around week 4 post tumor inoculation. FIG. 21B is a line graph showing the effect on circulating myeloma cells in peripheral blood over time. Weekly blood draws were performed and the isolated cells were analyzed for human CD38+ cells in circulation. A significant increase in circulating myeloma cells was evident in the "myeloma alone" arm compared to Treg recipients (p=0.002). FIG. 21C depicts a series of images showing tumor load visualization. As monitored by weekly bioluminescence imaging, minimal evidence of MM1S cells was visualized in CB Treg recipients as compared to widespread tumor in the "myeloma alone" mice. FIG. 21D is a line graph showing tumor load quantification over time. On the qualification of bioluminescence imaging, significantly higher signal was observed on day 17, 24 and 31. The triangle indicates CB Treg i.v. injection and the arrow indicates MM1S cell i.v. injection.

FIG. 29 is a table providing cord blood selection criteria for various products comprising populations of activated human Treg cells. "AABB" refers to the American Association of Blood Banks. "FACT" refers to the Foundation for the Accreditation for Cellular Therapy. "CLIA" refers to the Clinical Laboratory Improvement Amendments.

FIG. 30 is a table providing cord blood selection criteria for various products comprising populations of activated human Treg cells.

FIG. 35A shows the percentage of human CD45 cells. FIG. 35B shows the percentage of human CD45 cells that co-express CD4 and CD45. FIG. 35C shows the percentage of human CD45 cells that are labeled CB Treg cells. Rux or R=ruxolitinib.

FIG. 36A shows the normalized levels of plasma IL-7. FIG. 36B shows the normalized levels of plasma IL-15. FIG. 36C shows the normalized levels of plasma IL-4. Ruxo=ruxolitinib.

FIG. 37A shows the normalized levels of plasma IL-1a. FIG. 37B shows the normalized levels of plasma IL-17. FIG. 37C shows the normalized levels of plasma IFNa2. FIG. 37D shows the normalized levels of plasma FGF-12. FIG. 37E shows the normalized levels of plasma Macrophage-Derived Chemokine (MDC). Ruxo=ruxolitinib.

FIG. 38A shows the normalized levels of plasma IL-1RA. FIG. 38B shows the normalized levels of plasma IL-1a3. FIG. 38C shows the normalized levels of plasma IL-12p70. Ruxo=ruxolitinib.

FIG. 39A shows hemoglobin levels. FIG. 39B shows platelet levels. Rux or R=ruxolitinib.

FIG. 40B shows that CB Tregs decrease and Teff cells completely block MM1S (myeloma cell line) migration (p<0.001). FIG. 40C shows that CB Tregs decrease and Teff cells completely block RPMI8226 (myeloma cell line) migration (p=0.04). FIG. 40D show that CB Tregs decrease U266 (myeloma cell line) migration but not significantly. Teff cells block U266 migration. FIG. 40E shows that CB Tregs and Teff cells do not have any effect on migration of HL-60 (acute myeloid leukemia cell line). FIG. 40F shows that CB Tregs and Teff cells do not have any effect on migration of Nalm6 (pre-B cell leukemia cell line). P<0.05 were determined by unpaired Student t-test at each time point. The y-axis in FIG. 40B-FIG. 40**D depicts cell number×10³/μL.

FIG. 43 depicts a table summarizing clinical data from a Phase 1 clinical trial of allogeneic cord blood-derived Treg cells in patients with BMF.

FIG. 47 is a series of graphs depicting inflammatory cytokine levels of Patient 1 in a Phase 1 clinical trial of allogeneic cord blood-derived Treg cells in patients with BMF. The x-axis shows days after administration of Treg cells. Upper left panel: CXCL-5. Upper right panel: IL-17. Lower left panel: IL-15. Lower right panel: MCP.

FIG. 60A-FIG. 60B depict tables summarizing data from a study of a xenogeneic lymphoma mouse model treated with i) mock-chimeric antigen receptor (CAR) T cells, ii) cord blood-derived Treg cells, iii) CD19-CAR T cells, or (iv) cord blood-derived Treg cells+CD19-CAR T cells. FIG. 60A depicts comparisons of survival times for various groups. FIG. 60B depicts CD19-CAR T cells/μL in various organs.

FIG. 61A-FIG. 61H depict a series of graphs and images showing the effect of administration of multiple doses of Tregs in a xenogeneic mouse model of multiple myeloma. FIG. 61A is a line graph showing the effect on mouse weight over time of mice administered (1) MM.1S myeloma cells alone; (2) myeloma cells and CD3+ T conventional cells (Tcon); (3) myeloma cells and cord blood-derived Treg cells (Treg); or (4) myeloma cells, Tcon cells and Treg cells (Tcon Treg). FIG. 61B shows a series of images produced with non-invasive bioluminescent imaging (BLI) of mice treated with CD3+ T conventional cells (Tcons) or a combination of Tcon cells and Treg cells (Tcons w Tregs). FIG. 61C is a line graph depicting tumor load quantification by BLI. FIG. 61D is an image showing an example of extramedullary relapse in a mouse treated with Tcon cells alone. FIG. 61E depicts the experimental design for administration of a bispecific T-cell engager against CD3 and BCMA (BiTE®) with Treg cells. FIG. 61F shows a series of images produced with non-invasive BLI of mice treated with the BiTE® and PanT cells or a combination of the BiTE®, PanT and Treg cells. FIG. 61G is a line graph showing the effect of Treg administration on BiTE®-mediated weight loss. FIG. 61H is a bar graph showing the effect of Treg administration on the GVHD (graft versus host disease) score.

FIG. 64A depicts the percentage of CXCR4$^{hi}$ cells in the fractions. FIG. 64B depicts MFI (mean fluorescence intensity) in the fractions. FIG. 64C depicts MFI fold change in the fractions.

FIG. 65A-FIG. 65C depict histogram and contour plots for CXCR4 expression on different separation populations of the D3 (day 3) CB Treg cells.

FIG. 66A shows data for the Culture 1. FIG. 66B shows data for the Culture 2. FIG. 66C shows data for the Culture 3.

FIG. 68A shows the CXCR4 expression in the CXCR4 enriched vs. Treg control cells. FIG. 68B shows the intra-cellular expression of the FOXP3 and Helios in the D12 (day 12) CXCR4 enriched CB Treg cells.

FIG. 70A shows the diagrammatic representation of the transwell migration assay experiment. FIG. 70B shows photomicrographs of the cell concentration of different cells: Treg control; CXCR4-negative and CXCR4-enriched CB Treg cells in the lower chamber of the transwell migration assay.

DETAILED DESCRIPTION

Figure 1:
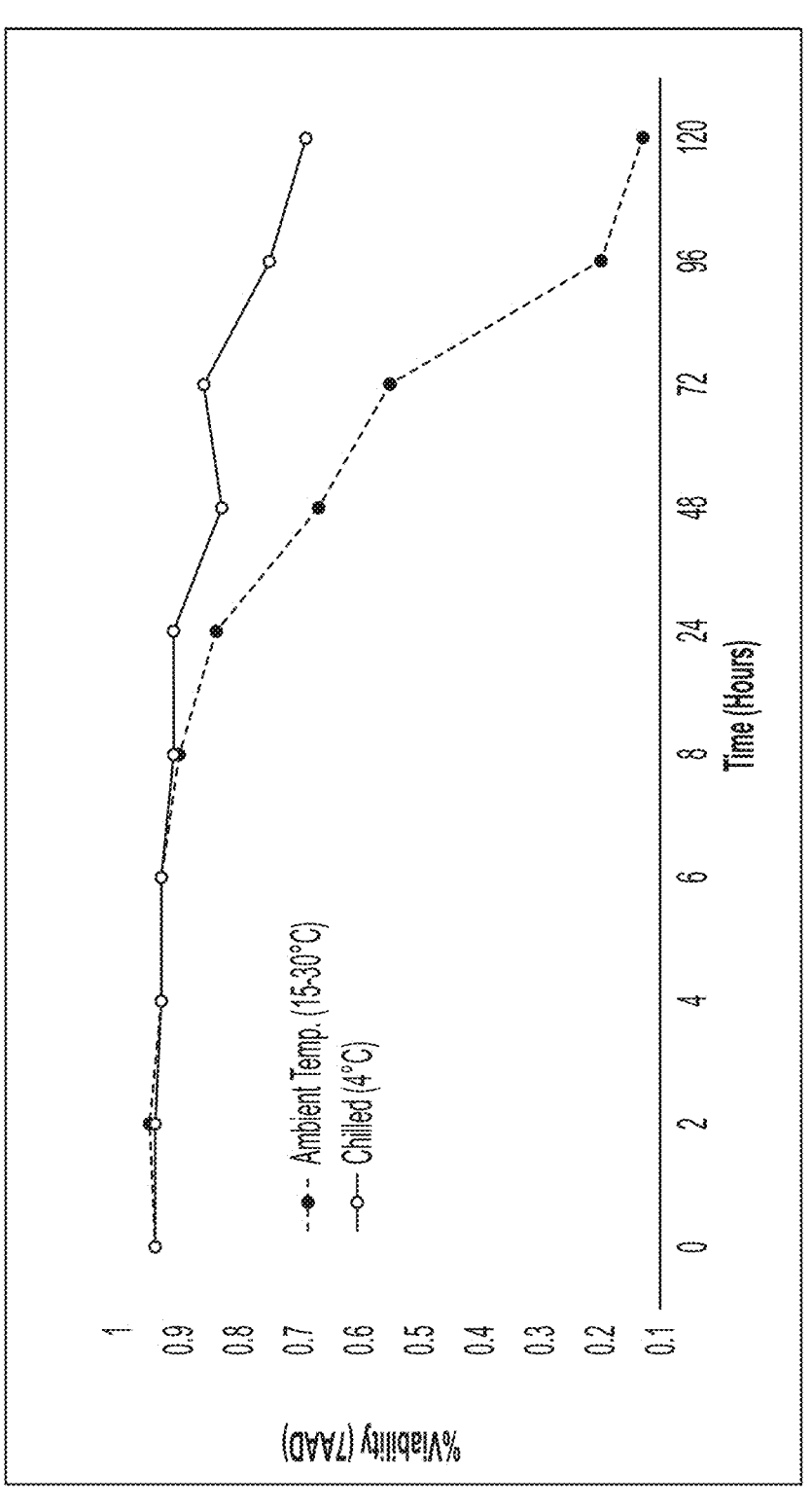
FIG. 1 is a line graph showing results from an assay measuring percent viability (7AAD) of fresh activated Treg cells stored at room temperature (15-30° C.) or at 4° C. N=9.

Healthy regulatory T cells (Treg) protect the body from auto-reactive cytotoxic T cells by preventing the activation and proliferation of these cells that have escaped thymic deletion or recognize extrathymic antigens. Thus, Tregs are critical for homeostasis and immune regulation, as well as for protecting the host against the development of autoimmunity. Additionally, both infused and innate Tregs home to areas of inflammation due to i) proliferating effector T cells producing surplus IL-2 which is essential for the survival of Treg; and ii) homing signals released by the injured antigen presenting cells/dendritic cells residing in the tissue.

Although several types of Tregs have been described, the best characterized and most potent subset expresses CD4 and high levels of CD25 (IL-2Ra) and FoxP3, a Forkhead box P3 gene product and CD127$^{lo}$. These CD4$^+$CD25$^+$ FoxP3$^+$CD127$^{lo}$ Tregs can be further subdivided into natural Tregs (nTregs), which develop in the thymus and undergo thymic selection, and induced Tregs (iTregs), which develop in the periphery under the influence of cytokines such as transforming growth factor β (TGFβ). (See Ohkura et al., Immunity 38(3):414-23 (2013)).

In their natural state, Treg cells play an important role in maintaining immune homeostasis and limiting autoimmune responses by modulating both innate and adaptive immunity. Tregs are essential for immune homeostasis by maintaining peripheral tolerance and inhibiting autoimmune responses and pathogenic tissue damage. (See Burrell et al., J. Immunol 189(10):4705-11 (2012); Schneidawind et al., Blood 122(18):3116-21 (2013); and Tang et al., Col Spring Harb Perspect Biol 5(11):a015552 (2013)). However, in autoimmune disease, defective endogenous Tregs cannot protect the body effectively from the onslaught of self-reactive cytotoxic/effector T cells.

One hurdle to the development of Treg therapy is the instability of regulatory T-cells, which often "flip" to an inflammatory effector T-cell phenotype. For example, Treg cells can down-regulate expression of FOXP3, thereby permitting gain of effector T cells-like functions by activation of E3 ubiquitin ligase Stub 1 in and Hsp70-dependent manner (Chen et al., Immunity. 2013 Aug. 22; 39(2):272-85)

To address this difficulty, the present disclosure uses umbilical cord blood-derived Tregs. Cord blood is less immunogenic and is available in surplus in public and private cord blood banks. Cord blood (CB) is distinct from peripheral blood (PB), as it is more suppressive, has different epigenetic properties and a different ratio of blood cells. Moreover, cord blood cells are primitive, less immune-reactive, naïve, exhibit a higher proliferative index, and can function across the human leukocyte antigen (HLA) border. Cord blood source is unique because Tregs derived from cord blood are naïve, more suppressive and lack plasticity compared to other sources of Tregs. Likewise, because cord blood cells are constantly stimulated by many cytokines during the stress of childbirth, they are less sensitive to possible toxic environmental substances.

Another hurdle to the development of Treg therapy is clinically adequate cell numbers that can be repeatedly infused over a period of time to quell ongoing inflammation. Disclosed herein are methods for producing an expanded population of human T regulatory (Treg) cells from at least one cryopreserved human umbilical cord blood unit, wherein the population is enriched for Treg cells expressing CXCR4 (C-X-C Motif Chemokine Receptor 4). Treg cells enriched for CXCR4 expression preferentially home to the bone marrow and abbreviate the transit time from the point of infusion to the site of bone marrow inflammation. Splenomegaly is one of the major clinical manifestations of primary myelofibrosis and is directly linked to splenic extramedullary hematopoiesis (EMH). Alteration of CXCL12/CXCR4 pathway could also lead to splenic EMH by migrated clonal hematopoietic cells from the bone marrow to the spleen (Song et al., *Int J Mol Sci,* 2018. 19(3)). Uniform delivery of healthy allogeneic CXCR4-expressing Treg cells can lead to resolution of inflammation and restoration of normal hematopoiesis.

Also disclosed are populations of activated and CXCR4-expression enriched human Treg cells produced by the methods described herein. Further disclosed herein are methods for treating diseases or disorders by administering to a subject an effective amount of a population of activated human Treg cells. Additionally disclosed herein are methods for cryopreserving an expanded population of activated human Treg cells produced from at least one cryopreserved human umbilical cord blood unit. Further disclosed herein are populations of immunosuppressive Treg cells.

Definitions

Unless otherwise defined, all technical and scientific terms used herein have the same meaning as commonly understood by one of ordinary skill in the art to which this disclosure belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

Unless specifically stated or obvious from context, as used herein, the terms "a," "an," and "the" are understood to be singular or plural.

Unless specifically stated or obvious from context, as used herein, the term "or" is understood to be inclusive.

The term "about" when immediately preceding a numerical value means±0% to 10% of the numerical value, ±0% to 10%, ±0% to 9%, ±0% to 8%, ±0% to 7%, ±0% to 6%, ±0% to 5%, ±0% to 4%, ±0% to 3%, ±0% to 2%, ±0% to 1%, ±0% to less than 1%, or any other value or range of values therein. For example, "about 40" means±0% to 10% of 40 (i.e., from 36 to 44).

A population of "activated" Treg cells can be defined as a homogenous cell population that has been generated as a result of continuous exposure to high concentrations of interleukin-2 (IL-2) under culture conditions and cell density specified herein in the presence of T cell receptor (TCR) stimulation by the CD3/28 beads that allow for a stimulated Treg cell that leads to consistent suppression of inflammation.

As used herein, an "antibody fragment" or "antigen-binding fragment" refers to a molecule other than a conventional or intact antibody that includes a portion of a conventional or intact antibody containing at least a variable region that binds an antigen. Examples of antibody fragments include but are not limited to Fv, single chain Fv (scFv), Fab, Fab', Fab'-SH, F(ab')2; diabodies; linear antibodies; and single-domain antibodies containing only the VH region (VHH).

As used herein, the terms "patient" or "subject" are used interchangeably herein to refer to any mammal, including humans, domestic and farm animals, and zoo, sports, and pet animals, such as dogs, horses, cats, and agricultural use animals including cattle, sheep, pigs, and goats. One preferred mammal is a human, including adults, children, and the elderly. A subject may also be a pet animal, including dogs, cats and horses. Examples of agricultural animals include pigs, cattle and goats.

The terms "treat", "treating", "treatment" and the like, as used herein, unless otherwise indicated, refers to reversing, alleviating, inhibiting the process of, or preventing the disease, disorder or condition to which such term applies, or one or more symptoms of such disease, disorder or condition and includes the administration of any of the compositions, pharmaceutical compositions, or dosage forms described herein, to prevent the onset of the symptoms or the complications, or alleviating the symptoms or the complications, or eliminating the disease, condition, or disorder. In some instances, treatment is curative or ameliorating.

As used herein, "preventing" means preventing in whole or in part, or ameliorating or controlling, or reducing or halting the production or occurrence of the thing or event, for example, the disease, disorder or condition, to be prevented.

The phrases "therapeutically effective amount" and "effective amount" and the like, as used herein, indicate an amount necessary to administer to a patient, or to a cell, tissue, or organ of a patient, to achieve a therapeutic effect, such as an ameliorating or alternatively a curative effect. The effective amount is sufficient to elicit the biological or medical response of a cell, tissue, system, animal, or human that is being sought by a researcher, veterinarian, medical doctor, or clinician. Determination of the appropriate effective amount or therapeutically effective amount is within the routine level of skill in the art.

The terms "administering", "administer", "administration" and the like, as used herein, refer to any mode of transferring, delivering, introducing, or transporting a therapeutic agent to a subject in need of treatment with such an agent. Such modes include, but are not limited to, intraocular, oral, topical, intravenous, intraperitoneal, intramuscular, intradermal, intranasal, and subcutaneous administration.

The term "CXCR4-enriched", as used herein, refers to a population of Treg cells that has undergone a method to increase the number of CXCR4-expressing (or CXCR4$^+$) Treg cells in the population compared to a population that has not undergone the method.

Methods for Producing an Expanded Population of T Regulatory Cells

Because Treg cells are present only at low frequency in circulating blood or umbilical cord blood, production of clinically relevant Treg cell doses requires ex vivo enrichment and expansion of Treg cells with a CD4$^+$CD25$^+$ phenotype.

In any of the methods described herein, cord blood banks and donors can be qualified prior to use of human umbilical cord blood in the methods described herein. In some embodiments, a unit of human umbilical cord blood is supplied by a public cord blood bank in the United States, European Union, or other region that has met supplier qualification criteria. Qualification of the cord blood unit may include verification that the donor has no evidence of relevant communicable diseases based on screening and testing. Additional selection criteria may be applied, including one or more of maternal age, gestational age, total nucleated cell (TNC) count, pre-freeze percent cell viability, cryopreserved volume, collection date, storage conditions, race, ethnicity, maternal donor history (e.g., infectious disease history, travel history), family medical history, cytomegalovirus seropositivity, gestational diabetes, high blood pressure and the like. Selection criteria may be relevant to insure consistency of the umbilical cord blood units before use. Cord blood selection criteria for various products comprising populations of activated human Treg cells are provided in FIG. 29 and FIG. 30.

In some embodiments, the cellular starting material (CBU) is thawed, washed, and enriched for CD25$^+$ mononuclear cells (MNCs) using immunomagnetic selection. The CD25$^+$ MNCs are placed into a gas permeable culture device with interleukin-2 (IL-2) and anti-CD3/anti-CD28 beads. The cells are culture-expanded for up to a 10-day period, up to a 12-day period, or up to a 14-day period. In some embodiments, the cells are culture-expanded for 8 to 10 days or for 10 to 12 days. On day 8, day 9, day 10, day 11, day 12 or day 14, the expanded cells are harvested and washed, and the CD3/CD28 beads are removed by an immunomagnetic method. The de-beaded cells are then formulated and packaged.

In some embodiments, disclosed herein is a method for producing an expanded population of activated human T regulatory (Treg) cells from at least one cryopreserved human umbilical cord blood unit, the method comprising: a) thawing the cryopreserved human umbilical cord blood unit; b) diluting and washing the thawed umbilical cord blood unit in a functionally closed system or a closed system; c) isolating naturally occurring Treg cells using a double selection method based on CD25$^+$ cell surface expression; d) ex-vivo expanding the isolated CD25$^+$ Treg cells in a culture medium(s), in a gas permeable cultureware, in the presence of an effective amount of interleukin-2 (IL-2) and in the presence of a reagent that specifically binds to CD3 and CD28, for up to 14 days, wherein the culture medium is replaced about every 48 hours, to produce a population of activated CD25$^+$ Treg cells; and e) harvesting the activated CD25$^+$ cells from the culture medium to produce an expanded population of activated human Treg cells. In some embodiments, the activated human Treg cells have a specified phenotype. In some embodiments, the method further comprises using an algorithm to select an optimal cryopreserved umbilical cord blood unit before the thawing step (i.e., step a)). In some embodiments, the method further comprises, after the harvesting step (i.e., step f)) releasing the expanded population of activated human Treg cells with a characteristic phenotype for clinical use based on defined criteria.

In some embodiments, a single umbilical cord blood unit (CBU) is used. In some embodiments, two or more (e.g., 2, 3, 4, 5, 6, 7, 8, 9, 10, 11, 12, 13, 14, 15, 16, 17, 18, 19, 20, or more) pooled CBUs are used. In some embodiments, between two and four pooled CBUs are used. In some embodiments, the CBUs are collected from healthy donors and frozen prior to use.

In some embodiments, the cryopreserved human umbilical cord blood unit is thawed in a single step in a water bath (e.g., at 37° C.+/−1 degree). In some embodiments, the thawing of the cryopreserved umbilical cord blood units comprises gentle massaging of the bag while it is submerged in a 37° C. (+/−1 degree) water bath, until the bag feels slushy. Then, the cells are immediately transferred for the washing process.

In some embodiments, the thawed cord blood unit is subjected to an automated wash using an automated cell processing system (e.g., a functionally closed system or a closed system). In some embodiments, an automated cell processing system is a Sepax system (Biosafe). A Sepax system is a centrifugation and pump device intended for use in cell therapy where specific blood components need to be isolated. Its principle is based on centrifugal separation, allowing separation according to density and size of the blood particles. Blood components are collected in individual bags and are readily available for transfusion. An automated cell processing system may allow for starting volumes of up to 100 ml to a final volume of 50-150 ml. The dilution ratio between the initial volume and the dilution volume is adjustable with a range of 0.5 to 2.0 times. The wash cycles can include a standard wash of one cycle or in certain circumstances, a high wash of two cycles. The automated cell processing system is programmed to automatically perform the dilution of the initial product, osmolarity restoration, washing, centrifugation, supernatant extraction and cell re-suspension. Usually, the starting volume is set at 25 ml; the final volume is set at 100 ml and a dilution factor of 1.0. The washing reagent comprises 5% human serum albumin (HSA) (CSL Behring) and 10% dextran-40 (D-40) (Hospira). Post-wash, the cord blood cells are collected into a cord blood wash bag.

In some embodiments, a basic wash media comprises about 20 ml of 25% HSA and about 1000 ml PBS/EDTA buffer. In some embodiments, a working wash media comprises about 300 ml of basic wash buffer and about 50 mg of Magnesium chloride (MgCl$_2$) and about 2500 Units of DNase. In some embodiments, a modified media comprises X-Vivo 15 media (Lonza) and about 10 ml of GlutaMAX-1 and about 100 ml of thawed human AB serum. In some embodiments, the wash media comprises PBS, EDTA, and 0.5% HSA.

In some embodiments, the washing step does not comprise manual washing.

In some embodiments, the automated washed cord blood cells undergo an additional manual wash using working wash media; where the final volume is constituted at 200 ml and the reconstituted cells under centrifugation at room temperature at 300 g for 10 minutes. Finally, the washed cells are resuspended at a concentration of 100×10$^6$ cells in 0.09 ml.

In some embodiments, the reagent that specifically binds to CD25 is an anti-CD25 antibody or an antigen-binding fragment thereof. In some embodiments, the reagent that specifically binds to CD25 is conjugated to a solid support. In some embodiments, the solid support is a bead, a column or a plate. In some embodiments, the solid support is a magnetic microbead. In some embodiments, a bead comprises cellulose, a cellulose derivative, an acrylic resin, glass, a silica gel, polystyrene, gelatin, polyvinyl pyrrolidone, a co-polymer of vinyl and acrylamide, polystyrene cross-linked with divinylbenzene, a polyacrylamide, a latex gel, polystyrene, dextran, rubber, silicon, a plastic, nitrocellulose, a natural sponge, control pore glass, a metal, cross-linked dextran or agarose gel.

In some embodiments, the CD25 microbeads are added to washed cord blood cells at a ratio of 0.02 ml CD25 microbeads per 100×10$^6$ cells. The cells and microbeads are incubated together at 4° C. for 30 minutes. In some embodiments, LS columns (Miltenyi) made of ferromagnetic spheres are used in combination with an external magnetic field, where the unlabeled cells are allowed to pass through freely, whereas the magnetically labeled CD25$^+$ cells are held in suspension within the column and do not actually "bind" the column matrix. This suspension minimizes stress on the cells and allows for efficient sterile washing by avoiding cell aggregation. The LS columns are primed using the working wash media and the CD25$^+$ microbead labeled cells are allowed to pass through the LS columns attached to the magnetic field. The LS columns are then removed from the magnetic field, and a plunger is used to push out the loosely retained cells bound to the CD25 microbeads and labeled as positive fraction 1. In the double selection method, the positive fraction 1 now behaves as the starting solution to be allowed to pass through the primed LS column and the steps are repeated where the positive fraction 2 is collected and finally, the two positive fractions are mixed to get a final selection of CD25$^+$ cells. In some embodiments, a double ferromagnetic column (e.g., LS column) method is used to isolate CD25$^+$ cells.

In some embodiments, the reagent that specifically binds to CD3 and CD28 comprises an anti-CD3 antibody or an antigen-binding fragment thereof and an anti-CD28 antibody or an antigen-binding fragment thereof. In some embodiments, the reagent that specifically binds to CD3 and CD28 comprises anti-CD3 coated beads and anti-CD28 coated beads (i.e., "anti-CD3/anti-CD28 coated beads"). In some embodiments, the anti-CD3 coated beads and the anti-CD28 coated beads are at a 1:1 ratio in the reagent that specifically binds to CD3 and CD28. In some embodiments, the CD25$^+$ cells and the anti-CD3/anti-CD28 coated beads are at a 1:1 ratio when the CD25$^+$ cells are cultured in the presence of a reagent that specifically binds to CD3 and CD28.

In some embodiments, the effective amount of IL-2 used in a method for producing an expanded population of activated human Treg cells is up to about 1000 IU/ml. In some embodiments, the effective amount of IL-2 is about 1000 IU/ml. In some embodiments, the IL-2 is human IL-2. In some embodiments, the isolated CD25$^+$ Treg cells are suspended in a culture medium comprising IL-2 at the immediate beginning of the culturing step of the methods described herein.

In some embodiments, during the culturing step, the culture medium is replaced about every 48 hours without disturbing the cells. In some embodiments, the culture is not mixed and resuspended in the culturing step of the methods described herein.

In some embodiments, about 1×10$^6$ CD25$^+$ cells/ml are cultured in the presence of a reagent that specifically binds to CD3 and CD28 in a method for producing an expanded population of activated human Treg cells. In some embodiments, the CD25$^+$ cells are initially cultured in gas-permeable cultureware that has a membrane surface area of 10 cm$^2$. In some embodiments, the culture is subsequently transferred to gas-permeable cultureware that has a membrane surface area of 100 cm$^2$.

In some embodiments, from about 0.5×10$^9$ to about 12×10$^9$, or from about 1×10$^9$ to about 2×10$^9$, activated CD25$^+$ cells are harvested following 14 days of culture in the presence of a reagent that specifically binds to CD3 and CD28. In some embodiments, the manufacturing process described herein results in 50-fold or greater expansion of the CD4$^+$CD25$^+$ Treg population. In some embodiments, the expanded population of activated human Treg cells is cryopreserved following the harvesting step. In some embodiments, the expanded population of activated human Treg cells is not cryopreserved following the harvesting step and is released rapidly for administration.

Additionally provided herein is a method for producing an expanded population of activated human T regulatory (Treg) cells from at least one cryopreserved human umbilical cord blood unit, the method comprising: a) thawing the cryopreserved human umbilical cord blood unit in a single step in a water bath; b) diluting and washing the thawed umbilical cord blood unit in a solution comprising PBS, EDTA, and about 0.5% human serum albumin in a functionally closed system without manual washing; c) isolating naturally occurring Treg cells using a double selection method based on CD25$^+$ cell surface expression using a double ferromagnetic column method; d) ex-vivo expanding the isolated CD25$^+$ Treg cells in a culture medium(s), in a gas permeable cultureware, in the presence of about 1000 IU/ml of interleukin-2 (IL-2) and in the presence of anti-CD3 and anti-CD28 coated beads, for up to 10 days, up to 12 days or up to 14 days, wherein the culture medium is replaced about every 48 hours, to produce a population of activated CD25$^+$ Treg cells; wherein the CD25$^+$ Treg cells and the anti-CD3 and anti-CD28 coated beads are at a 1:1 ratio; wherein the culture is not mixed and resuspended; and e) harvesting the activated CD25$^+$ cells from the culture medium to produce an expanded population of activated human Treg cells.

Following harvesting, the Treg cells may be tested for contamination, viability, purity, counted for cell number, and/or examined using flow cytometry.

In some embodiments, the active substance (DS) is a liquid cell suspension comprising or consisting of nucleated cord blood cells which have a T-regulatory cell phenotype (CD4$^+$CD25$^+$). In some embodiments, the DS is a liquid cell suspension comprising or consisting of nucleated cord blood cells, of which ≥ about 60% have a T-regulatory cell phenotype (CD4$^+$CD25$^+$) and < about 10% have a T-cytotoxic/suppressor cell phenotype (CD4$^-$CD8$^+$). In some embodiments, the final product (DP) is a liquid cell suspension comprising or consisting of the active substance suspended in an excipient solution comprising or consisting of Plasma-Lyte A with 0.5% human serum albumin (HSA), in a final volume of 50 mL.

In some embodiments, a conditional CD8$^+$ cell depletion step is used, if needed, to reduce the content of CD4$^-$CD8$^+$ cytotoxic/suppressor T-cells in the population of activated Treg cells, prior to final formulation. Prior to harvesting, CD8$^+$ cells can be depleted from the culture medium using a reagent that specifically binds to CD8 (i.e., an anti-CD8 antibody or antigen binding fragment thereof) and removing any cells that bind to the reagent. In some embodiments, this reagent can be conjugated to a solid support, such as, for example, beads, columns, and plates. For example, the beads may be magnetic microbeads coated with an anti-CD8 antibody. Beads may be made from any material commonly used in the art, including, but not limited to, cellulose, cellulose derivatives, acrylic resins, glass, silica gels, polystyrene, gelatin, polyvinyl pyrrolidone, co-polymers of vinyl and acrylamide, polystyrene cross-linked with divinylbenzene or the like, polyacrylamides, latex gels, polystyrene, dextran, rubber, silicon, plastics, nitrocellulose, natural sponges, silica gels, control pore glass, metals, cross-linked dextrans, and agarose gel.

Following CD8$^+$ cell depletion, the methods described herein may further involve the step of analyzing the cells remaining in the culture medium for the presence of CD4$^-$CD8$^+$ cells. For example, the analyzing may involve determining the number of cells remaining in the culture medium that are CD4$^-$CD8$^+$. When ≥10% of the cells remaining in the culture medium are CD4$^-$CD8$^+$ cells, a second round of CD8$^+$ cell depletion can be performed.

At the end of the cell culture, an additional step of removal of anti-CD3/anti-CD28 coated beads can be performed if the concentration is higher than 100 per 3×10$^6$ cells.

Criteria for releasing the expanded population of activated human Treg cells with a characteristic phenotype for clinical use may include: 7 amino-actinomycin-D (7-AAD) viability ≥70%, CD4$^+$CD25$^+$ purity ≥60%, gram stain with 'no organisms', and endotoxin <5 EU/kg.

In some embodiments, a large volume product with massive scale of expansion up to greater than 1000-fold can be generated, where the final population of cells is homogenous, well-defined Treg cells with cell numbers ranging from approximately 0.5×10$^9$ to 12×10$^9$ Treg cells that are harvested following up to 14 days of culture. In some embodiments, the final product can remain stable for up to 8 hours when stored at room temperature and 96 hours when stored at 4° C.

A. Methods for Producing an Expanded Population of CXCR4-Expressing T Regulatory Cells Exploiting CXCR4 expression on the Treg cell surface allows for Treg cell homing to the areas of dysregulation of the CXCR4/CXCL12 axis. In the case of primary myelofibrosis, these areas would be bone marrow and potentially ongoing extramedullary hematopoiesis due to the clonal hematopoietic cells in spleen. Targeting of CXCR4/CXCL12 axis allows the repeated infusion of the CB Treg cells to capture any residual disease or escaped cells.

CK0804 is a product where additional enrichment is performed to ensure that there is consistent cell surface expression of CXCR4 in the cultured CB Treg cells and that the cell surface expression of CXCR4 is retained during the freeze/thaw process. The starting material for CK0804 remains HLA agnostic but fulfils predetermined qualification testing for the purpose of manufacturing. One batch manufacturing process result in multiple doses that are cryopreserved in single doses of 100 million cells each. The product generated from a single expansion can be cryopreserved and administered to different patients. The same patient can receive multiple doses from different batches.

A population of CB-derived CXCR4-expressing Treg cells (e.g., the CK0804 product) can be manufactured in a 10-12-day process, starting with thaw and wash of the CBU, and immunomagnetic enrichment of CD25$^+$ mononuclear cells (MNCs). The CD25$^+$ enriched MNCs are placed into culture with X-Vivo 15 supplemented by GlutaMax (2 mM) and IL-2 (1000 IU/ml), and anti-CD3/CD8 beads, and incubated at 37° C. with 5% CO$_2$. The cultured cells are enriched for CXCR4 on the third feed of culture expansion. The enrichment can be performed by using magnetic microbeads coated with anti-CXCR4 antibody to isolate CXCR4-expressing Treg cells from the culture medium. The final formulation and fill of the CK0804 final product (DP) occurs on the last day of the 4$^{th}$ or 5$^{th}$ expansion-day process. If necessary, the cells undergo CD8 depletion prior to harvest and final formulation to ensure that the CD4$^-$CD8$^+$ T-cytotoxic/suppressor cell content is less than 10%.

The ex-vivo expanded Treg cells are harvested, washed, depleted of residual CD3/CD28 beads, and formulated in infusable cryopreservation medium containing 10% dimethyl sulfoxide (DMSO). This product can then be cryopreserved in cryobags utilizing a controlled rate freezer and transferred to vapor phase LN$_2$ (<minus 150° C.).

Provided herein is a method for producing an expanded population of human Treg cells enriched for CXCR4$^+$ Treg cells from a cryopreserved human umbilical cord blood unit, the method comprising: (a) thawing the cryopreserved human umbilical cord blood unit; (b) diluting and washing the thawed umbilical cord blood unit in a functionally closed system; (c) isolating Treg cells using a double selection method based on CD25$^+$ cell surface expression; (d) ex vivo expanding the isolated CD25$^+$ Treg cells in a culture medium, in a gas permeable cultureware, in the presence of: (1) an effective amount of interleukin-2 (IL-2); (2) a reagent that specifically binds to CD3 and CD28; and (3) anti-CXCR4 magnetic microbeads, for up to 10 days or up to 12 days, wherein the culture medium is replaced about every 48 hours, to produce a CXCR4-enriched culture of CD25$^+$ Treg cells; and (e) harvesting the activated CD25$^+$ CXCR4$^+$ cells from the culture medium to produce an expanded population of human Treg cells enriched for CXCR4$^+$ Treg cells.

In some embodiments, in step (d), (1) the ex vivo expansion is initiated at day 0; (2) the effective amount of IL-2 is added to the isolated CD25$^+$ Treg cells at day 0; and (3) the reagent that specifically binds to CD3 and CD28 is added to the isolated CD25$^+$ Treg cells at day 0. In some embodiments, in step (d), an effective amount of IL-2 is added to the culture medium comprising isolated CD25$^+$ Treg cells about every 48 hours.

In some embodiments, the reagent that specifically binds to CD3 and CD28 is added to the culture medium twice: the first time along with the IL-2 at the beginning of the expansion step, and the second time after anti-CXCR4 magnetic microbeads are removed. In some embodiments, the reagent that specifically binds to CD3 and CD28 is removed from the culture medium before the anti-CXCR4 magnetic microbeads are added to the culture medium. In some embodiments, the reagent that specifically binds to CD3 and CD28 is added again to the culture medium after the CXCR4 enrichment step is completed. In some embodiments, the reagent that specifically binds to CD3 and CD28 comprises anti-CD3 coated beads and anti-CD28 coated beads (e.g., magnetic microbeads). In some embodiments, the anti-CD3 coated beads and anti-CD28 coated beads are removed by an immunomagnetic method.

In some embodiments, in step (d), the anti-CXCR4 magnetic microbeads are added to the culture medium 3 or 4 days after the ex vivo expansion is initiated. In some embodiments, in step (d), the anti-CXCR4 magnetic microbeads are added to the culture medium for about 30 minutes before a double ferromagnetic column is used to isolate CXCR4$^+$ Treg cells.

In some embodiments, the effective amount of IL-2 is about 1000 IU/ml.

In some embodiments, the isolated CD25$^+$ Treg cells are enriched for CXCR4 on the third feed of ex vivo expansion.

In some embodiments, step (d) takes place over 4 or 5 days.

Provided herein is a method for producing an expanded population of human Treg cells enriched for CXCR4$^+$ Treg cells from a cryopreserved human umbilical cord blood unit, the method comprising: (a) thawing the cryopreserved human umbilical cord blood unit; (b) diluting and washing the thawed umbilical cord blood unit in a functionally closed system; (c) isolating Treg cells using a double selection method based on CD25$^+$ cell surface expression; (d) ex vivo expanding the isolated CD25$^+$ Treg cells in a culture medium, in a gas permeable cultureware, wherein the ex vivo expansion step comprises: (1) at day 0, adding anti-CD3 and anti-CD28 coated beads to the CD25$^+$ Treg cells in the culture medium; (2) at day 2, adding about 1000 IU/ml IL-2 to the culture medium; (3) at day 3 or 4, removing the anti-CD3 and anti-CD28 coated beads from the culture medium and adding anti-CXCR4 magnetic microbeads to the culture medium; and (4) at day 3 or 4, removing the anti-CXCR4 magnetic microbeads attached to CXCR4$^+$ Treg cells from the culture medium, and adding fresh anti-CD3 and anti-CD28 coated beads to the CXCR4$^+$ Treg cells, wherein the ex vivo expansion takes place for up to 10 days or up to 12 days, wherein the culture medium is replaced about every 48 hours, to produce a CXCR4-enriched culture of CD25$^+$ Treg cells; and (e) harvesting the activated CD25$^+$ CXCR4$^+$ cells from the culture medium to produce an expanded population of human Treg cells enriched for CXCR4$^+$ Treg cells.

In some embodiments, in step (d), IL-2 is added to the culture medium comprising isolated CD25$^+$ Treg cells about every 48 hours.

In some embodiments, the anti-CD3 coated beads and the anti-CD28 coated beads are at a 1:1 ratio. In some embodiments, the CD25$^+$ cells and the anti-CD3 and anti-CD28 coated beads are at a 1:1 ratio.

In some embodiments, in step (e), about 1×10$^6$ CD25$^+$ cells/ml are cultured.

In some embodiments, in step (e), the cells are initially cultured in gas-permeable cultureware that has a membrane surface area of 10 cm$^2$. In some embodiments, the culture is subsequently transferred to gas-permeable cultureware that has a membrane surface area of 100 cm$^2$. In some embodiments, in step (d), the culture is not rocked or agitated when the IL-2 is added.

In some embodiments, in step (a), the cryopreserved human umbilical cord blood unit is thawed in a single step in a water bath.

In some embodiments, step (b) does not comprise manual washing. In some embodiments, step (b) takes place in a solution comprising PBS, EDTA, and about 0.5% human serum albumin.

In some embodiments, a double ferromagnetic column method is used in step (c) to isolate CD25$^+$ Treg cells.

In some embodiments, the method further comprising cryopreserving the expanded population of human Treg cells enriched for CXCR4$^+$ Treg cells.

Provided below is an exemplary manufacturing process to produce a population enriched for Treg cells expressing CXCR4 (e.g., the CK0804 product). The step to deplete CD8$^+$ cells from the culture is optional and performed only if the % CD3$^+$CD4$^-$CD8$^+$ cell population represents >10% of the culture-expanded cells.

Step 1: Thaw CBU (Day 0)

Input: CBU

Output: CBU Post-Thaw

The frozen CBU is removed from LN$_2$ vapor phase storage, placed in a plastic overwrap bag to prevent contamination of the ports during thaw. The overwrapped cryobag is placed immediately in a 37° C. water bath and thawed rapidly, using gentle kneading of the bag to ensure even thawing. The output, CBU Post-Thaw, is sampled for:

TNC (total nucleated cell) count (Cellometer)

% Viability of NCs (nucleated cells) (Cellometer)

Test results are used for process monitoring.

Step 2: Dilute & Wash CBU (Day 0)

Input: CBU Post-Thaw

Output: CBU Post-Wash

Immediately after the rapid thaw, the contents of the CBU post-thaw bag is attached to the input line of the Sepax single-use disposable kit. The cells are diluted and washed within the Sepax system with 10% LMD in 0.9% NaCl. The output of the Sepax wash (CBU Post-Wash) is approximately 100 mL, and is sampled for:

TNC (total nucleated cell) count (Cellometer)

% Viability of NCs (nucleated cells) (Cellometer)

% Viability of NCs (flow cytometry—7-AAD)

% CD3+CD4−CD8+(flow cytometry)

% CD3+CD4+CD25+(flow cytometry)

Test results are used for process monitoring.

Step 3: Pre-Selection Wash (Day 0)

Input: CBU Post-Wash

Output: CB Mononuclear Cells (MNCs)

The CBU post-wash cells are centrifuged at 300×g for 10 minutes at room temperature. After removal of the supernatant by gentle aspiration, the cells (CB MNCs) are resuspended to a volume of approximately 8-10 mL in Miltenyi PBS/EDTA buffer, supplemented with Pulmozyme and $MgCl_2$. The output, CB MNCs, is not sampled.

Step 4: CD25 Antibody Incubation (Day 0)

Input: CB MNCs

Output: CB MNCs Post Inc

The CB mononuclear cells are incubated with Miltenyi anti-CD25 microbeads for 30 minutes at 2-8° C., with automated mixing. Following incubation, the cells and anti-CD25 microbead mixture is washed and resuspended to a volume of approximately 10 mL in Miltenyi PBS/EDTA buffer, supplemented with Pulmozyme and $MgCl_2$. The output, CB MNCs Post incubation, is not sampled.

Step 5: CD25 Positive Selection (Day 0)

Input: CB MNCs Post Inc

Output: $CD25^+$ MNCs

Following the incubation step with Miltenyi CD25 antibody reagent, the CB MNCs Post Inc are transferred into the Miltenyi LS column attached to the MidiMACS device, which captures the anti-CD25 labeled cells by use of a magnet. After the immunomagnetic selection, the cells are released from the magnetic field. This selection is done on each of 2 separate fractions of CB MNCs Post Inc, and the outputs are combined. The output, $CD25^+$ MNCs, is sampled for:

TNC Count (Cellometer)

% Viability of NCs (Cellometer)

% Viability NCs (flow cytometry—7-AAD flow cytometry)

% CD3+CD4−CD8+(flow cytometry)

% CD3+CD4+CD25+(flow cytometry)

Sterility (Negative fraction)

Test results are used for process monitoring.

Step 6: Initiate Culture-Expansion (Day 0)

Input: $CD25^+$ MNCs

Output: Day 0 Culture

The $CD25^+$ selected MNCs are washed and suspended in X-Vivo 15 with 1% Glutamine and 10% human AB serum with interleukin-2 (IL-2, 1000 IU/mL) and then mixed with CD3/CD28 beads at a bead to cell ratio of 1:1. The cells+ bead mixture is transferred into the G-Rex 10M system, and into incubation at 37° C. with 5% $CO_2$. There is no rocking or agitation of the cell suspension. No sampling is done at this step.

The Bioreactor 10M system consists of a sterile, single-use, disposable plastic device with a cylindrical shape. After transfer of the cells and media to the Bioreactor, the cells reside on the bottom of the container, where the surface is gas-permeable. The gas-permeable membrane of the Bioreactor 10M system has a surface area of 10 $cm^2$. The system is placed in a conventional incubator, but can be removed intermittently as needed for sampling, media removal, media addition, or cell harvest.

Step 7: Add IL-2 (Day 2)

Input: Day 0 Culture

Output: Day 2 Culture+IL-2

At day 2, fresh IL-2 is added to the cultured cells in the G-Rex 10M system at 1000 IU/mL to replenish the IL-2, which is presumed to have been consumed. No sampling is done at this step. The cells in the G-Rex 10M system are returned to incubation at 37° C. with 5% $CO_2$. There is no rocking or agitation of the cell suspension.

To monitor the culture-expansion process, sampling for Lactate in the culture supernatant is obtained on Day 2 or 3, Day 4, Day 6, Day 8, Day 10, Day 12, and Day 14 Harvest.

Step 8: CXCR4 Enrichment (Day 3 or 4)

Input: Day 2 Culture+IL-2

Output: Day 3 or 4 CXCR4 Enriched cells

At Day 3 or 4, the cultured cells are incubated with Miltenyi anti-CXCR4 microbeads for 30 minutes at 2-8° C., with automated mixing. Following incubation, the cells and anti-CXCR4 microbead mixture is washed and resuspended to a volume of approximately 10 mL in Miltenyi PBS/EDTA buffer, supplemented with Pulmozyme and $MgCl_2$. The output, cell culture Post incubation, is not sampled.

Step 9: CXCR4 Enrichment Selection (Day 3 or 4)

Input: Day 3 or 4 Cultured cells, Post Incubation

Output: Day 3 or 4 CXCR4 Enriched cells

Following the incubation step with Miltenyi CXCR4 antibody reagent, the CB MNCs Post Inc are transferred into the Miltenyi LS column attached to the MidiMACS device, which captures the anti-CXCR4 labeled cells by use of a magnet. The output, CXCR4 enriched cells, are sampled for:

TNC Count (Cellometer)

% Viability of NCs (Cellometer)

% Viability NCs (flow cytometry—7-AAD flow cytometry)

% CD3+CD4−CD8+(flow cytometry)

% CD3+CD4+CD25+(flow cytometry)

% CD3+CD4+CD25+CXCR4+(flow cytometry)

Sterility (Negative fraction)

Test results are used for process monitoring.

Step 10: Transfer & Feed (Day 3 or 4)

Input: Day 4 CXCR4 Enriched Culture

Output: Day 4 CXCR4 Culture+IL-2

CXCR4 enriched cells are returned to culture with Fresh Media+IL-2 (1000 IU/mL) in the G-Rex 10M system. No sampling is done at this step. The cells in the G-Rex 10M system are returned to incubation at 37° C. with 5% $CO_2$. There is no rocking or agitation of the cell suspension.

Step 11: Transfer & Feed (Day 6, or 7)

Input: Day 3 or 4 Culture+IL-2

Output: Day 6/7 Culture+Fresh media+IL-2

At day 6 or 7 (<66 hours since last media/IL-2 change), an aliquot of the cultured cells in the G-Rex 10M system is removed, and sampled for:

TNC Count (Cellometer)

% Viability of NCs (Cellometer)

The TNC Count and % Viability are used for process monitoring of the culture-expansion. The remaining cultured cells in the G-Rex 10M system are transferred to the G-Rex 100M system, with fresh media added to obtain a concentration of $2 \times 10^6$ cells/mL (X-Vivo 15 with 1% Glutamine and 10% human AB serum, and IL-2 1000 IU/mL). The cells in the G-Rex 100M system are returned to incubation at 37° C. with 5% $CO_2$. There is no rocking or agitation of the cell suspension.

The Bioreactor 100M system consists of a sterile, single-use, disposable plastic device with a cylindrical shape. After transfer of the cells and media to the G-Rex, the cells reside on the bottom of the container, where the surface is gas-permeable. The gas-permeable membrane of the Bioreactor 100M system has a surface area of 100 $cm^2$. The system is placed in a conventional incubator, but can be removed intermittently as needed for sampling, media removal, media addition, or cell harvest.

US 12,692,478 B2

23

Step 12: Add IL-2 (Day 8 or 9)
Input: Day 6/7 Culture+Fresh media+IL-2
Output: Day 8/9 Culture+IL-2
At day 8 or 9 (<66 hours since last media/IL-2 change), fresh IL-2 is added to the cultured cells in the G-Rex 100M system, to replenish the IL-2, which is presumed to have been consumed. The cell suspension is sampled for TNC and % Viability (Cellometer), used for process monitoring. The cells in the G-Rex 100M system are returned to incubation at 37° C. with 5% $CO_2$. There is no rocking or agitation of the cell suspension.
Step 13: (Day 10)
Input: Day 10 Culture+IL-2
Output: Day 10 Harvest if CXCR4 meets criteria (proceed to step 15)
An aliquot of the cultured cells in the G-Rex 100M system is removed, and sampled for:
TNC Count (Cellometer)
% Viability of NCs (Cellometer)
% Viability NCs (flow cytometry—7-AAD flow cytometry)
% CD3+CD4–CD8+(flow cytometry)
% CD3+CD4+CD25+(flow cytometry)
% CD3+CD4+CD25+CXCR4+(flow cytometry)
or
Day 10 Culture (if CXCR4 criteria is not met)
At day 10, the cells in the G-Rex 100M system are returned to incubation at 37° C. with 5% $CO_2$. There is no rocking or agitation of the cell suspension. Proceed to step 14.
Step 14: Add IL-2 (Day 10)
Input: Day 8/9 Culture+IL-2
Output: Day 10 Culture+IL-2
At day 10 (<66 hours since last media/IL-2 change), fresh IL-2 is added to the cultured cells in the G-Rex 100M system, to replenish the IL-2, which is presumed to have been consumed. The cell suspension is sampled for TNC and % Viability (Cellometer), used for process monitoring. The cells in the G-Rex 100M system are returned to incubation at 37° C. with 5% $CO_2$. There is no rocking or agitation of the cell suspension.
Step 15: Sample Pre Harvest (Day 10 or 12)
Input: Day 10 or 12 Culture+IL-2
Output: Pre-Harvest Day 10 or 12, sampled
On day 10 or 12, prior to harvesting the culture-expanded T-Reg cells, the cell suspension is sampled for:
*Mycoplasma*
The *mycoplasma* test result is included in final release criteria.
After sampling for *Mycoplasma*, 60% of the total culture volume is removed from the cell suspension volume in the G-Rex 100M system, the remaining culture is sampled for
TNC Count (Cellometer)
% Viability of NCs (Cellometer)
% Viability NCs (flow cytometry—7-AAD flow cytometry)
% CD3+CD4–CD8+(flow cytometry)
% CD3+CD4+CD25+(flow cytometry)
% CD3+CD4+CD25+CXCR4+(flow cytometry)
The TNC count and % Viability are used for process monitoring. The % CD3+CD4–CD8+ is used to determine the need for immunomagnetic depletion of CD8+ cells if the % CD3+CD4–CD8+ cell population represents >10% of the culture-expanded cells. If CD8 depletion is required, the cells will be depleted prior to Harvest on Day 10 or 12.

24

Step 17: Harvest (Day 10 or 12)
Input: Pre-Harvest Day 10 or 12, sampled
Output: T-Reg Harvest
Following the sampling, the remaining volume in the G-Rex 100M system is transferred, with rinsing of the G-Rex to optimize cell recovery, to one or more 500 mL conical tubes in 150 mL increments. The volume in each tube is brought up to 400 mL with the infusion buffer (Plasma-Lyte A with 0.5% HSA). The 500 mL conical tube(s) is centrifuged twice at 400×g for 10 minutes at room temperature to wash the cells with Plasma-Lyte A with 0.5% HSA, and the cell suspension is brought to a volume of 10 mL with Plasma-Lyte A with 0.5% HSA in a 15 mL conical tube for Bead Removal (Step 15).
Conditional Step: CD8 Depletion (Day 10 or 12)
Input: Day 10 or 12 T-Reg Harvest
Output: Post CD8 Depletion
If the % CD3+CD4–CD8+ flow cytometry result from sampling at Step 14 indicates that the CD3+CD4–CD8+ cell population represents >10% of the culture-expanded cells, CD8 depletion is performed. For CD8 depletion, the T-Reg Harvest is incubated with Miltenyi CD8 microbeads for 15 minutes at 4-8° C. with gentle agitation, then transferred to a Miltenyi LS column, and then immunomagnetically selected using the MidiMACS device. The output, Post CD8 Depletion, is sampled for:
TNC Count (Cellometer)
% Viability of NCs (Cellometer)
% CD3+CD4–CD8+(flow cytometry)
The NC count and % Viability are used for process monitoring. The process is resumed at the following step (Wash & Remove CD3/CD28 Beads, Step 15) if the % CD3+CD4–CD8+ is ≤10% after the CD8 depletion. If the % CD3+CD4–CD8+ is >10%, a second CD8 depletion is performed.
Step 18: Wash & Remove CD3/CD28 Beads (Day 10 or 12)
Input: Harvest Day 10 or 12
Output: T-Reg Harvest, De-Bead
The 15 mL conical tube containing the harvested T-Reg cell suspension is placed in the Dynal MPC-1 magnet for 2 minutes. The supernatant (containing the cells, without CD3/CD28 beads) is collected in another 15 mL conical tube before releasing the magnet ("De-bead #1"). Once the magnet is released, the remaining beads and cells are resuspended in 2 mL of Plasma-Lyte A with 0.5% HSA and placed in the Dynal MPC-1 magnet for 2 minutes; the supernatant is collected and transferred to the "De-bead #1 tube. The "De-bead #1" tube is then placed in the Dynal MPC-1 magnet for 2 minutes, and the supernatant is collected in another 15 mL conical tube before releasing the magnet ("De-bead #2). This process may be performed up to three times depending on Harvest volume. The cell suspension in the "De-bead #2" tube, which now has a volume of ~17 mL, is pooled with any additional Debead #2 tubes and sampled for:
TNC Count (Cellometer)
% Viability of NCs (Cellometer)
% CD3+CD4–CD8+(flow cytometry)
% CD3+CD4+CD25+(flow cytometry)
% CD3+CD4+CD25+CXCR4+(flow cytometry)
% Viability of NCs (flow cytometry—7-AAD)
Residual Beads
The output of this step, T-Reg Harvest, De-Bead, is the active substance (drug substance). The TNC count and % Viability (Cellometer) are used for process monitoring. The TNC is also used in the calculation of cell dose for lot release. The % CD3+CD4−CD8+, % CD3+CD4+CD25+, % Viability (7-AAD), and Residual Beads assay are used for release of the final product.

Step 19: Wash & Concentrate T-Regs (Day 10-12)
Input: T-Reg Harvest, De-Bead
Output: T-Regs, Washed/Concentrated The T-Reg Harvest, De-Bead is transferred from a 15 mL conical tube to a 500 mL conical tube. The conical tube is rinsed with 10 mL of Plasma-Lyte A+0.5% HSA, and the rinse is added to the 500 mL conical tube. The cellular suspension in the conical tube is brought to a volume of 150 mL with Plasma-Lyte A+0.5% HSA and centrifuged at 400×g for 10 minutes at room temperature. The supernatant is removed, leaving a concentrated cell pellet in the tube.

Step 20: Add Cryoprotectant & Fill Bags (Day 10 or 12)
Input: T-Regs, Washed/Concentrated
Output: CK0804 Final Product, Pre-Freeze CryoStor® Freeze Medium CS10 is added to the concentrated cell pellet, with volume based on total number of cells and a target final cell concentration of 10-12 Treg cells/mL. The cell suspension containing CryoStor® CS10 is filled into OriGen CryoStor® CS50N freeze bags, each with a fill volume of 10 mL (100×10$^6$ Tregs) or 30 mL (300×10$^6$ Tregs).

The remaining cell suspension is sampled for:
Endotoxin
Sterility

Results of Endotoxin and Sterility are used for release of the final product.

Step 21: Controlled Rate Freeze (Day 10 or 12)
Input: CK0804 Final Product, Pre-Freeze
Output: CK0804 Final Product, Frozen in Bags Bags containing the CK0804 final product are placed into aluminum cassettes and transferred to a controlled rate freeze device, frozen according to a pre-set program, and then overwrapped in a plastic bag, which is sealed and transferred to a LN$_2$ vapor phase freezer for storage.

Process Controls
Process control at Step 16 (Sample before Harvest):

If the % CD3$^+$CD4$^-$CD8$^+$ cells (assayed by flow cytometry) is >10%, the Conditional Step (CD8 Depletion) is performed. If the post-CD8 depletion value for % CD3$^+$CD4$^-$CD8$^+$ cells is ≤10%, the manufacturing process resumes at Step 17. If the post-CD8 depletion value for % CD3$^+$CD4$^-$CD8$^+$ cells is still >10%, a second CD8 Depletion procedure is performed. This ensures that the final product will meet the lot release criterion for % CD3$^+$CD4$^-$CD8$^+$ cells.

An overview of analytical procedures for CK0804 is provided in Tables 1a and 1b.

TABLE 1a

Quality Control Testing: Analytical Procedures for CK0804

| Test | Method | Report Timing (In-process, Lot release) |
| --- | --- | --- |
| Total nucleated cell (TNC) count (concentration) | Cellometer K2 automated cell counter | In-process Lot release |
| % Viability of nucleated cells (NCs) | Cellometer K2 automated cell counter, AOPI method | In-process |
| % Viability of nucleated cells (TNCs) | 7-AAD and Flow cytometry | In-process Lot release |

TABLE 1a-continued

Quality Control Testing: Analytical Procedures for CK0804

| Test | Method | Report Timing (In-process, Lot release) |
| --- | --- | --- |
| % CD3$^+$CD4$^+$CD25$^+$ cells | Flow cytometry | In-process Lot release |
| Treg Cell Dose | Calculation | Lot release |
| % CD3$^+$CD4$^+$CD8$^+$ cells | Flow cytometry | In-process Lot release |
| Endotoxin | Endosafe ™ PTS (Charles River) | Lot release |
| Sterility (bacterial & fungal) | VersaTREK ™ (Aerobic, Anaerobic) | In-process Lot release |
| Mycoplasma | MycoAlert ™ (bioluminescence) | Lot release |
| Residual Beads Test | Light microscopy Method | Lot release Report Timing (In-process, Lot release) |
| Treg Suppression Assay | Cell culture, Invitrogen CellTrace ™ Violet Proliferation assay kit, and flow cytometry | Characterization only |

TABLE 1b

Analytical Testing

| Assay | Method |
| --- | --- |
| Total nucleated cell (TNC) count and Viability | Cellometer K2 automated cell counter, Acridine Orange/Propidium Iodide |
| % CD3$^+$CD4$^+$CD25$^+$ T-regulatory cells % CD3$^+$CD4$^+$CD8$^+$ T-cytotoxic suppressor cells | Flow cytometric surface phenotyping |
| Sterility (bacterial & fungal) | VersaTREK ™ (Aerobic, Anaerobic) |
| Endotoxin | Endosafe ™ PTS (Charles River) |
| Mycoplasma | MycoAlert ™ (bioluminescence) |
| Residual CD3/CD28 beads | Light Microscopy |

B. Methods for Characterizing an Expanded Population of CXCR4-Expressing T Regulatory Cells An expanded population of CXCR4-expressing T regulatory cells (e.g. the CK0804 product) can be characterized by the following methods.

Phenotypic analysis: Fresh or "in process" samples can be analyzed from each run for the phenotype markers including: CD3, CD4, CD25, CD127, CXCR4, FOXP3 and Helios at Day 0, 3 and 12. Phenotypic analysis of cryopreserved samples can be performed for CK0804 for: CD3, CD4, CD25, CD127, CXCR4, FOXP3 and Helios. Samples can be used at pre-determined time points post cryopreservation. Post thaw stability of the product can be analyzed for viability and phenotype markers including: CD3, CD4, CD25, CD127, CXCR4, FOXP3 and Helios. Phenotypic analysis of CK0804 can be performed with anti-human specific antibodies including CD4/APC eFluor780 (Thermo Fischer Scientific, Waltham, MA, USA), CD8/FITC (Becton Dickinson, Franklin Lakes, NJ, USA), CD25/PE (Becton Dickinson, Franklin Lakes, NJ, USA), CD127/Alexa Fluor647 (Becton Dickinson, Franklin Lakes, NJ, USA), CXCR4 (CD184)/PE-Cy™5 (Becton Dickinson, Franklin Lakes, NJ, USA), for surface staining and FoxP3/PECy7 (Thermo Fischer Scientific, Waltham, MA, USA), and Helios/APC (Thermo Fischer Scientific, Waltham, MA, USA) for intracellular. True-Nuclear Transcription Factor Buffer Set (BioLegend, SanDiego, CA, USA) can be used for intracellular staining. As a viability dye, 7-amino-actino-mycin-D (7AAD, TONBO biosciences, Tucson, AZ, USA) for surface and Ghost dye V510 (TONBO biosciences, Tucson, AZ, USA) for intracellular staining, respectively, can be used. Cells will be acquired with BD FACSCanto II (Becton Dickinson, Franklin Lakes, NJ, USA) or a BD LSRFortessa X20 (Becton Dickinson, Franklin Lakes, NJ, USA). The flow cytometry data can be analyzed using FlowJo software ver.10 (Becton Dickinson, Franklin Lakes, NJ, USA).

Cell suppression assay: In process samples can be collected and analyzed for their suppressor function at Day 12. Suppressor function analysis can also be performed on samples collected at the predetermined time points post cryopreservation.

Conventional T cells (Tcons) CD4$^+$25$^-$ phenotype (ReachBio LLC, Seattle, WA) can be stained using the CellTrace™ Violet Cell Proliferation Kit (Invitrogen, Carlsbad, CA, USA) to trace multiple generations using dye dilution by flow cytometry. 50,000 Tcons are be seeded in a 96 well U-bottom plate and co-cultured with the different numbers of CB Tregs at ratios of 4:1, 2:1, 1:1, 1:2, 1:4, and 1:8. CD3/28 T-cell activator beads are added at a ratio of 1:1 with Tcons cultured in RPMI Medium 1640+ Glutamax-I (Thermo Fischer Scientific, Waltham, MA, USA) supplemented with 10% Fetal Bovine Serum, heat inactivated (Thermo Fischer Scientific, Waltham, MA, USA). Cells are incubated for four days at 37° C. in a 5% $CO_2$-in-air atmosphere. Tcon-proliferation can be measured using flow cytometry. Cells will be acquired using either a BD FACSCanto or a BD LSRFortessaX20 Flow Cytometer. The data can be analyzed using FlowJo software. For a Cell-Trace™ based measurement, the suppressive capacity can be calculated as the following formula: 100×(1–% Cell-Trace$^{low}$ Tcons in a target well/% CellTrace$^{low}$ Tcons alone).

Migration assay: The transwell cell migration assay measures the chemotactic capability of cells toward a chemoattractant. The purpose of this experiment is to capture the chemotaxis of the enriched population and compare it to the standard (non-enriched) population. It would be expected that CXCR4-expression enriched cells have the ability for a faster transit across the transwell membrane in response to SDF1α signaling. The desired amount of chemo-attractant (SDF-1alpha=500 ng/ml) is placed into the bottom of the lower chamber in a 24-well plate. The transwell chamber with 0.5 micron size is placed. The CXCR4 enriched cell population or the standard is placed at a cell concentration of 1×10ˆ6 cells/ml ate the top of the transwell. The cells are allowed to migrate from the top chamber into the bottom well. Images and cell counts are captured at 0.5 hr, 1.0 hr and 1.5 hr.

In vivo analyses can be performed to examine the biodistribution of the injected CK0804 cells as well as quantify their persistence in the target organs as well as circulation. For the purpose of differentiation and to detect the cell of origin, the CK0804 can be mismatched on HLA-A2 loci with the donor cells.

Bone marrow homing studies: The transit time of the CXCR4-enriched Tregs or the standard Tregs can be analyzed by evaluating their concentration in the target organ of interest. Eight to ten-week-old NOD-scid IL2Rgamma$^{null}$ (NSG) mice purchased from Jackson Laboratories can be utilized. CXCR4-enriched Tregs or the standard Tregs can be injected intravenously (i.v.) into NSG mice at a dose of 1×10$^7$ cells/animal. Animals will receive 100,000 IU of IL-2 intraperitoneally immediately following injection. Femur bone marrow will be harvested 24 h post-injection and human Treg cells identified based on CD25-positivity by flow cytometry. Data will be analyzed with FlowJo software.

At least 3 mice will be assigned to each arm in each experiment. The experiment will be repeated at least 3 times. Organs including lung, liver, bone marrow, spleen, skin, gut will be harvested for flow analysis and pathological study upon euthanasia.

The above experiment will be repeated with the addition of 2 arms of i) ruxolitinib alone and ii) ruxolitinib+CK0804. 100 mg ruxolitinib powder will be dissolved in with DMSO, PEG-300, and sterile water to 10 mL total volume (1 mg/100 μL) and 100 μl aliquots will be stored at −20° C. Mice will be fed 1 mg (100 μl) ruxolitinib daily for the duration of the study.

Methods for Cryopreservation of Activated T-Regulatory Cells

Provided herein are methods for cryopreserving an ex vivo expanded population of human Treg cells (e.g., activated human Treg cells).

In some embodiments, a method for cryopreserving an expanded population of activated human T regulatory (Treg) cells produced from at least one cryopreserved human umbilical cord blood unit comprises: a) thawing the cryopreserved human umbilical cord blood unit; b) diluting and washing the thawed umbilical cord blood unit in a functionally closed system; c) isolating naturally occurring Treg cells using a double selection method based on CD25$^+$ cell surface expression; d) ex-vivo expanding the isolated CD25$^+$ Treg cells in a culture medium(s), in a gas permeable cultureware, in the presence of an effective amount of interleukin-2 (IL-2) and in the presence of a reagent that specifically binds to CD3 and CD28, for up to 14 days, wherein the culture medium is replaced about every 48 hours, to produce a population of activated CD25$^+$ Treg cells; e) harvesting the activated CD25$^+$ cells from the culture medium to produce an expanded population of activated human Treg cells; and f) cryopreserving the expanded population of activated human Treg cells.

In some embodiments, the method further comprises releasing the activated cultured human Treg cells for clinical use based on defined criteria between step e) and step f).

Any suitable cryopreservation process known in the art can be used in the methods described herein. For example, an expanded population of human Treg cells can be cryopreserved by using a freezing cocktail comprising dimethyl sulfoxide (DMSO) and subsequent placement in a controlled rate freezer with a specially defined program(s). The cryopreserved product can be stored at −180° C. for at least several months. Upon thawing the cryopreserved product, the Treg cells can maintain their cell surface and intracellular phenotype with high expression of FOXP3 (forkhead box P3) and of Helios and retain their suppressive function as demonstrated by in vitro cell suppression assays (FIG. 8A-FIG. 8C) as well as in vivo data in different animal models (FIG. 9A-FIG. 9B).

In some embodiments, up to about 50×10$^6$ cells are cryopreserved per 5 ml vial at a concentration of about 10×10$^6$ cells per ml. In some embodiments, from about 100×10$^6$ cells to about 1×10$^8$ cells can be cryopreserved in a single cryogenic bag in a volume of up to 10 ml to 100 ml.

In some embodiments, for the purpose of cryopreservation, the harvested expanded population of human Treg cells can be centrifuged at 400 g for 10 minutes at a temperature of 4° C. The total cell number can be calculated using the automated cell counter and the number of cryovials can be estimated by dividing the total cell number by $50\times10^6$ cells. Subsequently, up to $50\times10^6$ cells can be cryopreserved per 5 ml cryovial using a freezing stock solution where the freezing stock solution comprises a pre-formulated solution with 5% or 10% dimethyl sulfoxide (DMSO) (Cryostor®). While the cells are undergoing centrifugation, the controlled rate freezer is turned on and once the controlled rate freezer has reached appropriate start temperature, then a command appears "Program Waiting for User-click here to continue". Once admixed with the freezing stock solution, the cryovial consisting up to $50\times10^6$ cells are placed in the controlled rate freezer using the freezing algorithm to allow for paced freezing of the cells to avoid cell death and preserving the cell function. After the freeze program is complete, the cryovials are removed from the controlled rate freezer and placed in the liquid nitrogen cryogenic freezer at a temperature of as low as −190° C. for long term cryopreservation.

The expanded Treg population can be cryopreserved into several aliquots to generate appropriate clinical dose(s) for therapeutic administration.

Populations of T-regulatory Cells and Pharmaceutical Compositions

Disclosed herein are populations of human Treg cells produced by the methods described herein. The populations are suitable for allogeneic cell therapy uses. In some aspects, the human Treg cells are immunosuppressive.

In some embodiments, a population of human Treg cells is positive for CD4 and CD25. In some embodiments, a population of human Treg cells is positive for CD3, CD4 and CD25. In some embodiments, a population of human Treg cells is positive for CD3, CD4, CD25, CD45RO, CD45RA, CD95 and CD28.

Provided herein is a population of human Treg cells that are at least about 60% CD4$^+$CD25$^+$ and less than or equal to about 10% CD4$^-$CD8$^+$. In some embodiments, a population of human Treg cells that are at least about 60% CD4$^+$CD25$^+$ and less than or equal to about 10% CD4$^-$CD8$^+$ further co-express CD45RA and CD45RO.

In some embodiments, a population of human Treg cells is at least about 90% CXCR4$^+$. In some embodiments, a population of human Treg cells is at least about 95% CXCR4$^+$, at least about 95% CD45RA$^+$ and at least about 80% CD45RO$^+$. In some embodiments, a population of human Treg cells is at least about 95% CXCR4$^+$, at least about 95% CD45RA$^+$, at least about 80% CD45RO$^+$, at least about 95% CD95$^+$, at least about 95% HLADR$^+$, at least about 95% alpha4beta7$^+$, at least about 15% CXCR3hi$^+$, at least about 95% CCR6$^+$, at least about 95% CD54$^+$, at least about 95% CD11A$^+$, at least about 85% CD45RARO$^+$, at least about 80% CTLA4$^+$, at least about 80% GPR83$^+$ and at least about 80% CD62L$^+$. In some embodiments, the expression of such cell surface markers is measured by flow cytometry. In some embodiments, a population of human Treg cells has been expanded ex vivo.

In some embodiments, a population of human Treg cells comprises human Treg cells that have a phenotype of CD4$^+$CD25$^+$CD127$^{lo}$ FOXP3$^{hi}$ and show additional co-expression of CD45RA$^+$CD45RO$^+$. In some embodiments, a population of human Treg cells comprises human Treg cells that have a phenotype of CD4$^+$CD25$^+$CD127$^-$FoxP3$^{hi}$ and Helios$^+$. In some embodiments, the extended phenotype of the activated human Tregs is: $\alpha 4\beta 7^{hi}$CCR3$^{lo}$ CCR4$^{hi}$CCR6$^{hi}$CCR7$^{hi}$CD103$^{lo}$CD11a$^{hi}$CD137$^{lo}$CD28$^{hi}$ CD31$^+$CD39$^{lo}$ CD54$^{hi}$ CD62L$^{hi}$CD7$^{hi}$CD95$^{hi}$CXCR3$^{lo}$ CXCR4$^{hi}$HLA-ABC$^{hi}$HLADR$^{hi}$PD1$^{lo}$PD-L1$^{lo}$ and intracellular CD154$^{hi}$FOXP3$^{hi}$Helios$^{hi}$GITR$^{hi}$RORγt$^{lo}$ Tbet$^{lo}$. In some embodiments, a population of neurotropic human Tregs has a phenotype of CD95/CXCR4/CD31/CD39$^{hi}$/CTLA4/HELIOS/CXCR3/CD28.

In some embodiments, a population of human Treg cells has a flow cytometry phenotype of > about 60% CD4$^+$ CD25$^+$ Treg cells and < about 10% CD4$^-$CD8$^+$ T-cytotoxic/suppressor cells.

In some embodiments, a population of human Treg cells comprises human Treg cells that exhibit high expression of FOXP3 and low expression of RORγt. In some embodiments, a population of human Treg cells comprises human Treg cells that do not secrete IL-17 or exhibit RORγT under stressful conditions. In some embodiments, a population of human Treg cells comprises human Treg cells that maintain their polyclonal T cell receptor Vβ (TCR Vβ) repertoire. In some embodiments, a population of human Treg cells is cryopreserved prior to use.

In some embodiments, a population of human Treg cells expresses intracellular Helios. In some embodiments, the human Treg cells produced by the methods disclosed herein retain their immunosuppressive function and phenotype under stressful conditions. In some embodiments, the human Treg cells produced by the methods disclosed herein retain their viability and suppressive function in the presence of steroids (for example, dexamethasone, prednisone or prednisolone). In some embodiments, the human Treg cells produced by the methods disclosed herein resist interleukin-17 (IL-17) secretion and are much less likely to "flip" to pro-inflammatory TH17 cells than peripheral blood Tregs due to their epigenetic signature and the nature of the selection/expansion protocols described herein.

The biological activity of interest for Treg cells in the populations described herein is an immunosuppressive function, which can be measured by an in vitro suppressor assay using the intracellular staining dye of CFSE (carboxyfluorescein succinimidyl ester) or CellTrace™ Violet dye. In this assay, Treg cells are co-cultured with normal peripheral blood T-responder (Tresp) cells, at various ratios, and the proliferating cells are detected using the method of flow cytometry to detect the incorporation of the intracellular dye of CFSE or CellTrace™ Violet, which allows tracking of cell proliferation for up to 8 cell divisions. The degree of suppression of T-responder (Tresp) cells by Treg cells can be quantitated in relation to the ratio of Treg cells to Tresp cells and the generation of divided cells. If effective suppression by Treg cells is present, suppression within the first generation of dividing responder cells is greater at higher ratios of Treg to Tresp cells compared to lower ratios of Treg to Tresp cells. In some embodiments, Treg cells in the population described herein are considered immunosuppressive when the Treg cells inhibit at least about 50%, at least about 60%, at least about 70%, at least about 80%, or at least about 90% of the proliferating T conventional (Tcon) cells, when the Treg:Tcon ratio is 4:1.

In some embodiments, a population of human Treg cells exhibits paracrine functions, such as increasing production of the inhibitory cytokines interleukin-10 (IL-10) but not of transforming growth factor β (TGFβ). In some embodiments, a population of human Treg cells secretes Granzyme B in response to IL-6 treatment (see, e.g., FIG. 25).

Provided herein is a population of human Treg cells, comprising at least about $1\times10^8$ human Treg cells that are: (i) ≥60% CD4$^+$CD25$^+$; and (ii) ≤10% CD4$^-$CD8$^+$; wherein the human Treg cells are immunosuppressive. Further provided herein is a population of human Treg cells, comprising at least about $1\times10^8$ human Treg cells that are: (i) ≥60% CD4$^+$CD25$^+$; (ii) ≥60% CD4$^+$CD25$^+$ CXCR4$^+$; and (iii) ≤10% CD4$^-$CD8$^+$; wherein the human Treg cells are immunosuppressive. Further provided herein is a population of human Treg cells, comprising at least about $1\times10^8$ human Treg cells that are: (i) $\geq60\%$ CD4$^+$CD25$^+$; (ii)) $\geq60\%$ CD4$^+$CD25$^+\alpha4\beta7^+$; and (iii) $\leq10\%$ CD4$^-$CD8$^+$; wherein the human Treg cells are immunosuppressive. Also provided herein is a population of human Treg cells, comprising at least about $1\times10^8$ human Treg cells that are: (i) $\geq60\%$ CD4$^+$CD25$^+$; (ii)) $\geq60\%$ CD4$^+$CD25$^+$CD11a$^+$; and (iii) $\leq10\%$ CD4$^-$CD8$^+$; wherein the human Treg cells are immunosuppressive. In some embodiments, a population of human Treg cells disclosed herein comprises at least about $1\times10^9$ human Treg cells or at least about $1\times10^{10}$ human Treg cells. In some embodiments, a population of human Treg cells disclosed herein comprises from about $1\times10^8$ to $1\times10^{10}$, from about $1\times10^8$ to $1\times10^9$, or from about $1\times10^9$ to $1\times10^{10}$ human Treg cells.

In some embodiments, a population of human Treg cells is formulated as a fresh single dose product (e.g., CK0801). The CK0801 product is produced from cord blood that is at least a 3 out of 6 HLA (human leukocyte antigen) match (e.g., 3 out of 6, 4 out of 6, 5 out of 6, or 6 out 6 HLA match) for the subject to whom the product is administered. The CK0801 product is administered to a subject as a single infusion with a dose based on the subject's weight. This product comprises immunosuppressive Treg cells.

In some embodiments, the CK0801 product is isolated via CD25$^+$ selection and after a culture duration of 14 days. In some embodiments, the release criteria for the CK0801 product are (i) $\geq60\%$ CD4$^+$CD25$^+$ (T-regulatory phenotype); and (ii) $\leq10\%$ CD4$^-$CD8$^+$ (T-cytotoxic/suppressor phenotype). In some embodiments, the CK0801 product is administered to a subject to treat inflammatory bone marrow disease or Guillain-Barre Syndrome.

In some embodiments, a population of human Treg cells is formulated as a cryopreserved and/or multiple dose product (e.g., CK0804, CK0802, CK0803 or CK0805). In some embodiments, CK0804, CK0802, CK0803 or CK0805 is formulated in an infusible cryopreservation medium containing 10% Dimethyl Sulfoxide (DMSO). The CK0804, CK0802, CK0803 and CK0805 are not HLA matched for the subject to whom the product is administered. In some embodiments, these products are a 2 out of 6, a 1 out of 6, or a 0 out of 6 HLA match for the subject to whom the product is administered. Each of these products is administered to a subject as a multiple dose infusion with a fixed dose. These products comprise immunosuppressive Treg cells.

In some embodiments, the CK0802 product is isolated via CD25$^+$ selection and after a culture duration of 14 days. In some embodiments, the release criteria for the CK0802 product are (i) $100\times10^6$ Tregs/bag in 10 mL ($10\times10^6$ Treg/ml); (ii) $\geq60\%$ CD4$^+$CD25$^+$ (T-regulatory phenotype); and (iii) $\leq10\%$ CD4$^-$CD8$^+$ (T-cytotoxic/suppressor phenotype). In some embodiments, the CK0802 product is administered to a subject to treat acute respiratory distress syndrome (ARDS) (e.g., CoV-ARDS) or cytokine release syndrome (CRS) (for example, CRS due to chimeric antigen receptor T-cell therapy). In some embodiments, the CK0802 product is administered to a subject on days 0, 3 and 7.

In some embodiments, the CK0804 product is isolated via CD25$^+$ selection and additional enrichment on CXCR4 and after a culture duration of 10-12 days. In some embodiments, the release criteria for the CK0804 product are (i) $100\times10^6$ Tregs/bag in 10 mL ($10\times10^6$ Treg/ml); (ii) $\geq60\%$ CD4$^+$CD25$^+$ (T-regulatory phenotype); (iii) $\geq60\%$ CD4$^+$CD25$^+$ CXCR4$^+$ (bone marrow homing subtype); and (iv) $\leq10\%$ CD4$^-$CD8$^+$ (T-cytotoxic/suppressor phenotype). In some embodiments, the CK0804 product is administered to a subject to treat myelofibrosis, aplastic anemia or immune thrombocytopenia. In some embodiments, the CK0804 product is administered to a subject monthly for up to 6 months.

CK0804 is a product comprising cord blood (CB)-derived, Treg cells that are enriched for CXCR4 expression in order to allow for faster delivery to the bone marrow stroma in patients suffering from inflammatory bone marrow disorders including primary myelofibrosis. CK0804 is an off-the-shelf, cryopreserved product. CK0804 is prepared from a single unit of umbilical cord blood (CBU) for each batch. One batch manufacturing process generates multiple products that are frozen in cryobags at a fixed dose of 100 million cells per bag.

In some embodiments, the CK0805 product is isolated via CD25$^+$ selection and additional enrichment on $\alpha4\beta7$ and after a culture duration of 8-10 days. In some embodiments, the release criteria for the CK0805 product are (i) $100\times10^6$ Tregs/bag in 10 mL ($10\times10^6$ Treg/ml); (ii) $\geq60\%$ CD4$^+$CD25$^+$ (T-regulatory phenotype); (iii) $\geq60\%$ CK0805 (gastrointestinal homing subtype); and (iv) $\leq10\%$ CD4$^-$CD8$^+$ (T-cytotoxic/suppressor phenotype). In some embodiments, the CK0805 product is administered to a subject to treat gastrointestinal graft versus host disease or inflammatory bowel disease. In some embodiments, the CK0805 product is administered to a subject in the following dosing regimen: (i) induction: weekly for up to 4 weeks; and (ii) maintenance: monthly for up to 6 months.

In some embodiments, the CK0803 product is isolated via CD25$^+$ selection and additional enrichment on CD11a and after a culture duration of 8-10 days. In some embodiments, the release criteria for the CK0803 product are (i) $100\times10^6$ Tregs/bag in 10 mL ($10\times10^6$ Treg/ml); (ii) $\geq60\%$ CD4$^+$CD25$^+$ (T-regulatory phenotype); (iii) $\geq60\%$ CD4$^+$CD25$^+$ CD11a$^+$ (neuron homing subtype); and (iv) $\leq10\%$ CD4$^-$CD8$^+$ (T-cytotoxic/suppressor phenotype). In some embodiments, the CK0803 product is administered to a subject to treat amyotrophic lateral sclerosis, multiple sclerosis or demyelinating neuropathy. In some embodiments, the CK0803 product is administered to a subject in the following dosing regimen: (i) induction: weekly for up to 4 weeks; and (ii) maintenance: monthly for up to 6 months.

The cord blood unit selection criteria for the various populations of human Treg cells are provided in FIG. 29 and FIG. 30.

The cellular starting material of CK0802 is a single unit of umbilical cord blood (CBU) from a normal, healthy unrelated donor. Production of clinically relevant Treg cell doses comprises ex vivo enrichment and expansion of Treg cells with a CD4$^+$CD25$^+$ phenotype. In some embodiments, the 14 day manufacturing process results in 50-fold or greater expansion of the CD4$^+$CD25$^+$ Treg population. Multiple doses intended for different recipients can be manufactured from a single expansion process. The Treg cells are harvested, cryopreserved, tested and released for clinical use prior to being transported to the clinical site for infusion.

CK0802 is polyclonal, with wide representation of V-beta repertoire and high representation of intracellular FOXP3 staining. CK0802 is also associated with consistent hypomethylation of the TSDR (Treg-specific demethylated region), which is common in naturally occurring human Tregs.

In some embodiments, the CK0802 active drug substance (DS) is a liquid cell suspension consisting of nucleated cord blood cells, of which $\geq60\%$ have a T-regulatory cell phenotype (CD3$^+$CD4$^+$CD25$^+$) and $<10\%$ have a T-cytotoxic/suppressor cell phenotype (CD3$^+$CD4$^-$CD8$^+$). In some embodiments, the CK0802 final drug product (DP) is a suspension of live cells comprising the CK0802 active drug substance suspended at a cell concentration of $10\times10^6$ Treg cells/mL in infusable cryopreservation medium containing 10% dimethyl sulfoxide (DMSO).

An example of a composition of a CK0802 drug product is provided in Table 2.

mour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax.

TABLE 2

| Component | Function | Amount per 10 mL | Quality Standard |
|---|---|---|---|
| Cord blood-derived T-regulatory cells | Active drug Substance (DS) | $100 \times 10^6$ Tregs/bag in 10 mL ($10 \times 10^6$ Treg/ml) ≥60% CD4$^+$CD25$^+$ (T-regulatory phenotype) ≤10% CD4$^-$CD8$^+$ (T-cytotoxic/suppressor phenotype) | In-house |
| Plasma-Lyte A Injection pH 7.4 (Multiple Electrolytes Injection, Type 1, USP) | Excipient (Residual) | <1 mL | USP FDA-approved |
| Albumin (Human) 25% | Excipient (Residual) | <0.2 mL | USP/EP FDA-approved |
| CryoStor ® CS10 | Excipient | ~10 mL | FDA MF# 13671 Package Insert |

Further disclosed herein are pharmaceutical compositions comprising populations of activated human Treg cells and one or more pharmaceutically or veterinarily acceptable carriers, diluents, excipients, or vehicles.

The terms "pharmaceutically acceptable" and "veterinarily acceptable" refer to a pharmaceutically- or veterinarily-acceptable material, composition, or vehicle, such as a liquid or solid filler, diluent, excipient, solvent, or encapsulating material. Each component must be "pharmaceutically acceptable" or "veterinarily acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. (See, Remington: The Science and Practice of Pharmacy, 21st Edition; Lippincott Williams & Wilkins: Philadelphia, PA, 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Pre-formulation and Formulation, Gibson Ed., CRC Press LLC: Boca Raton, FL, 2004)).

A pharmaceutical composition of the disclosure is formulated to be compatible with its intended route of administration (i.e., intraocular, subretinal, parenteral, intravenous, intra-arterial, intradermal, subcutaneous, oral, inhalation, transdermal, topical, transmucosal, intraperitoneal or intrapleural, and/or rectal administration).

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Sey- Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Pharmaceutical compositions suitable for injectable use include sterile aqueous solutions (where water soluble) or dispersions and sterile powders for the extemporaneous preparation of sterile injectable solutions or dispersions of cells. In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active substance in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

disclosure are dictated by and directly dependent on the unique characteristics of the active compound and the particular therapeutic effect to be achieved, and the limitations inherent in the art of compounding such an active compound for the treatment of individuals.

One example of a final product composition (which consists of the active substance suspended in excipients) is shown in the table below. In some embodiments, the final dosage form has a volume of from about 50 mL to about 100 mL. In some embodiments, the cellular component of the final product consists of cord blood-derived mononuclear cells that are predominantly T-regulatory cells with a $CD4^+$ $CD25^+$ phenotype, which have been culture-expanded from a single umbilical cord blood unit or multiple pooled umbilical cord blood units.

TABLE 3

| Component | Function | Amount per 50 mL | Quality Standard |
|---|---|---|---|
| Cord blood-derived T-regulatory Cells | Active Substance (DS) | Mononuclear cells with total nucleated cell (TNC)* content of $1 \times 10^6 - 1.5 \times \times 10^7$ per kg recipient body weight OR FIXED DOSE $1 \times 10^8$ cells $3 \times 10^8$ cells $5 \times 10^8$ cells $1 \times 10^9$ cells $\geq 60\%$ $CD4^+CD25^+$ (T-regulatory phenotype) $\leq 10\%$ $CD4^-CD8^+$(T-cytotoxic/ suppressor phenotype) | In-house |
| Plasma-Lyte A Injection pH 7.4 (Multiple Electrolytes Injection, Type 1, USP) | Excipient | ~49 mL | USP FDA-approved |
| Flexbumin 25%, Albumin (Human) USP, 25% Solution | Excipient | ~1 mL | USP FDA-approved |

*Total nucleated cells in in-process and final product samples are enumerated by a conventional, manual method, which uses a hemocytometer and light microscopy, and the results are expressed as nucleated cells per volume, and a calculation is performed, using the volume of the product, to express the content of total nucleated cells in the product.

In some embodiments, the active substance is prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Dosage unit form as used herein refers to physically discrete units suited as unitary dosages for the subject to be treated; each unit containing a predetermined quantity of active substance calculated to produce the desired therapeutic effect in association with the required pharmaceutical carrier. The specification for the dosage unit forms of the In some embodiments, the final formulated product is contained and provided for use in a sealed 300 mL polyvinyl chloride (PVC) plastic blood bag. The bag has a port that can be accessed with the plastic spike of a conventional intravenous (IV) administration set used for administration to the patient.

In some embodiments, the excipients used to formulate the final product can include the following:

TABLE 4

| Excipient | Final Concentration | Function |
|---|---|---|
| Plasma-Lyte A Injection pH 7.4 (Multiple Electrolytes Injection, Type 1, USP) | >95% of final concentrations of all electrolyte components | In combination with HSA, supports/stabilizes and provides infusible solution for cord blood-derived T-regulatory cells. |
| Flexbumin 25%, Albumin (Human) USP, | ~0.5% HSA | In combination with Plasma-Lyte A, supports/ stabilizes and provide |

TABLE 4-continued

| Excipient | Final Concentration | Function |
|---|---|---|
| 25% Solution (HSA) | | infusible solution for cord blood-derived T-regulatory cells. |

In some embodiments, a composition comprises a population of activated human Treg cells produced by a method described herein and one or more other therapeutic agents. Also provided herein are kits for treating one or more autoimmune diseases, disorders, or conditions, comprising a composition described herein (e.g., in a container, pack, or dispenser) along with instructions for use or administration. Articles of manufacture are also provided, which include a vessel containing any of the populations of activated human Treg cells described herein and instructions for use.

Methods of Treatment and Therapeutic Uses

Provided herein are methods for treating a disease, disorder or condition in a subject in need thereof, comprising administering to the subject an effective amount of a population of human Treg cells (e.g., activated human Treg cells) produced by any of the methods described herein. Further provided herein are methods for treating a disease, disorder or condition in a subject in need thereof, comprising administering to the subject an effective amount of a population of human Treg cells disclosed herein. In some embodiments, the disease, disorder or condition is an autoimmune disease, disorder, or condition. In some embodiments, the disease, disorder or condition is an inflammatory disease, disorder, or condition. In some embodiments, the disease, disorder or condition is graft versus host disease (GVHD), inflammatory bowel disease, bone marrow failure (e.g., aplastic anemia, primary myelofibrosis or myelodysplastic syndrome), systemic lupus erythematosus (SLE), inflammatory cancer (e.g., multiple myeloma or inflammatory breast cancer), a neuro-inflammatory disorder (e.g., Guillain-Barre Syndrome, amyotrophic lateral sclerosis (ALS), multiple sclerosis or demyelinating neuropathy), cytokine release syndrome (CRS) or immunodeficiency syndromes (e.g., iPEX (immunodysregulation polyendocrinopathy enteropathy X-linked)). In some embodiments, the disease, disorder or condition is a respiratory disease, disorder or condition associated with severe acute respiratory syndrome coronavirus 2 (SARS-CoV-2) infection. In some embodiments, the disease, disorder or condition is COVID-19 (coronavirus disease) mediated acute respiratory distress syndrome (CoV-ARDS).

In some embodiments, a population of human Treg cells is produced from one or more umbilical cord blood units that are human leukocyte antigen (HLA)-matched to the intended recipient. In some embodiments, a population of human Treg cells is produced from one or more umbilical cord blood units that are not HLA-matched to the intended recipient. In some embodiments, the population of human Treg cells is prepared from one or more umbilical cord blood units of a compatible blood type for the subject.

In some embodiments, umbilical cord blood-derived Tregs may exhibit one or more of the following properties to generate anti-inflammatory effects: (1) direct engagement with a recipient antigen presenting cell (APC) and blocking interaction with T-effector (Teff) cells (i.e., by suppressing pro-inflammatory immune cells through direct interaction); (2) release of suppressor cytokines including transforming growth factor β (TGFβ), interleukin-10 (IL-10), and interleukin-35 (IL-35); (3) depletion of the IL-2 supply for Teff leading to their apoptosis; and/or (4) playing a role in granzyme/perforin production (i.e., by secreting granzyme B or Perforin, thereby leading to natural killer (NK) cells and $CD8^+$ T cell death). Moreover, local proliferation of the infused cord blood-derived Tregs at the site of inflammation can confer a survival advantage and generate anti-inflammatory action that is necessary for disease control.

The Treg cell dose in the final product may be expressed as number of cells per kg of the subject's body weight. Determination of the appropriate cell dose for use in any of the methods described herein is within the routine level of skill in the art. In some embodiments, the effective amount of the population of activated human Treg cells is between about $1\times10^5$ and about $1\times10^8$ Treg cells/kg of body weight of the subject, or between about $1\times10^6$ and about $1\times10^7$ Treg cells/kg of body weight of the subject. In some embodiments, the cell doses for any of the methods described herein may be:

Dose Level 1: about $1\times10^6$ Treg cells/kg

Dose Level 2: about $3\times10^6$ Treg cells/kg

Dose Level 3: about $1\times10^7$ Treg cells/kg

In some embodiments, fixed doses without relying on a subject's weight can be administered. In some embodiments, a dose may be between about $1\times10^8$ activated human Treg cells and about $3\times10^8$ Treg cells. For example, a dose may be about $1\times10^8$, about $3\times10^8$ or about $1\times10^9$ activated human Treg cells.

In some embodiments, the effective amount of the population of activated human Treg cells is administered intravenously to the subject.

In some embodiments, a single dose of an effective amount of the population of human Treg cells is administered to the subject. In some embodiments, multiple doses of an effective amount of the population of activated human Treg cells are administered to the subject. In some embodiments, up to 10 (i.e., 2, 3, 4, 5, 6, 7, 8, 9, or 10) or more repeat doses of Treg cells can be administered. If multiple doses are administered, these doses can be administered at regular intervals (i.e., every 3 days, every 4 days, every 5 days, every 6 days, every week, every 2 weeks, every 3 weeks, every 4 weeks, every 5 weeks, every 6 weeks, every 1-2 weeks, every 1-3 weeks, every 1-4 weeks, every 1-5 weeks, every 1-6 weeks, every 2-3 weeks, every 2-4 weeks, every 2-5 weeks, every 2-6 weeks, every 3-4 weeks, every 3-5 weeks, every 3-6 weeks, every 4-5 weeks, every 4-6 weeks, or every 5-6 weeks). In some embodiments, the doses are administered to the subject about every 4-6 weeks. In some embodiments, the Treg cells can be administered weekly for a period of four weeks followed by monthly for a period of at least 6-9 (i.e., 6, 7, 8, or 9) months.

In some embodiments, following administration of the effective amount of the population of activated human Treg cells, circulating inflammatory cytokine levels in the subject are decreased compared to the circulating inflammatory cytokine levels in the subject prior to the administration. In some embodiments, circulating inflammatory cytokines are interleukin-6 (IL-6), Interferon gamma (IFNγ) or Tumor Necrosis Factor-alpha (TNFα).

In some embodiments, prior to treatment, serum biomarkers of the subject are examined in order to determine whether the subject will respond to the effective amount of the population of activated human Treg cells. In some embodiments, following treatment, serum biomarkers of the subject are examined in order to determine a correlation with clinical response. In some embodiments, serum biomarkers are examined serially to examine whether subsequent retreatment with Treg cells is needed.

In some embodiments, diphenhydramine is administered to the subject prior to administration of the effective amount of the population of activated human Treg cells. In some embodiments, about 50 mg of diphenhydramine is administered. In some embodiments, diphenhydramine is administered about 30 minutes before administration of the effective amount of the population of activated human Treg cells.

Further provided herein is a use of a population of human Treg cells disclosed herein in the preparation of a medicament. The medicament may be used for treating or preventing a disease, disorder or condition.

Graft Versus Host Disease (GVHD)

Provided herein is a method for treating or preventing graft versus host disease (GVHD) in a subject, the method comprising administering to the subject an effective amount of the population of activated human Treg cells produced by a method disclosed herein or the population or an effective amount of the population of human Treg cells disclosed herein.

In some embodiments, a method described herein ameliorates, reduces or prevents one or more symptoms of GVHD in a subject. In some embodiments, a method described herein prolongs survival of a subject having GVHD. In some embodiments, a method described herein prevents a subject from developing GVHD after receiving a transplant.

Further provided herein is a method for treating or preventing GVHD in a subject, the method comprising administering to the subject (i) an effective amount of the population of activated human Treg cells produced by a method disclosed herein or the population or an effective amount of the population of human Treg cells disclosed herein and (ii) ruxolitinib. In some embodiments, ruxolitinib is administered to the subject continuously and the human Treg cells are administered to the subject every 2, 3 or 4 weeks. In some embodiments, ruxolitinib taken twice a day by mouth as a 5 mg, 10 mg, 15 mg, 20 mg, or 25 mg tablet.

Allogeneic hematopoietic stem cell transplant (HSCT) is the only curative option for many hematological malignancies. However, a major barrier to more widespread use of this procedure is the development of GVHD, which occurs when T cells from the graft recognize the tissues of the host as foreign and is a major cause of morbidity and mortality. (See Warren et al., Tissue Antigens 81(4):183-93 (2013); Sung et al., Stem Cells Transl Med 2(1):25-32 (2013); and Qian et al., J Cell Mol Med 17(8):966-75 (2013)). Acute GVHD (aGVHD) generally occurs within the first 100 days post-HSCT and involves a "cytokine storm" from activated T cells that recruit other inflammatory cell types such as NK cells and macrophages, causing inflammatory lesions in tissues such as skin, gut and liver. aGVHD causes death in approximately 15% of transplant patients. (See Sung et al., Stem Cells Transl Med 2(1):25-32 (2013); and Qian et al., J Cell Mol Med 17(8):966-75 (2013)). Chronic GVHD (cGVHD) occurs subsequent to the first 100 days after transplant and is characterized by systemic inflammation and tissue destruction affecting multiple organs, particularly the gut, liver, lungs, bone marrow, thymus and skin. cGVHD occurs in 30-65% of allogeneic HSCT recipients causing extreme morbidity with a 5-year mortality of 30-50% due predominantly to impaired ability to fight infections. aGVHD is thought to be mainly a Th1/Th17-driven process whereas cGVHD is thought to be predominantly driven by Th2-driven responses. In some embodiments, a method described herein ameliorates, reduces or prevents one or more symptoms of aGVHD in a subject. In some embodiments, a method described herein ameliorates, reduces or prevents one or more symptoms of cGVHD in a subject. In some embodiments, the methods of treatment described herein can be used to suppress GVHD without loss of the benefits of graft-versus-leukemia (GVL) activity, a beneficial immune response by allogeneic immune cells that kills leukemic cells (see Edinger et al., Nat Med 9(9):1144-50 (2003)).

Current strategies for minimizing GVHD call for prolonged immunosuppressive therapies with drugs such as the calcineurin inhibitors (CNI), cyclosporine and tacrolimus. However, this prolonged immunosuppression results in delayed immune function leading to infectious complications as well as the risk of post-transplant lymphoproliferative disorders. In some embodiments, provided herein is a method for treating or preventing GVHD in a subject, the method comprising administering to the subject an effective amount of the population of activated human Treg cells produced by a method disclosed herein or an effective amount of the population of human Treg cells disclosed herein, without administering any other immunosuppressive therapy.

A xenogeneic mouse model of GVHD may be used to assess function of umbilical cord blood-derived T-regulatory cells in treating GVHD. (See Parmar et al., Cytotherapy 16(10:90-100

Bone Marrow Failure Syndrome (BMF)

Provided herein is a method for treating or preventing bone marrow failure syndrome (BMF) in a subject, the method comprising administering to the subject an effective amount of the population of activated human Treg cells produced by a method disclosed herein or an effective amount of the population of human Treg cells disclosed herein. In some embodiments, an effective amount of a cryopreserved Treg cell product enriched for CXCR4 expression (e.g., CK0804) is administered to treat or prevent BMF.

In some embodiments, a method described herein ameliorates, reduces or prevents one or more symptoms of BMF in a subject. In some embodiments, a method described herein prolongs survival of a subject having BMF.

BMF refers to the decreased production of one or more major hematopoietic lineages which leads to diminished or absent hematopoietic precursors in the bone marrow (BM). It can be divided into two categories: acquired and inherited. Acquired BMF syndromes include aplastic anemia, myelodysplastic syndrome, and primary myelofibrosis. Pathogenesis of the acquired BMF syndromes involves BM microenvironment as well as environmental factors. For a vast majority of these syndromes, the role of immune dysfunction is being recognized as being important in both the origin as well as maintenance of the BM defect.

Aplastic Anemia (AA)

Provided herein is a method for treating or preventing aplastic anemia (AA) in a subject, the method comprising administering to the subject an effective amount of the population of activated human Treg cells produced by a method disclosed herein or an effective amount of the population of human Treg cells disclosed herein.

AA is characterized by pancytopenia in peripheral blood (PB) and bone marrow (BM) hypoplasia AA is a BMF syndrome characterized by an attack by autoreactive cytotoxic T cells, such as CD8$^+$ cytotoxic T cells, CD4$^+$ Th1 cells, and Th17 cells, on BM hematopoietic progenitors. (See Brodksy et al., Lancet 365(9471):1647-56 (2005); Li et al., Crit Rev Oncol Hematol 75(2):79-93 (2010); Young et al., Curr Opin Hematol 15(3):162068 (2008); and de Latour et al., Blood 116(20):4175-84 (2010)).

Mechanisms of immune mediated destruction of hematopoiesis include Th1 polarization response conferring excessive production of inhibitory cytokines such as interferon-$\gamma$ (IFN-$\gamma$), tumor necrosis factor-$\alpha$ (TNF-$\alpha$), and interleukin-2 (IL-2), direct toxicity to autologous CD34$^+$ cells by T-cell populations, and Th17 immune response. (See de Latour et al., Blood 116(20):4175-84 (2010); Giannakoulas et al., Br J Haematol 124(1):97-105 (2004): Sloand et al., Blood 100(4):1185-91 (2002); and Solomou et al., Blood 107(10):3983-91 (2006)). In that sense, AA is a specific autoimmune disease because of the overactive cytotoxic auto-reactive T cells in combination with the defective as well as deficient regulatory T cells leading to aberrant T-cell immune homeostasis and BM is the main target organ.

Also provided herein are methods of treating acquired idiopathic aplastic anemia in a subject, wherein the subject is ineligible for matched sibling donor hematopoietic stem cell transplant (MSD-HSCT) or is predicted to be a poor responder to immunosuppressive therapy (IST).

The diagnosis of acquired AA can be based on the exclusion of other disorders that can cause pancytopenia and on the well-known Camitta criteria. (See Camitta et al., Blood 45(3):355-63 (1975)).

AA response criteria (see Killick et al., *Br J Haematol* 172(2):187-207 (2016)), as shown in the table below, can be used to determine response of a subject with AA to the therapeutic methods described herein:

TABLE 5

| (a) Response criteria following immune suppressive therapy (IST) in severe AA | |
| --- | --- |
| None | Still fulfill severe disease criteria |
| Partial | Transfusion independent |
| | No longer meet criteria for severe disease |
| Complete | Hemoglobin concentration normal for age and gender |
| | Neutrophil count > 1.0 × 10$^9$/l |
| | Platelet count > 100 × 10$^9$/l |
| (b) Response criteria following IST for non-severe AA | |
| None | Blood counts are worse, or do not meet criteria below |
| Partial | Transfusion independence (if previously dependent) |
| | or doubling or normalization of at least one cell line |
| | or increase of baseline |
| | Hemoglobin concentration of > 30 g/l (if initially < 60) |
| | neutrophils of > 0.5 × 10$^9$/l (if initially < 0.5) |
| | platelets of > 20 × 10$^9$/l (if initially < 20) |
| Complete | Same criteria as for severe disease |

Myelodysplastic Syndrome (MDS)

Provided herein is a method for treating or preventing myelodysplastic syndrome (MDS) in a subject, the method comprising administering to the subject an effective amount of the population of activated human Treg cells produced by a method disclosed herein or an effective amount of the population of human Treg cells disclosed herein.

MDS is characterized by ineffective hematopoiesis where impaired blood cell production may be a result of increased apoptosis. Clonal expansion of abnormal progenitor cells escaping apoptosis may cause evolution to overt acute leukemia. (See Rosenfeld, Leukemia 14(1):2-8 (2000) and Barrett et al., Semin Hematol 37(1):15-29 (2000)). Dysregulation of the immune function is an accepted fact in MDS. (See Fozza et al., Exp Hematol 37(8):947-55 (2009)). Among the possible mechanisms, T cell-mediated inhibition of hematopoiesis has been recognized as a typical feature of especially low-risk and hypocellular MDS. (See Epperson et al., Leuk Res 25(12):1075-83 (2001)). Cytopenia in some types of MDS may be due to either cytokine or cell-mediated autoimmune suppression of normal and abnormal bone marrow (BM) progenitor cells. (See Barrett et al., Semin Hematol 37(1):15-29 (2000)). These mechanisms may operate especially in the hypoplastic forms of MDS (HMDS) (see Tuzuner et al., Br J Haematol 91(3):612-17 (1995)), which often overlap clinically with aplastic anemia (AA), a disease with established autoimmune pathogenesis. (See Young et al., N Engl J Med 336(19):1365-72 (1997)).

Patients with MDS show a decreased CD4-to-CD8 ratio, expansion of multiple activated CD8$^+$ T-cell clones, and overproduction of inhibitory cytokines. (See Selleri et al., Cancer 95(9):1911-22 (2002)). The immune effector mechanisms in MDS patients may include not only direct killing, but also release of cytokines with inhibitory activity on hematopoietic progenitors, such as interferon-$\gamma$ (IFN-$\gamma$), tumor necrosis factor-$\alpha$ (TNF-$\alpha$), and Fas-ligand (Fas-L). (See Zang et al., Blood 98(10):3058-65 (2001)). Consistent with these pathophysiologic pathways, increased levels of these cytokines have been described in blood and marrow of MDS patients and are likely the cause for the high number of apoptotic myeloid cells found in these patients. (See Selleri et al., Cancer 95(9):1911-22 (2002)).

Currently, the diagnosis of MDS (see Gangat et la., Am J Hematol 91(1):76-89 (2016)) is established based on the presence of (i) persistent (>6 month duration) and significant cytopenia(s) hemoglobin <10 g/dL, absolute neutrophil count <1.8×10$^9$/L, platelet count <100×10$^{109}$/L, (ii) significant bone marrow dysplasia, or blast excess or typical cytogenetic abnormality, and (iii) exclusion of differential diagnoses. (See Barrett et al., Semin Hematol 37(1):15-29 (2000)). Common peripheral blood findings include macrocytic anemia, reticulocytopenia, neutropenia with hyposegmented neutrophils (pseudo Pelger-Huet), circulating immature myeloid cells, including myeloblasts and thrombocytopenia.

International Working Group (IWG) response criteria (see Cheson et al., Blood 108(2):419-25 (2006)), as shown in the table below, can be used to determine response of a subject with MDS to the therapeutic methods described herein:

TABLE 6

| IWG Criteria for Response | | |
| --- | --- | --- |
| Category | Original (sustained ≥ weeks) | Modified (sustained ≥ 4 weeks) |
| CR: Marrow | <5% blasts; no dysplasia; normal maturation of all cell lines | ≤5% blasts; normal maturation of all cells lines |
| CR: Peripheral blood | Hgb ≥ 11 g/dL; ANC ≥ 1,500/mL; platelets ≥ 100,000/mL; 0% blasts; no dysplasia | Hgb ≥ 11 g/dL; ANC ≥ 1000/mL; platelets ≥ 100,000/mL; 0% blasts; hematologic improvement responses noted in addition to marrow CR |
| PR | Same as CR, except blasts ↓ by ≥ 50% or lower FAB | Same as CR, except blasts ↓ by ≥50%, still greater than 5% in marrow |

TABLE 6-continued

IWG Criteria for Hematological Improvement

| | | Modified IWG Response |
|---|---|---|
| Category | Pretreatment | Criteria* (≥8 weeks) |
| Erythroid (HI-E) | Hgb < 11 g/dL | Hgb ↑ of ≥1.5 g/dL ↓ of ≥4 RBC transfusions/8 weeks versus pretreatment requirement in previous 8 weeks; only RBC transfusions given for a pretreatment Hgb of ≤9.0 g/dL count |
| Platelet (HI-P) | <100,000/mL | ↑ of ≥30,000/mL (starting with >20,000/mL) ↑ from <20,000/mL to >20,000/mL by >100% |
| Neutrophil (HI-N) | <1,000/mL | ↑ of ≥100% and >500/μL |
| Progression/Relapse after hematological improvement | | ≥1 of the following: ≥50% decrement from maximum response levels in granulocytes or platelets; ↓ in Hgb by ≥1.5 g/dL; transfusion dependence |

Primary Myelofibrosis (PMF)

Provided herein is a method for treating or preventing primary myelofibrosis (PMF) in a subject, the method comprising administering to the subject an effective amount of the population of activated human Treg cells produced by a method disclosed herein or an effective amount of the population of human Treg cells disclosed herein. In some embodiments, the population of human Treg cells administered to a subject for treating or preventing PMF is at least about 90% CXCR4+. In some embodiments, an effective amount of a cryopreserved Treg cell product enriched for CXCR4 expression (e.g., CK0804) is administered to treat or prevent PMF. In some embodiments, the unit dose of a cryopreserved Treg cell product enriched for CXCR4 expression administered to a subject is 100 million cells in 10-20 ml. A unit dose can be administered on Day 1 of each 28-day cycle for up to six doses (i.e., up to six cycles).

Further provided herein is a method for treating or preventing PMF in a subject, the method comprising administering to the subject (i) an effective amount of the population of activated human Treg cells produced by a method disclosed herein or an effective amount of the population of human Treg cells disclosed herein (e.g., CK0804) and (ii) ruxolitinib. In some embodiments, ruxolitinib is administered to the subject continuously and the human Treg cells are administered to the subject every 2, 3 or 4 weeks. In some embodiments, ruxolitinib taken twice a day by mouth as a 5 mg, 10 mg, 15 mg, 20 mg, or 25 mg tablet.

PMF is a clonal hematopoietic stem cell disorder in which 50% of patients have a constitutively activated mutation in the Janus kinase (JAK)2 gene, JAK2V617F. Although PMF is generally regarded as arising from a mutated stem or progenitor hematopoietic cell, immune dysregulation is common. For example, there are increased plasma levels of inflammatory cytokines and clinical and laboratory manifestations of autoimmunity. (See Barosi Curr Hematol Malig Rep 9(4):331-39 (2014)). This clonal myeloproliferation is characteristically accompanied by reactive myelofibrosis (bone marrow fibrosis) and by extramedullary hematopoiesis in the spleen or in multiple organs.

Pro-inflammatory cytokines are known to be at very high levels in PMF and to contribute to the disease pathogenesis. In fact, treatment with ruxolitinib is associated with a dramatic decrease in circulating levels of pro-inflammatory cytokines including IL-6, and tumor necrosis factor (TNF)-α.

The diagnosis of PMF can be made using the criteria set forth in Table 7 (see Barbui et al., Blood Cancer Journal 8(2):15 (2018)):

TABLE 7

| Primary Myelofibrosis (PMF)[a] | |
|---|---|
| Prefibrotic/early PMF (pre-PMF) | Overt PMF |
| Major criteria | |
| Megakaryocytic proliferation and atypia[b], without reticulin fibrosis > grade 1[c], accompanied by increased age-adjusted BM cellularity, granulocytic proliferation and often decreased erythropoiesis | Megakaryocyte proliferation and atypiab accompanied by either reticulin and/or collagen fibrosis (grade 2 or 3) |
| Not meeting WHO criteria for BCR-ABL1 + CML, PV, ET, MDS, or other myeloid neoplasm | Not meeting WHO criteria for BCR-ABL1 + CML, PV, ET, MDS or other myeloid neoplasm |
| Presence of JAK2, CALR, or MPL mutation or int he absence of these mutations, presence of another clonal marker[d] or absence of minor reactive BM reticulin fibrosis[e] | Presence of JAK2, CALR, or MPL mutation or in the absence, the presence of another clonal marker[d] or absence of evidence for reactive BM fibrosis[f] |
| Minor criteria | |
| Presence of one or more of the following, confirmed in two consecutive determinations: | |
| Anemia not attributed to a comorbid condition | Anemia not attributed to a comorbid condition |
| Leukocytosis ≥ 11 × 10⁹/L | Leukocytosis ≥ 11 × 10⁹/L |
| Palpable splenomegaly | Palpable splenomegaly |

TABLE 7-continued

| Primary Myelofibrosis (PMF)[a] | |
|---|---|
| Prefibrotic/early PMF (pre-PMF) | Overt PMF |
| LDH level above the upper limit of the institutional reference range | LDH level above the upper limit of the institutional reference range<br>Leukoerythroblastosis |

[a]Diagnosis of prefibrotic/early PMF requires all three major criteria and at least one minor criterion. Diagnosis of overt PMF requires meeting all three major criteria and at least one minor criterion
[b]Small-to-large megakaryocytes with aberrant nuclear/cytoplasmic ratio and hyperchromatic and irregularly folded nuclei and dense clustering
[c]In cases with grade 1 reticulin fibrosis, the megakaryocyte changes must be accompanied by increased BM cellularity, granulocytic proliferation, and often decreased erythropoiesis (that is, pre-PMF)
[d]In the absence of any of the three major clonal mutations, the search for the most frequent accompanying mutations (ASXL1, EZH2, TET2, IDH1/IDH2, SRSF2, SF3B1) are of help in determining the clonal nature of the disease
[e]Minor (grade 1) reticulin fibrosis secondary to infection, autoimmune disorder or other chronic inflammatory conditions, hairy cell leukemia or other lymphoid neoplasm, metastatic malignancy, or toxic (chronic) myelopathies
[f]BM fibrosis secondary to infection, autoimmune disorder, or other chronic inflammatory conditions, hairy cell leukemia, or other lymphoid neoplasm, metastatic malignancy or toxic (chronic) myelopathies The revised International Working Group-Myeloproliferative Neoplasms Research and Treatment (IWG-MRT) and European-Leukemia Network (ELN) response criteria (see Tefferi et al., Blood 122(8):1395-98 (2013), as shown in Table 8, can be used to determine response of a subject with PMF to the therapeutic methods described herein. In some embodiments, administration of an effective amount of a cryopreserved Treg cell product enriched for CXCR4 expression (e.g., CK0804) to a subject with PMF reduces or improves a symptom listed in Table 8.

TABLE 8

| Response Categories | Required criteria (for all response categories, benefit must last for ‡12 wk to qualify as a response) |
|---|---|
| Complete Response (CR) | Bone marrow*: Age-adjusted normocellularity; ‚5% blasts; #grade 1 MF† and Peripheral blood: Hemoglobin ≥ 100 g/L and UNL; neutrophil count ≥ 1 × 10⁹/Land UNL;<br>Platelet count ≥ 100 × 10⁹/L and < UNL; <2% immature myeloid cellst and Clinical: Resolution of disease symptoms; spleen and liver not palpable; no evidence of EMH |
| Partial Response (PR) | Peripheral blood: Hemoglobin ≥ 100 g/L and < UNL; neutrophil count ≥ 1 × 10⁹/L and < UNL; platelet count ≥ 100 × 10⁹/L and < UNL; <2% immature myeloid cellst and<br>Clinical: Resolution of disease symptoms; spleen and liver not palpable; no evidence of EMH or<br>Bone marrow*: Age-adjusted normocellularity; <5% blasts; ≥grade 1 MF†, and peripheral blood:<br>Hemoglobin ≥ 85 but < 100 g/L and < UNL; neutrophil count ≥ 1 × 10⁹/L and < UNL; platelet count ≥ 50, but < 100 × 10⁹/L and < UNL; <2% immature myeloid cells‡ and<br>Clinical: Resolution of disease symptoms; spleen and liver not palpable; no evidence of extra-medullary hematopoiesis (EMH) |
| Clinical improvement (CI) | The achievement of anemia, spleen or symptoms response without progressive disease or increase in severity of anemia, thrombocytopenia, or neutropenia |
| Anemia response | Transfusion-independent patients: a >20 g/L increase in hemoglobin level<br>Transfusion-dependent patients: becoming transfusion-independent |
| Spleen response# | A baseline splenomegaly that is palpable at 5-10 cm, below the LCM, becomes not palpable or<br>A baseline splenomegaly that is palpable at >10 cm, below the LCM, decreases by ≥50%<br>A baseline splenomegaly that is palpable at <5 cm, below the LCM, is not eligible for spleen response<br>A spleen response requires confirmation by MRI or computed tomography showing ≥35% spleen volume reduction |
| Symptoms response | A ≥50% reduction in the MPN Symptom Assessment Form Total Symptom Score (MPN-SAF TSS) |
| Progressive disease‡‡ | Appearance of a new splenomegaly that is palpable at least 5 cm below the LCM or<br>A ≥100% increase in palpable distance, below LCM, for baseline splenomegaly of 5-10 cm or<br>A 50% increase in palpable distance, below LCM, for baseline splenomegaly of >10 cm or<br>Leukemic transformation confirmed by a bone marrow blast count of ≥20% or<br>A peripheral blood blast content of ≥20% associated with an absolute blast count of ≥1 × 10⁹/L that lasts for at least 2 weeks |
| Stable disease | Belonging to none of the above listed response categories |
| Relapse | No longer meeting criteria for at least CI after achieving CR, PR, or CI, or<br>Loss of anemia response persisting for at least 1 month or<br>Loss of spleen response persisting for at least 1 month |

TABLE 8-continued

| Response Categories | Required criteria (for all response categories, benefit must last for ‡12 wk to qualify as a response) |
|---|---|
| | Recommendations for assessing treatment-induced cytogenetic and molecular changes |
| Cytogenetic Remission | At least 10 metaphases must be analyzed for cytogenetic response evaluation and requires confirmation by repeat testing within 6 month window<br>CR: eradication of a preexisting abnormality<br>PR: ≥50% reduction in abnormal metaphases<br>(partial response applies only to patients with at least ten abnormal metaphases at baseline) |
| Molecular remission | Molecular response evaluation must be analyzed in peripheral blood granulocytes and requires confirmation by repeat testing within 6 month window<br>CR: Eradication of a pre-existing abnormality<br>PR: ≥50% decrease in allele burden<br>(partial response applies only to patients with at least 20% mutant allele burden at baseline) |
| Cytogenetic/ molecular relapse | Re-emergence of a pre-existing cytogenetic or molecular abnormality that is confirmed by repeat testing |

Systemic Lupus Erythematosus (SLE)

Provided herein is a method for treating or preventing systemic lupus erythematosus (SLE) in a subject, the method comprising administering to the subject an effective amount of the population of activated human Treg cells produced by a method disclosed herein or an effective amount of the population of human Treg cells disclosed herein.

In some embodiments, a method described herein ameliorates, reduces or prevents one or more symptoms of SLE in a subject. In some embodiments, following administration of the activated human Treg cells to the subject, the spillover of albumin in urine is decreased; the SLE cell infiltration in the glomeruli is decreased; and/or the hair follicles are preserved. In some embodiments, a method described herein prolongs survival of a subject having SLE.

SLE is a chronic, multisystem, inflammatory autoimmune disorder. Lupus can affect many parts of the body, including the joints, skin, kidney, heart, lungs, blood vessels, and/or brain. For example, SLE may manifest as arthralgia or arthritis, Raynaud phenomenon, malar and other rashes, pleuritis or pericarditis, renal or CNS involvement, and/or hematologic cytopenias.

Inflammatory Cancers

Provided herein is a method for treating or preventing an inflammatory cancer in a subject, the method comprising administering to the subject an effective amount of the population of activated human Treg cells produced by a method disclosed herein or an effective amount of the population of human Treg cells disclosed herein. In some embodiments, an inflammatory cancer is multiple myeloma or inflammatory breast cancer. In some embodiments, the treatment regimen for multiple myeloma comprises administration of an effective amount of the population of human Treg cells and administration of a bispecific protein (e.g., antibody) useful for treating an inflammatory cancer. In some embodiments, the bispecific protein is a bispecific T-cell engager. In some embodiments, a bispecific T-cell engager binds to CD3 and BCMA.

In some embodiments, a method described herein ameliorates, reduces or prevents one or more symptoms of an inflammatory cancer in a subject. In some embodiments, a method described herein prolongs survival of a subject having an inflammatory cancer.

Neuro-Inflammatory Disorders

Provided herein is a method for treating or preventing a neuro-inflammatory disorder in a subject, the method comprising administering to the subject an effective amount of the population of activated human Treg cells produced by a method disclosed herein or an effective amount of the population of human Treg cells disclosed herein. In some embodiments, an inflammatory cancer is Guillain-Barre Syndrome or amyotrophic lateral sclerosis.

In some embodiments, a method described herein ameliorates, reduces or prevents one or more symptoms of a neuro-inflammatory disorder in a subject. In some embodiments, a method described herein prolongs survival of a subject having a neuro-inflammatory disorder.

Guillain-Barre Syndrome (GBS)

Provided herein is a method for treating or preventing Guillain-Barre Syndrome (GB S) in a subject, the method comprising administering to the subject an effective amount of the population of activated human Treg cells produced by a method disclosed herein or an effective amount of the population of human Treg cells disclosed herein.

Also provided herein are methods of treating GBS in a subject, wherein the subject is unresponsive to treatment with intravenous immunoglobulin (IVIG) or plasma exchange.

GBS is an autoimmune disorder characterized by rapid-onset of muscle weakness due to inflammation of the nerves. There are two major subtypes: (1) acute inflammatory demyelinating polyneuropathy (AIDP) and (2) acute axonal neuropathy (AMAN). Although the exact cause of GBS is unknown, there is strong evidence that immune response to infection produces an autoimmune response that damages the nerves.

Experimental autoimmune neuritis (EAN) is an immune-mediated inflammatory demyelinating disorder of the peripheral nervous system that serves as an animal model of AIDP. The therapeutic methods described herein may be tested in this animal model. It is commonly induced in susceptible animal strains by immunization with myelin proteins such as P0 or P2, which provoke breakdown of the blood-nerve barrier, infiltration of autoreactive T cells and macrophages, and demyelination of the peripheral nervous system (Soliven, B., Autoimmune neuropathies: insights from animal models. J Peripher Nery Syst, 2012. 17 Suppl 2: p. 28-33). EAN can be actively initiated with neuritogenic epitopes of peripheral nerve proteins P0, P2, and peripheral myelin protein 22 (PMP22) (Hughes, R. A., et al., Patho-genesis of Guillain-Barre syndrome. J Neuroimmunol, 1999. 100(1-2): p. 74-97) or by adoptive transfer of sensitized T cells.

Amyotrophic Lateral Sclerosis (ALS)

Provided herein is a method for treating or preventing amyotrophic lateral sclerosis (ALS) in a subject, the method comprising administering to the subject an effective amount of the population of activated human Treg cells produced by a method disclosed herein or an effective amount of the population of human Treg cells disclosed herein (e.g., $1\times10^8$, $3\times10^8$ or $1\times10^9$ activated human Treg cells).

In some embodiments, provided herein is a method for treating or preventing a neuro-inflammatory disorder in a subject, the method comprising administering to the subject an effective amount of the population of human Treg cells disclosed herein.

ALS is a rare neurological disease involving the death of neurons controlling voluntary muscles. It results in severe muscle atrophy with a loss of the ability to walk and speak. The disease is characterized by an approximately 80% 5-year mortality rate. Autoimmune neuro-inflammation forms the cornerstone for ALS pathogenesis and progression. In fact, ALS patients present with enhanced inflammation in the spinal cord and the degree of microglial activation corresponds to disease severity.

In ALS, Tregs are dysfunctional and less effective in suppressing responder T-lymphocyte proliferation. Moreover, late-stage ALS is characterized by M1-like macrophages/microglia and infiltration of proinflammatory effector T cells. ALS patients tend to have a decrease in Tregs (CD4+/CD25+) and the rate of progression is negatively correlated with Treg cell counts. Likewise, low FoxP3 mRNA levels are predictors of rapid ALS progression. Moreover, Tregs taken from ALS patients have a decreased ability to suppress proliferation of Th17 cells compared to healthy subjects.

COVID-19 (Coronavirus Disease) Mediated Acute Respiratory Distress Syndrome (CoV-ARDS)

Provided herein is a method for treating or preventing COVID-19 (coronavirus disease) mediated acute respiratory distress syndrome (CoV-ARDS) in a subject, the method comprising administering to the subject an effective amount of the population of activated human Treg cells produced by a method disclosed herein or an effective amount of the population of human Treg cells disclosed herein (e.g., about $1\times10^8$ or about $3\times10^8$ activated human Treg cells). In some embodiments, about $1\times10^8$ or about $3\times10^8$ activated human Treg cells are administered to a subject at day 0 and day 3. In some embodiments, about $1\times10^8$ or about $3\times10^8$ human Treg cells are administered to a subject at day 0, day 3 and day 7. In some embodiments, the human Treg cells are cryopreserved allogeneic, cord blood-derived Treg cells (CK0802). In some embodiments, the human Treg cells are administered as a single agent.

In some embodiments, a subject is infected or suspected of being infected with severe acute respiratory syndrome coronavirus 2 (SARS-CoV-2).

The highly pathogenic SARS-CoV-2 is associated with rapid virus replication, massive inflammatory cell infiltration and elevated pro-inflammatory cytokine/chemokine responses resulting in acute lung injury leading to acute respiratory distress syndrome (ARDS); pulmonary fibrosis and death. The initial phase of viral infection includes robust virus replication and clinical symptoms, including fever, cough, and others. The second phase of viral infection includes high fever, hypoxemia, progression to pneumonialike symptoms, and progressive decline in virus titers towards the end. The third phase of viral infection includes exuberant host inflammatory responses, excessive production of cytokines and chemokines, dysregulated innate immune response, and ARDS. Clinically, ARDS is characterized by acute hypoxemic respiratory failure and bilateral pulmonary infiltrates on chest x-ray.

An uncontrolled cytokine storm may be responsible for the acuity of the respiratory complications in some subjects infected with SARS-CoV-2. In some embodiments, a CoV-ARDS cytokine storm includes an increase in pro-inflammatory cytokines (for example, IFN-γ, IL-1, IL-6, IL-12, or TGFβ) and chemokines (for example, CCL2, CXCL10, CXCL9, and IL-8). Higher virus titers and dysregulated cytokine/chemokine responses orchestrate massive infiltration of inflammatory cells into the lungs. In some embodiments, a CoV-ARDS cytokine storm includes a decrease in anti-inflammatory cytokines (for example, IL-10). In a pre-clinical lung injury model, injection of CB-Treg cells led to: i) decrease in inflammatory T-cells; ii) decrease of alveolar hemorrhage; iii) regeneration of lung epithelium and alveoli; and iv) decrease in inflammatory cytokines including IL-17 and IL-6, both implicated in CoV-ARDS.

No specific treatment exists except for supportive care including mechanical ventilation where mortality rates exceed 50%. Novel therapeutic options are urgently needed. Regulatory T cells (Tregs) are a special type of T-cell that restrict inflammation-induced lung damage via multiple mechanisms leading to tissue-repair and regeneration.

In some embodiments, administration of an effective amount of the population of human Treg cells disclosed herein may treat CoV-ARDS or a symptom of CoV-ARDS by resolving inflammation. In some embodiments, administration of the population or an effective amount of the population of activated human Treg cells disclosed herein may induce the release of suppressor cytokines (for example, TGF-β, IL-6, IL-10, IL-17, IL-18, or IL-33).

In some embodiments, the human Treg cells used in these treatment methods express CCR4, a homing marker for lung tissue responsible for transport to CoV-ARDS-related sites of inflammation.

All publications, patents and patent applications are herein incorporated by reference in their entirety to the same extent as if each individual publication, patent or patent application was specifically and individually indicated to be incorporated by reference in its entirety Any of the aspects and embodiments described herein can be combined with any other aspect or embodiment as disclosed here in the Summary, in the Drawings, and/or in the Detailed Description, including the below specific, non-limiting, examples/embodiments of the present disclosure.

NUMBERED EMBODIMENTS

Notwithstanding the appended claims, the disclosure sets forth the following numbered embodiments:

1. A method for producing an expanded population of human T regulatory (Treg) cells enriched for CXCR4+ Treg cells from a cryopreserved human umbilical cord blood unit, the method comprising:
   (a) thawing the cryopreserved human umbilical cord blood unit;
   (b) diluting and washing the thawed umbilical cord blood unit in a functionally closed system;
   (c) isolating Treg cells using a double selection method based on CD25+ cell surface expression;

51

(d) ex vivo expanding the isolated CD25$^+$ Treg cells in a culture medium, in a gas permeable cultureware, in the presence of:
(1) an effective amount of interleukin-2 (IL-2);
(2) a reagent that specifically binds to CD3 and CD28; and
(3) anti-CXCR4 magnetic microbeads,
for up to 10 days or up to 12 days, wherein the culture medium is replaced about every 48 hours, to produce a CXCR4-enriched culture of CD25$^+$ Treg cells; and
(e) harvesting the activated CD25$^+$ CXCR4$^+$ cells from the culture medium to produce an expanded population of human Treg cells enriched for CXCR4$^+$ Treg cells.

2. The method of embodiment 1, wherein in step (d),
(1) the ex vivo expansion is initiated at day 0;
(2) the effective amount of IL-2 is added to the isolated CD25$^+$ Treg cells at day 0; and
(3) the reagent that specifically binds to CD3 and CD28 is added to the isolated CD25$^+$ Treg cells at day 0.

3. The method of embodiment 1 or 2, wherein the reagent that specifically binds to CD3 and CD28 is removed from the culture medium before the anti-CXCR4 magnetic microbeads are added to the culture medium.

4. The method of any one of embodiments 1-3, wherein in step (d), the anti-CXCR4 magnetic microbeads are added to the culture medium 3 or 4 days after the ex vivo expansion is initiated.

5. The method of any one of embodiments 1-4, wherein in step (d), the anti-CXCR4 magnetic microbeads are added to the culture medium for about 30 minutes before a double ferromagnetic column is used to isolate CXCR4$^+$ Treg cells.

6. The method of any one of embodiments 1-5, wherein the isolated CD25$^+$ Treg cells are enriched for CXCR4 on the third feed of ex vivo expansion.

7. The method of any one of embodiments 1-6, wherein step (d) takes place over 4 or 5 days.

8. The method of any one of embodiments 1-7, wherein the reagent that specifically binds to CD25 is an anti-CD25 antibody or an antigen-binding fragment thereof.

9. The method of any one of embodiments 1-8, wherein the reagent that specifically binds to CD25 is conjugated to a solid support.

10. The method of embodiment 9, wherein the solid support is a magnetic microbead.

11. The method of any one of embodiments 1-10, wherein the reagent that specifically binds to CD3 and CD28 comprises an anti-CD3 antibody or an antigen-binding fragment thereof and an anti-CD28 antibody or an antigen-binding fragment thereof.

12. The method of any one of embodiments 1-11, wherein the reagent that specifically binds to CD3 and CD28 comprises anti-CD3 coated beads and anti-CD28 coated beads.

13. The method of any one of embodiments 1-12, wherein the effective amount of IL-2 is about 1000 IU/ml.

14. A method for producing an expanded population of human Treg cells enriched for CXCR4$^+$ Treg cells from a cryopreserved human umbilical cord blood unit, the method comprising:
(a) thawing the cryopreserved human umbilical cord blood unit;
(b) diluting and washing the thawed umbilical cord blood unit in a functionally closed system;
(c) isolating Treg cells using a double selection method based on CD25$^+$ cell surface expression;
(d) ex vivo expanding the isolated CD25$^+$ Treg cells in a culture medium, in a gas permeable cultureware, wherein the ex vivo expansion step comprises:

52

(1) at day 0, adding anti-CD3 and anti-CD28 coated beads to the CD25$^+$ Treg cells in the culture medium;
(2) at day 2, adding about 1000 IU/ml IL-2 to the culture medium;
(3) at day 3 or 4, removing the anti-CD3 and anti-CD28 coated beads from the culture medium and adding anti-CXCR4 magnetic microbeads to the culture medium; and
(4) at day 3 or 4, removing the anti-CXCR4 magnetic microbeads attached to CXCR4$^+$ Treg cells from the culture medium, and adding fresh anti-CD3 and anti-CD28 coated beads to the CXCR4$^+$ Treg cells,
wherein the ex vivo expansion takes place for up to 10 days or up to 12 days, wherein the culture medium is replaced about every 48 hours, to produce a CXCR4-enriched culture of CD25$^+$ Treg cells; and
(e) harvesting the activated CD25$^+$ CXCR4$^+$ cells from the culture medium to produce an expanded population of human Treg cells enriched for CXCR4$^+$ Treg cells.

15. The method of any one of embodiments 1-14, wherein in step (d), IL-2 is added to the culture medium comprising isolated CD25$^+$ Treg cells about every 48 hours.

16. The method of any one of embodiments 12-15 wherein the anti-CD3 coated beads and the anti-CD28 coated beads are at a 1:1 ratio.

17. The method of embodiment 8 or 9, wherein the CD25$^+$ cells and the anti-CD3 and anti-CD28 coated beads are at a 1:1 ratio.

18. The method of any one of embodiments 1-17, wherein in step (e), about $1\times10^6$ CD25$^+$ cells/ml are cultured.

19. The method of any one of embodiments 1-18, wherein in step (e), the cells are initially cultured in gas-permeable cultureware that has a membrane surface area of 10 cm$^2$.

20. The method of embodiment 19, wherein the culture is subsequently transferred to gas-permeable cultureware that has a membrane surface area of 100 cm$^2$.

21. The method of any one of embodiments 1-20, wherein in step (d), the culture is not rocked or agitated when the IL-2 is added.

22. The method of any one of embodiments 1-21, wherein in step (a), the cryopreserved human umbilical cord blood unit is thawed in a single step in a water bath.

23. The method of any one of embodiments 1-22, wherein step (b) does not comprise manual washing.

24. The method of any one of embodiments 1-23, wherein step (b) takes place in a solution comprising PBS, EDTA, and about 0.5% human serum albumin.

25. The method of any one of embodiments 1-24, wherein a double ferromagnetic column method is used in step (c) to isolate CD25$^+$ Treg cells.

26. The method of any one of embodiments 1-25, the method further comprising cryopreserving the expanded population of human Treg cells enriched for CXCR4$^+$ Treg cells.

27. The method of any one of embodiments 1-26, wherein the expanded population of human Treg cells enriched for CXCR4$^+$ Treg cells is:
(i) ≥60% CD4$^+$CD25$^+$;
(ii) ≥60% CD4$^+$CD25$^+$ CXCR4$^+$; and
(iii) ≤10% CD4$^-$CD8$^+$, as measured by flow cytometry.

28. An expanded population of human Treg cells enriched for CXCR4$^+$ Treg cells produced by the method of any one of embodiments 1-27.

29. A method for treating or preventing a bone marrow failure syndrome in a subject, the method comprising administering to the subject an effective amount of the population of activated human Treg cells produced by the method of any one of embodiments 1-23 or the population of embodiment 28.

30. The method of embodiment 29, wherein the bone marrow failure syndrome is aplastic anemia, primary myelo- fibrosis or myelodysplastic syndrome.

31. A method for treating or preventing primary myelo- fibrosis in a subject, the method comprising administering to the subject an effective amount of the population of activated human Treg cells produced by the method of any one of embodiments 1-27 or the population of embodiment 28, wherein a dose of 100 million Treg cells is administered to the subject on day 1 of a 28-day cycle for up to 6 cycles.

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric.

EXAMPLES

Example 1: Producing an Expanded Population of Activated T-Regulatory Cells from Umbilical Cord Blood A cryopreserved human umbilical cord blood unit (CBU) was obtained from a qualified public United States cord human AB serum. After completing the automated wash, the washed cord blood cells underwent an additional manual wash using working wash media; where the final volume was constituted at 200 ml and the reconstituted cells under- went centrifugation at room temperature at 300 g for 10 minutes. Finally, the washed cells were resuspended in a concentration of a total nucleated cell (TNC) count of $100 \times 10^6$ cells in 0.09 ml.

Subsequently, the CD25 microbeads were added at a ratio of 0.02 ml human CD25 reagent per $100 \times 10^6$ TNCs. The cells and microbeads were incubated together at 4 degree centigrade for 30 minutes. Following the incubation step, the cells were transferred into the Miltenyi LS column attached to a MidiMACS device, which captured the anti-CD25 labeled cells by use of a magnet. After the immunomagnetic selection, the cells were released from the magnetic field.

Approximately $1 \times 10^6$ CD25+ cells were washed and sus- pended in X-VIVO, with 1% L-glutamine, 10% human serum albumin (HSA) and interleukin-2 (IL-2, 1000 IU/mL). The solution was then mixed with anti-CD3/anti- CD28 beads at a bead to cell ratio of 1:1. The mixture was transferred to gas-permeable cultureware with a membrane surface area of 10 cm², 0 and the culture was subsequently transferred to gas-permeable cultureware with a membrane surface area of 100 cm² and incubated for a total of 14 days where the culture medium was replaced every 48 hours without disturbing the cells. After 14 days, the cells were harvested, and the anti-CD3/anti-CD28 beads were removed with a Magnetic Particle Concentrator. The cells were then resuspended in final media.

Cells were sampled at various points in the manufacturing process, and their properties are shown in Table 9.

TABLE 9

|  |  | | |
| --- | --- | --- | --- |
|  | pre-CD25 selection TNC ($\times 10^8$) | median (range) | 14 (10-15.4) |
| Post CD25 |  | n | 5 |
| selection | TNC ($\times 10^6$) | median (range) | 16.5 (9-26) |
|  | % CD4+CD25+ | median (range) | 44 (35-70) |
|  | Absolute CD4+CD25+ ($\times 10^6$) | median (range) | 7.5 (3-8) |
| Post- | TNC ($\times 10^6$) | median (range) | 2106 (1481-3307) |
| Expansion | Viability (%) | median (range) | 93 (91-98) |
|  | % CD4+ CD25+ | median (range) | 77.4 (70-86) |
|  | Absolute CD4+CD25+ ($\times 10^6$) | median (range) | 1790 (1262-2559) |
|  | Fold expansion | median (range) | 289 (194-596) |

TNC = total nucleated cells blood bank. The CBU was rapidly thawed. The thawed cord blood unit was subjected to automated wash using a Sepax device (Biosafe), with a starting volume set at 25 ml; the final volume set at 100 ml and a dilution factor of 1.0. The washing reagent used was 5% human serum albumin (HSA) (CSL Behring) and 10% dextran-40 (D-40) (Hospira). Post- wash, the cord blood cells were collected into cord blood wash bag.

For the purpose of washing, the basic wash media was 20 ml of 25% HSA to 1000 ml PBS/EDTA buffer; and the working wash media was 300 ml of basic wash buffer and 50 mg of Magnesium chloride (MgCl₂) and 2500 Units of DNase; and then a modified media was X-Vivo 15 media (Lonza) and 10 ml of GlutaMAX-1 and 100 ml of thawed As shown in FIG. 1, the expanded activated Treg cells produced by the method described above were stable when stored at room temperature (15-30° C.) or at 4° C. FIG. 1 shows results of a flow cytometry based assay where 7-ami- noactinomycin D (7AAD), a fluorescent intercalator that undergoes a spectral shift upon association with DNA, is used to evaluate live cells, as 7AAD appears to be generally excluded from live cells. Cells are incubated on ice in the presence of 1 microliter 7AAD stock solution for 30 min- utes. As soon as possible after the incubation period, the stained cells are analyzed by flow cytometry, using violet and 488 nm excitation and measuring the fluorescence emission using 440 nm and 670 nm bandpass filters (or their near equivalents). The live cells show only a low level of fluorescence.

The phenotype of the expanded activated Treg cells was measured by flow cytometry at initiation of the cell culture (day 0), as well as 8 days and 14 days after initiation of the cell culture. Results are shown in Table 10.

TABLE 10

| Marker | Day 0 Percentage median (range) | Day 8 Percentage median (range) | Day 14 Percentage median (range) |
|---|---|---|---|
| CD95 | 69.5 (54-95) | 98.8 (98-100) | 98.5 (90-100) |
| CXCR4 | 68.7 (60-80) | N/A | 97.8 (90-100) |
| PD1 | 9.2 (5-15) | N/A | 11.0 (5-20) |
| PDL1 | 2.9 (0-10) | N/A | 2.8 (0-10) |
| HLA ABC | 98.9 (90-100) | 99.8 (90-100) | 99.3 (90-100) |
| HL ADR | 6.2 (5-10) | 6.1 (5-10) | 97.2 (90-100) |
| CD31$^{hi}$ | 58.8 (60-80) | 31.6 (20-50) | 56.6 (15-60) |
| alpha4beta7 | 64.5 (50-100) | 96.6 (80-100) | 97.0 (90-100) |
| CXCR3$^{hi}$ | 2.8 (0-10) | 45.2 (30-60) | 20.2 (15-30) |
| CCR3 | 1 (0-5) | 0.5 (0-5) | 0.2 (0-5) |
| CCR6 | 66.6 (60-100) | 12.1 (0-20) | 99.3 (60-100) |
| CD54 | 46.5 (30-60) | 97.4 (80-100) | 97.3 (80-100) |
| CD11A | 71.3 (60-100) | 99.1 (80-100) | 97.9 (90-100) |
| CD45RA | 88.4 (80-100) | 88.9 (80-100) | 96.5 (80-100) |
| CD45RO | 10.8 (0-50) | 92.5 (80-100) | 85.6 (80-100) |
| CD45RARO | 67.6 (40-80) | 68.0 (50-90) | 86.7 (70-90) |
| CD39$^{HI}$ | 10.7 (0-20) | 18.5 (5-30) | 10.3 (0-20) |
| CD7 | 97.2 (90-100) | 98.6 (90-100) | 95.6 (90-100) |
| CD137 | 1.2 (0-5) | 2.0 (0-5) | 1.3 (0-10) |
| HELIOS | 92.1 (70-100) | 96.1 (80-100) | 93.2 (80-100) |
| GITR | 98.3 (80-100) | 93.7 (80-100) | 99.3 (80-100) |
| RORgT | 0.35 (0-5) | 0.7 (0-5) | 0.56 (0-5) |
| Tbet | 0.77 (0-5) | 1.0 (0-5) | 0.325 (0-5) |
| CTLA4 (CD152) | 49.6 (30-70) | N/A | 83.6 (70-100) |
| CCR7 | 98.8 (80-100) | N/A | 99.65 (80-100) |
| GPR83 | 14.85 (0-20) | N/A | 83.55 (70-100) |
| CD62L | 12.7 (0-20) | N/A | 82.5 (70-100) |
| CD28 | 84.4 (70-100) | 94.6 (70-100) | 84.9 (70-100) |

N/A = not done

Figure 2A:
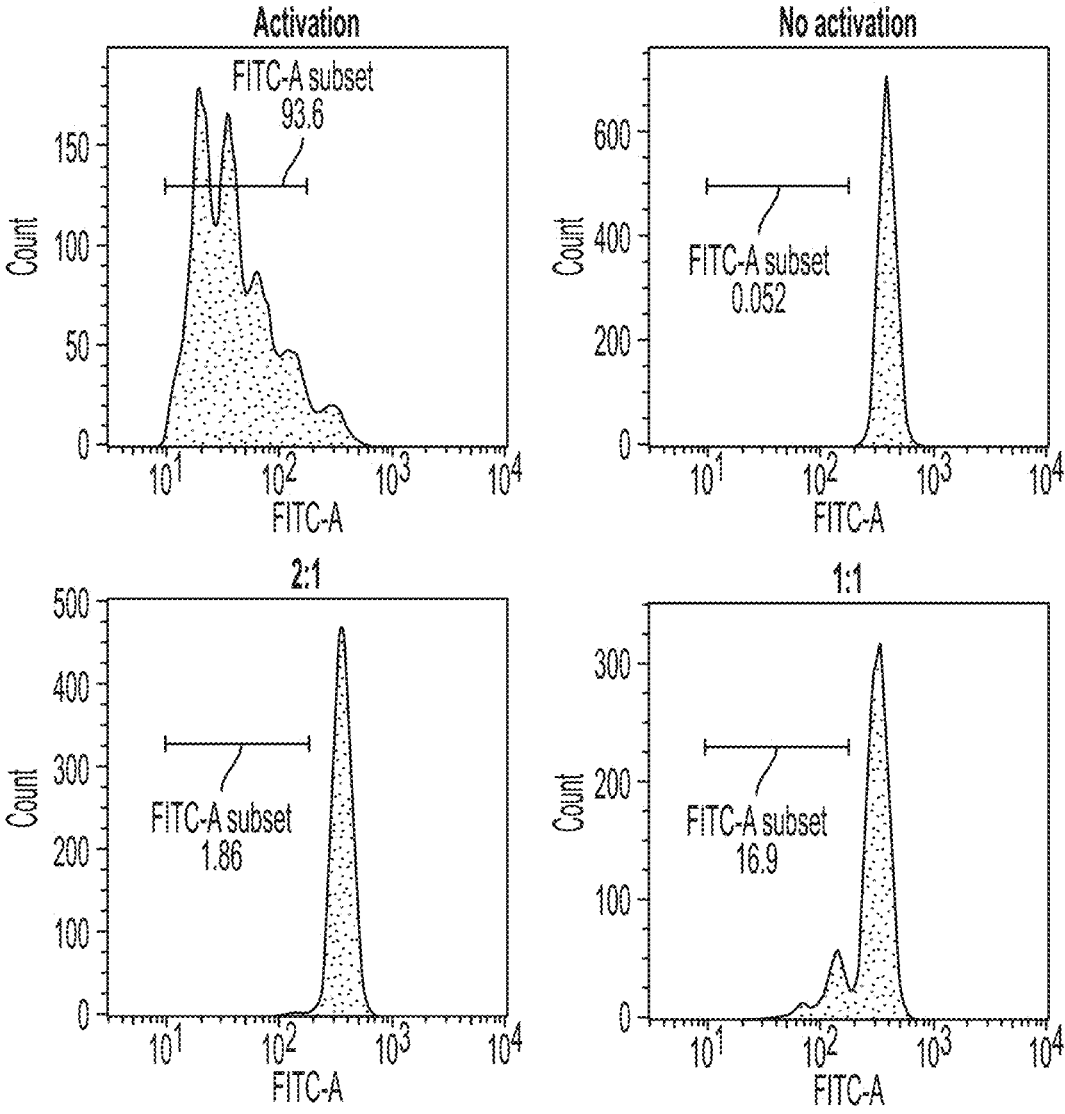
FIG. 2A-FIG. 2B depict a series of graphs showing that expanded activated Treg cells are immunosuppressive. For the suppression assay, conventional T cells (Tcon) (CD4$^+$ CD25$^-$) cells were thawed and stained with CellTrace™ Violet (ThermoFisher) following manufacturer instructions. Cord blood Tregs and Tcons were placed into various ratios in the presence of continued activation by CD3/CD28 beads and analyzed after 3 days using flow cytometry.
Figure 2B:
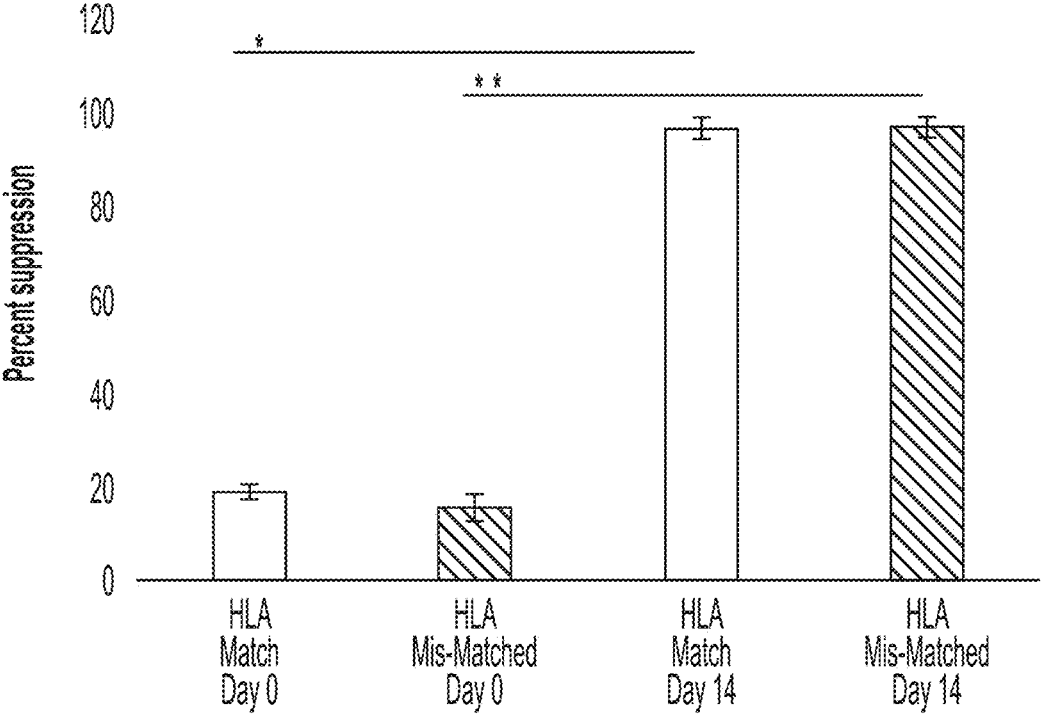
Figure 3:
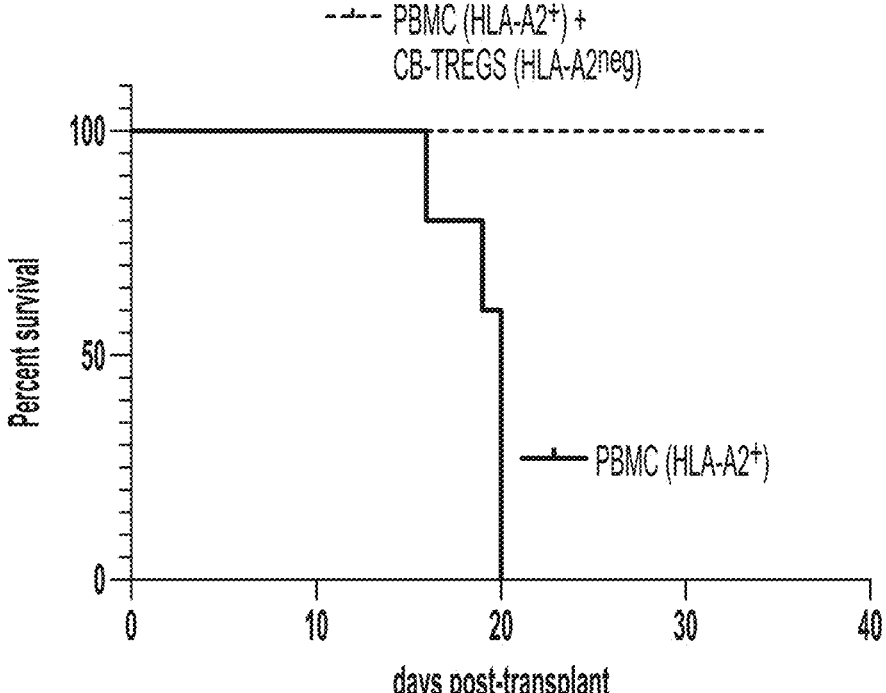
FIG. 3 is a line graph showing that activated Treg cells can be immunosuppressive across the HLA barrier. Using a xenogeneic graft vs. host disease (GVHD) model (Parmar et al., *Cytotherapy* 16 (10:90-100 (2013)), non-SCID gamma null (NSG) mice were sublethally irradiated, followed by injection of peripheral blood mononuclear cells (PBMC) derived from an HLA A2 positive donor, at a dose of 1×10$^7$ cells to induce GVHD. In the treatment arm, cord blood Tregs derived from an HLA A2 negative donor were injected at a dose of 1×10$^6$ cells at one day prior to the PBMC injection. Mice were followed for survival. Even at a one log lesser dose, the CB Tregs were able to rescue the detrimental effect of GVHD and resulted in a statistically significant superior survival (log rank; p=0.003) at day 40 when compared to the PBMC only arm.
Figure 4C:
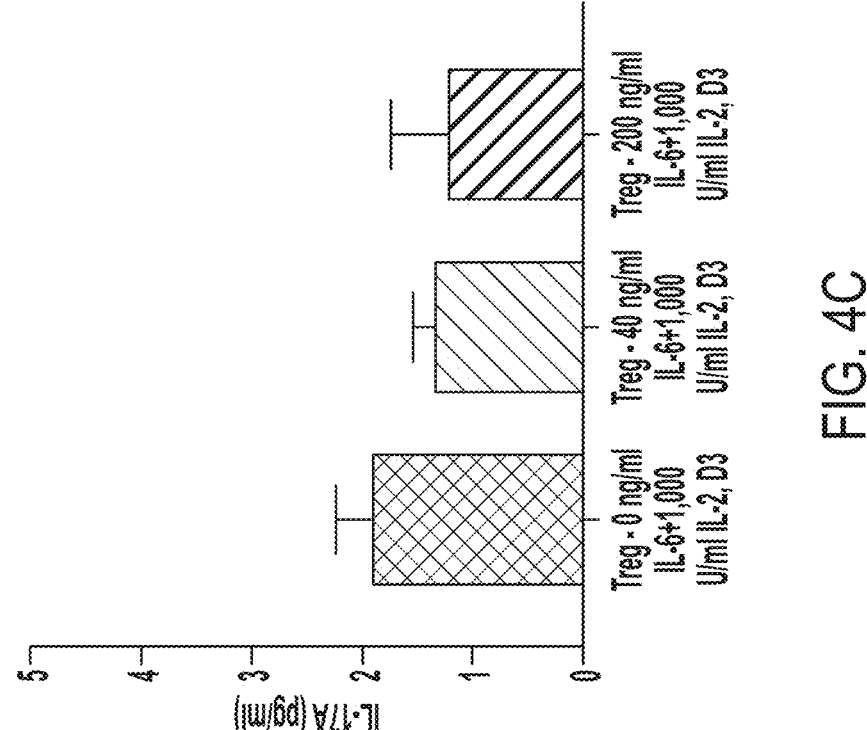
Figure 4D:
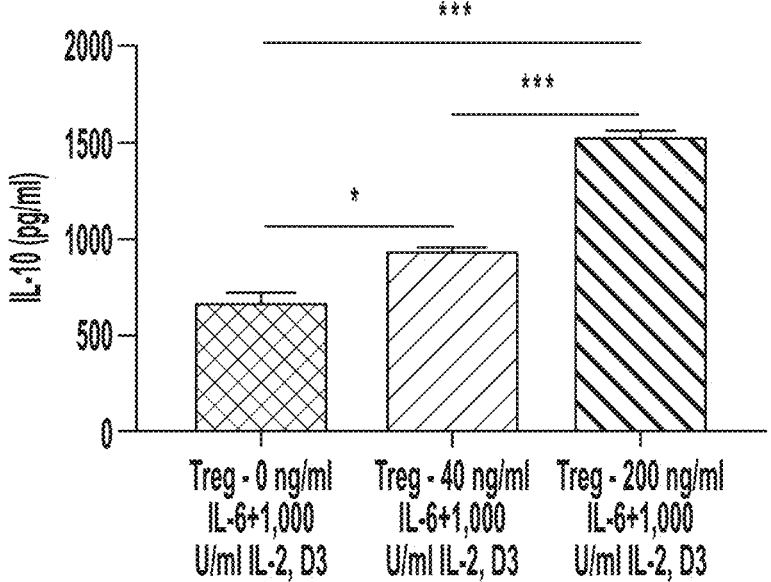
Figure 6:
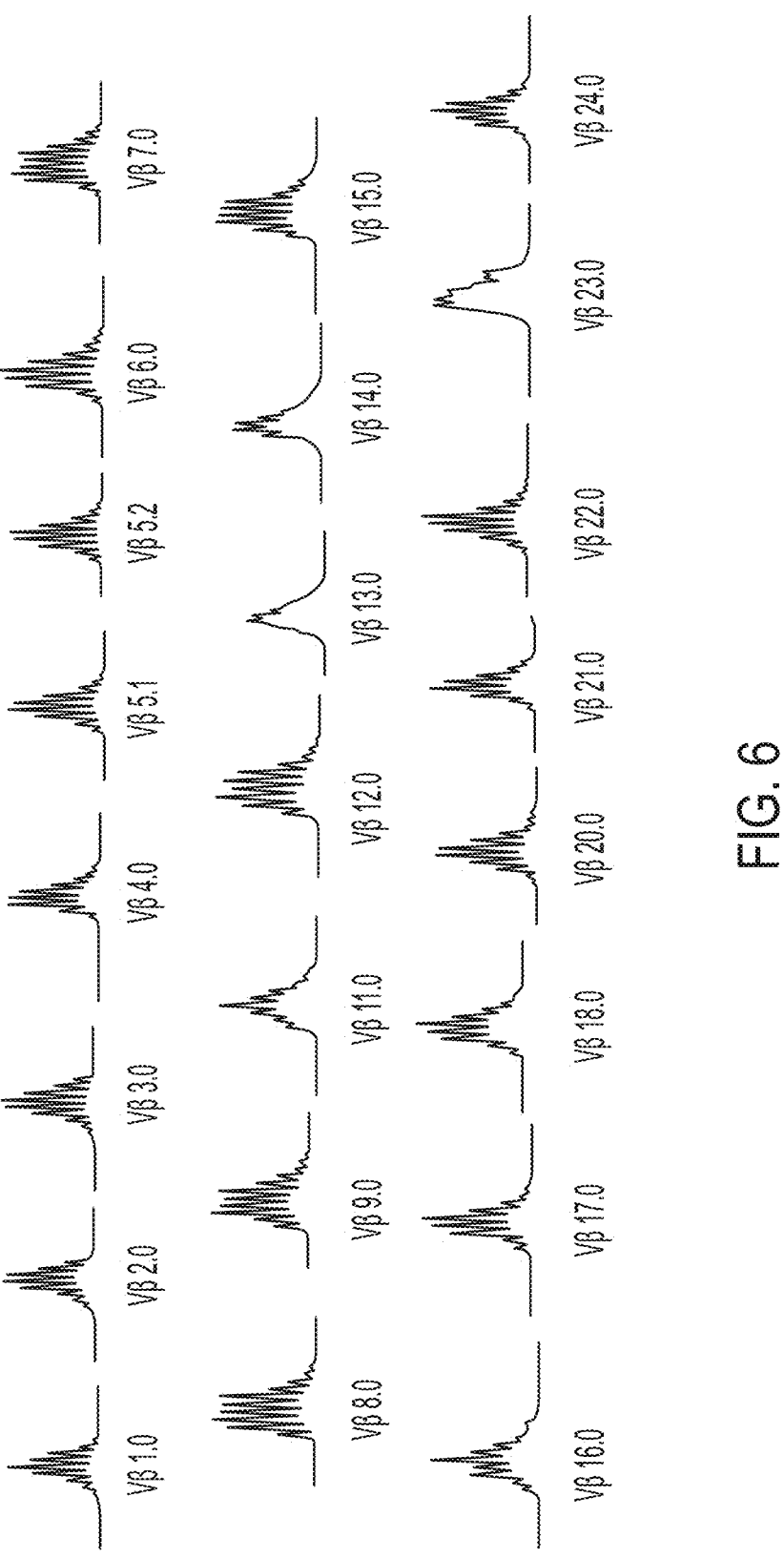
FIG. 6 is a series of graphs showing that expanded cord blood Tregs show a Gaussian (polyclonal) distribution of the T cell receptor Vβ repertoire. Total RNA was extracted from the Treg using a commercial kit (Tel-Test, Friendswood, TX), and cDNA was prepared using reverse transcription (Applied Biosystems, Foster City, CA). The CDR3 regions were then amplified for 23 TCR Vβ subsets by polymerase chain reaction (PCR). The resulting PCR products were subjected to capillary electrophoresis and quantitative densitometry to assess the diversity of fragment length within each of the TCR Vβ families.
Figure 25:
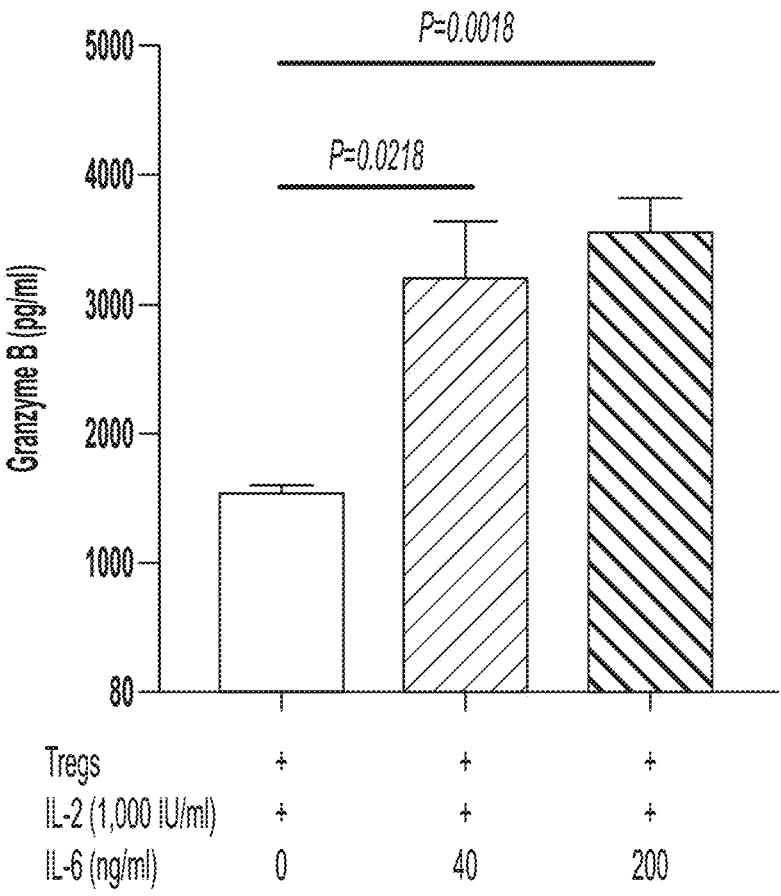
FIG. 25 depicts secretion of the cytokine Granzyme B by activated Treg cells isolated from umbilical cord blood when the cells are exposed to IL-6.

The expanded activated Treg cells are suppressive, demonstrating 70-96% suppression, as shown in FIG. 2A and FIG. 2B. As shown in FIG. 4A-FIG. 4D, expanded activated Treg cells do not express RORγt and show reciprocal increase in IL-10 expression in response to stress. FIG. 4A shows that IL-6 has no impact on suppressive activity of Treg cells. FIG. 4B shows that IL-6 has no impact on RORγ expression by Treg cells. FIG. 4C shows that IL-6 has no impact on IL-17A production by Treg cells. FIG. 4D shows that IL-6 induces increased IL-10 production by Treg cells. FIG. 25 shows that IL-6 induces Granzyme B production by Treg cells. Furthermore, expanded activated Treg cells can be immunosuppressive across the HLA barrier (FIG. 3). Expanded activated Tregs show a Gaussian (polyclonal) distribution of the T cell receptor Vβ repertoire (FIG. 6).

Figure 7B:
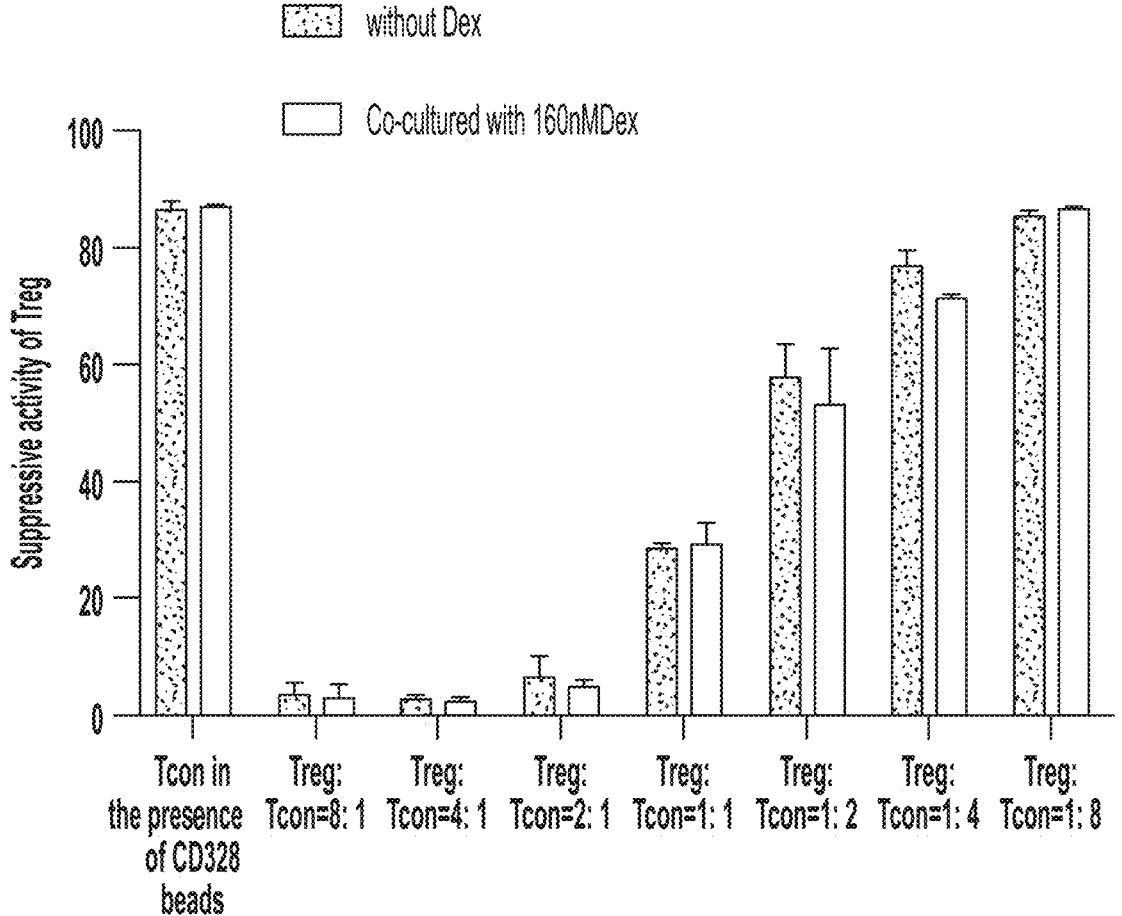

The expanded activated Treg cells remain suppressive in the presence of steroids. FIG. 7A and FIG. 7B show that the Treg cells remain suppressive in the presence of dexamethasone. The effects of prednisone on viability of Treg and Tcon cells are shown below.

TABLE 11

| | Alive (no prednisone) | Alive (with prednisone 100 μg/ml for 72 hrs) |
|---|---|---|
| Treg | 95% | 90.3% |
| Tcon | 82% | 64.7% |

Treg cells remain suppressive in the presence of prednisone, as shown below.

TABLE 12

| Treg:Tcon | Suppressive capacity (without prednisone) | Treg:Tcon Suppressive capacity (100 μg/ml prednisone) |
|---|---|---|
| 2:1 | 98.13% | 97.41% |
| 1:1 | 95.6% | 94.12% |
| 1:2 | 84.94% | 79.9% |

Example 2: Cryopreservation of an Expanded Population of Activated T-Regulatory Cells from Umbilical Cord Blood Expanded activated Treg cells produced by the method described in Example 1 were cryopreserved as follows.

A total of $50 \times 10^6$ cells were cryopreserved per 5 ml vial at a concentration of $10 \times 10^6$ cells per ml. The harvested expanded population of activated human Treg cells were centrifuged at 400 g for 10 minutes at a temperature of 4° C. The total cell number was calculated using the automated cell counter, and the number of cryovials were estimated by dividing the total cell number by $50 \times 10^6$ cells. Subsequently, up to $50 \times 10^6$ cells were cryopreserved per 5 ml cryovial using the freezing stock solution where the freezing stock solution consists of a pre-formulated solution with 10% dimethyl sulfoxide (DMSO) (CryoStor'). While the cells were undergoing centrifugation, the controlled rate freezer was turned on and once the controlled rate freezer reached the appropriate start temperature, then a command appeared "Program Waiting for User-click here to continue". Once admixed with the freezing stock solution, the cryovials containing up to $50 \times 10^6$ cells each were placed in the controlled rate freezer using the freezing algorithm to allow for paced freezing of the cells to avoid cell death and preserving the cell function. After the freeze program was complete, the cryovials were removed from the controlled rate freezer and placed in the liquid nitrogen cryogenic freezer at a temperature of −190° C. for long term cryopreservation.

Figures 8A, 8B:
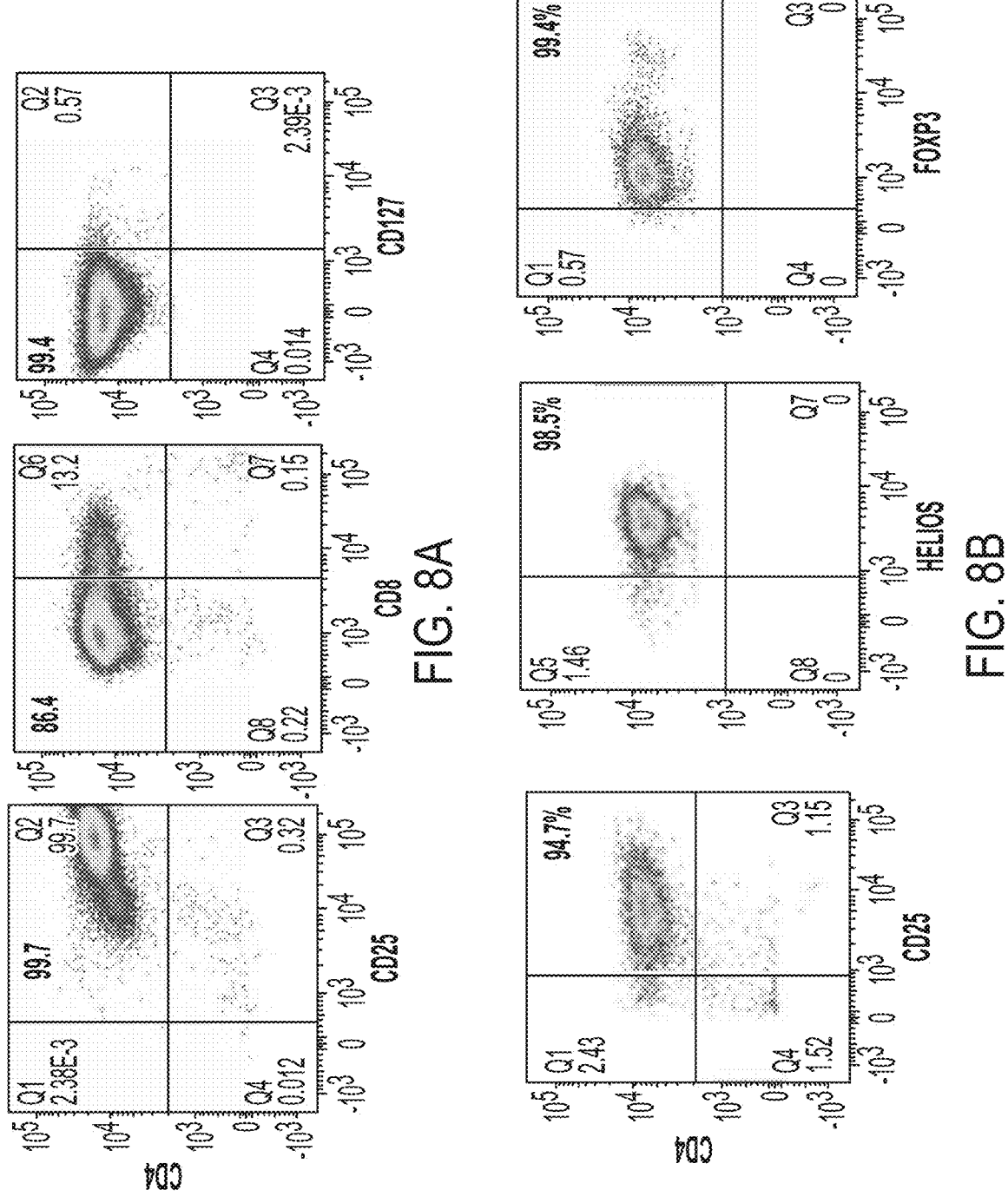
FIG. 8A-FIG. 8C show that cryopreserved activated Treg cells show consistent phenotype and are capable of immunosuppression similar to fresh activated Treg cells.
Figure 8C:
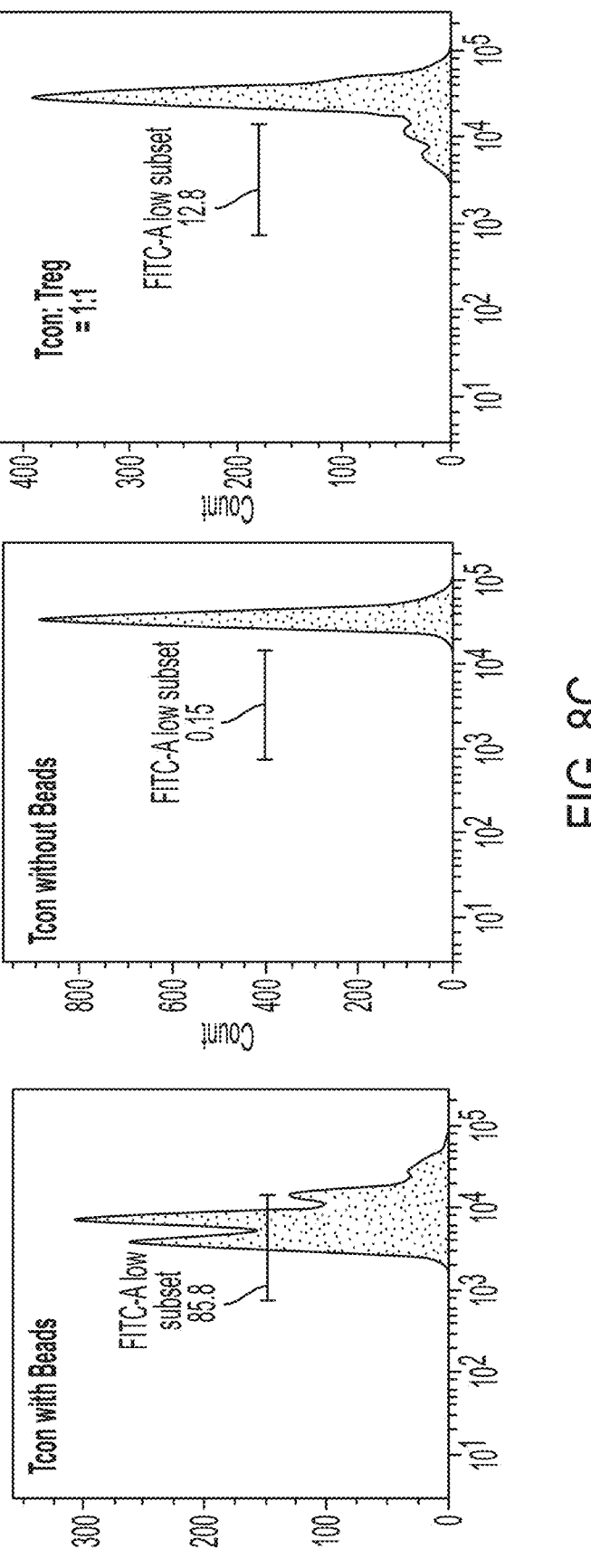
Figure 9B:
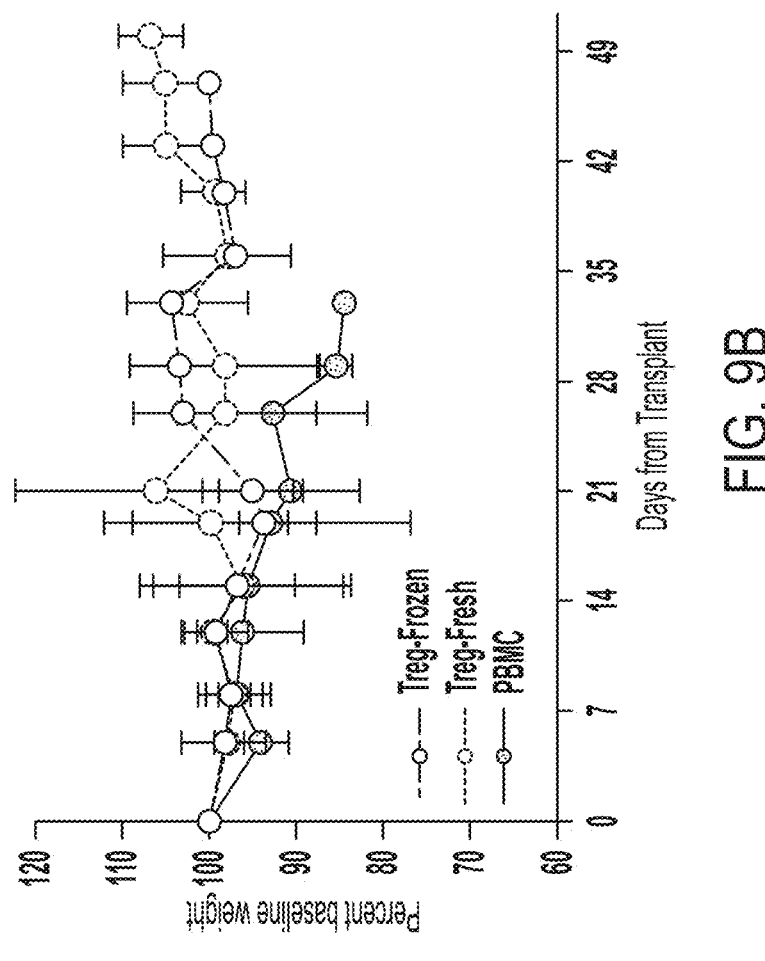
FIG. 9A-FIG. 9B show the results of studies using a xenogeneic mouse graft versus host disease (GVHD) model. Using a xenogeneic graft vs. host disease (GVHD) model (Parmar et al., Cytotherapy 16(10:90-100 (2013)), fresh activated Treg cells or cryopreserved (frozen) activated Treg cells were administered at a dose of 1×10$^7$ cells one day prior to the donor peripheral blood mononuclear cells at a dose of 1×10$^7$ cells on GVHD prevention.
Figure 9A:
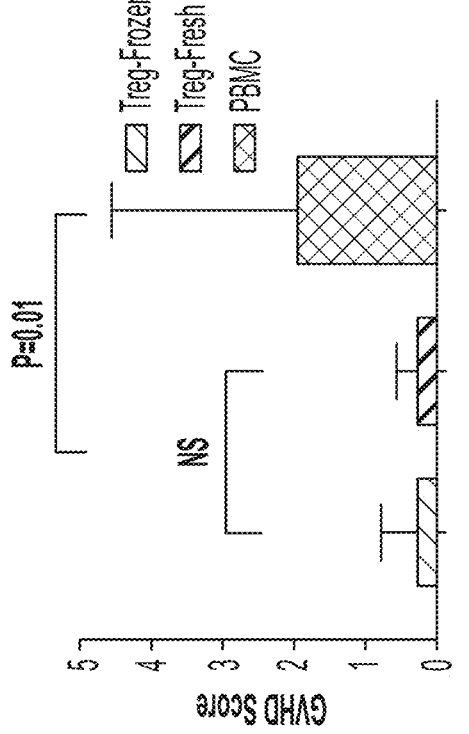

Cryopreserved activated Treg cells show consistent phenotype and are capable of immunosuppression similar to fresh activated Treg cells (FIG. 8A-FIG. 8C). Cryopreserved activated Treg cells show high expression of Helios (FIG. 8B) and suppression of proliferating conventional T cells (FIG. 8C). As further described in Example 3, cryopreserved and fresh expanded activated Treg cells are comparable in preventing or treating graft versus host disease.

Example 3: Prevention and Treatment of Graft Versus Host Disease with Cord Blood-Derived T-Regulatory Cells A xenogeneic mouse model of graft versus host disease (GVHD) was used to assess function of umbilical cord blood-derived T-regulatory cells produced by the methods described in Examples 1 and 2. The model of GVHD is described in Parmar et al., Cytotherapy 16 (10:90-100 (2013)). To study the effect of Tregs on prevention of GVHD, NOD/SCID IL-2Rγnull (NSG) mice (Jackson Laboratory, Bar Harbor, ME) received sublethal whole body irradiation (300 cGy from a 137Cs source delivered over 1 minute by a J. L. Shepherd and Associates Mark 1-25 Irradiator, San Fernando, CA) 1 day prior to injection with $1 \times 10^7$ Treg cells and 2 days prior to intravenous infusion of $1\times10^7$ human PBMCs. Mice were evaluated using a clinical GVHD scoring system. (See Reddy et al., Transplantation 69(4):691-93 (2000)). Treatment with fresh cord blood-derived Tregs and cryopreserved Tregs produced comparable GVHD scores (FIG. 9A) and effect on weight (FIG. 9B).

Figures 10A, 10B:
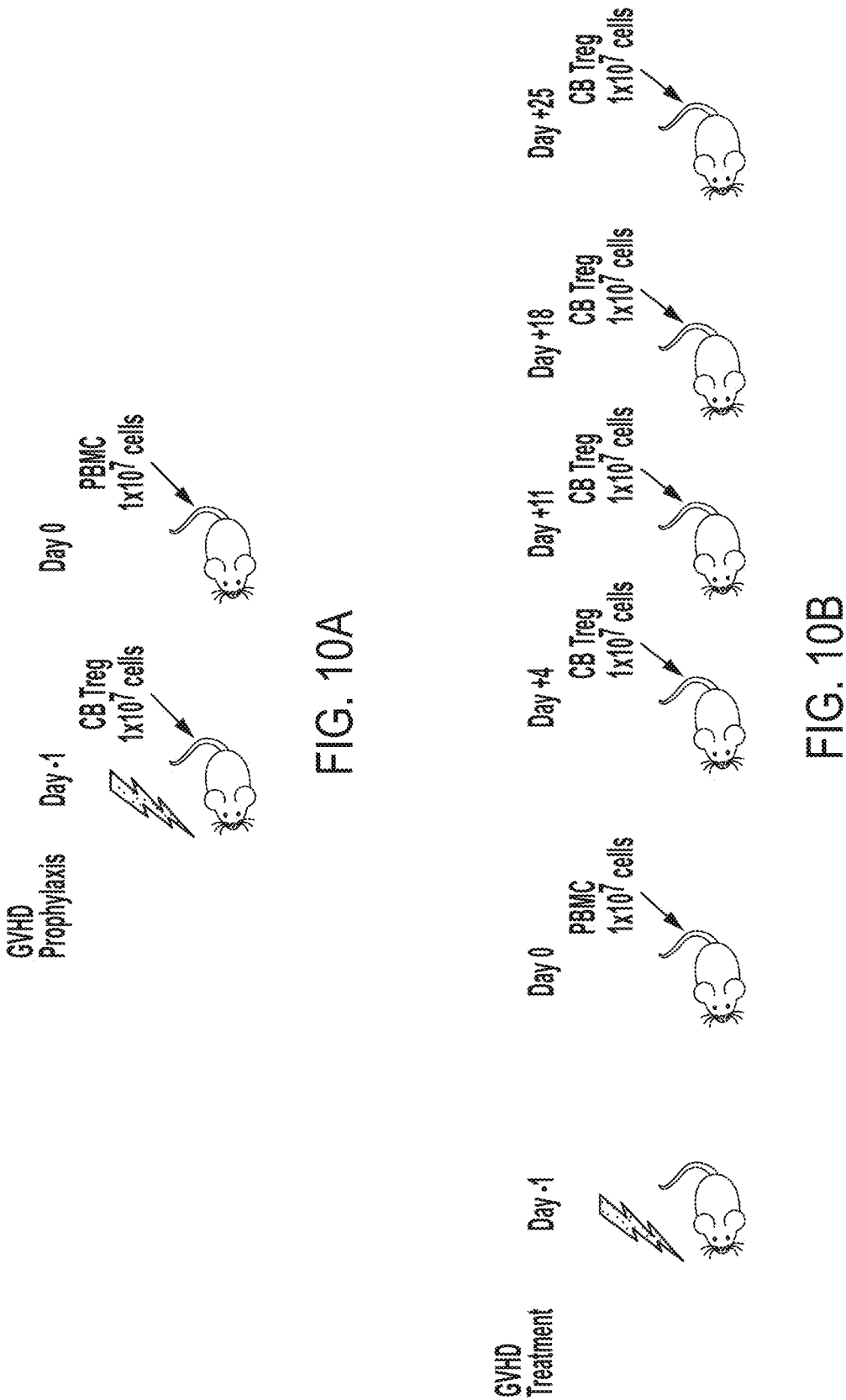
FIG. 10A-FIG. 10B show the design of studies using a xenogeneic mouse graft versus host disease (GVHD) model.
Figure 11A:
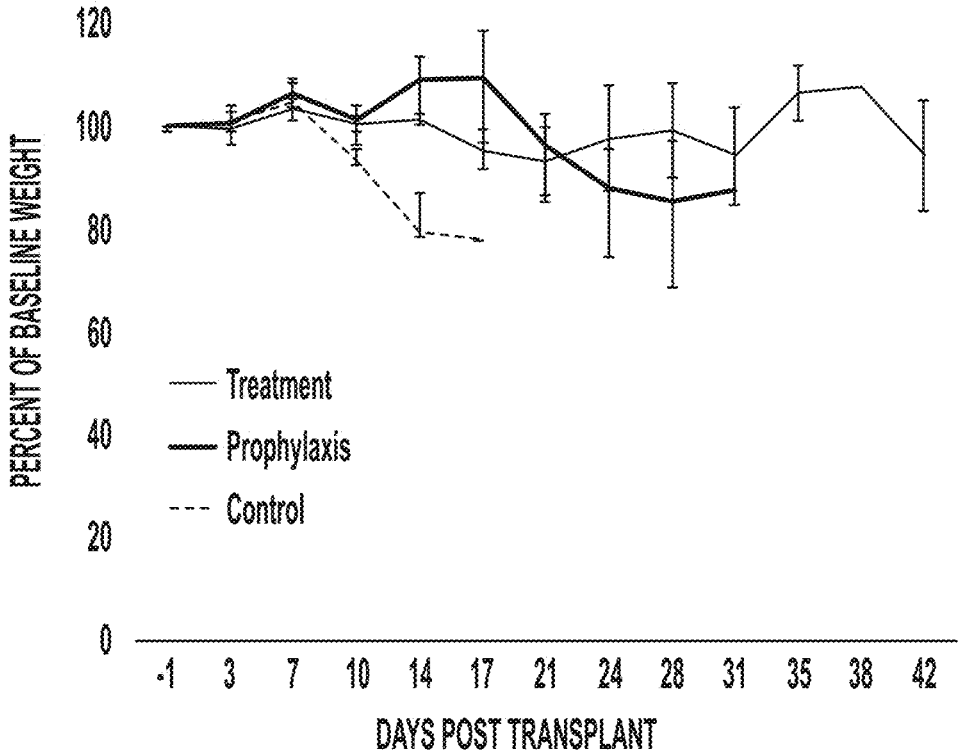
FIG. 11A-FIG. 11B depict the effects of administration of cryopreserved activated Tregs on weight fluctuation (FIG. 11A) and survival (FIG. 11B) in a xenogeneic mouse graft versus host disease (GVHD) model. "Prophylaxis" refers to the study design depicted in FIG. 10A. "Treatment" refers to the study design depicted in FIG. 10B. "Control" refers to a negative control with no Treg cells being administered.
Figure 11B:
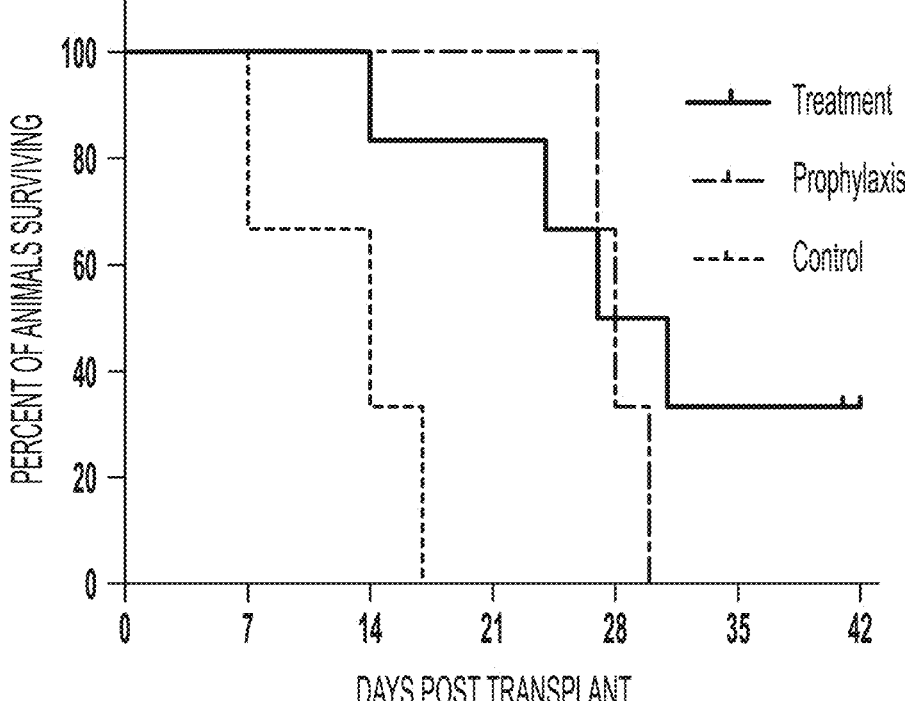
Figures 12A, 12B, 12C, 12D, 12E, 12F:
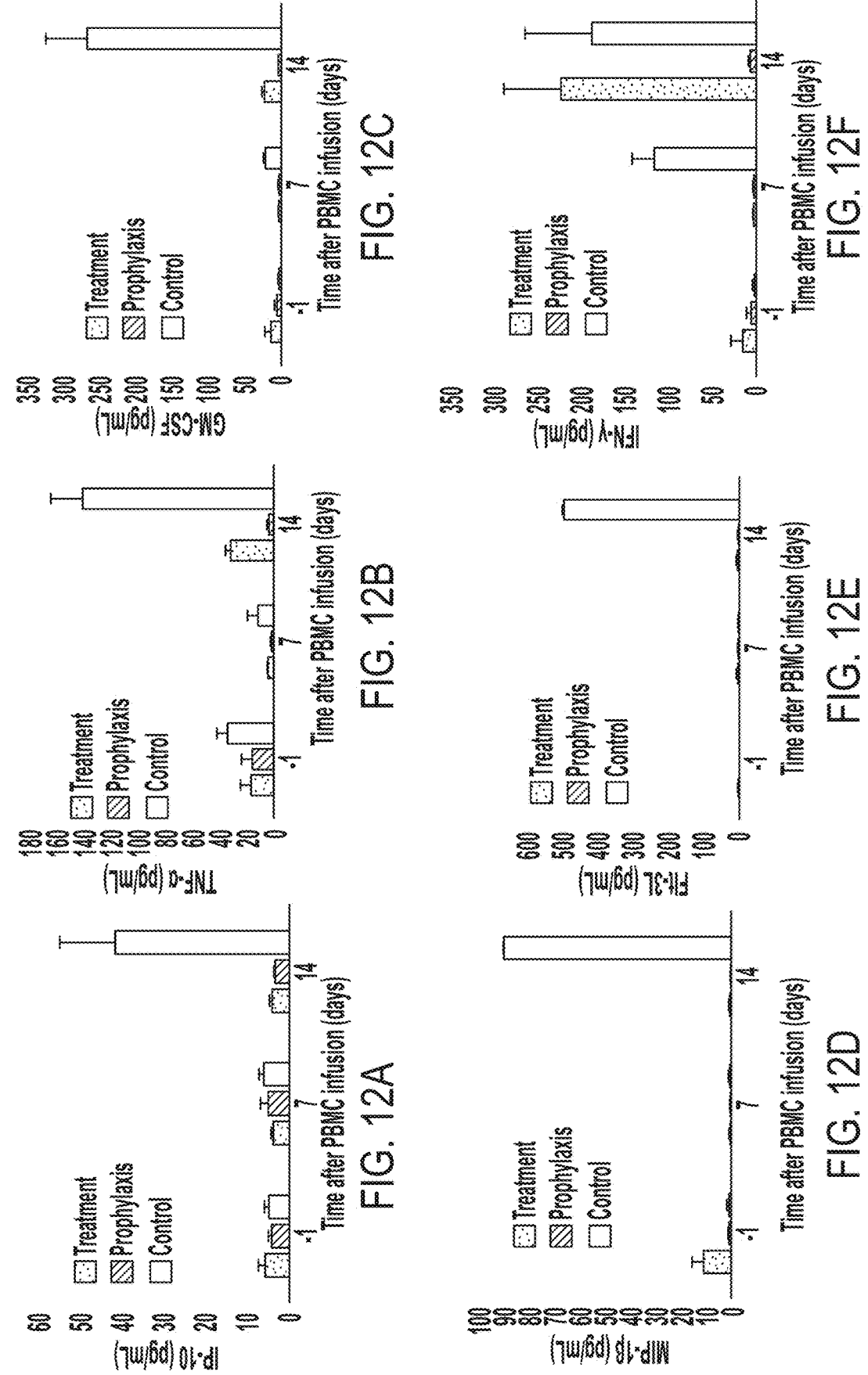
FIG. 12A-FIG. 12F show the results of peripheral blood cytokine analysis at day Baseline, Day +7 and Day +14 post-PBMC infusion in a xenogeneic mouse graft versus host disease (GVHD) model of the Control, Prophylaxis and Treatment arm.
Figure 13:
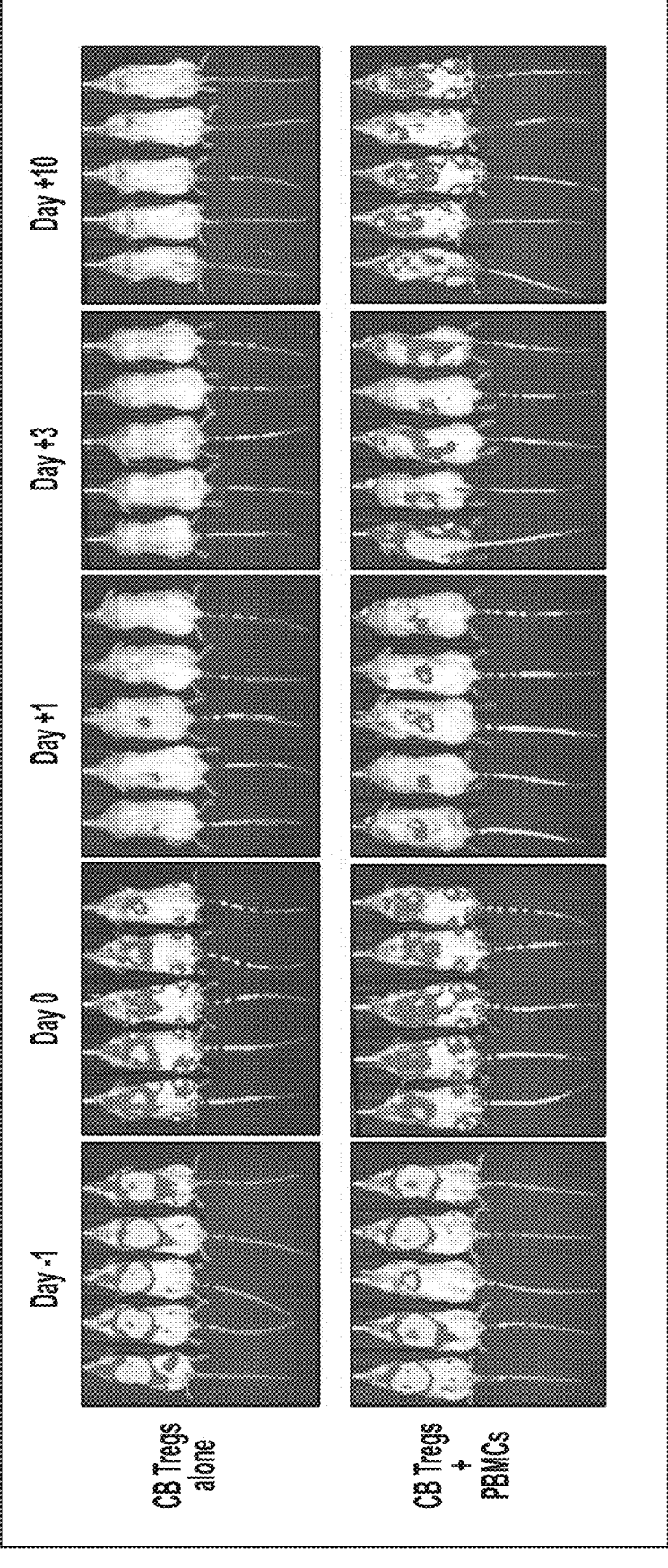
FIG. 13 depicts images of mice treated with activated Tregs (cord blood (CB) Tregs alone) or activated Tregs and PBMCs (CB Tregs+PBMCs). Bioluminescence scanning after infusion of firefly luciferase-labeled CB Tregs showed that by Day +1 after their injection, CB Tregs were detected in lungs, liver, and spleen of all mice, regardless of the injection of PBMC. By Day +3, CB Tregs could no longer be detected in mice without the continued presence of PBMCs (CB Tregs alone) but continued to be detected in the PBMC recipient mice (CB Tregs+PBMC). In mice with proliferating PBMCs, the scans suggest persistence and even proliferation in GVHD target organs.
Figure 14:
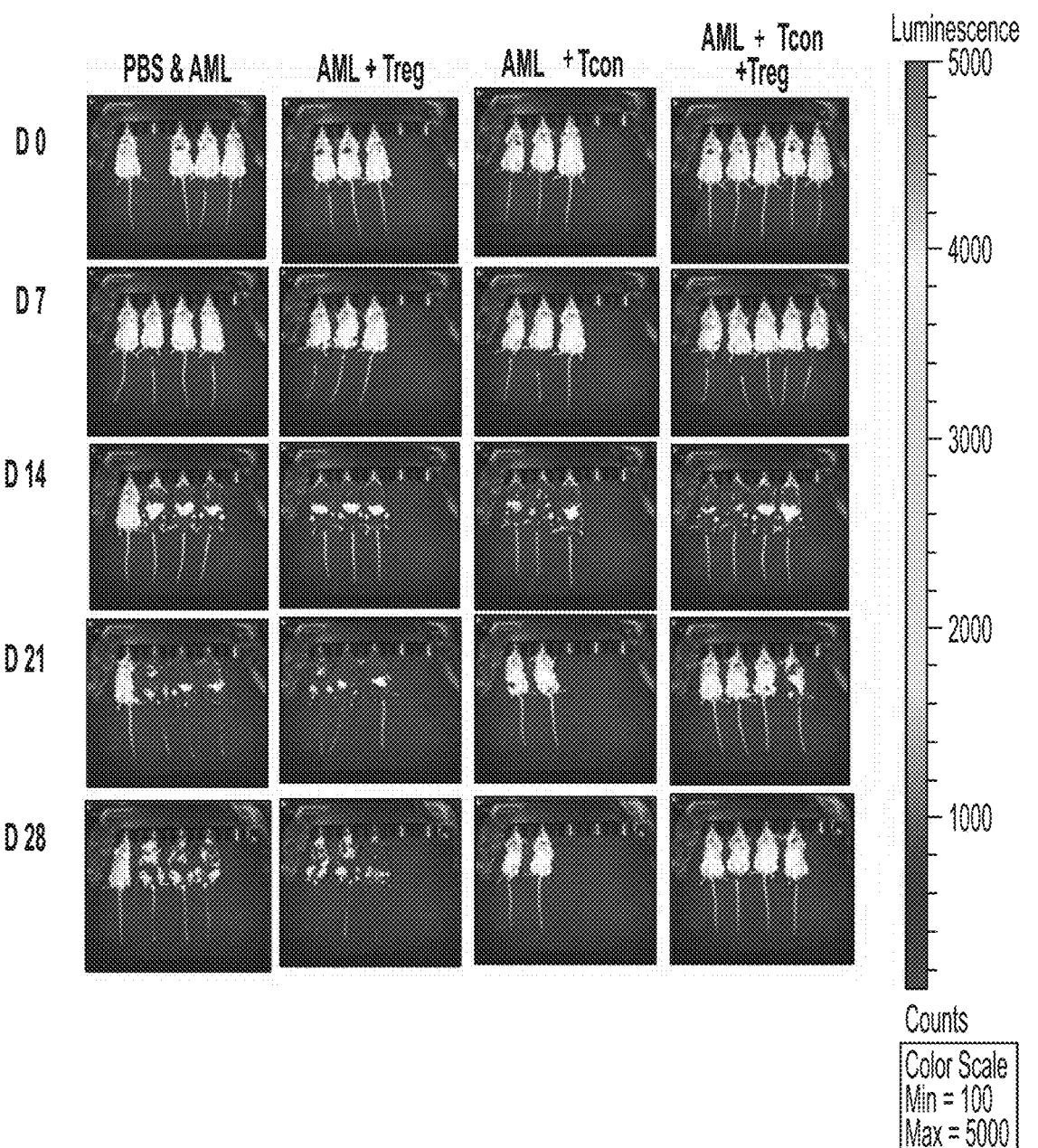
FIG. 14 depicts images of mice treated with activated Tregs. GFP-labeled HL-60 acute myeloid leukemia (AML) cell line was injected at a dose of $3\times10^6$ cells into NSG mouse in all 4 arms: 1) Control mice (PBS & AML): received HL60+PBS; 2) Treg mice (AML+Treg): received HL60+Tregs ($1\times10^7$ cells); 3) Tcon mice (AML+Tcon): received HL60+Tcons ($1\times10^7$ cells); 4) Tcon+Treg mice (AML+Tcon+Treg): received HL60+Tcons ($1\times10^7$ cells)+ Tregs ($1\times10^7$ cells). Mice were imaged at weekly intervals to understand the impact of the injected Tcon and Tregs on the tumor volume load. Mice succumbed to the tumor in the control (PBS treated) and the CB Treg alone treated mice. Recipients of Tcon were able to eliminate the tumor but died of GVHD. Recipients of Tcons and Tregs were able to have prolonged survival with tumor control and absence of GVHD.

Administration of cryopreserved Tregs both prevented and treated GVHD in the xenogeneic mouse model. FIG. 10A depicts the study design for monitoring the effect of a single Treg infusion on GVHD prevention. FIG. 10B depicts the study design for monitoring the effect of multiple Treg infusions on GVHD treatment. As shown in FIG. 11A-FIG. 11B, administration of activated Tregs can both prevent and treat GVHD. Administration of activated Tregs suppresses the levels of inflammatory cytokines in peripheral blood at day 14 post-PBMC infusion (FIG. 12A-FIG. 12F). Activated Tregs distribute to the sites of inflammation in treated mice (FIG. 13). Moreover, activated Tregs do not interfere in the conventional T cell-mediated anti-leukemia effect (FIG. 14).

Example 4: Treatment of Systemic Lupus Erythematosus with Cryopreserved Cord Blood-Derived T-Regulatory Cells A xenogeneic mouse model of systemic lupus erythematosus (SLE) (Andrade et al., Arthritis Rheum. 2011 September; 63(9): 2764-2773) was utilized where the peripheral blood mononuclear cells from systemic lupus erythematosus were engrafted into Non-SCID gamma null (NSG) mice. Female $Rag2^{-/-}\gamma c^{-/-}$ mice transplanted with $3\times10^6$ human SLE-peripheral blood mononuclear cells (PBMCs) by intravenous injection on day 0. The mice were allowed to develop disease and on day 30 post-transplant, they were divided into 2 groups: i) control and ii) treatment. $1\times10^7$ ex vivo-expanded, cryopreserved, allogeneic, non-HLA matched CB Tregs were injected into SLE xenografts intravenously once per week for 4 weeks through the tail vein. Serial blood draws were performed for the phenotypic analysis, cytokine assay and anti-double stranded (ds)DNA IgG antibody analysis. Serial examination of the urine samples was performed for creatinine and albumin quantification. Histopathologic examination of the harvested organs was performed at the time of planned euthanasia at 13 weeks.

Figure 15:
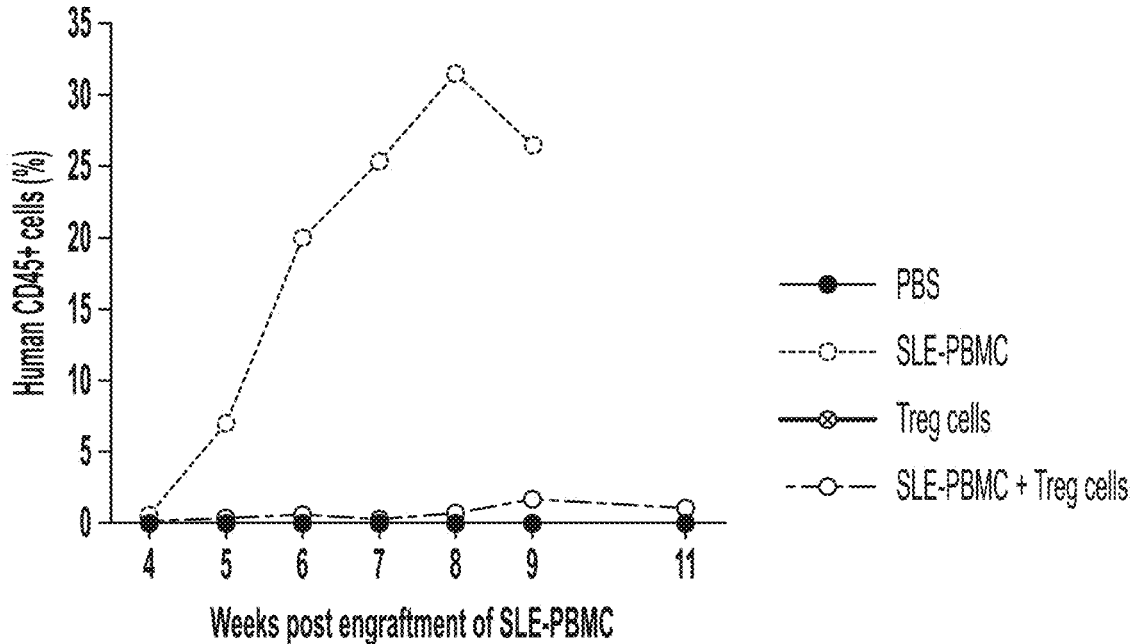
FIG. 15 depicts a line graph showing that a single injection of activated Treg cells decreased the levels of CD45+ effector T cells for 9 weeks post engraftment of SLE-PBMCs in a xenogeneic mouse model of systemic lupus erythematosus (SLE) where the SLE-PBMCs ($3\times10^6$ cells) are injected in NSG mice and CB Tregs ($1\times10^7$ cells) are injected 1 week after the SLE-PBMC injection. "PBMC" refers to peripheral blood mononuclear cells.
Figure 16B:
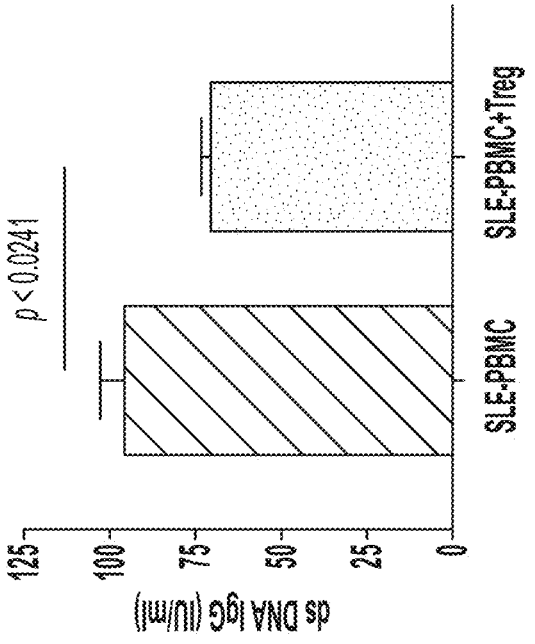
FIG. 16B depicts a bar graph showing that four weekly injections of activated Treg cells decreased the levels of anti-double-stranded DNA antibody (ds DNA Ig) in a xenogeneic mouse model of systemic lupus erythematosus (SLE).
Figure 16A:
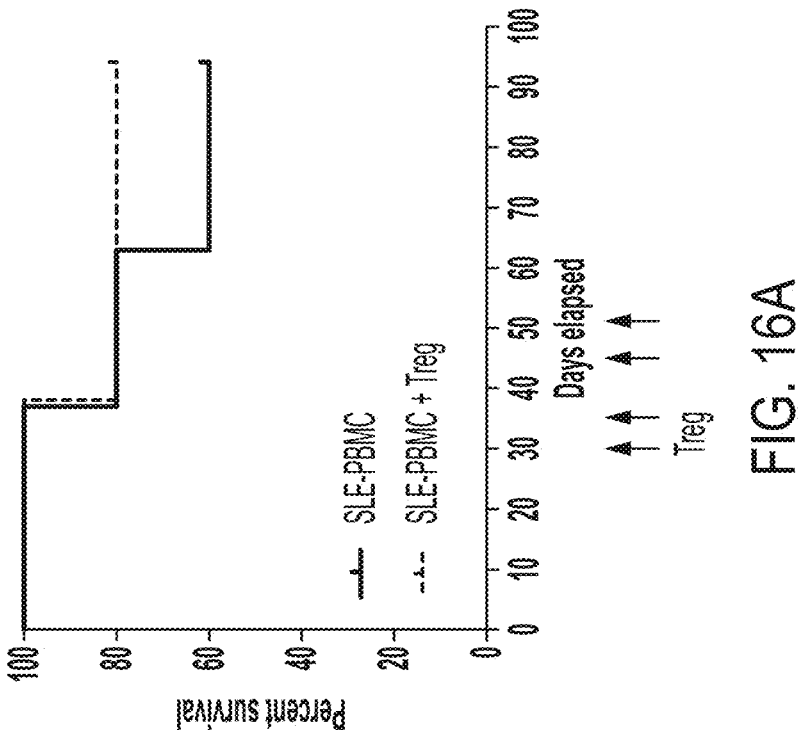
FIG. 16A depicts a graph showing that four weekly injections of activated Treg cells ($1\times10^7$ cells) starting at 4 weeks after the injection of SLE-PBMC ($3\times10^6$ cells) improved survival in a xenogeneic mouse model of systemic lupus erythematosus (SLE).
Figure 17B:
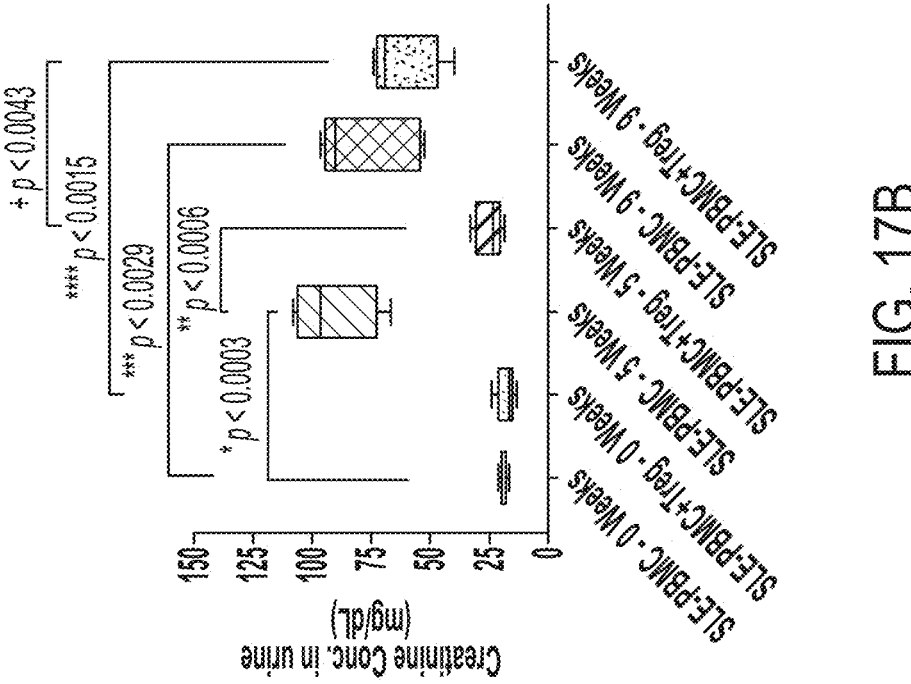
FIG. 17A-FIG. 17B depict plots showing that four weekly injections of activated Treg cells decreased the level of urine albumin (FIG. 17A) and decreased urine creatinine leakage (FIG. 17B) in a xenogeneic mouse model of systemic lupus erythematosus (SLE).
Figure 17A:
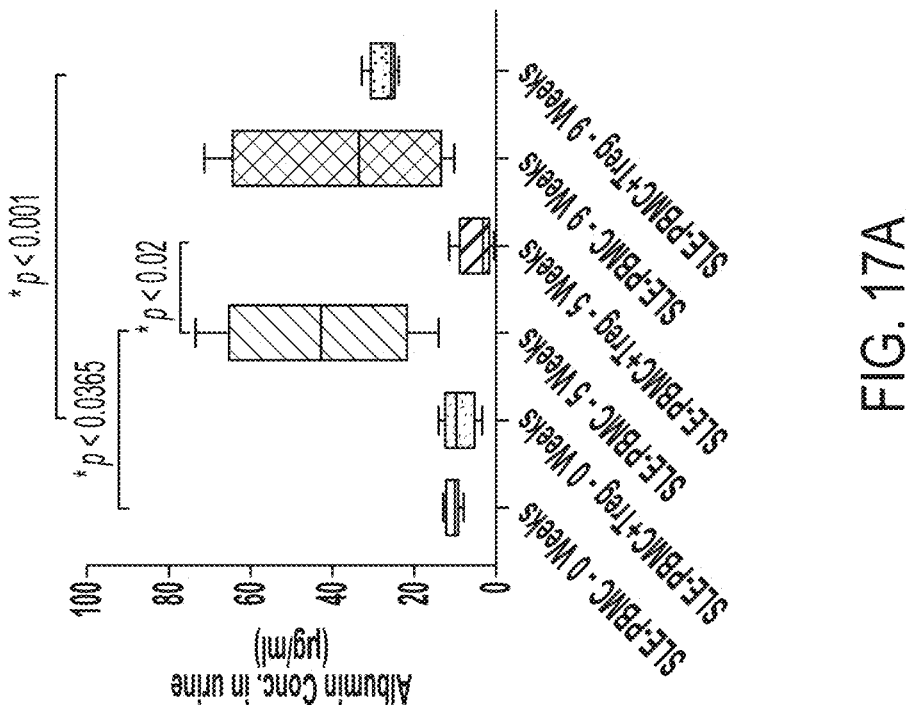
Figure 18:
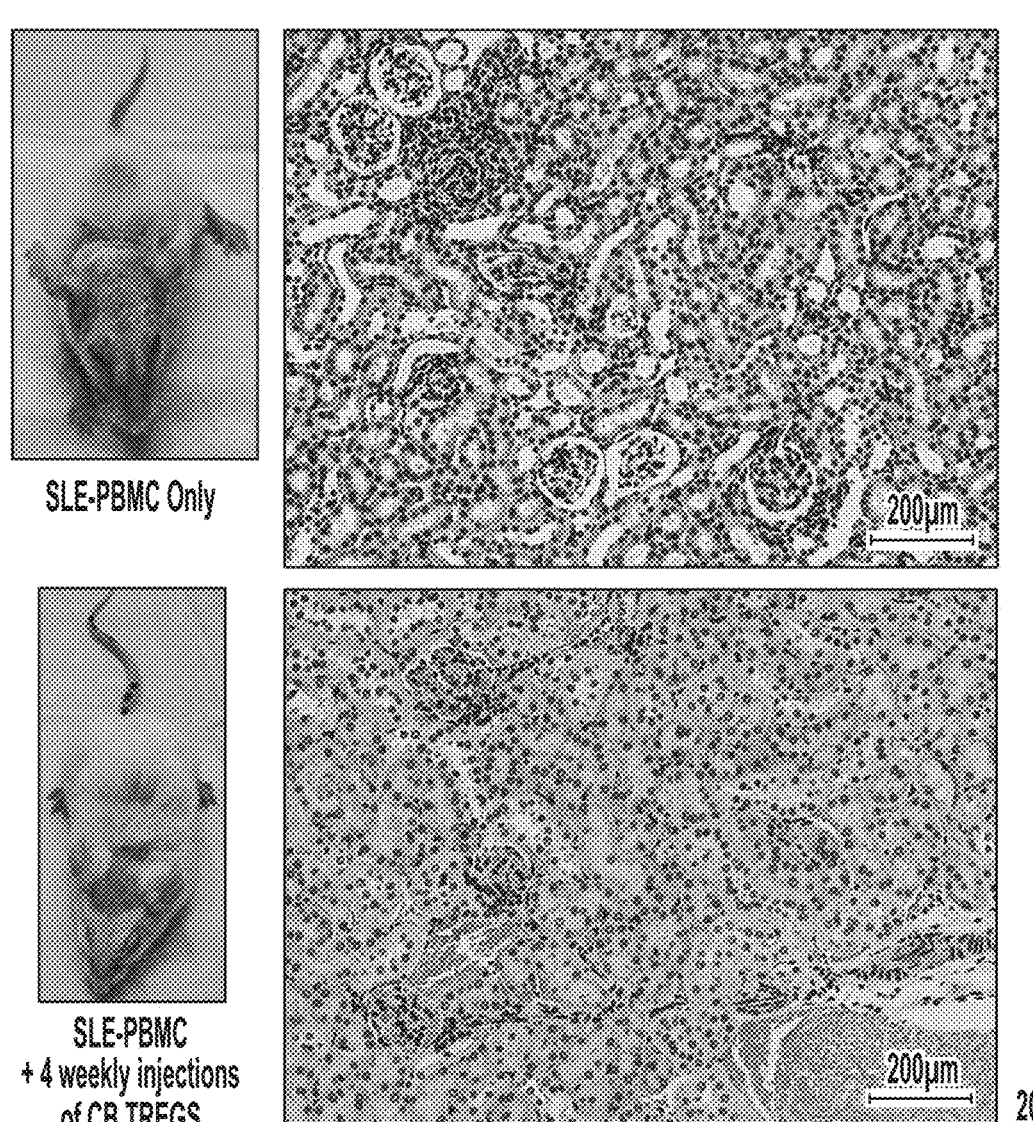
FIG. 18 depicts a series of images showing that four weekly injections of activated Treg cells improved renal histology in a xenogeneic mouse model of systemic lupus erythematosus (SLE).
Figure 19:
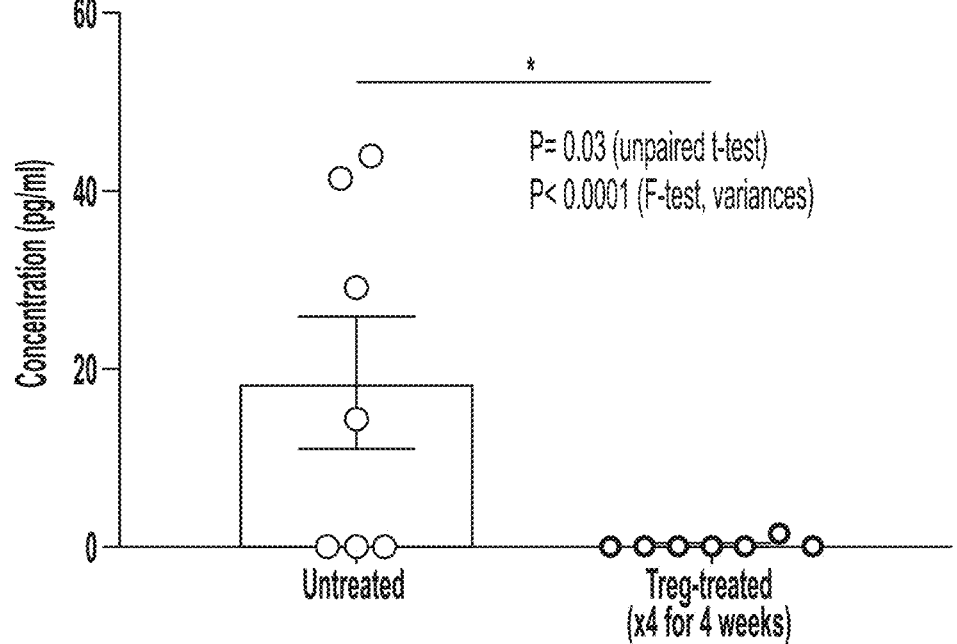
FIG. 19 depicts a graph and results of statistical analysis showing that administration of activated Tregs reduces the serum concentration of human sCD40L in a xenogeneic mouse model of systemic lupus erythematosus (SLE).
Figures 20A, 20B:
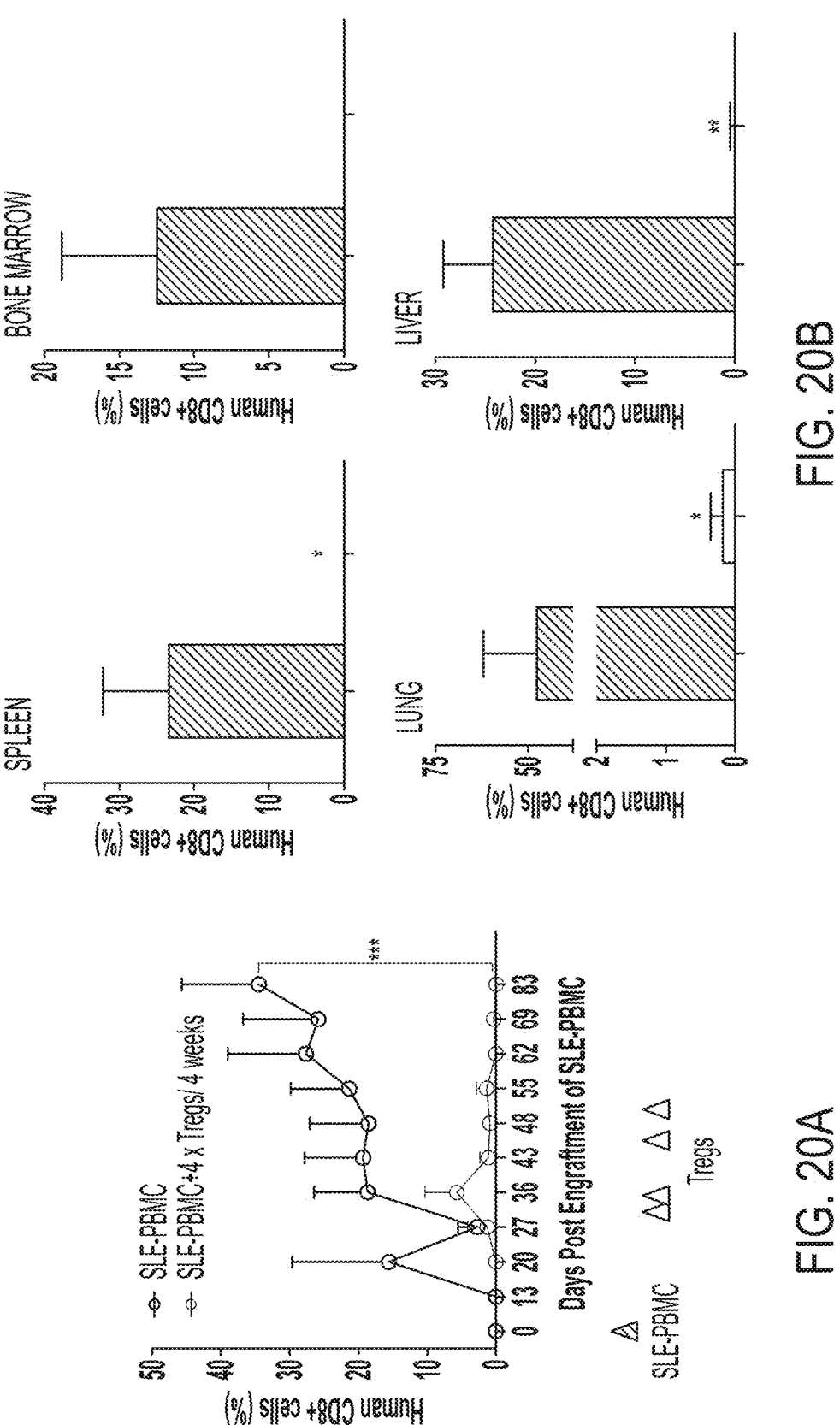
FIG. 20A-FIG. 20B depict graphs showing that weekly injections of activated cryopreserved Tregs led to a sustained decrease in the circulating CD8+ effector T cells (FIG. 20A), as well as decreased infiltration of the CD8+ effector T cells in the spleen, bone marrow, lung and liver (FIG. 20B), in a xenogeneic mouse model of systemic lupus erythematosus (SLE). "PBMC" refers to peripheral blood mononuclear cells.

This SLE model was used to assess function of umbilical cord blood-derived T-regulatory cells produced by the methods described in Examples 1 and 2. As shown in FIG. 15, a single injection of activated Treg cells decreased the levels of $CD45^+$ effector T cells for 9 weeks post engraftment of SLE-PBMCs. SLE-PBMCs were injected on day 0, and the cord blood (CB) Treg weekly injections were given starting week +4. Four weekly injections of activated Treg cells improved survival (FIG. 16A) and decreased the levels of anti-double-stranded DNA antibody (dsDNA Ig) (FIG. 16B) in SLE mice. The presence of anti-double-stranded DNA antibody is a marker of lupus disease activity. Treg recipients showed preserved weight gain and a lower GVHD score. Four weekly injections of activated Treg cells also decreased the level of urine albumin (FIG. 17A), decreased urine creatinine spill (FIG. 17B) and improved renal histology (FIG. 18) in SLE mice. As shown in FIG. 19, administration of activated Tregs reduces the concentration of human sCD40L in SLE mice. Also, the weekly injections of activated cryopreserved Tregs led to a sustained decrease in the circulating $CD8^+$ effector T cells (FIG. 20A) as well as decreased infiltration of the $CD8^+$ effector T cells in the spleen, bone marrow, lung and liver (FIG. 20B). Histopathological results from two index cases from each arm demonstrated that Treg recipients show reduced T-cells ($CD3^+$) and B-cells ($CD20^+$) in the kidneys, as well as a decrease in the lymphoid infiltration into glomeruli and renal parenchyma as compared to the control arm.

Figure 40B:
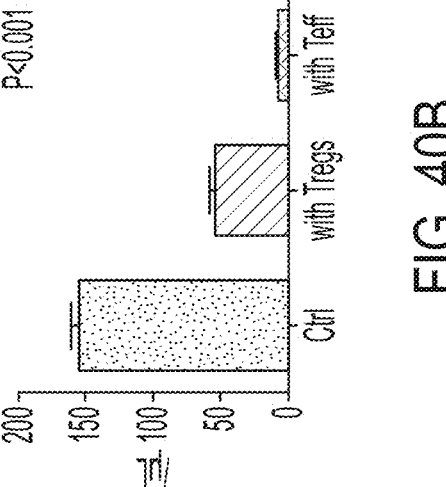
FIG. 40B-FIG. 40F depicts a series of bar graphs showing the effect CB Treg cells on myeloma and leukemia target cell migration.
Figure 40A:
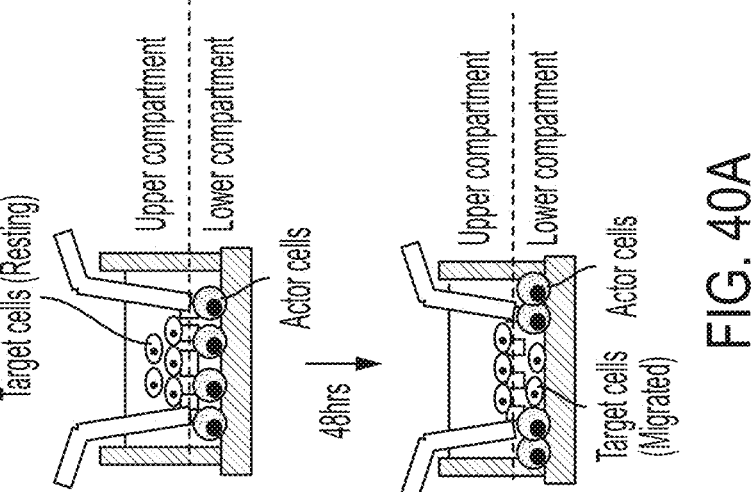
FIG. 40A is a schematic representation of a transwell migration assay. The Target cells are myeloma cells or leukemia cells (negative control). The actor cells are CB Treg cells or Teff cells.

Example 5: Treatment of Multiple Myeloma with Fresh Cord Blood-Derived T-Regulatory Cells Transwell Migration Assay A 6.5 mm 24-well transwell plate with 8.0 μm Pore Polycarbonate Membrane Inserts (Corning, Corning, NY, US) was used. T effector cells (Teffs) were isolated using $CD3^+$ MicroBeads (Miltenyi Biotec). Firefly luciferase/GFP labelled MM1.S and wild type RPMI 8226 cells were obtained from Orlowski laboratory (MD Anderson Cancer Center (MDACC)). U266 and HL-60 cells were purchased from American Type Culture Collection (Manassas, VA). Nalm6 cells were provided by Department of Hematopathology Laboratory (MDACC). RPMI 8226 and Nalm6 cells were stained with Carboxyfluorescein succinimidyl ester (CFSE) (Invitrogen) according to the manufacturer's instruction. Target cells: GFP labeled MM1.S ($3\times10^5$ cells); GFP labeled U266 ($3\times10^5$ cells); and CFSE stained RPMI 8226 ($3\times10^5$ cells); or negative control GFP labelled HL-60 ($1.5\times10^5$ cells) or CFSE stained Nalm6 ($6\times10^5$ cells), respectively, resuspended in 300 μL of media and seeded into upper compartment of transwell. The Actor cells CB Tregs ($1\times10^6$ cells) or positive control $CD3^+$ Teffs ($1\times10^6$ cells) were resuspended in 750 μL media and added to lower compartment. A schematic of the experiment is shown in FIG. 40A. The migrated Target cells were analyzed using a flow cytometer (BD FACSCanto™)

Figure 40C:
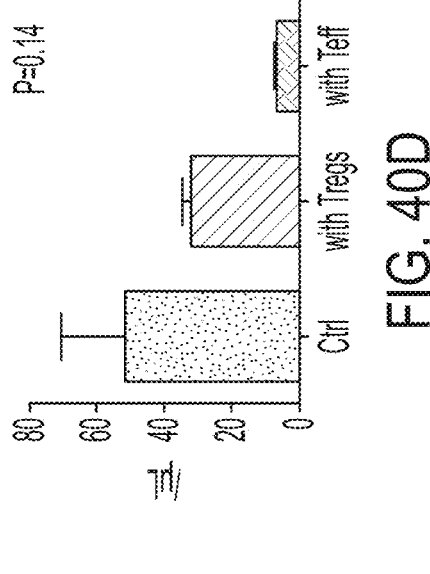
Figure 40D:
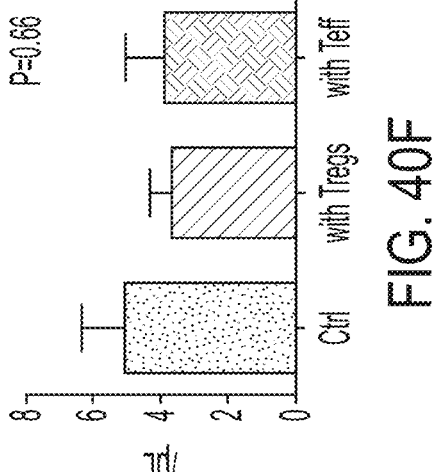
Figure 40E:
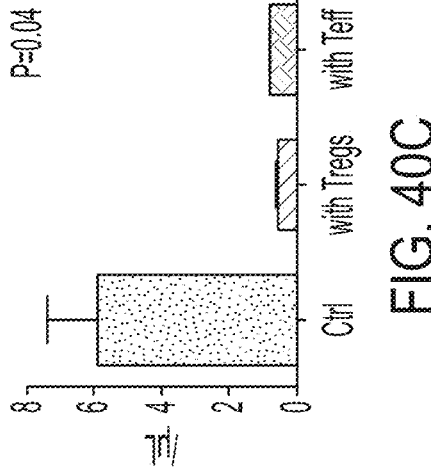
Figure 40F:
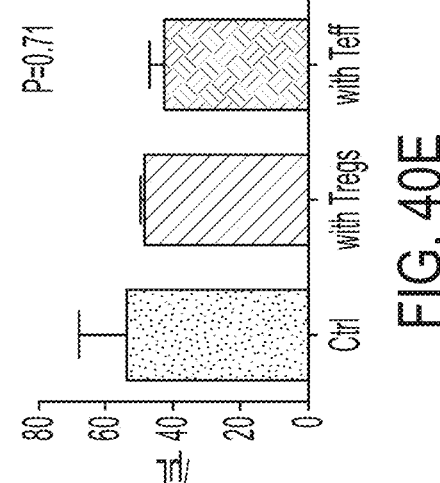

In order to understand the impact of CB Treg cells on the trafficking of the myeloma cells, the transwell experiments were set up where the Target cells were seeded in the upper compartment of the transwell (FIG. 40A). These Target cells were myeloma cells: GFP-MM1.S, GFP-U266 or CFSE-RPMI 8226. Additionally, two leukemic cell lines were used as negative control Target cells: GFP-HL60 (acute myeloid leukemia) or CFSE-Nalm6 (pre-B leukemia). The Actor cells were seeded in the lower compartment and were CB Treg cells or, as a positive control, Teff cells. Such measures were taken to isolate the myeloma specific effect of CB Tregs. The CB Tregs were able to prevent the migration of MM1.S (FIG. 40B; p<0.01)) and RPMI 8226 (FIG. 40C; p=0.04) but not U266 (FIG. 40D; p=0.14). No effect of CB Tregs was seen on the migration pattern of leukemic cells lines including HL-60 (FIG. 40E) or Nalm6 (FIG. 40F).

Xenogeneic Multiple Myeloma Mouse Model

A xenogeneic mouse model of multiple myeloma was used to assess function of umbilical cord blood-derived T-regulatory cells produced by the methods described in Examples 1 and 2. Non-SCID γ-null female mice (Jackson Laboratory, Bar Harbor, ME) were injected intravenously via tail vein with Firefly luciferase-labeled MM1.S cells (ATCC, Manassas, VA) ($3\times10^6$ cells/mouse) with or without $1\times10^7$ ex-vivo expanded CB Treg cells. The CB Treg cells were injected one day before the MM1.S cell injection. The mice were subsequently imaged as described previously (Parmar et al., Cytotherapy, 2014. 16(1): p. 90-100). Mice were bled once a week. Plasma samples were sent to Eve Technologies (Calgary, AB, Canada) to measure mouse cytokine levels. Lysed blood was stained with anti-human CD45/APC (Thermo Fisher Scientific), anti-human CD25/PE (Becton Dickinson), anti-human CD38/APCeFluor780 (Thermo Fisher Scientific), and anti-mouse CD45/Pacific Blue (Thermo Fisher Scientific). Cells were acquired by BD FACSCanto™ II. At euthanasia, bone marrow and spleen were harvested.

Survival was estimated using Kaplan Meier method, and groups were compared using log-rank test. Two groups were compared by unpaired Student t-test and three or more means by one-way ANOVA followed by Bonferroni test for multiple comparison. The values are expressed as the means and standard error of means. A P value <0.05 was considered to be statistically significant. All statistical analyses and generation of graphs were conducted using GraphPad Prism7.0 (San Diego, CA).

Figure 21A:
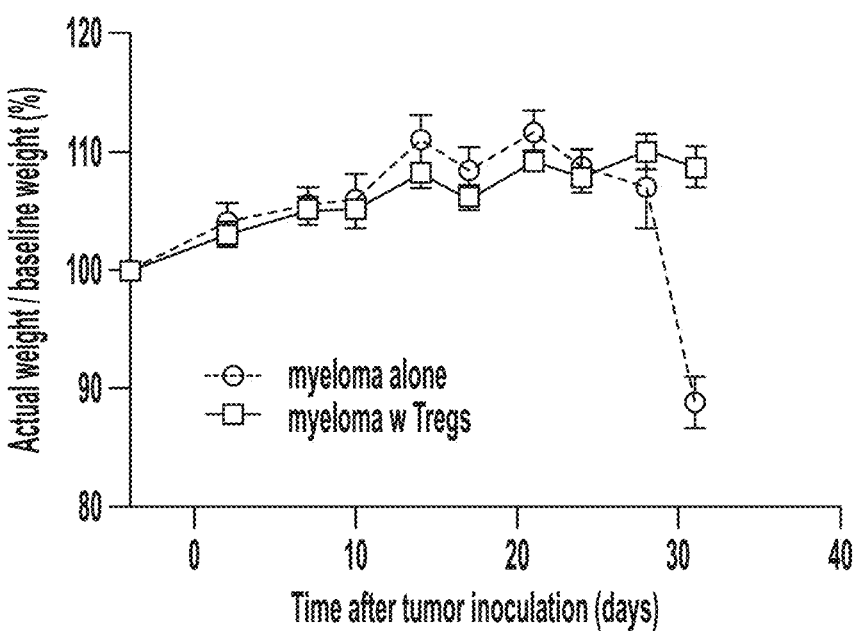
FIG. 21A-FIG. 21D depict a series of graphs and images showing the effect of administration of Tregs in a xenogeneic mouse model of multiple myeloma.
Figure 21B:
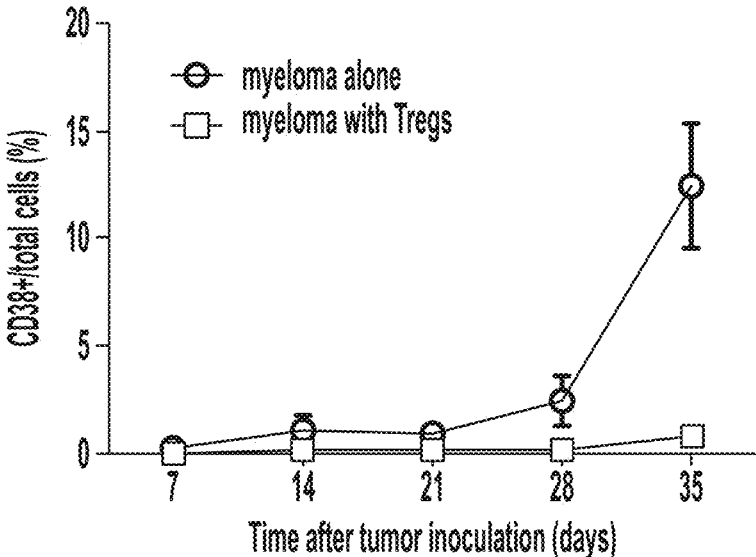

In order to understand the effect of the CB Tregs on blocking myeloma engraftment, a xenogeneic myeloma mouse model where $3 \times 10^6$ MM1.S cells were injected intravenously to allow for tumor development (control arm). In the treatment arm, CB Tregs ($1 \times 10^7$ cells) were injected one day prior to the injection of myeloma cells. Mice were weighed twice weekly and the weight remained comparable in the two arms until week 3 post tumor inoculation, when a drop in the weight of the "myeloma alone" mice was visible and a significant difference was evident at the time of euthanasia (FIG. 21A). The myeloma burden was quantified in the peripheral blood where a similar trend was observed with slight increase in the circulating $CD38^+$ myeloma cells by day 28 in the control arm compared to the Treg recipients where the difference became statistically significant by the time of euthanasia (FIG. 21B; myeloma alone: 0.8%±0.3 vs. Myeloma with Tregs: 12.4%±2.9, P=0.002)

Figure 21C:
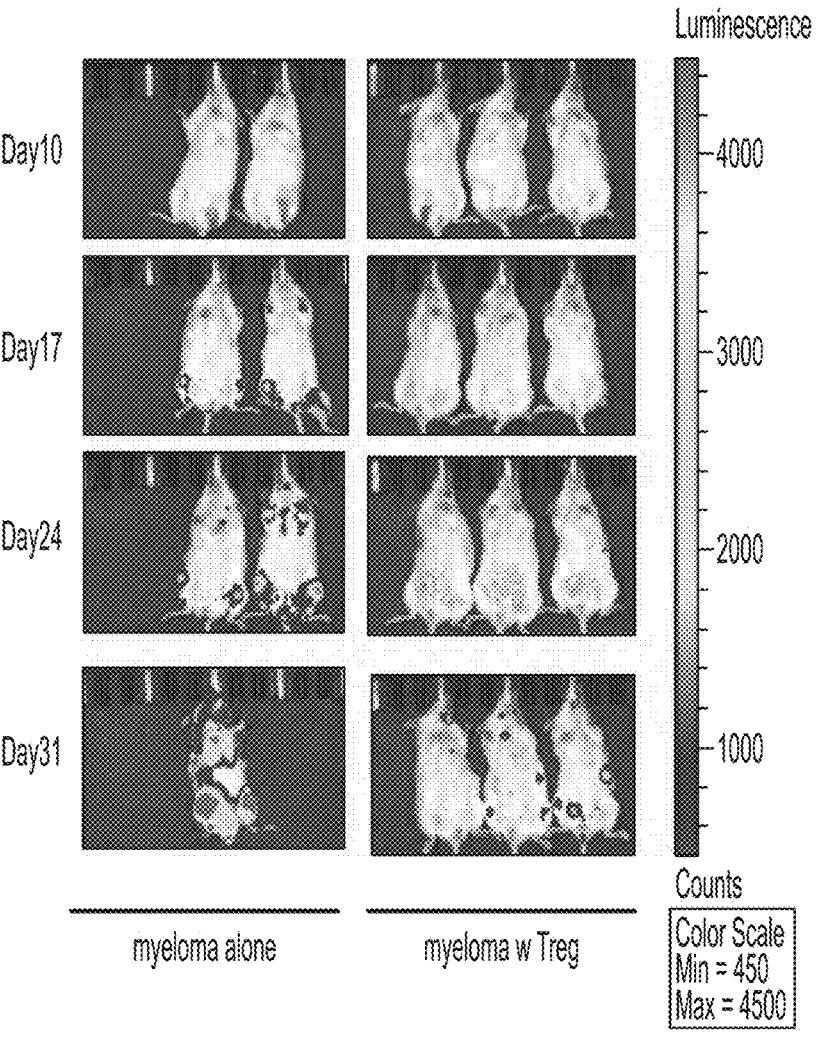
Figure 21D:
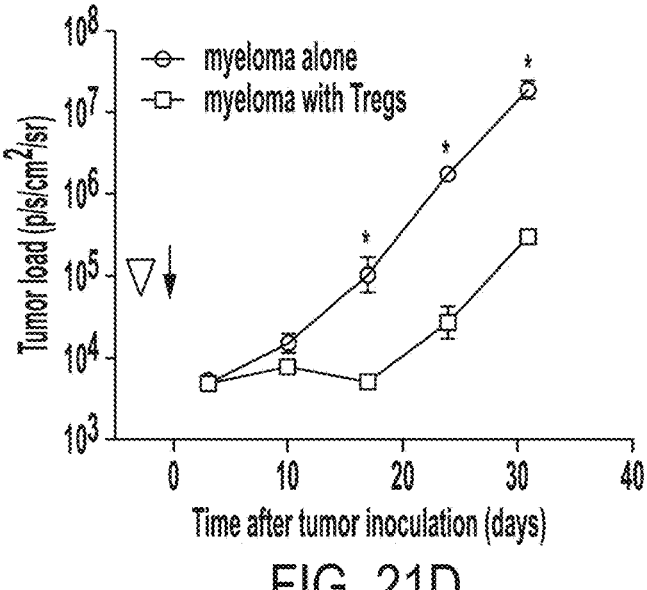

Using non-invasive bioluminescence, mice were imaged weekly and a significant uptake of the GFP-labeled MM1.S cells was evident in the control arm again at approximately 3 weeks post tumor inoculation and became widespread by the 4th week whereas minimal luminescence was detected in the CB Treg recipients (FIG. 21C). The tumor progression was rapid, and the increment of tumor load quantified by BLI in CB Treg recipients was significantly delayed compared to that in the control arm over the period of observation (FIG. 21D).

Figure 22:
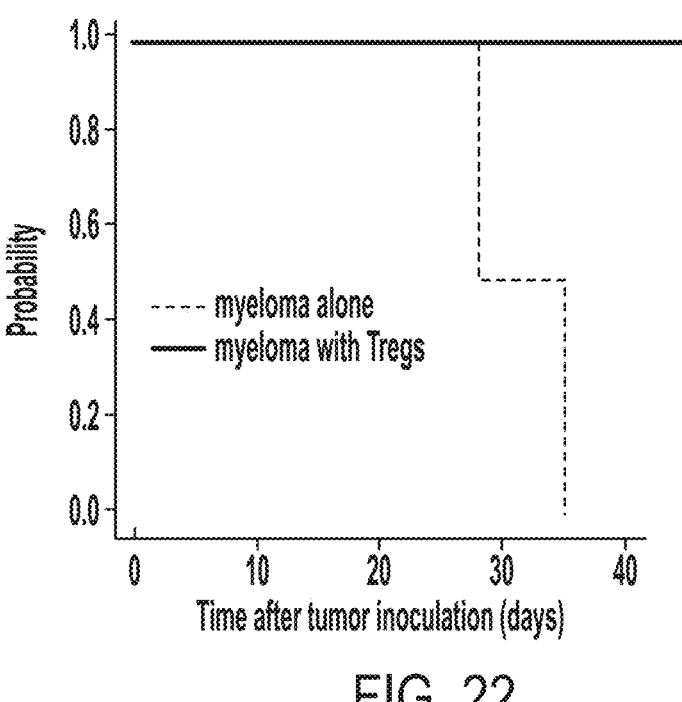
FIG. 22 depicts a graph showing that administration of activated Tregs improves survival in a xenogeneic mouse model of multiple myeloma. In a xenogeneic myeloma model, cord blood (CB) Treg injection prior to the myeloma cell injection led to improvement in overall survival compared to the "myeloma alone" arm. P=0.039 was determined by log-rank test.
Figure 23:
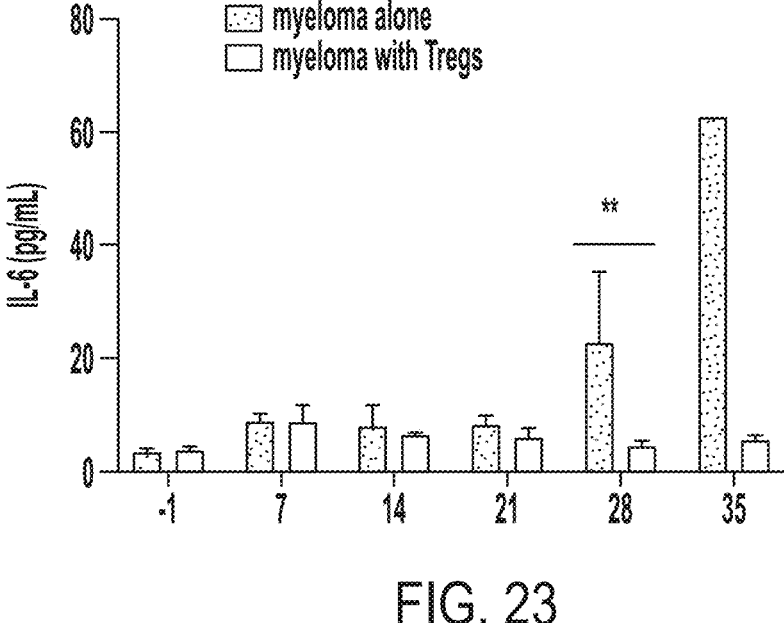
FIG. 23 depicts a bar graph showing that administration of activated Tregs decreases plasma IL-6 levels in a xenogeneic mouse model of multiple myeloma. In a xenogeneic myeloma mouse model, injection of cord blood (CB) Tregs one day prior to the injection of myeloma cells prevented myeloma engraftment and led to improved overall survival which correlated with decreased levels of serum inflammatory cytokine IL-6. Measurement of circulating plasma mouse IL-6 level showed lower levels compared with the "myeloma alone" mice on days 28 and 35. Mean±SEM. *P<0.0001, P<0.001, *P<0.01 were determined by unpaired Student t-test at each time point.
Figure 24A:
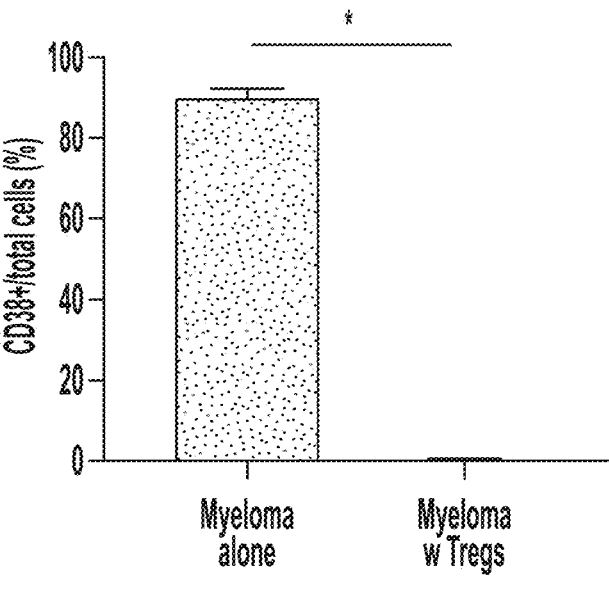
FIG. 24A-FIG. 24B depict bar graphs showing that administration of activated Treg cells decreased myeloma burden in the bone marrow (FIG. 24A) and the spleen (FIG. 24B) in a xenogeneic mouse model of multiple myeloma. Three mice in each group were euthanized, and the organs were harvested on day 25. The cells of bone marrow and spleen were stained with CD38 antibody and analyzed the population of MM.1S cells by flow cytometry.
Figure 24B:
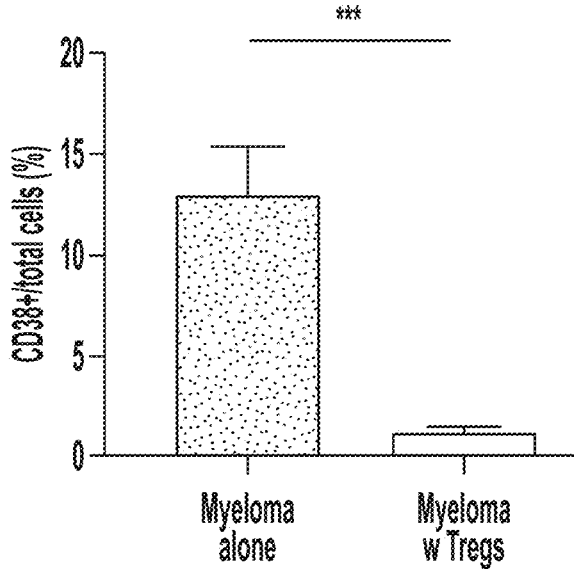

Since myeloma cells thrive in the inflammatory tumor microenvironment and interleukin-6 (IL-6) has been implicated as a major driver of the myeloma disease progression (Harmer et al. Front Endocrinol (Lausanne), 2018, 9: p. 788), the impact of CB Tregs on this inflammatory cytokine was examined. As shown in FIG. 23, the circulating IL-6 level was comparable in the 2 arms until week 4 post tumor inoculation when a significant increase in the plasma IL-6 level in the "myeloma alone" arm was measured and continued to increase until week 5. Finally, the increase in tumor load as well as increase in inflammatory burden translated into mortality in the "myeloma alone" arm leading to a statistically significant survival advantage for the Treg recipients (FIG. 22). Upon euthanasia, the tumor cells were measured in the harvested organs and compared between the 2 arms. The myeloma cells were barely detectable in bone marrow of the Treg recipients compared to the "myeloma alone" arm (FIG. 24A; 0.6%±0.1 vs 90.0%±2.2, P<0.0001). A similar pattern was also observed in the spleen (FIG. 24B; Myeloma+Tregs: 1.3%±0.4 vs Myeloma alone: 12.9%±4.2, P=0.009).

The data support the hypothesis that a single injection of CB Treg cells prior to the injection of myeloma cells gives them enough proliferative advantage that allows for dampening of the inflammatory signals generated by myeloma cells in vivo as shown by the lack of IL-6 production which ultimately translates into hostile conditions for myeloma engraftment. The overlay of tumor burden with the physical signs of weight loss as well as circulating and organ infiltrating myeloma cells strengthens systemic anti-inflammatory effect of the CB Treg cells.

Effects on Established Myeloma Disease

Methods: $3 \times 10^6$ GFP-labeled MM.1S cells were injected in NSG mice followed by $5 \times 10^6$ $CD3^+$ T conventional (Tcon) cells on day +14. In a subset of the Tcon treated mice, $1 \times 10^7$ CB Treg cells were injected on day +16, +23 and +30 (see experimental design table below). Mice were followed every other day for weight and GVHD score. Non-invasive bioluminescent imaging (BLI) were performed serially. Weekly blood draw was performed for cell analysis and cytokine assays. At the time of euthanasia, blood, spleen and marrow were harvested for histopathology and flow analysis. In a subsequent experiment, intra-peritoneal injection of the bispecific antibody against CD3 and BCMA (BCMA-BiTE® (bispecific T-cell engager)) was administered in the xenogeneic myeloma model in presence or absence of CB Treg cells. Pan T cells were added to all mice to facilitate the anti-tumor action of BiTE®. The experimental design is shown in FIG. 61E.

TABLE 13

| Experimental Design: Treg + Tcon | | | | | |
|---|---|---|---|---|---|
| | Day 0 | Day +14 | Day +16 | Day +23 | Day +30 |
| MM1.S | X | | | | |
| Tcon | | X | | | |
| Treg | | | X | X | X |

Figure 61A:
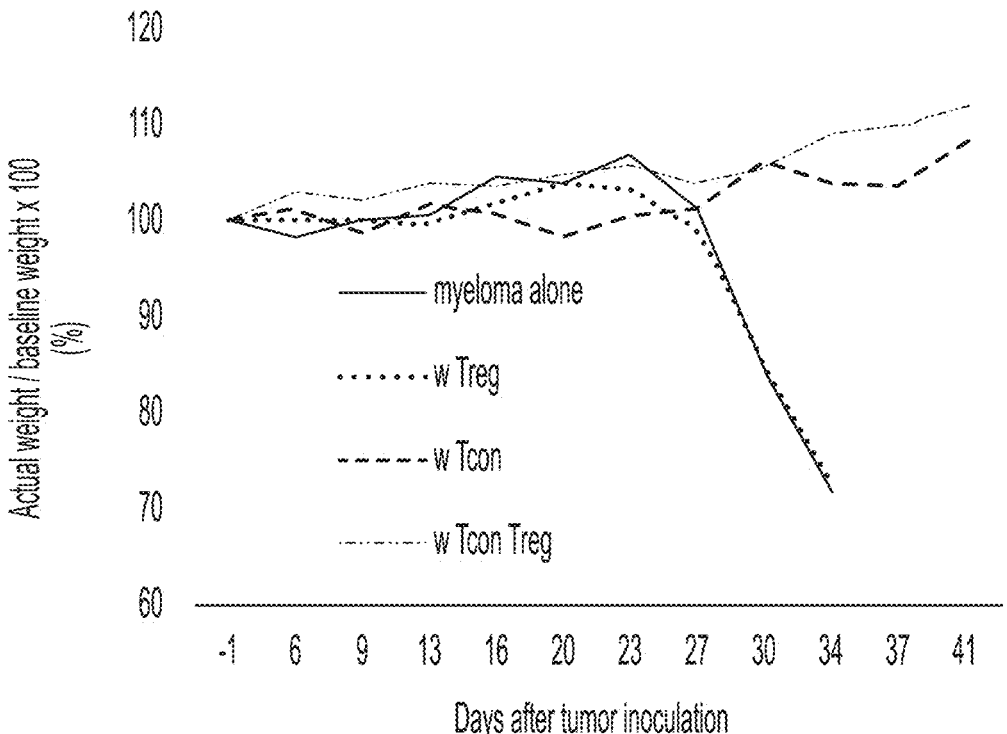
Figures 61B, 61C, 61D:
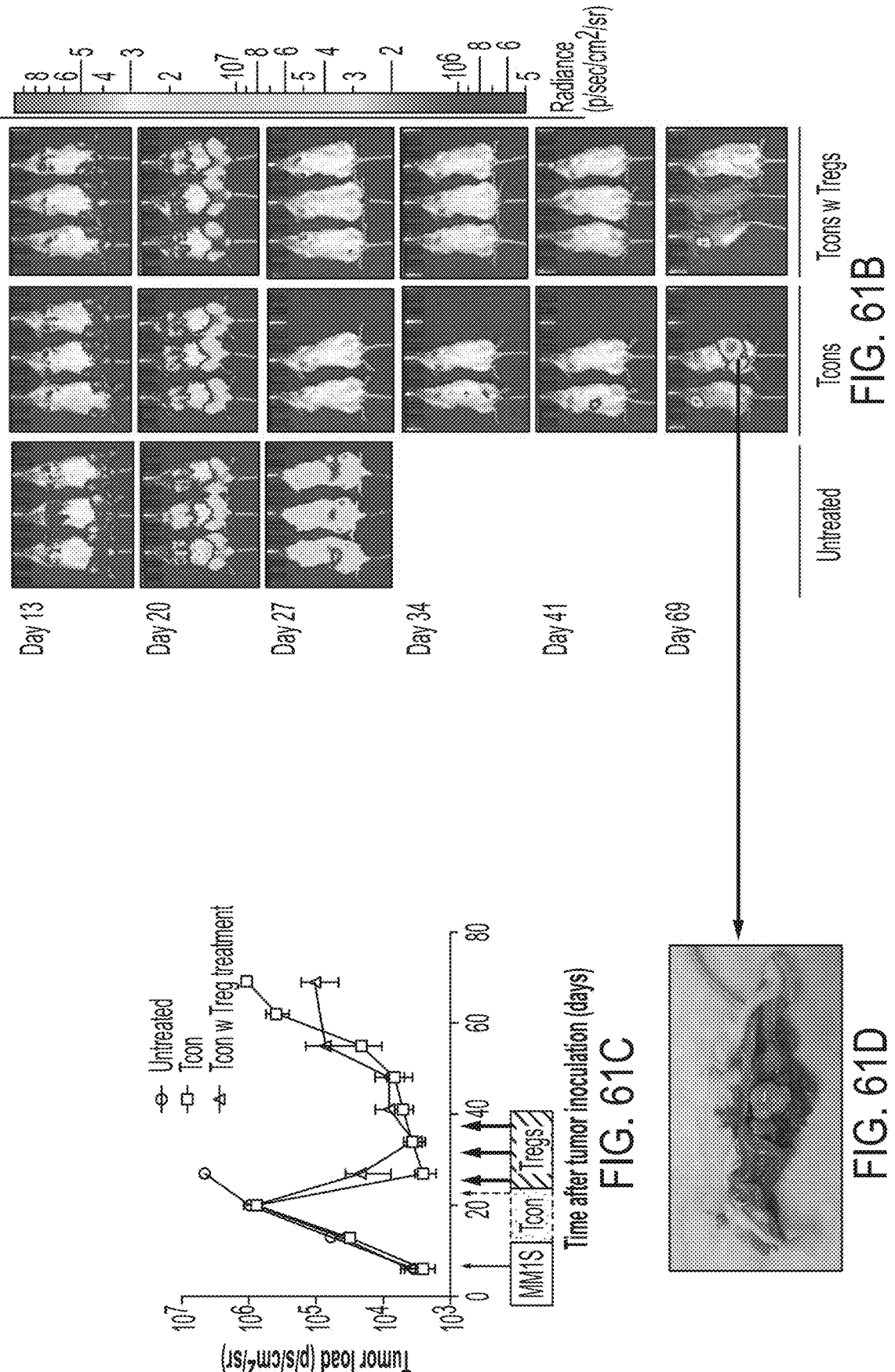
Figure 61F:
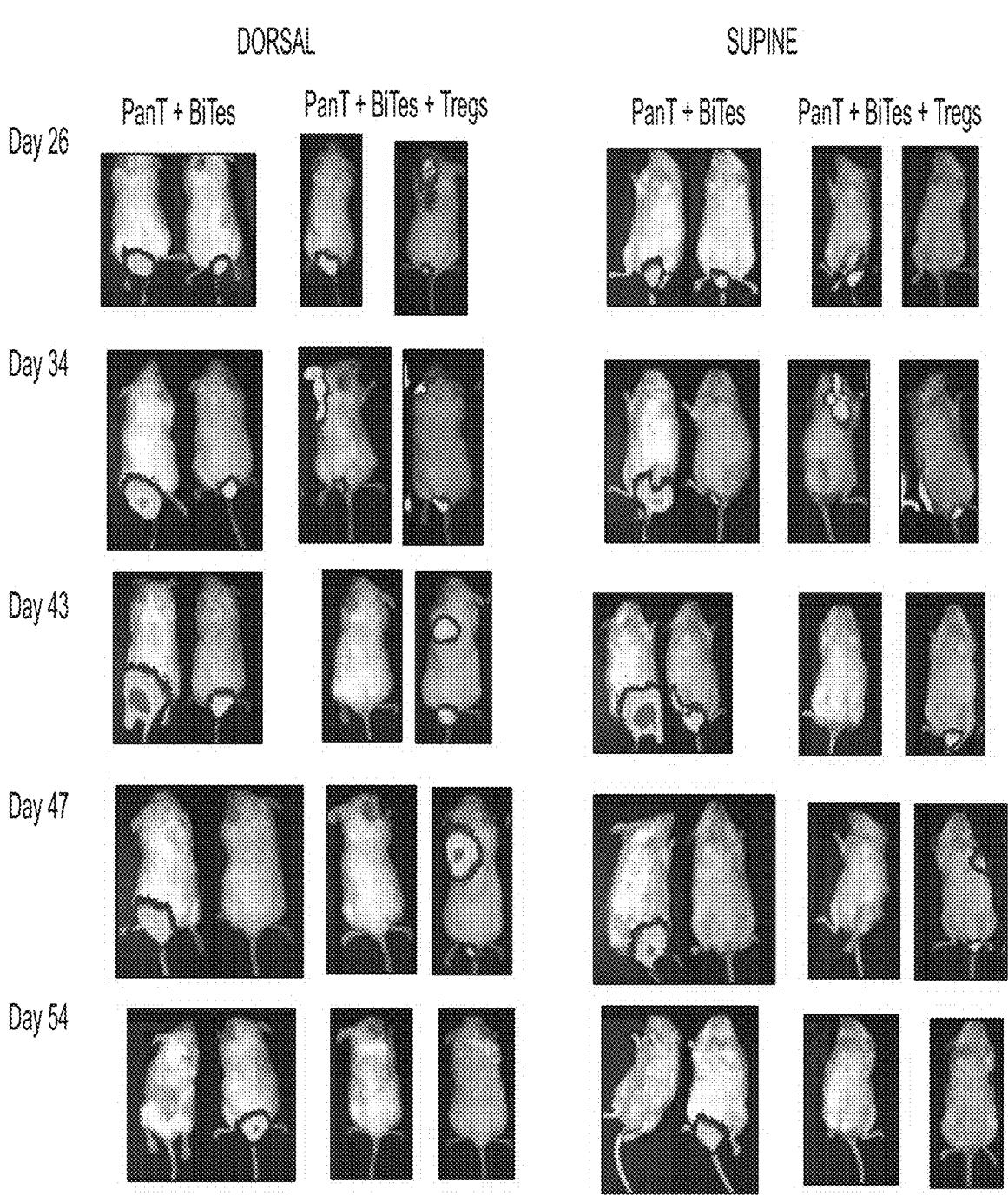
Figure 61G:
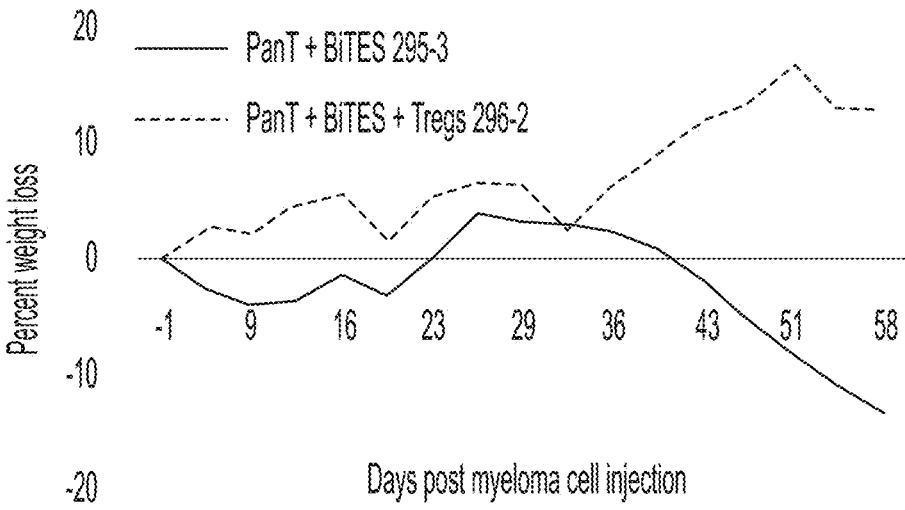
Figure 61H:
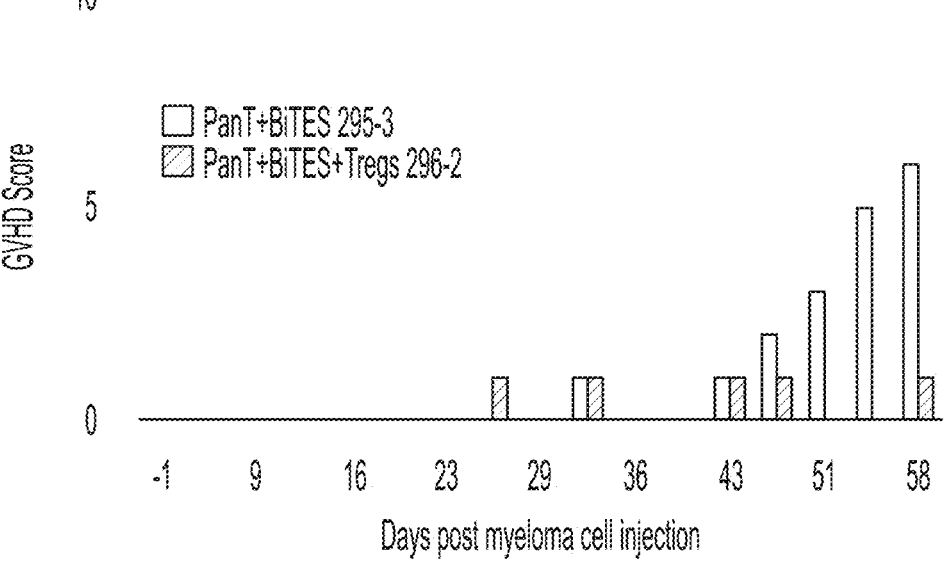

Results: Both Tcon and Tcon+Treg recipients maintained their body weight compared to myeloma alone or myeloma+Treg arm (FIG. 61A). The addition of Tregs did not interfere in Tcon mediated anti-myeloma effect and prevented delayed relapse (FIG. 61B-FIG. 61D). The addition of Treg+BiTE® led to a similar degree of tumor control compared to BiTE® alone treated mice (FIG. 61F). The addition of Tregs did not interfere in BiTE®-mediated anti-myeloma effect. The addition of Tregs mitigated BiTE®-induced weight loss (FIG. 61G) with a corresponding high GVHD score (FIG. 61H).

Example 6: Evaluation of Safety and Efficacy for Administering Cord Blood-Derived T-Regulatory Cells in the Treatment of Bone Marrow Failure Syndromes and Other Autoimmune Disorders Study Rationale Adoptive therapy with cord blood-derived T-regulatory cells may be able to decrease the circulating pro-inflammatory cytokines and improve outcomes. In previous studies, it has been demonstrated that infusion of cord blood-derived T-regulatory cells is safe and possibly effective in prophylaxis of GVHD, though the effects in both preclinical and clinical studies appear to be strongly dependent on the ratio of Tregs to Tcons in vivo. Current strategies for minimizing GVHD call for prolonged immunosuppressive therapies with drugs such as the calcineurin inhibitors (CNI), cyclosporine and tacrolimus. However, this prolonged immunosuppression results in delayed immune function leading to infectious complications as well as the risk of post-transplant lymphoproliferative disorders. Adoptive therapy with cord blood-derived T-regulatory cells therefore may be an attractive alternative for treatment of GVHD as well as other autoimmune diseases.

The cord blood-derived T-regulatory cells cell product (CK0801) consists of the ex vivo expanded T-regulatory cells, derived from a single cord blood unit (CBU) and manufactured according to the methods described herein.

The purpose of this study is to evaluate whether it is safe and practical to give CK0801 to patients with treatment refractory bone marrow failure syndromes including myelo-dysplasia, myelofibrosis, and aplastic anemia. Only patients who have relapsed/refractory bone marrow failure and who have not responded to standard treatment will be enrolled in these studies. This study will determine the highest possible dose that is safe to be given and whether CK0801 may improve the symptoms of bone marrow failure syndrome.

Participants eligible to participate in this study are unable or unwilling to be treated with standard therapy or have failed standard therapy.

Primary Objective

The primary objective is to determine dose limiting toxicity of CK0801 as defined as any of the events each starting at the time of CK0801 infusion.

severe (grade 3 or 4) infusion toxicity within 24 hours (NCI-CTCAE V4.0)

regimen related death within 30 days severe (grade 3 or 4) cytokine release syndrome within 30 days Secondary Objective preliminary assessment of disease-specific response duration of disease-specific response Exploratory Objectives To assess Peripheral Blood and Bone Marrow immune reconstitution and inflammatory cytokines at baseline and scheduled follow ups in the post-treatment setting. Samples will be drawn on Day −10, day 0, day +3, day +7, day +14, day +21, day +30, day +60, day +90 and 1 year following each infusion.

Arms and Intervention

TABLE 14

| Arms | Assigned Interventions |
|------|------------------------|
| Experimental: CK0801 Adoptive therapy with infusion of unrelated cord blood-derived regulatory T cells: CK0801 | Biological/Vaccine: CK0801 CK0801 (a cord blood-derived T-regulatory cell product) |

Study Design

A standard 3+3 phase I statistical design will be utilized, where three patients will be treated at dose level 1: $1 \times 10^6$/kg. If no dose limiting toxicity (DLT) is observed, then the dose will be escalated to the dose level 2: (range) $>1 \times 10^6$/kg-$1 \times 10^7$/kg for the next cohort of 3 patients. If no DLT is observed, then the dose will be escalated to dose level 3: (range) $>1 \times 10^7$/kg-$1.5 \times 10^7$/kg.

If one DLT is observed at a dose level, then 3 additional patients will be treated at that level. If no additional DLTs, then that dose level will be defined as MTD.

If ≥2 DLTs at dose level 2 or 3, then prior dose level is defined as MTD. If >2 DLTs at dose level 1, the data safety monitoring board (DSMB) will review and evaluate for study continuation.

MTD is decided when 6 patients are treated at a dose level with <2 DLTs. A maximum of 18 patients will be treated.

Upon enrollment of subjects into each study cohort (3 or 6 patients), the cohort will close until 30 days after the final patient has completed Day 0 (infusion of CK0801). Dose escalation may only occur after DSMB review of the previously dosed cohort.

Subjects will be consented and enrolled on study providing the eligibility criteria are met.

Investigational Product

Source and Pharmacology

CK0801 (Cord blood-derived T-regulatory cells) is manufactured in the Cellenkos GMP facility, using a single allogeneic unrelated donor cord blood unit that has been selected on the predetermined criteria, and qualified for use in manufacturing. CK0801 is manufactured using immuno-magnetic selection of $CD25^+$ Tregs and a 14-day culture-expansion process, with harvest of the Tregs and final formulation in Plasma-Lyte A and 0.5% human serum albumin (HSA). The final cellular product is released only after a formal lot release process, including review of all available test results. Lot release criteria include 7AAD viability ≥70%, % $CD4^+CD25^+$ cell purity ≥60%, % $CD4^-$/$CD8^+$ cells <10%, anti-CD3/anti-CD28 Ab bead count <100 per $3 \times 10^6$ cells, gram stain with "no organisms", endotoxin <5 EU/kg, sterility (sampled 48-72 hours before final formulation) negative, and mycoplasma negative.

Cord Blood Search, Selection and Shipment to Manufacturing Facility

Cord blood units provided to Cellenkos, Inc. for generation of CK0801 will be obtained from individually qualified and selected Cord Blood Banks (CBB) that meet the minimum accreditation standards for Foundation for the Accreditation of Cellular Therapy (FACT) or American Association of Blood Banks (AABB). Eligible CB units may be classified as either licensed or unlicensed and will meet predetermined qualification criteria.

At the time of consent, subjects will provide a blood sample for HLA typing. Results will be provided to the sponsor's clinical coordinator in order to facilitate the cord blood search and selection process. The sponsor will identify available cord blood units according to standard search algorithms that are HLA-matched to the recipient (subject) at 3, 4, 5, or 6 of 6 antigens at the HLA-A, —B and DRB1 loci, and provide the list to the principal investigator (PI). The sponsor and PI will select the appropriate cord blood unit based upon predetermined criteria.

After the cord blood unit has been selected, the sponsor's clinical coordinator will arrange the shipment and transportation logistics and the unit will be shipped to Cellenkos' GMP Manufacturing Facility. Upon arrival at the manufacturing facility, the cord blood unit will be inspected, checked-in and verified against the CB donor/Recipient shipment request. Cord blood units meeting acceptance criteria (including identification, labeling, and temperature) will be stored in a liquid nitrogen, vapor phase storage freezer at ≤−150° C. until day −14 (initiation of manufacturing), which will be coordinated with the subject's planned infusion schedule.

Prior to the infusion, the sponsor's clinical coordinator and site clinical team will be responsible for arranging infusion of CK0801 at the predetermined time point and time window. CK0801 must be administered within 8 hours of final formulation.

The sponsor's clinical coordinator will arrange the transportation of CK0801 to the clinical site. The site's clinical team will be responsible for the receipt, acceptance, preparation and administration of CK0801.

Formulation and Stability

CK0801 is formulated to the final cell dose in Plasma-lyte+0.5% human serum albumin (HSA) buffer. Infusion of CK0801 must occur within 8 hours of final formulation.

Storage and Handling

CK0801 will be transported to the clinical site in a transport container validated to maintain temperatures between 15° C. to 30° C., and will be maintained at 15° C. to 30° C. prior to infusion.

Toxicity

Infusion of Cord blood-derived T-regulatory cells has been previously shown to be safe, however subjects should be monitored during infusion of CK0801 per standard of clinical practice. Recommended timing of vital signs on day of each infusion: pre-infusion, 15 minutes after start of infusion, 30 minutes after start of infusion, 1 hour after start of infusion, 2 hours after start of infusion and then per standard clinical practice.

Vital signs will include temperature, respiration, blood pressure, and pulse.

Route of Administration

CK0801 is administered via a central or peripheral line and not to exceed a rate of 5 ml/min. After administration, the bag and the line will be flushed repeatedly with normal saline.

CK0801 Infusion

Infusion of CK0801 at three different dose levels will be explored in this trial. A standard 3+3 phase I statistical design will be used.

No conditioning or lympho-depletion will be administered to the patient. Three patients will be treated at dose level 1: $1 \times 10^6$/kg IBW. If no dose limiting toxicity (DLT) is observed, then the dose will be escalated to dose level 2: (range) $3 \times 10^6$/kg IBW for the next cohort of 3 patients. If no DLT is observed, then the dose will be escalated to dose level 3: (range) $1 \times 10^7$/kg IBW.

If 1 DLT is observed at a dose level, then 3 additional patients will be treated at that level. If no additional DLTs, then that dose level will be defined as MTD.

If ≥2 DLTs at dose level 2 or 3, then prior dose level is defined as MTD. If ≥2 DLTs at dose level 1, then the data safety monitoring board (DSMB) will review and evaluate for study continuation.

MTD will be decided when 6 patients are treated at a dose level with <2 DLTs.

Patients will be pre-medicated with diphenhydramine (Benadryl®) 50 mg IV piggyback (IVPB) and acetaminophen 650 mg (orally) thirty (30) minutes before infusion of CK0801. CK0801 is infused by gravity flow over 15 to 30 minutes, via an IV line that must not contain any solution other than 0.9% Sodium Chloride (normal saline) USP. CK0801 is compatible with standard blood product tubing. Use of a filter is prohibited.

Selection of Study Population

Inclusion Criteria

1. Subjects who fulfill the diagnostic criteria of bone marrow failure syndrome including: aplastic anemia, myelodysplastic syndrome, or myelofibrosis.
2. HLA matched (≥3/6 at HLA-A, HLA-B, and HLA-DRB1) cord blood unit available for CK0801 generation.
3. Subjects age greater than 18 years.
4. Bilirubin ≤2×ULN and SGPT (ALT) ≤2×ULN (unless Gilbert's syndrome is documented).
5. Calculated creatinine clearance of >50 mL/min using the Cockcroft-Gault equation.
6. Zubrod performance status ≤2.

7. Female subjects of child bearing potential (FPCP) must have a negative urine or serum pregnancy test. NOTE: FPCP is defined as premenopausal and not surgically sterilized. FPCP must agree to use maximally effective birth control or to abstain from heterosexual activity throughout the study. Effective contraceptive methods include intra-uterine device, oral and/or injectable hormonal; contraception, or 2 adequate barrier methods (e.g., cervical cap with spermicide, diaphragm with spermicide).
8. Subject has agreed to abide by all protocol required procedures including study-related assessments, visits and long term follow up.
9. Subject is willing and able to provide informed consent.

Exclusion Criteria

1. Subject has received an investigational agent within 4 weeks prior to CK0801 infusion.
2. Subject has received radiation or chemotherapy within 21 days prior to CK0801 infusion.
3. Subject has received prior cord blood-derived T-regulatory cell therapy.
4. Known HIV seropositivity.
5. Subject has uncontrolled infection, not responding to appropriate antimicrobial agents after seven days of therapy. The Protocol PI is the final arbiter of eligibility.
6. Subjects with uncontrolled inter-current illness that in the opinion of the investigator would place the patient at greater risk of severe toxicity and/or impair the activity of CK0801.
7. Subjects is pregnant or breastfeeding.
8. Bone marrow failure caused by stem cell transplantation.
9. Subjects who are unable to provide consent or who, in the opinion of the Investigator will be unlikely to fully comply with protocol requirements.

Data Collection

Treatment and Toxicity data related to the infusion of CK0801 will be collected from the date of first CK0801 infusion up to 30 days post last infusion.

Subjects who experience study-related death or documented disease progression with subsequent alternative treatment, will be considered treatment failures and treated as censored observations at the time of the event with no further data collection. Subjects who withdraw informed consent or are taken off study for noncompliance will also be censored at that point.

Outcome Measures

Primary Outcome Measure:

1. Number of participants with treatment-related adverse events as assessed by CTCAE v4.0 Evaluate safety of infusing CK0801 in subjects suffering from bone marrow failure by collection of adverse events and serious adverse events Dose limiting toxicity will be defined to include any of the events each starting at the time of CK0801 infusion.

severe (grade 3 or 4) infusion toxicity within 24 hours (NCI-CTCAE V4.0)

regimen related death within 30 days severe (grade 3 or 4) cytokine release syndrome within 30 days

[Time Frame: 30 days from infusion]

Secondary Outcome Measure:

2. Preliminary assessment of disease-specific response to the therapy and the duration of the response

[Time Frame: 12 months]

Other Pre-Specified Outcome Measures:

3. To assess Bone Marrow (BM) immune reconstitution and inflammatory cytokines

A sample of bone marrow will be drawn at baseline and scheduled follow ups in the post-treatment setting and analyzed for immune reconstitution and inflammatory cytokines

[Time Frame: 12 months]

4. To assess peripheral blood (PB) immune reconstitution and inflammatory cytokines Peripheral blood will be drawn at baseline and scheduled follow ups in the post-treatment setting and analyzed for immune reconstitution and inflammatory cytokines

[Time Frame: 12 months]

Results of Phase 1 Clinical Trial of Allogeneic Cord Blood-Derived Treg Cells in Patients with Bone Marrow Failure (BMF)

Figure 28:
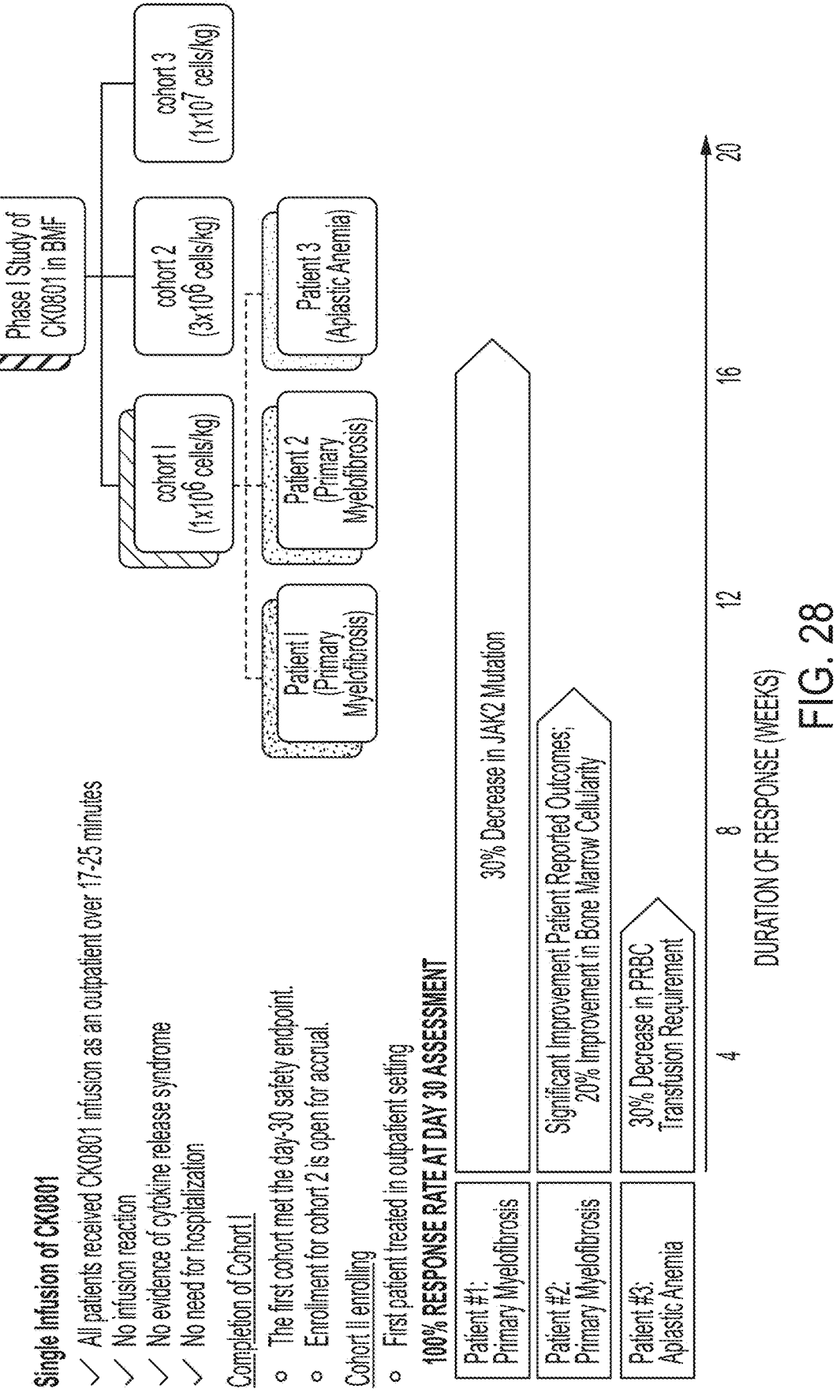
FIG. 28 depicts a summary of early results from a Phase 1 clinical trial to evaluate safety and efficacy of administering cord blood-derived T regulatory cells in the treatment of subjects suffering from bone marrow failure.
Figure 41:
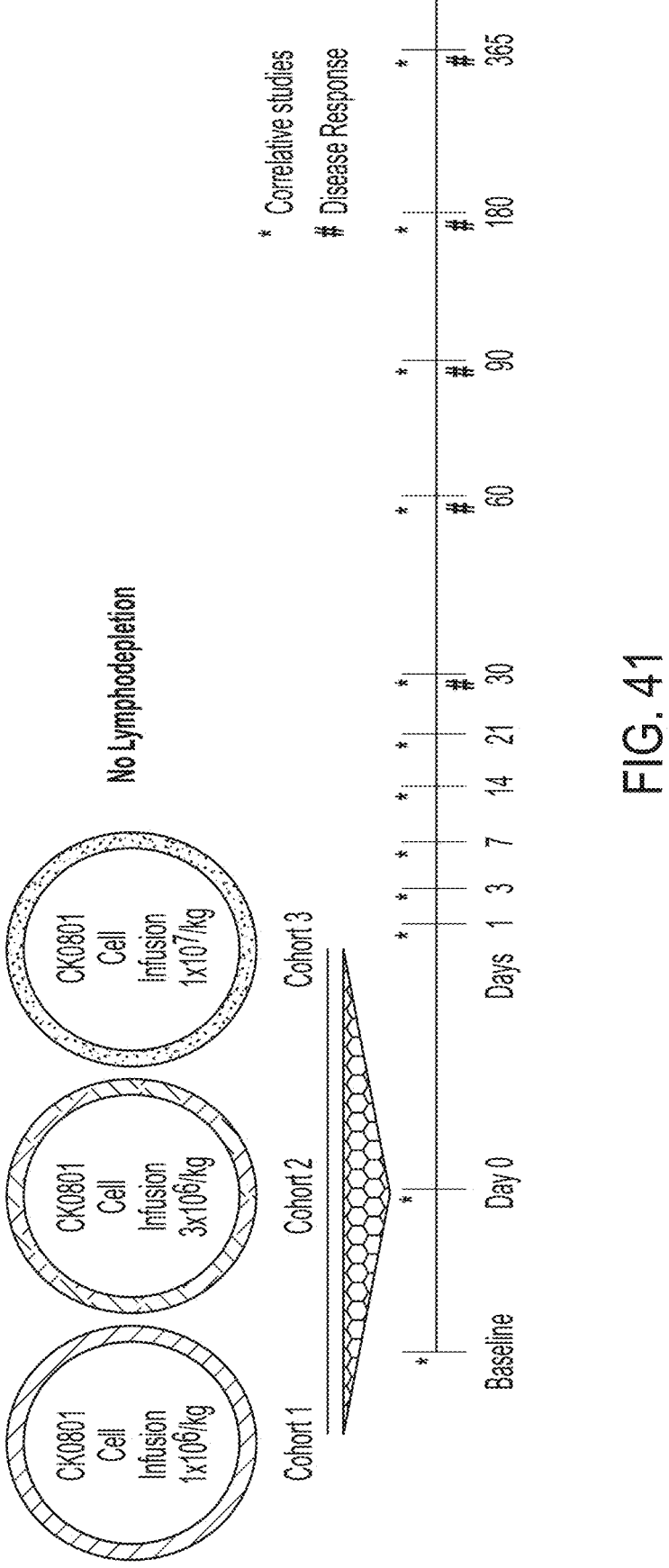
FIG. 41 depicts a schematic of a design for a Phase 1 clinical trial of allogeneic cord blood-derived Treg cells in patients with bone marrow failure (BMF).

A schematic of the trial design is shown in FIG. 41. Timing for correlative studies is shown in the table below. FIG. 28 depicts that the Phase 1 clinical trial for CK0801 in subjects suffering from bone marrow failure showed an early efficacy signal.

TABLE 15

| Study Timepoint | Screening/ Baseline | CK0801 Infusion (pre-infusion) | Post CK0801 Infusion | | | | | | | | | |
|---|---|---|---|---|---|---|---|---|---|---|---|---|
| Study Day | Day -10 to -7 | 0 | +1 | +3 | +7 | +14 | +21 | +30 | +60 | +90 | +180 | +365 |
| Visit Window (days) | N/A | N/A | | | | | | +/- 7 | +/- 7 | +/- 7 | +/- 28 | +/- 28 |
| Correlative Studies | X | X | X | X | X | X | X | X | X | X | X | X |

Figure 42:
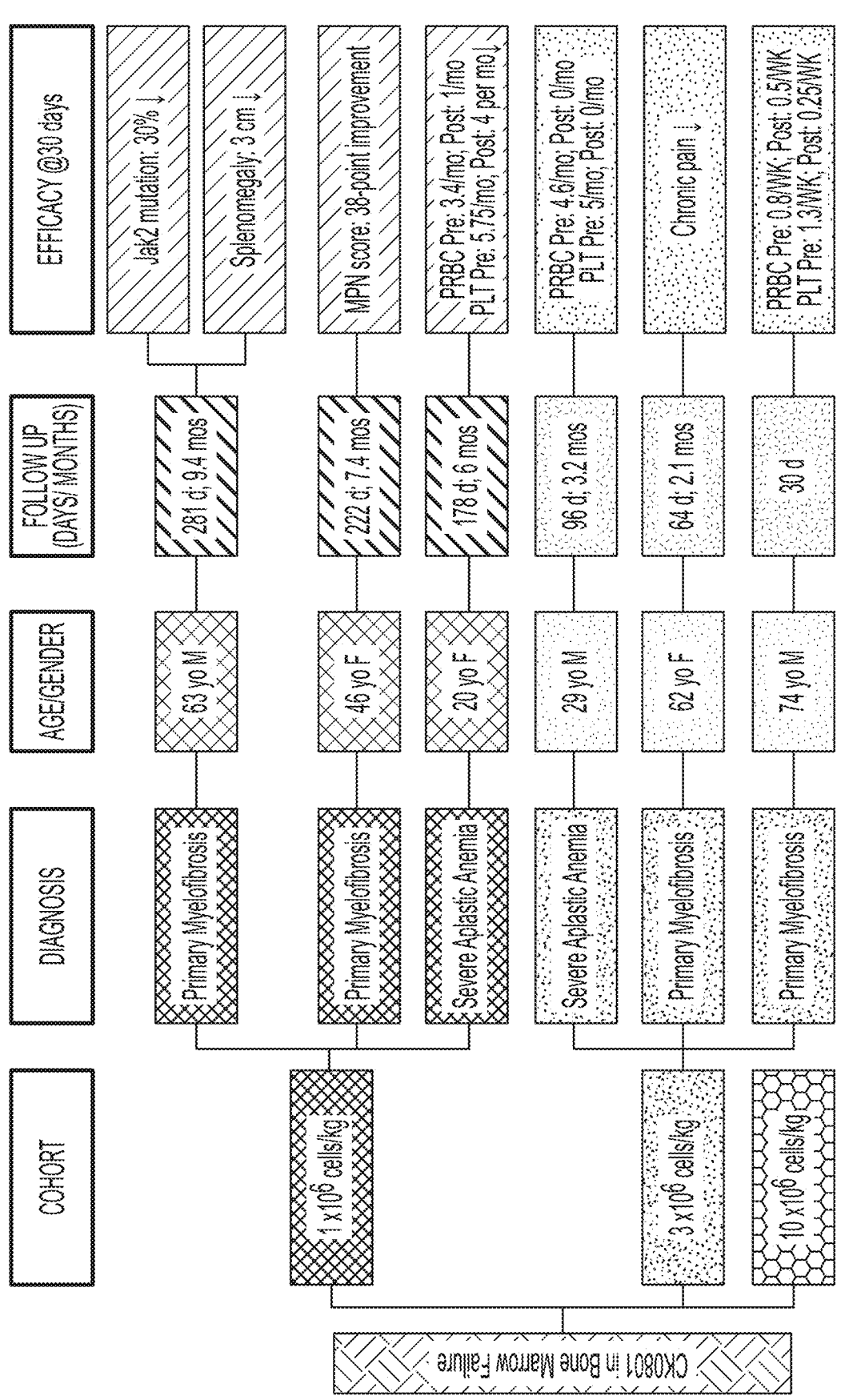
FIG. 42 depicts a diagram summarizing clinical data from a Phase 1 clinical trial of allogeneic cord blood-derived Treg cells in patients with BMF.
Figure 44:
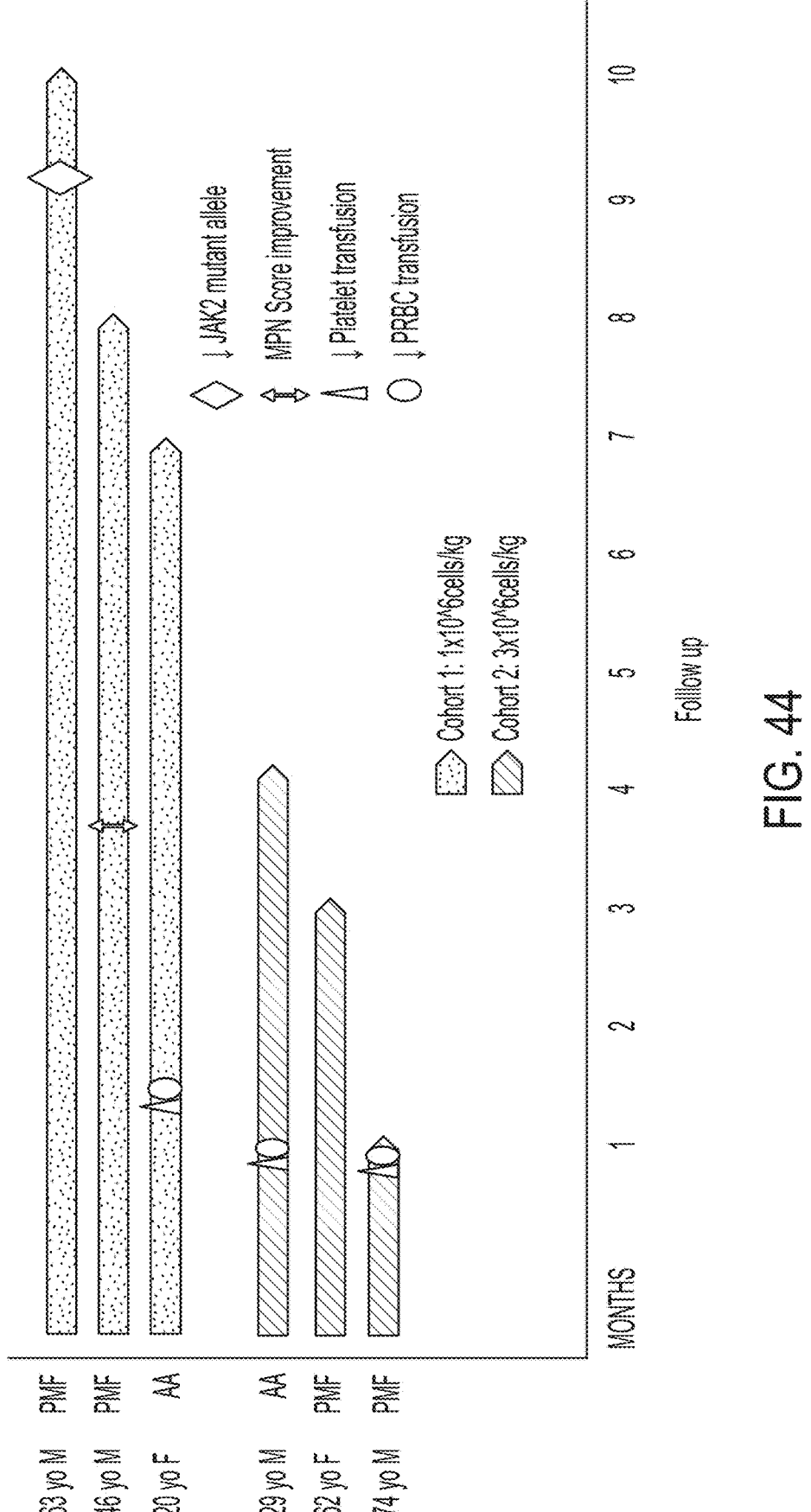
FIG. 44 depicts a graph summarizing the durability of response data from a Phase 1 clinical trial of allogeneic cord blood-derived Treg cells in patients with BMF.

FIG. 42 provides a description of the subjects undergoing treatment in the Phase 1 clinical trial. A summary of clinical data is provided in FIG. 43 and FIG. 44.

Cohort I

Figure 45:
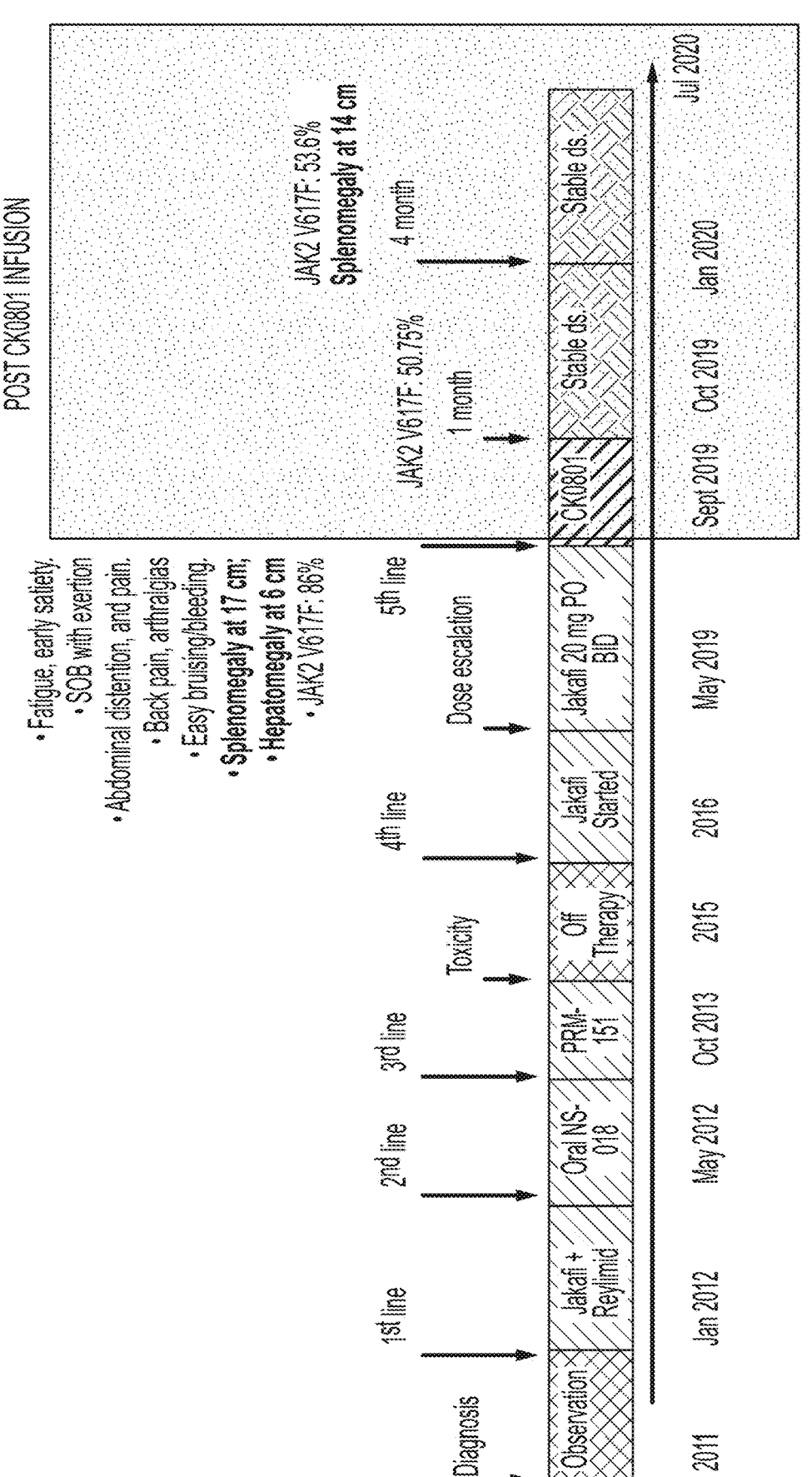
FIG. 45 depicts a diagram summarizing the treatment history of Patient 1 in a Phase 1 clinical trial of allogeneic cord blood-derived Treg cells in patients with BMF.
Figures 46A, 46B:
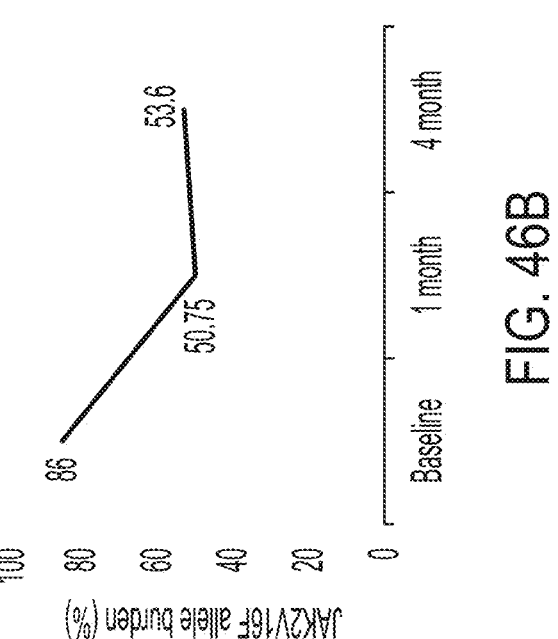
FIG. 46A-FIG. 46B depict the clinical data of Patient 1 in a Phase 1 clinical trial of allogeneic cord blood-derived Treg cells in patients with BMF at baseline and 1 month and 4 months after administration of Treg cells.
Figure 48:
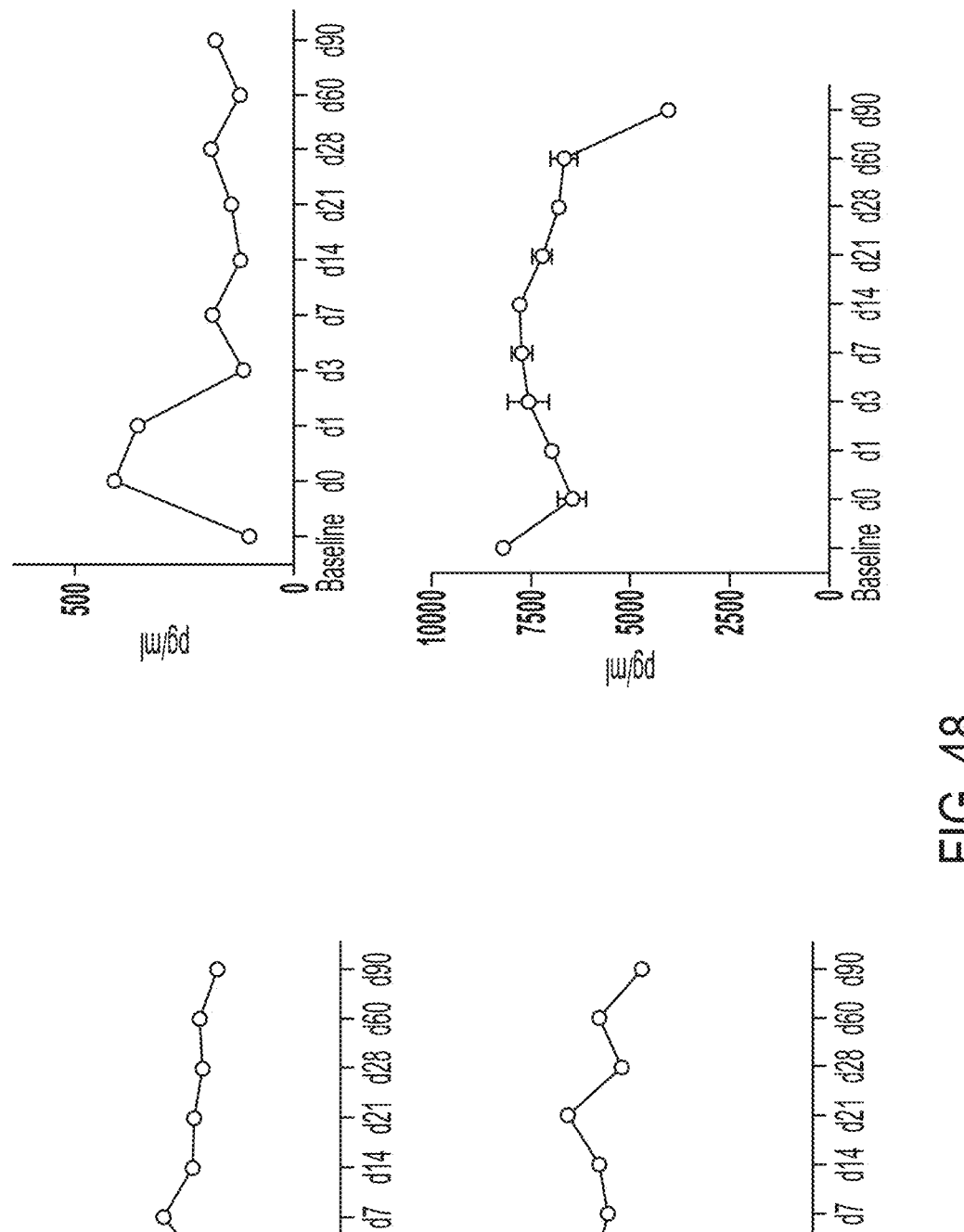
FIG. 48 is a series of graphs depicting inflammatory cytokine levels of Patient 1 in a Phase 1 clinical trial of allogeneic cord blood-derived Treg cells in patients with BMF. The x-axis shows days after administration of Treg cells. Upper left panel: IL-8. Upper right panel: sCD40L. Lower left panel: MIP-1. Lower right panel: SDF-1α+1β.
Figure 49:
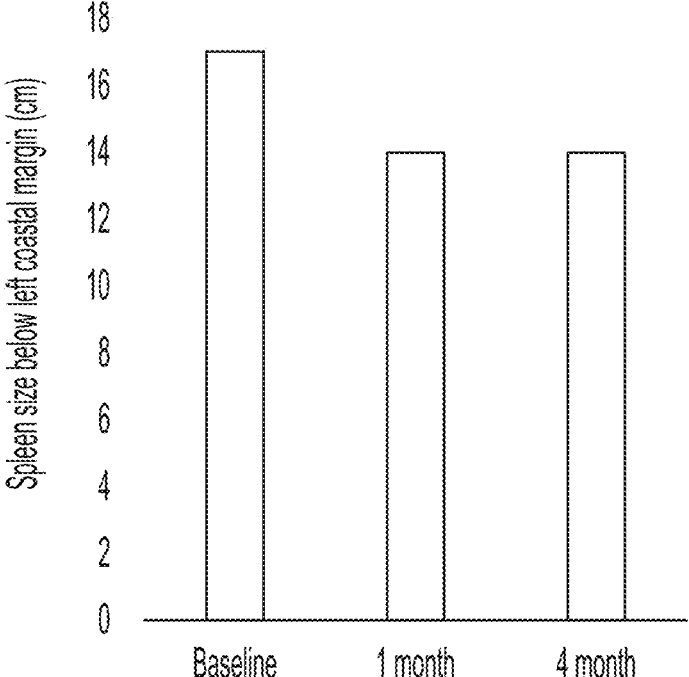
FIG. 49 depicts a bar graph showing the splenomegaly measurements of Patient 1 in a Phase 1 clinical trial of allogeneic cord blood-derived Treg cells in patients with BMF at baseline and 1 month and 4 months after administration of Treg cells.

The treatment history for Patient 1 is shown in FIG. 45. The patient is a 63-year-old male diagnosed with primary myelofibrosis. The patient was treated with $1 \times 10^6$ Treg cells/kg (67 million cells), infused over 17 minutes. The patient was also on ruxolitinib 20 mg PO (by mouth) BID (twice a day). The patient's clinical data is shown in FIG. 46A and FIG. 46B. Inflammatory cytokine levels are shown in FIG. 47 and FIG. 48. The patient had a decrease in JAK2 mutation burden (FIG. 46B) and splenomegaly (FIG. 49) correlated with SDF 1α-CXCR4 axis (FIG. 48). The patient's bone marrow assessments before (PRE) and after (POST) Treg cell administration are shown in Table 16, Table 17a and Table 17b.

TABLE 16

| Peripheral blood | | |
|---|---|---|
| | PRE | POST |
| WBC (K/μL) | 8.5 | 9.7 |
| HB (gm/dL) | 12.1 | 12.7 |
| PLT (K/μL) | 73 | 72 |
| ANC (K/μL) | 4.8 | 5.82 |
| BLAST (%) | 0 | 1 |

TABLE 17a

| Bone marrow | | |
|---|---|---|
| | PRE | POST |
| Blasts | 2 | 1 |
| Progranulocytes | 1 | 0 |
| Myelocytes | 6 | 2 |
| Metamyelocytes | 10 | 7 |
| Granulocytes | 50 | 62 |
| Eosinophils | 3 | 2 |
| Lymphocytes | 14 | 16 |
| Plasma Cells | 0 | 0 |
| Monocytes | 5 | 2 |
| Reticulum Cells | 0 | 0 |
| Pronormoblasts | 0 | 0 |
| Normoblasts | 6 | 7 |
| M:E ratio | 12.2 | 10.7 |
| Mast Cells | 0 | 0 |

TABLE 17b

| Bone marrow | | |
|---|---|---|
| | PRE | POST |
| Cellularity (%) | 5-20 | 20 |
| Diagnosis | Persistent Myelofibrosis, MF-3 Hypocelleular bone marrow with atypical megakaryocytic maturation | Persistent myeloproliferative neoplasm with myelofibrosis (MF-3) |
| JAK2 mutant allele (%) | 86 | 50.75 |
| Cytogenetics | 46XY, dell3q12q32, dellq23 | 46XY del 11423 |

Figure 50:
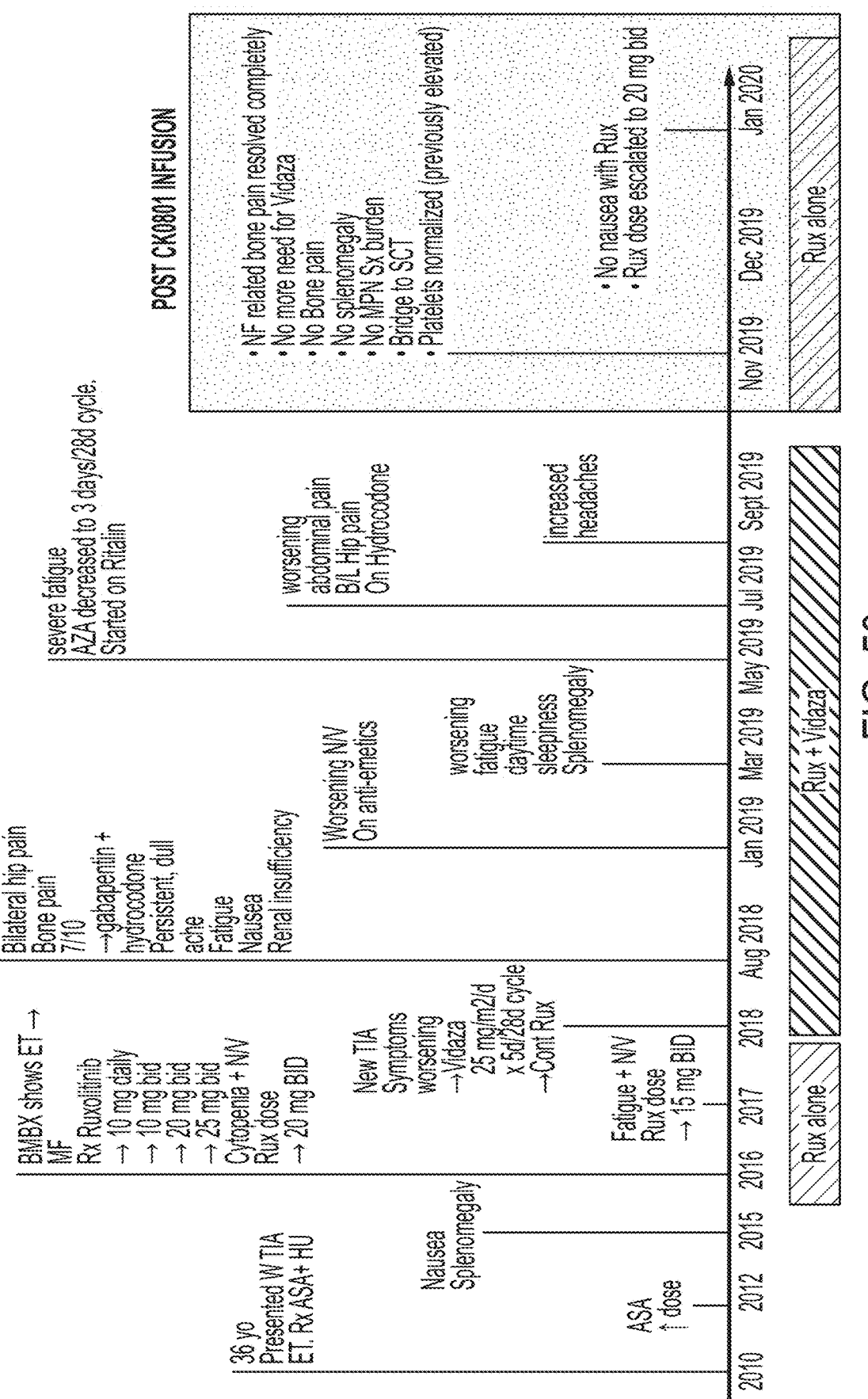
FIG. 50 depicts a diagram summarizing the treatment history of Patient 2 in a Phase 1 clinical trial of allogeneic cord blood-derived Treg cells in patients with BMF.
Figure 51:
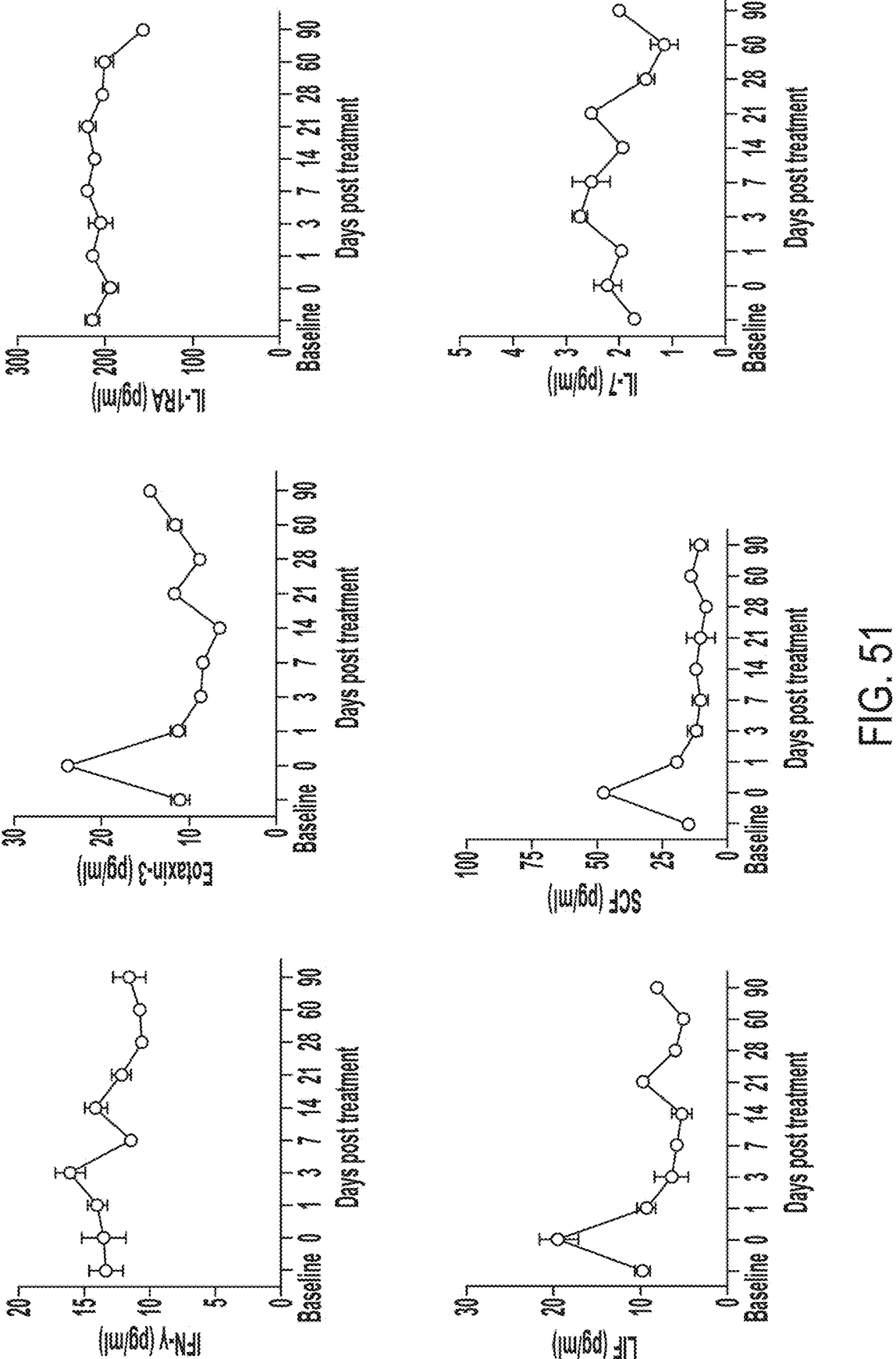
FIG. 51 is a series of graphs depicting inflammatory cytokine levels of Patient 2 in a Phase 1 clinical trial of allogeneic cord blood-derived Treg cells in patients with BMF. The x-axis shows days after administration of Treg cells.

The treatment history for Patient 2 is shown in FIG. 50. The patient is a 46-year-old female diagnosed with Myeloproliferative Neoplasm (MPN) in Adolescents and Young Adults (AYA). The patient was treated with $1 \times 10^6$ Treg cells/kg (60 million cells), infused over 20 minutes. The patient was also on ruxolitinib 20 mg PO (by mouth) BID (twice a day). Inflammatory cytokine levels are shown in FIG. 51. The patient's bone marrow assessments before (PRE) and after (POST) Treg cell administration are shown in Table 18, Table 19 and Table 20.

TABLE 18

| Peripheral blood | | |
| --- | --- | --- |
| | PRE | POST |
| WBC (K/µL) | 3.7 | 3.2 |
| HB (gm/dL0 | 10.8 | 10 |
| PLT (K/µL) | 329 | 291 |
| ANC (K/µL) | 2 | 2 |
| BLAST (%) | 0 | 0 |

TABLE 19

| Bone marrow | | |
| --- | --- | --- |
| | PRE | POST |
| Blasts | 1 | 1 |
| Progranulocytes | 0 | 1 |
| Myelocytes | 10 | 7 |
| Metamyelocytes | 13 | 11 |
| Granulocytes | 45 | 35 |
| Eosinophils | 1 | 1 |
| Lymphocytes | 18 | 20 |
| Plasma Cells | 1 | 1 |
| Monocytes | 2 | 2 |
| Reticulum Cells | 0 | 0 |
| Pronormoblasts | 0 | 2 |
| Normoblasts | 10 | 20 |
| M:E ratio | 6.9 | 2.5 |
| Mast Cells | 0 | 0 |

TABLE 20

| Bone marrow | | |
| --- | --- | --- |
| | PRE | POST |
| Cellularity (%) | <10% | 30% |
| Diagnosis | Hypocellular marrow with trilineage hypoplasia | Persistent myeloid neoplasm with increased hyperlobulated megakaryocytes consistent with ET with therapy effect, MF-1 |

Figure 52:
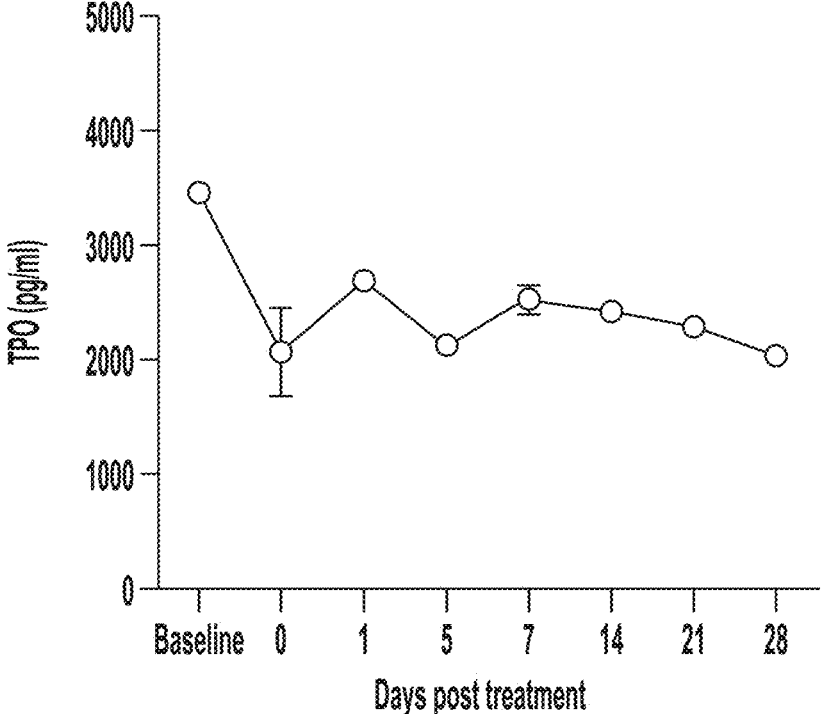
FIG. 52 depicts a graph showing TPO levels over time of Patient 3 in a Phase 1 clinical trial of allogeneic cord blood-derived Treg cells in patients with BMF.
Figure 53:
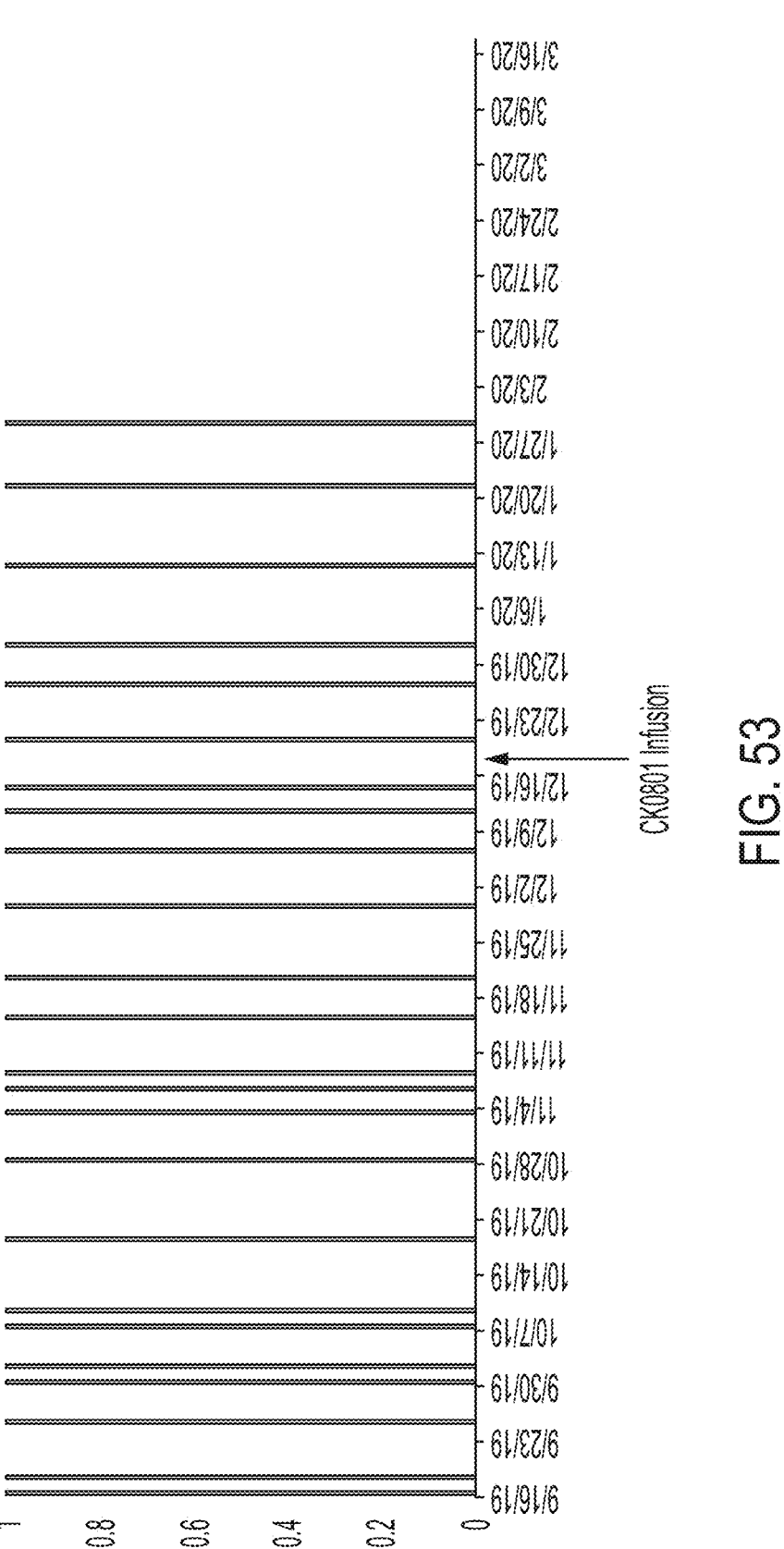
FIG. 53 depicts platelet (PLT) transfusion requirements over time for Patient 3 in a Phase 1 clinical trial of allogeneic cord blood-derived Treg cells in patients with BMF.
Figure 54:
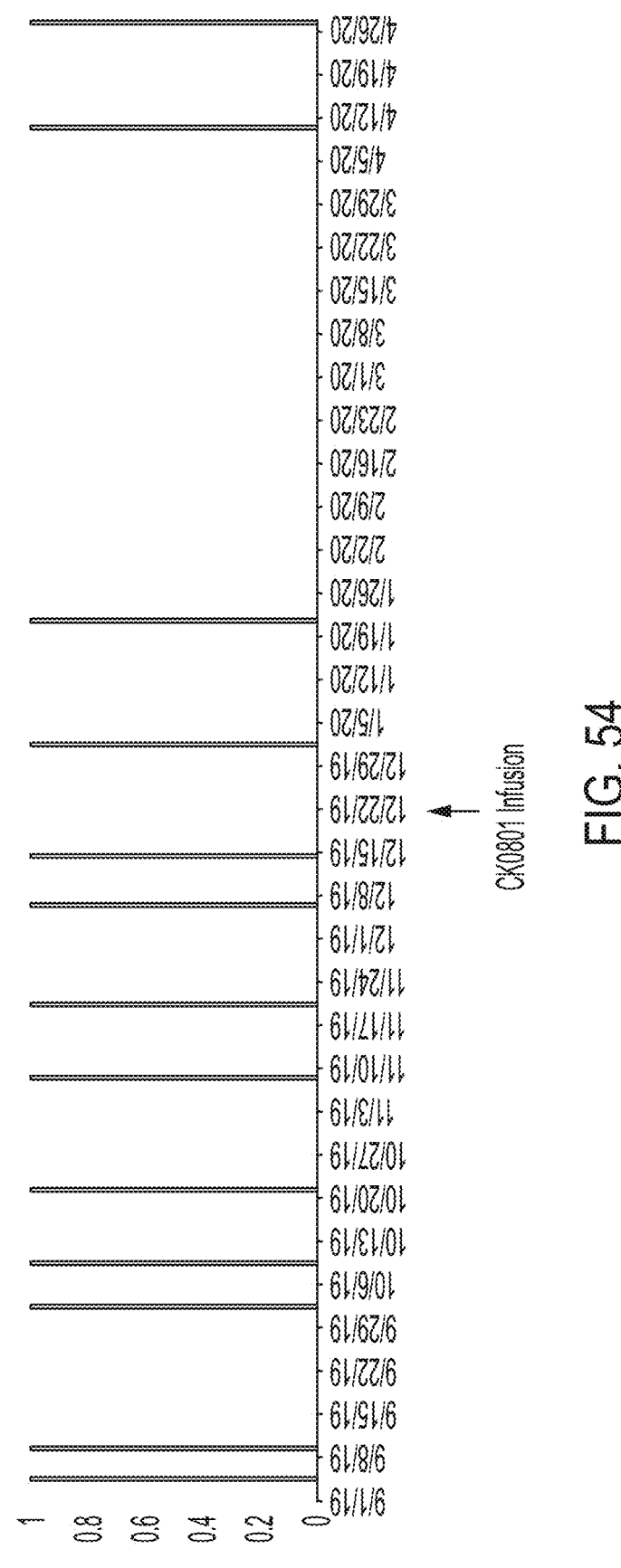
FIG. 54 depicts packed red blood cells (PRBC) transfusion requirement over time for Patient 3 in a Phase 1 clinical trial of allogeneic cord blood-derived Treg cells in patients with BMF.

Patient 3 is a 19-year-old female diagnosed with acquired aplastic anemia and is transfusion dependent. The patient was treated with $1 \times 10^6$ Treg cells/kg (50 million cells), infused over 25 minutes. The patient was also on eltrombopag and cyclosporine (CSA). The patient's TPO levels over time are shown in FIG. 52. The patient's platelet transfusion requirement over time is shown in FIG. 53. The patient's PRBC (packed red blood cells) transfusion requirement over time is shown in FIG. 54. The patient's bone marrow assessments before (PRE) and after (POST) Treg cell administration are shown in Table 21, Table 22 and Table 23.

TABLE 21

| Peripheral blood | | |
| --- | --- | --- |
| | PRE | POST |
| WBC (K/µL) | 3.1 | 2.1 |
| HB (gm/dL) | 9.8 | 8.2 |
| PLT (K/µL) | 10 | 47 |
| ANC (K/µL) | 1.54 | 1 |
| BLAST (%) | 0 | 0 |

TABLE 22

| Bone marrow | | |
| --- | --- | --- |
| | PRE | POST |
| Blasts | 2 | 0 |
| Progranulocytes | 2 | 1 |
| Myelocytes | 10 | 9 |
| Metamyelocytes | 19 | 8 |
| Granulocytes | 40 | 25 |
| Eosinophils | 0 | 2 |
| Lymphocytes | 6 | 13 |
| Plasma Cells | 0 | 2 |
| Monocytes | 4 | 3 |
| Reticulum Cells | 0 | 0 |
| Pronormoblasts | 1 | 1 |
| Normoblasts | 15 | 35 |
| M:E ratio | 4.4 | 1.3 |
| Mast Cells | 0 | 0 |

TABLE 23

| Bone marrow | | |
| --- | --- | --- |
| | PRE | POST |
| Cellularity (%) | 30-80, | 70% |
| Diagnosis | Megakaryocytic hypoplasia and dysgranulopoeisis | Cellular bone marrow with trilineage hematopoeisis |

Cohort II

Figure 55:
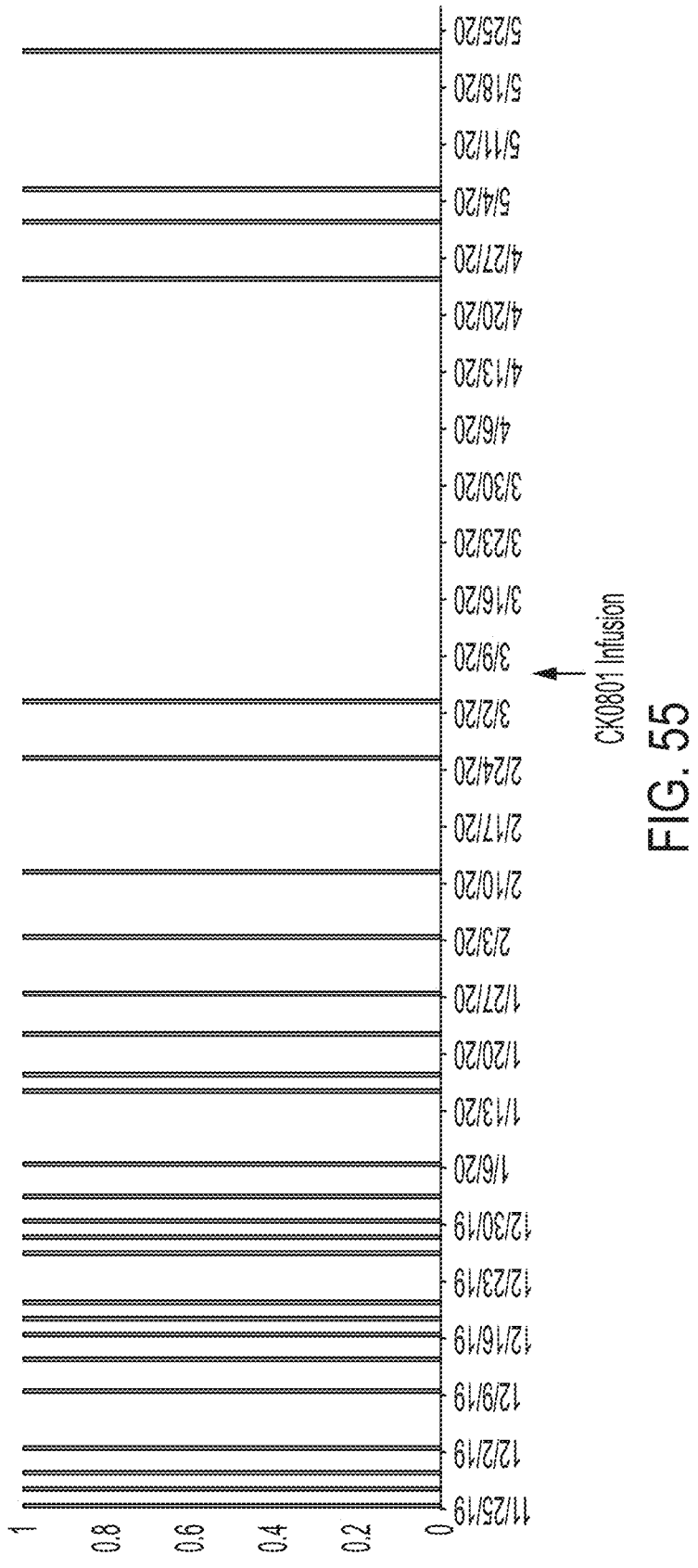
FIG. 55 depicts platelet (PLT) transfusion requirements over time for Patient 4 in a Phase 1 clinical trial of allogeneic cord blood-derived Treg cells in patients with BMF.
Figure 56:
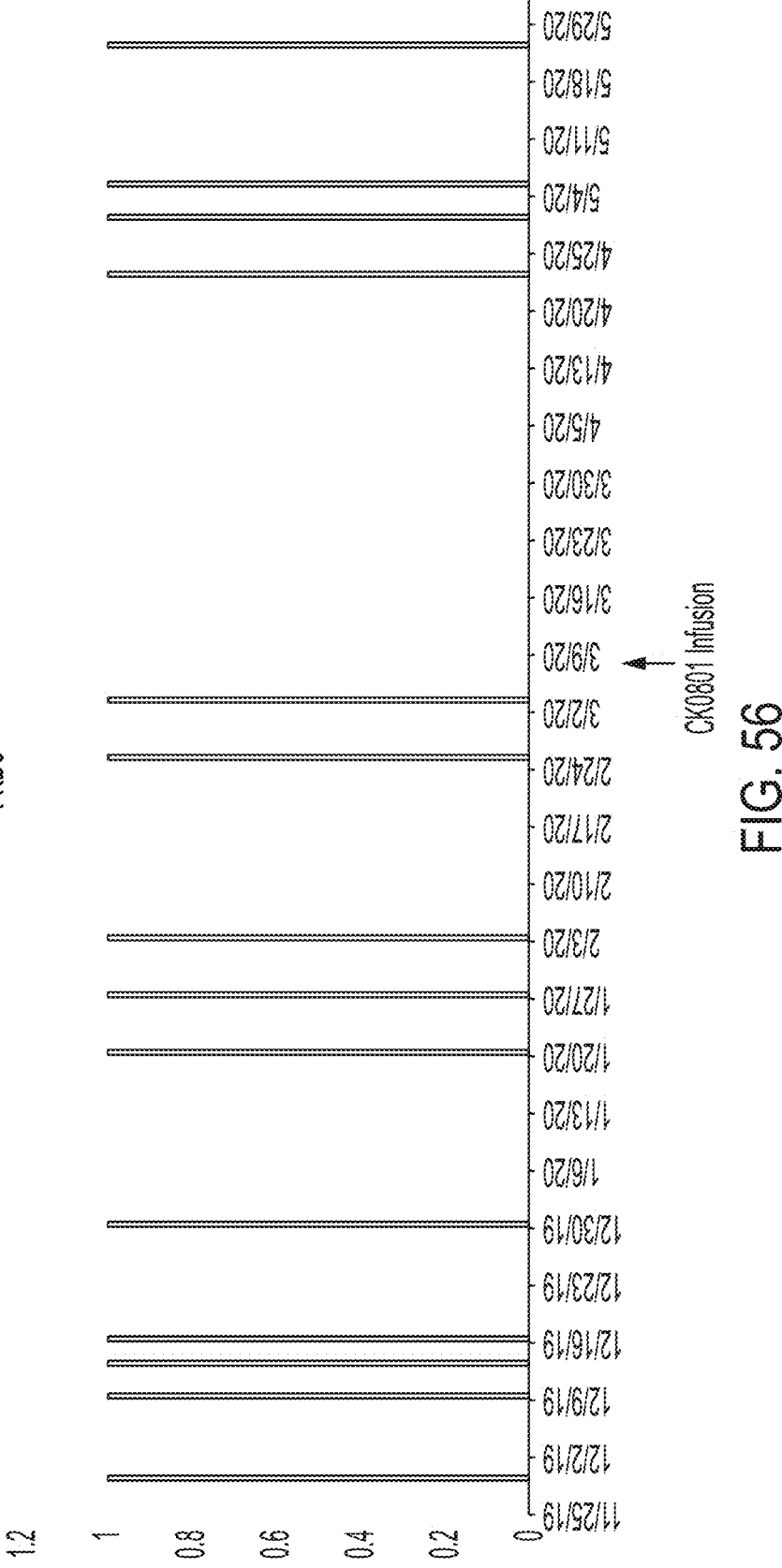
FIG. 56 depicts packed red blood cells (PRBC) transfusion requirement over time for Patient 4 in a Phase 1 clinical trial of allogeneic cord blood-derived Treg cells in patients with BMF.

Patient 4 is a 29-year-old male diagnosed with idiopathic severe aplastic anemia. The patient was treated with $3 \times 10^6$ Treg cells/kg. The patient was also on hATG+CSA+Steroids+eltrombopag+Peg-filgrastim. The patient's platelet transfusion requirement over time is shown in FIG. 55. The patient's PRBC (packed red blood cells) transfusion requirement over time is shown in FIG. 56. The patient's bone marrow assessments before (PRE) and after (POST) Treg cell administration are shown in Table 24, Table 25 and Table 26.

TABLE 24

| Peripheral blood | | |
| --- | --- | --- |
| | PRE | POST |
| WBC (K/µL) | 6.8 | 6.0 |
| HB (gm/dL) | 8.3 | 7.8 |
| PLT (K/µL) | 9 | 22 |
| ANC (K/µL) | 4.5 | 3.69 |
| BLAST (%) | | 0 |

TABLE 25

| Bone marrow | | |
| --- | --- | --- |
| | PRE | POST |
| Blasts | 2 | 1% |
| Progranulocytes | 2 | 2 |
| Myelocytes | 8 | 7 |
| Metamyelocytes | 12 | 13 |
| Granulocytes | 31 | 34 |
| Eosinophils | 2 | 1 |
| Lymphocytes | 15 | 14 |
| Plasma Cells | 2 | 2 |
| Monocytes | 3 | 3 |
| Reticulum Cells | 0 | 0 |
| Pronormoblasts | 1 | 1 |
| Normoblasts | 23 | 21 |

TABLE 25-continued

| Bone marrow | | |
| --- | --- | --- |
| | PRE | POST |
| M:E ratio | 2.3 | 2.6 |
| Mast Cells | 0 | 0 |

TABLE 26

| Bone marrow | | |
| --- | --- | --- |
| | PRE | POST |
| Cellularity (%) | 10-80, overall 60 | 40 |
| Diagnosis | Trilineage hematopoiesis with marked megakaryocytic hypoplasia and mild dysmyelopoiesis | Cellular (30-40%) bone marrow showing mild to moderate megakaryocytic hypoplasia. Mild plasmacytosis |

Patient 5 is a 62-year-old female diagnosed with primary myelofibrosis (essential thrombocythemia (ET). The patient was treated with $3 \times 10^6$ Treg cells/kg. The patient's bone marrow assessments before (PRE) and after (POST) Treg cell administration are shown in Table 27, Table 28 and Table 29.

TABLE 27

| Peripheral blood | | |
| --- | --- | --- |
| | PRE | POST |
| WBC (K/μL) | 10.3 | 12.1 |
| HB (gm/dL) | 12.5 | 12.3 |
| PLT (K/μL) | 465 | 481 |
| ANC (K/μL) | 6.69 | 9.44 |
| BLAST (%) | 0 | 0 |

TABLE 28

| Bone marrow | | |
| --- | --- | --- |
| | PRE | POST |
| Blasts | 1 | 1 |
| Progranulocytes | 0 | 0 |
| Myelocytes | 10 | 7 |
| Metamyelocytes | 14 | 8 |
| Granulocytes | 40 | 29 |
| Eosinophils | 2 | 3 |
| Lymphocytes | 12 | 12 |
| Plasma Cells | 0 | 0 |
| Monocytes | 3 | 3 |
| Reticulum Cells | 0 | 0 |
| Pronormoblasts | 1 | 1 |
| Normoblasts | 17 | 37 |
| M:E ratio | 3.7 | 1.2 |
| Mast Cells | 0 | 0 |

TABLE 29

| Bone marrow | | |
| --- | --- | --- |
| | PRE | POST |
| Cellularity (%) | 80 | 80 |
| Diagnosis | MF2 CONSISTENT W Primary Myelofibrosis | Peristent myeloproliferative neoplasm with interstitial fibrosis. MF2 |
| JAK2 mutant allele | 26 | 29.2 |

Figure 57:
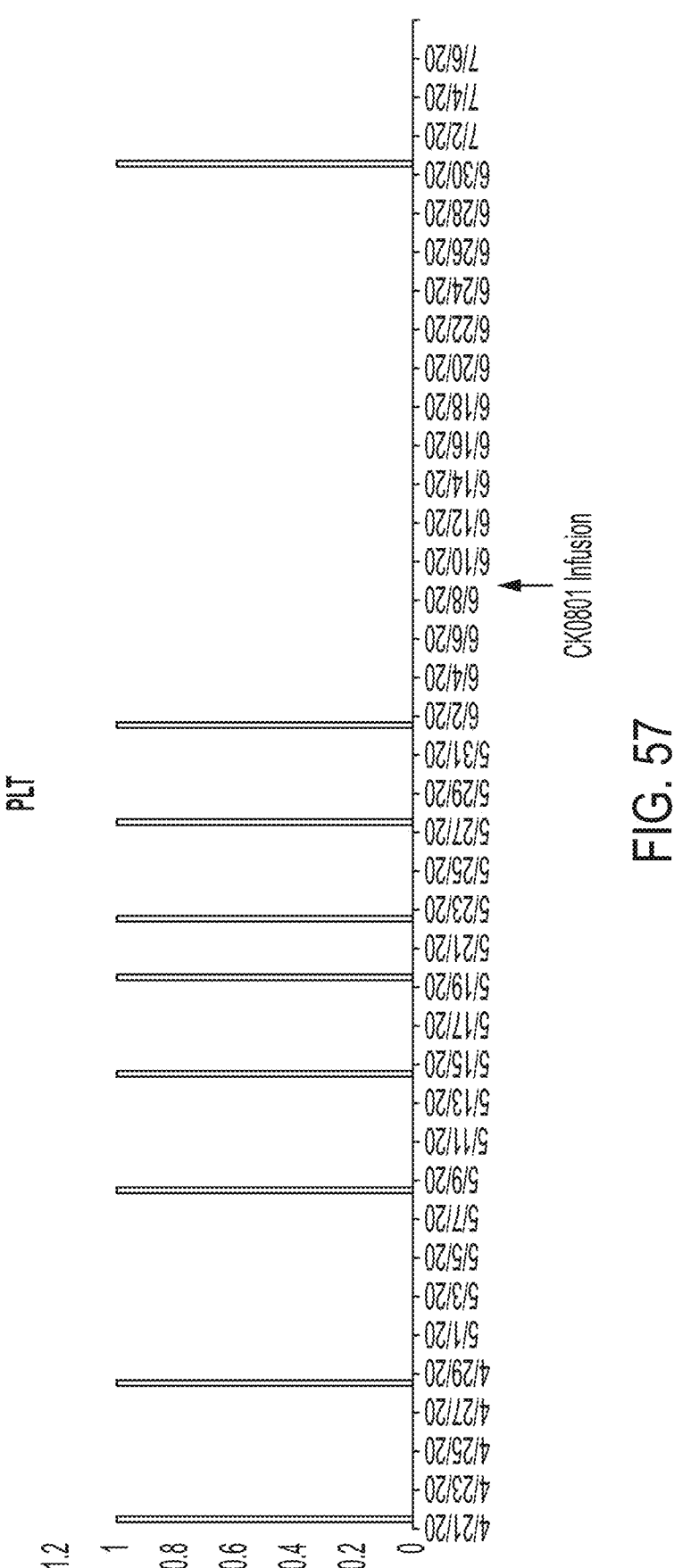
FIG. 57 depicts platelet (PLT) transfusion requirements over time for Patient 6 in a Phase 1 clinical trial of allogeneic cord blood-derived Treg cells in patients with BMF.
Figure 58:
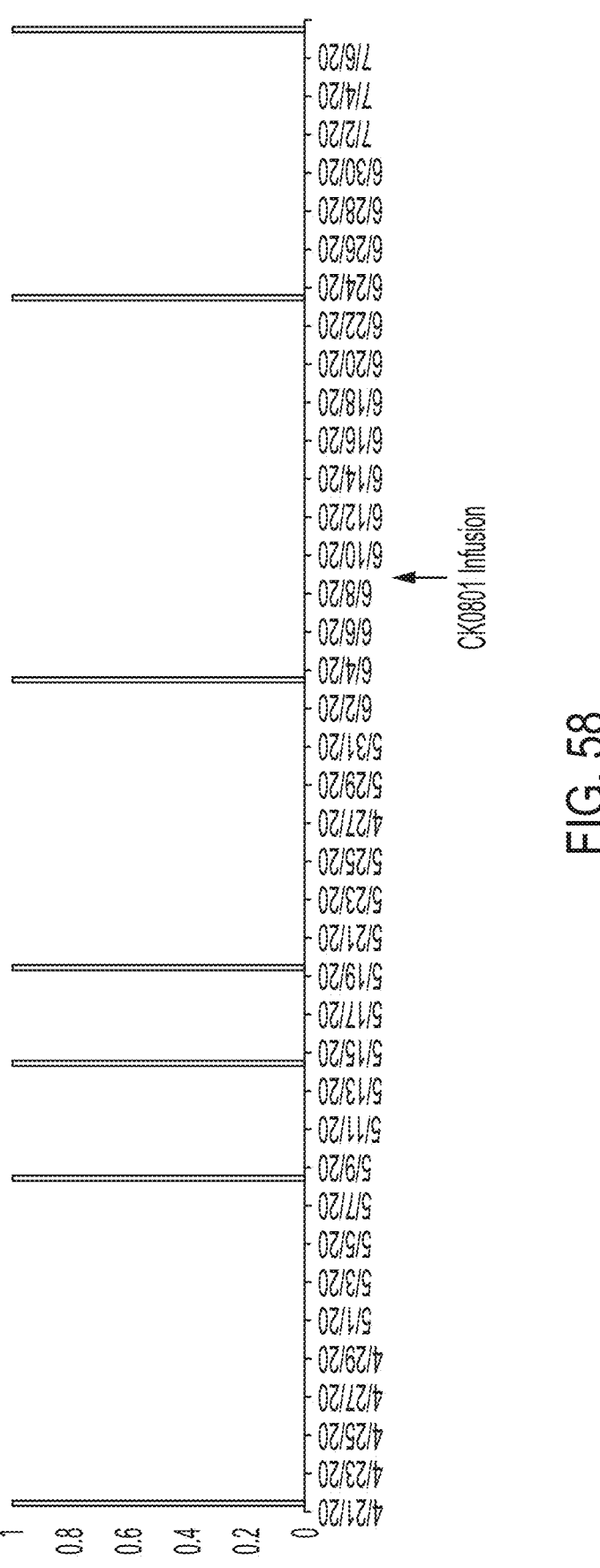
FIG. 58 depicts packed red blood cells (PRBC) transfusion requirement over time for Patient 6 in a Phase 1 clinical trial of allogeneic cord blood-derived Treg cells in patients with BMF.

Patient 6 is a 74-year-old male diagnosed with primary myelofibrosis (grade 2, hypocellularity transfusion dependent). The patient failed treatment with LCL-161 (Novartis, Basel, Switzerland). The patient was treated with $3 \times 10^6$ Treg cells/kg. The patient's platelet transfusion requirement over time is shown in FIG. 57. The patient's PRBC (packed red blood cells) transfusion requirement over time is shown in FIG. 58. The patient's bone marrow assessments before (PRE) and after (POST) Treg cell administration are shown in Table 30, Table 31 and Table 32.

TABLE 30

| Peripheral blood | | |
| --- | --- | --- |
| | PRE | POST |
| WBC (K/μL) | 5.8 | 6.9 |
| HB (gm/dL0 | 7.9 | 6.9 |
| PLT (K/μL) | 17 | 22 |
| ANC (K/μL) | 3.25 | 3.9 |
| BLAST (%) | 0 | 0 |

TABLE 31

| Bone marrow | | |
| --- | --- | --- |
| | PRE | POST |
| Blasts | 1 | 1 |
| Progranulocytes | 0 | 0 |
| Myelocytes | 2 | 8 |
| Metamyelocytes | 12 | 24 |
| Granulocytes | 38 | 29 |
| Eosinophils | 0 | 2 |
| Lymphocytes | 22 | 8 |
| Plasma Cells | 0 | 0 |
| Monocytes | 2 | 5 |
| Reticulum Cells | 0 | 0 |
| Pronormoblasts | 0 | 1 |
| Normoblasts | 22 | 33 |
| M:E ratio | 2.4 | 1.6 |
| Mast Cells | 0 | 0 |

TABLE 32

| Bone marrow | | |
|---|---|---|
| | PRE | POST |
| Cellularity (%) | 20 | Hypocellular smear |
| Diagnosis | Primary myelofibrosis, MF-3 | Persistent myelofibrosis (MF-3), increased sideroblastic iron incorporation, 16% ring sideroblasts. |
| JAK2 mutant allele | 7 | <5 |
| ASXL1 | present | present |
| U2AF1 | present | present |

CONCLUSIONS

No SAE observed in the 6 patients treated in cohort 1 (dose=1×10$^6$ cells/kg) and cohort 2 (dose=3×10$^6$ cells/ kg)

Improvement in JAK2 mutant allele in patient #1. Durability of response=6 months Improvement in MPN score in patient #2. Durability of response 4 months Improvement in red cell and platelet transfusion requirement in Patient #3. Durability of response 4 weeks Improvement in red cell and platelet transfusions in Patient #4. Durability of response 4 weeks Improvement in chronic pain in patient #5. durability 4 weeks Improvement in red cell and platelet transfusions in Patient #6. Assessment performed at 4 weeks Improvement in bone marrow cellularity in Patients #1; #2

Improvement in bone marrow dysplasia in Patients #3, #4

Decrease in M:E ratio is all cases except Patient #4 (stable)

Example 7: Evaluation of Safety and Efficacy for Administering Cord Blood-Derived T-Regulatory Cells in the Treatment of Treatment-Resistant Guillain-Barre Syndrome This study will examine whether it is safe and practical to give CK0801 (a cord-blood derived T-regulatory cell product) to patients with Guillain-Barré Syndrome (GB S). In addition, the highest possible dose that is safe to be given will be determined. Likewise, the study will also examine whether CK0801 may improve the symptoms of GBS.

Target Population

The target population for this study is patients unresponsive to standard treatment with intravenous immunoglobulin (IVIG) treatment or plasma exchange.

Enrollment

Up to 18 adult patients (ages 18-70) will be enrolled.

Eligibility

Inclusion Criteria:

1. Subject fulfills the diagnostic criteria for Guillain-Barré syndrome (GBS).
2. HLA matched (≥3/6 at HLA-A, HLA-B, and HLA-DRB1) cord blood unit available for CK0801 generation.
3. Subjects age 18 to 70 years.
4. Subject has GBS disability scale score of 4 and unchanged 1 week after IVIG or PE treatment.
5. Subject has completed IVIG/PE treatment ≥4 weeks prior to CK0801 infusion.
6. Subject has modified Erasmus GBS outcome score (mEGOS score) of ≥7 at the time of presentation and unchanged 1 week after IVIG or PE treatment.
7. Bilirubin ≤2×ULN and, ALT ≤2×ULN (unless Gilbert's syndrome).
8. Calculated creatinine clearance of >50 mL/min using the Cockroft-Gault equation for adult patients 18-70 years old.
9. Female subjects of child bearing potential (FPCP) must have a negative urine or serum pregnancy test. NOTE: FPCP is defined as premenopausal and not surgically sterilized. FPCP must agree to use maximally effective birth control or to abstain from heterosexual activity throughout the study. Effective contraceptive methods include intrauterine device, oral and/or injectable hormonal; contraception, or 2 adequate barrier methods (e.g., cervical cap with spermicide, diaphragm with spermicide).
10. Subject has agreed to abide by all protocol required procedures including study-related assessments, visits and long term follow up.
11. Subject is willing and able to provide written informed consent. If subject is temporarily unable to sign the consent due to disease-related complications (e.g., upper extremity paralysis), a legally authorized representative (LAR) will be used. The subject will sign the consent as soon as they are capable.

Exclusion Criteria:

1. Subject has received immunotherapy, chemotherapy, biologic or investigational agent within 4 weeks prior to CK0801 infusion.
2. Subject has received prior CB Treg therapy.
3. Subject has uncontrolled infection, not responding to appropriate antimicrobial agents after seven days of therapy. The Protocol PI is the final arbiter of eligibility.
4. Subject has received a vaccination with a live virus (e.g., Measles, Mumps, Rubella, Varicella).
5. Subject is pregnant or breastfeeding.
6. HIV seropositivity
7. Subjects who are unable to provide consent or who, in the opinion of the Investigator will be unlikely to fully comply with protocol requirements.

Arms and Interventions

TABLE 33

| Arms | Interventions |
|---|---|
| Experimental: CK0801 Adoptive therapy with infusion of unrelated cord blood-derived regulatory T cells: CK0801. Patients will receive one 50 mL intravenous dose of CK0801(on study Day 0). There will be a total of 3 dose cohorts. | Biological/Vaccine: CK0801 CK0801 (Cord blood-derived T-regulatory cells) |

TABLE 33-continued

| Arms | Interventions |
| --- | --- |

Cohort dosing will be as follows:
Dose level 1 = 1 × $10^6$/kg Treg cells per kg recipient
ideal body weight (IBW);
Dose level 2 = 3 × $10^6$/kg Treg cells per kg recipient
ideal body weight (IBW);
Dose level 3 = 1 × $10^7$/kg Treg cells per kg recipient
ideal body weight (IBW).

Dosing (phase I 3+3)

Three doses of CK0801 will be given during this study. A minimum of three patients will be treated in each dose level. The dose a patient receives is dependent on the timing of when they enter the study, as after each dose level is completed the following patients will receive the next highest dose level.

Dose Level 1: CK0801 IV 1×$10^6$/kg of ideal body weight
Dose Level 2: CK0801 IV 3×$10^6$/kg of ideal body weight
Dose Level 3: CK0801 IV 1×$10^7$/kg of ideal body weight Primary Endpoints The primary endpoints of this study will be dose limiting toxicity:

severe (grade 3 or 4) infusion toxicity within 24 hours;
severe (grade 3 or 4) cytokine release syndrome within 30 days;
regimen related death within 30 days Outcome Measures Primary Outcome Measure:

1. The number of adverse events and serious adverse events will be collected to provide a preliminary evaluation of the safety of infusing CK0801 in Guillain-Barré syndrome (GBS) patients unresponsive to standard treatment with intravenous immunoglobulin
[Time Frame: 30 days from infusion]
2. Dose limiting toxicity will be defined to include any of the following events (each starting at the time of CK0801 infusion).
severe (grade 3 or 4) infusion toxicity within 24 hours (NCI-CTCAE V4.0)
regimen related death within 30 days,
severe (grade 3 or 4) cytokine release syndrome (CRS) within 30 days
[Time Frame: 30 days from infusion]

Other Pre-Specified Outcome Measures:

3. Assessment of peripheral blood (PB) profiling after the infusion of CK0801 Evaluation whether infusion of CK0801 on Day 0 has caused the patient to develop changes in in their peripheral blood properties
[Time Frame: Screening, Day 0 and Week 1, 2, 4, 12, and 24]
4. Assessment of peripheral blood inflammatory cytokines after the infusion of CK0801 Evaluation whether infusion of CK0801 on Day 0 has caused the patient to develop inflammatory cytokines in their peripheral blood
[Time Frame: Screening, Day 0 and Week 1, 2, 4, 12, and 24]
5. Assessment of potential changes in the GBS disability score (a questionnaire)
Questionnaire that assesses 7 scores for disability, ranging from a healthy state (0) to dead (6)
[Time Frame: Screening, Day 0 and Week 1, 2, 4, 12, and 24]

6. Assessment of potential changes in the Overall Neuropathy Limitations Scale (ONLS) (a questionnaire)

The overall Neuropathy Limitation Scale (ONLS) is a questionnaire that determines symptoms in the patients' arms (numbness, tingling, weakness) and legs (ability to walk, run, gait changes, need for wheelchair) when performing normal daily activities. Arm scale is 0 (normal) to 5 (disability in both arms preventing all purposeful movements) and leg scale is 0 (walking/climbing stairs/running not affected to 7 (restricted to wheelchair or bed most of the day, unable to make any purposeful movements in the legs.
[Time Frame: Screening, Day 0 and Week 1, 2, 4, 12, and 24]

7. Assessment of potential changes in the Rasch-built Overall Disability Scale (a questionnaire)

A questionnaire that measures relationship between daily activities and health of the patient. The score is 0-2 where 0=not possible to perform activity and 2=the activity is easy to perform. The questionnaire includes activities such as walking indoors or outdoors, washing upper or lower body, dressing, eating, doing dishes, shopping. The overall summed raw score goes from 1-48 that correlates to a centrile metric of 0-100.
[Time Frame: Screening, Day 0 and Week 1, 2, 4, 12, and 24]

8. Assessment of potential changes in the MRC (Medical Research Council) sum score (a questionnaire)

MRC sum score is the sum of MRC scores of 6 muscle groups, including shoulder abductors, elbow flexors, wrist extensors, knee extensors, and foot dorsiflexors on both sides, ranging from 60 (normal) to 0 (quadriplegic).
[Time Frame: Screening, Day 0 and Week 1, 2, 4, 12, and 24]

9. Assessment of potential changes in the Rasch-built MRC model (a questionnaire) MRC sum score is the sum of MRC scores of 6 muscle groups, including shoulder abductors, elbow flexors, wrist extensors, knee extensors, and foot dorsiflexors on both sides, ranging from 48 (normal) to 0 (quadriplegic).
[Time Frame: Screening, Day 0 and Week 1, 2, 4, 12, and 24]

10. Assessment of potential changes in the Fatigue Severity Scale (FSS) (a questionnaire)

A questionnaire that measures activities related to fatigue on scales of 9 (no signs of fatigue) to 63 (most disabling fatigue)
[Time Frame: Screening, Day 0 and Week 1, 2, 4, 12, and 24]

11. Assessment of potential changes in the Rasch-built Fatigue Severity Scale (RFSS) (a questionnaire)

A questionnaire that measures activities related to fatigue on scales of 0 (no signs of fatigue) to 21 (most disabling fatigue)
[Time Frame: Screening, Day 0 and Week 1, 2, 4, 12, and 24]

12. Assessment of potential changes in the EuroQol E-5D Health Questionnaire (a questionnaire)

The EuroQol E-5D Health Questionnaire is a validated and simple Health Questionnaire for testing the patient's mobility, ability to conduct self-care activities, other usual activities (e.g., housework, leisure activities), their pain/discomfort level, and the presence of anxiety/depression. The scale is 0 (worst health patient can imagine) to 100 (best health the patient can imagine).

[Time Frame: Screening, Day 0 and Week 1, 2, 4, 12, and 24]

13. Assessment of potential changes in the patient condition based on comparison of Form A Entry Questionnaire to follow-up questionnaire Form B (week 1 and 2 questionnaires) (a questionnaire)

The Entry Questionnaire establishes a screening level baseline in the patients' overall status including comorbidity affecting respirations or mobility, other family members with GBS, antecedent events (e.g., common cold, gastroenteritis), type of pain (e.g., muscle pain, joint pain, neuropathic pain), location of pain, weakness in arms or legs, condition of reflexes, sensory deficits, ataxia, forced vital capacity. The form allows the user to predict if the patient will require ventilation or will be able to walk in 6 months.

[Time Frame: Screening, Day 0 and Week 1, and 2]

14. Assessment of potential changes in the patient condition based on comparison of Form A Entry Questionnaire to follow-up questionnaire Form B (week 4, 12, and 24 questionnaires) (a questionnaire)

This form (questionnaire) uses the same information as the Entry Questionnaire to provide a mechanism to document changes in patient status since enrollment.

[Time Frame: Screening, Day 0 and Week 1, 2, 4, 12, and 24]

15. Assessment of potential changes in the patient condition based on comparison of Form A Entry Questionnaire to follow-up questionnaire Form C (week 1, 2 4, 12, and 24 questionnaires) (a questionnaire)

This form (questionnaire) uses the same information as the Entry Questionnaire to provide a mechanism to document changes in patient status since enrollment.

[Time Frame: Screening, Day 0 and Week 1, 2, 4, 12, and 24]

16. Assessment of potential changes in the patient condition based on comparison of Form A Entry Questionnaire to follow-up questionnaire Form T (week 1, 2 4, 12, and 24 questionnaires) (a questionnaire)

This form (questionnaire) uses the same information as the Entry Questionnaire to provide a mechanism to document changes in patient status since enrollment.

[Time Frame: Screening, Day 0 and Week 1, 2, 4, 12, and 24]

Example 8: Evaluation of Safety and Efficacy for Administering Cord Blood-Derived T-Regulatory Cells in the Treatment of Acquired Idiopathic Aplastic Anemia and Hypoplastic Myelodysplastic Syndrome Target Population The target population for this study is patients that are ineligible for matched sibling donor hematopoietic stem cell transplant (MSD HSCT) or predicted to be poor responder to immunosuppressive therapy (IST).

Enrollment

Up to 18 adult patients will be enrolled.

Dosing

Dose Level 1: CK0804 IV $1\times10^8$ cells

Dose Level 2: CK0804 IV $3\times10^8$ cells

Primary Endpoints

The primary endpoints of this study will be time to infusion reaction; cytokine release syndrome, and/or death within 30 days.

Secondary Endpoints

The secondary endpoints for this study will be hematological improvement.

Example 9: Evaluation of Safety and Efficacy of Administering Cord Blood-Derived T-Regulatory Cells in the Treatment of Amyotrophic Lateral Sclerosis Target Population Adult ALS patients ($\geq18$ years of age) with acquired ALS Ability to provide informed consent Subjects with disease onset $\leq2$ years Forced Vital Capacity $\geq60\%$ predicted Subjects have a total ALSFRS-R score $\geq24$ and a score of at least 2 points on all 12 items of the scale Patients with greater than 0.3 point/month progression from onset to screen Enrollment 52 adult patients.

Study Drug

CK0803 (Cryopreserved, multi-dose, Cord blood-derived T-regulatory cells enriched in CD11a)

Dosing

Induction: Weekly IV CK0803 dose×4 at the following dose levels

Cohort 1: CK0803 IV $1\times10^8$ Treg cells

Cohort 2: CK0803 IV $3\times10^8$ Treg cells

Maintenance: Additional 6 doses every 4 weeks for both cohorts

Arms and Interventions

TABLE 34

| Arms | Interventions |
|---|---|
| Experimental: CK0803<br>Adoptive therapy with infusion of multiple doses of cryopreserved unrelated cord blood-derived regulatory T cells: CK0803.<br>Patients will receive 30 mL intravenous dose of CK0803 (on study days).<br>There will be a total of 2 dose cohorts.<br>Cohorts will use fixed dosing as follows:<br>Dose level 1 = 1 × 10⁸ Treg cells<br>Dose level 2 = 3 × 10⁸ Treg cells | Biological/Vaccine: CK0803<br>CK0803 (Cryopreserved, multi-dose, Cord blood-derived T-regulatory cells enriched in CD11a) |

Figure 26:
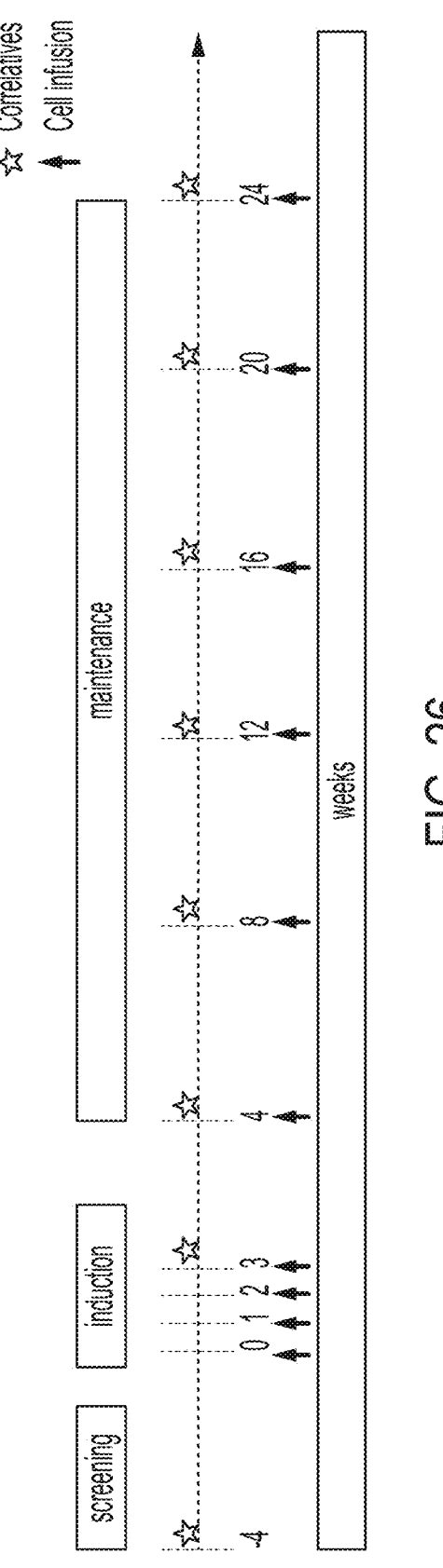
FIG. 26 depicts a time line for a clinical trial to evaluate safety and efficacy of administering cord blood-derived T regulatory cells in the treatment of Amyotrophic Lateral Sclerosis as described in Example 9.

The treatment time line is shown in FIG. 26.

Phase IB:

Primary Objective

Safety and tolerability

Treatment related adverse events per CTCAE v 4.03 (AE, SAE, DLT)

Secondary Objective

Efficacy

Revised ALS Functional Rating Scale (ALSFRS-R)

Forced Vital Capacity (FVC)

Hand-Held Dynamometry (HHD) for muscle strength

Exploratory

Inflammatory biomarkers and immune reconstitution

Study Endpoints

Clinical Response:

1. Improvement on the revised ALS Functional Rating Scale (ALSFRS-R) by six points over a 6-month period.
2. Rate of change of functional status
3. Change in the slope of Amyotrophic Lateral Sclerosis Functional Rating Scale (ALSFRS-R) score
4. Change in Forced Vital Capacity (FVC) and
5. Change in muscle strength ALSFR Responder Analysis (the percentage of subjects who improved post-treatment compared with pre-treatment)

The pre-specified responder analysis examines both percentage improvements and absolute point improvement per month in post treatment ALSFRS-R slope compared to pre-treatment slope.

Patient assessment for 25%, 50%, 75% and 100% improvement.

Clinically meaningful=25%

Significantly clinically meaningful=50%

Statistical significance defined as a one-sided p value <0.05 using Fisher's exact test.

Assessment Performed at 4, 8, 12, 16 and 24 Weeks

Clinical Trial Design: Phase Ib CLINICAL TRIAL

Study Design:

This study will be a Phase I, 3+3 study design, single ascending dose, SAFETY, TOLERABILITY of CK0803.

Fixed Dose Strategy will study 2 dose levels:

Low Dose: $1 \times 10^8$ cells;

High Dose: $3 \times 10^8$ cells;

A Minimum of 6 Patients and a Maximum of 12 Patients Will be Enrolled in this Study.

A cohort of 12 subjects will be randomized to one of the three treatment sequences with 3 subjects per sequence as displayed in the table above with a total (minimum) patients=12

Clinical Trial Design: Exploratory Studies.

PERIPHERAL BLOOD

T cell compartment: Treg, Effector T cell, anti-viral activity

Serum for inflammatory cytokines: Interleukin (IL) 1, IL-1beta, IL-2, IL-4, IL-6, IL7, IL-8, IL-10, IL-13, IL-17, IL-18

Interferon gamma, ST2, REG3a, OPN, Follistatin, Elafin, TGF-beta, TNF-alpha, TNFR-1

C-Reactive Protein (CRP)

Macrophage chemotactic protein-1 (MCP-1)

8-hydroxy-2'-deoxyguanosine (8-OHdG)

Malondialdehyde (MDA)

Ratio: glutathione disulfide, GSSG/reduced glutathione, GSH

Additional exploratory cytokines: SCF, G-CSF, GM-CSF, HGF, VEGF, SDF1a, MCP1, MCP2, TARC, MIP3a, TECK, CTACK, CCL28, FGF, PDGF, EGF, TGF-α, TLR

CEREBRO SPINAL FLUID phosphorylated neurofilament heavy chain (pNFH)

Chit-1

Prostaglandin E2

VEGF

IL-6

GMC SF

IL-2, IL-8, IL-15, IL-17

MIP-1β

FGF

G-CSF

MIP-1α

MCP-1

IFN-γ

RADIOGRAPHIC

Glial activation measured by in vivo [$^{11}$C]-PBR28 PET is increased in pathologically relevant regions in people with ALS and correlates with clinical measures. (Alshikho, ANN NEUROL 2018)

Integrated PET-MR and $^1$-MRS imaging demonstrates associations between markers for neuronal integrity and neuroinflammation and may provide valuable insights into disease mechanisms in ALS. (Ratai, *NeuroImage: Clinical* 20 (2018) 357-364)

Example 10: Evaluation of Safety and Efficacy of Administering Cord Blood-Derived T Regulatory Cells in the Treatment of COVID-19 (Coronavirus Disease) Mediated Acute Respiratory Distress Syndrome (CoV-ARDS)

Figure 27:
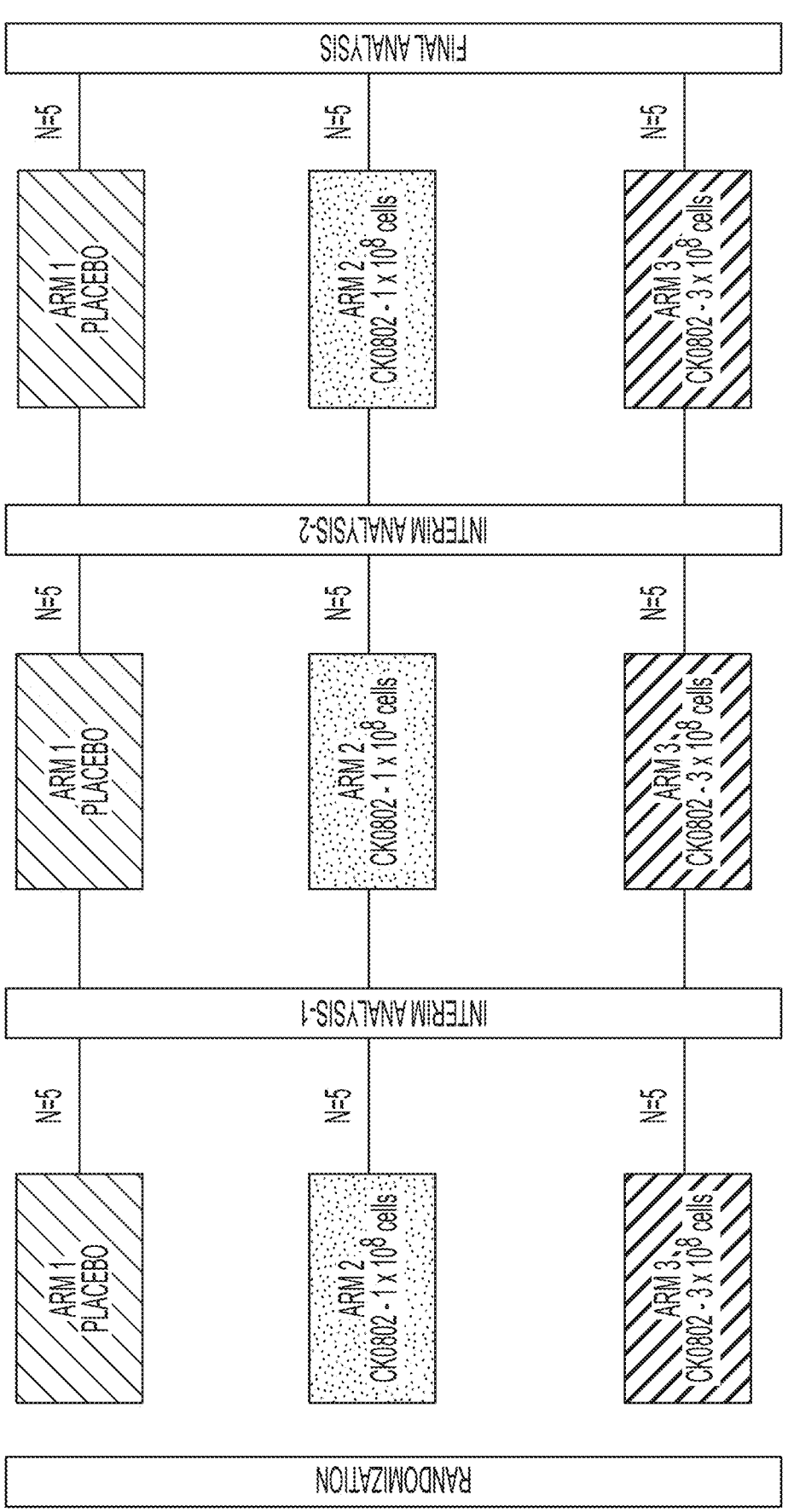
FIG. 27 depicts a diagram of a protocol for a clinical trial to evaluate safety and efficacy of administering cord blood-derived T regulatory cells in the treatment of COVID-19 (coronavirus disease) mediated acute respiratory distress syndrome (CoV-ARDS) as described in Example 10.

A clinical trial design for a Phase IB/IIa trial of cryopreserved, multi-dose cord blood-derived T regulatory (Treg) cells (CK0802) for treatment of CoV-ARDS is depicted in FIG. 27. There will be three treatment arms: Treatment arm 1: Placebo; Treatment Arm 2: $1 \times 10^8$ CK0802 cells; Treatment Arm 3: $3 \times 10^8$ CK0802 cells. The dosing regimen is three doses to be infused on day 0, day 3 (+/−1) and day 7 (+/−1). CK0802 will be administered intravenously. The study population is intubated adults with COVID-19 induced moderate to severe acute respiratory distress syndrome (ARDS). A minimum of 15 patients and a maximum of up to 45 patients will be enrolled.

Objective

Primary Objective

The objective of this protocol is to determine if regulatory T-cell infusions expanded from banked cord blood units (CK0802) can safely decrease the morbidity and mortality of intubated patients suffering from moderate to severe ARDS secondary to COVID-19 infection.

Endpoints and Correlatives

Primary Endpoint

The two co-primary outcomes will be

Regimen related, severe ≥grade 3 toxicity within 48 hours of CK0802 infusion (NCI-CTCAE (U.S. National Cancer Institute Common Terminology Criteria for Adverse Events) V4.0)

28-day treatment success, defined as S28=[Alive and not intubated 28 days after the date of first infusion].

Secondary Endpoint

Secondary outcomes, recorded from the day of first infusion up to 28 days from the date of first infusion, will include Time to extubation Oxygenation requirement (PaO2:FiO2 ratio) change between day 0 and day +11

Ventilator free days

Organ failure free days

ICU free days during the first 28 days 28-day all-cause mortality

Planned Non-Endpoint Correlative Analysis

Laboratory correlates and general assessment Days 0, 3, 7, 11, 21 and 28

Sequential Organ Failure Assessment (SOFA) Score [Vincent et al., Intensive Care Med, 1996. 22(7): p. 707-10]

Inflammatory markers: serum ferritin, procalcitonin, D-dimer and C-Reactive Protein (CRP), interleukin-6 (IL-6)

Peripheral blood lymphocyte subset analysis

Ventilator status parameters (if intubated) and ABG (if available)

Investigational Product

CK0802 (Cryopreserved cord blood-derived T-regulatory cells) refers to the allogeneic, off-the-shelf, regulatory T cells that are cryopreserved and ready to use as an intravenous infusion for the treatment of ARDS.

Source and Pharmacology

Tregs will be isolated from allogeneic, unrelated umbilical cord blood (CB) units derived from qualified public, licensed or unlicensed US CB banks, based on pre-determined selection criteria. The CB unit will be thawed and processed according to standard procedures in a 37° C. water bath using 10% dextran 40 and 5% human serum albumin as a wash solution. The CB cells will be resuspended in a $MgCl_2$/rHuDNAse/sodium citrate cocktail prior to immunomagnetic selection to prevent clumping. Enrichment of CD25+Treg cells will be accomplished by positive selection with directly conjugated anti-CD25 magnetic microbeads (Miltenyi Biotec, Bergish Gladbach, Germany) and MACS separation device. After the selection, the CD25+ cells will be suspended at a concentration of approximately $1 \times 10^6$ cells/mL in X-VIVO 15 media (Cambrex BioScience, Walkersville, MD) supplemented with 10% human AB serum (heat-inactivated; Valley Biomedical Products and Services, Inc., Winchester, VA), L-glutamine (2 mM), in the GREX flask. The CD25+ cells will be cultured with anti-CD3/anti-CD28 monoclonal antibody (mAb)-coated Dynabeads (Invitrogen) at a 1:1 bead to cell ratio for 14±1 days. On day 0, cultures will be supplemented with 1000 IU/ml IL-2 (Proleukin, Chiron Corporation, Emeryville, CA). Cells will be maintained at a density of $1.0 \times 106$ viable nucleated cells/mL and cultured at 37° C. in 5% $CO_2$ for 14 days.

On day 14 of culture, the cells will be harvested, the Dynabeads will be removed by magnetic separation and the Treg cells will be re-suspended in Plasmalyte+0.5% I buffer. The Treg product (CK0802) must pass release criteria for infusion and includes: 7AAD viability ≥70%, CD4+CD25+ cell purity ≥60%, CD4−/CD8+ cells <10%, anti-CD3/anti-CD28 mAB bead count <100 per $3 \times 10^6$ cells, gram stain with 'no organisms', and endotoxin <5 EU/kg.

The harvested cells will then be aliquoted into clinical cryobags and cryopreserved using controlled rate freezer and labeled as CK0802 product including the cell dose.

CK0802 Infusion

Infusion of CK0802 dose level 1=$1.0 \times 10^8$ cells and dose level 2: $3.0 \times 10^8$ cells will be explored in this trial. Patients will be pre-medicated with Benadryl® 50 mg IVPB (IV piggyback) thirty (30) minutes before infusion of CK0802. CK0802 should be infused by gravity over at least thirty (30) minutes and within one hour preferably. CK0802 is compatible with standard blood product tubing and filter.

Placebo Infusion

Infusion of cryopreserved excipient in 30 ml cryobag. Patients will be pre-medicated with Benadryl® 50 mg IVPB (IV piggyback) thirty (30) minutes before infusion of Placebo. Placebo should be infused by gravity within thirty (30) minutes and within one hour preferably of thawing. Placebo is compatible with standard blood product tubing and filter.

Study Population

This study will recruit subjects that meet all of the inclusion/exclusion criteria detailed below.

Inclusion Criteria

1. Documented to have an RT-PCR-based diagnosis of SARS-CoV-2 infection.

2. Moderate-to-severe ARDS as defined by the Berlin Criteria [Force et al., JAMA, 2012. 307(23): p. 2526-33]: ratio of partial pressure of arterial oxygen (PaO2) to the fraction of inspired oxygen (FiO2) of 200 mm Hg or less assessed with a positive end-expiratory pressure (PEEP) of >5 cm H2O.

3. Intubated for less than 120 hours

4. Age ≥18

5. Ability to provide informed consent or duly appointment health care proxy with the authority to provide informed consent Exclusion Criteria 1. In the opinion of the investigator, unlikely to survive for >48 hours from screening.

2. Any physical examination findings and/or history of any illness that, in the opinion of the study investigator, might confound the results of the study or pose an additional risk to the patient by their participation in the study.

3. Currently receiving extracorporeal membrane oxygenation (ECMO) or high frequency oscillatory ventilation (HFOV)

4. Females who are pregnant

5. Patients with active bacteremia at start of therapy enrollment or concurrently active moderate to severe other infection which in the opinion of the investigator may possibly affect the safety of CK0802 treatment.

6. Patients who have been intubated for more than >120 hours

7. Known hypersensitivity to DMSO or to porcine or bovine protein

8. Any end-stage organ disease which in the opinion of the investigator may possibly affect the safety of CK0802 treatment 9. Steroids are lympholytic and can be detrimental to the infused Treg cells. More than stress dose steroid therapy is an exclusion: hydrocortisone greater than 50 mg every 6 hours or other systemic steroids equivalent to methylprednisolone greater than 0.5 mg/kg/day administered intravenously or methylprednisolone greater than 60 mg orally daily.

10. Receiving an investigational cellular therapy agent

Evaluations During Study

Clinical Assessment

Baseline assessment on the day of infusion of first dose of assigned treatment arm: CK0802 or placebo and then subsequent daily assessment for 14 days post infusion of the first dose of assigned treatment arm: CK0802 or placebo.

81

Ventilatory Parameters:
average daily recording with range (minimum and maximum value)
    Plateau pressure
    Tidal volume
    Mean airway pressure
    FiO2
    PEEP
    PaO2/FiO2 ratio
    C-STAT/compliance (static compliance of the lungs)
Arterial Blood Gas:
average daily recording with range (minimum and maximum value)
    Arterial pH
    Partial pressure of oxygen (PaO2)
    Partial pressure of carbon dioxide (PaCO2)
    Bicarbonate (HCO3)
    Oxygen saturation ($O_2$ Sat)
Vital Signs:
average daily recording with range (minimum and maximum value)
    Body temperature
    Blood pressure (BP): systolic and diastolic BP readings
    Respiratory Rate
    Heart Rate
SOFA Score
    The Sequential Organ Failure Assessment (SOFA) Score predicts ICU mortality based on lab results and clinical data. SOFA score

82 a similar degree of suppression of the proliferating Tcon cells was demonstrated by the lack of dilution of the CellTrace™ Violet dye.

Example 12: Effects of Ruxolitinib on Activity of Cord Blood-Derived T Regulatory Cells Ruxolitinib improved cord blood-derived Treg cell function both in vitro and in vivo. These findings were unexpected because previous reports described negative effects of ruxolitinib on Treg cells in patients.

Figure 31:
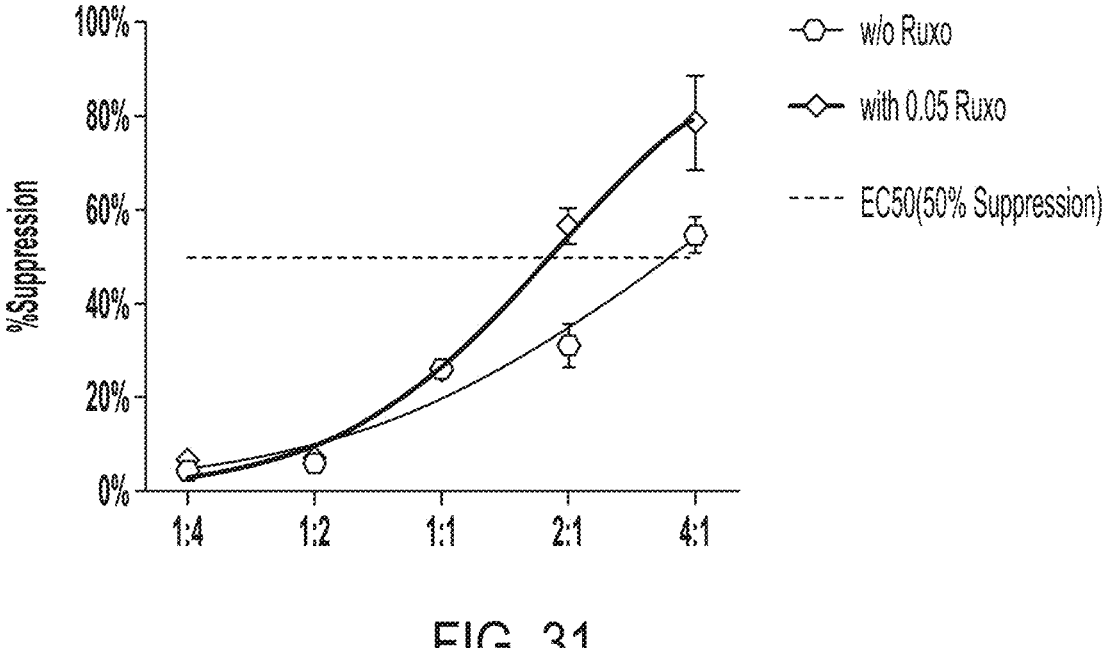
FIG. 31 is a line graph depicting percent suppression by activated Treg cells in the absence or in the presence of 0.05 μM ruxolitinib at 96 hours after initiation of co-culture of the Treg cells, Tcon cells and ruxolitinib. The x-axis shows a ratio of Treg cells to Tcon cells. Ruxo=ruxolitinib.

As shown in FIG. 31, the addition of ruxolitinib to thawed cryopreserved cord blood (CB) Treg cells restored the suppressive function of the Treg cells in vitro. When thawed CB Treg cells are put into secondary cultures, the Treg cells lose their suppressor function over time. The suppressor function can be restored by addition of ruxolitinib.

Figure 32:
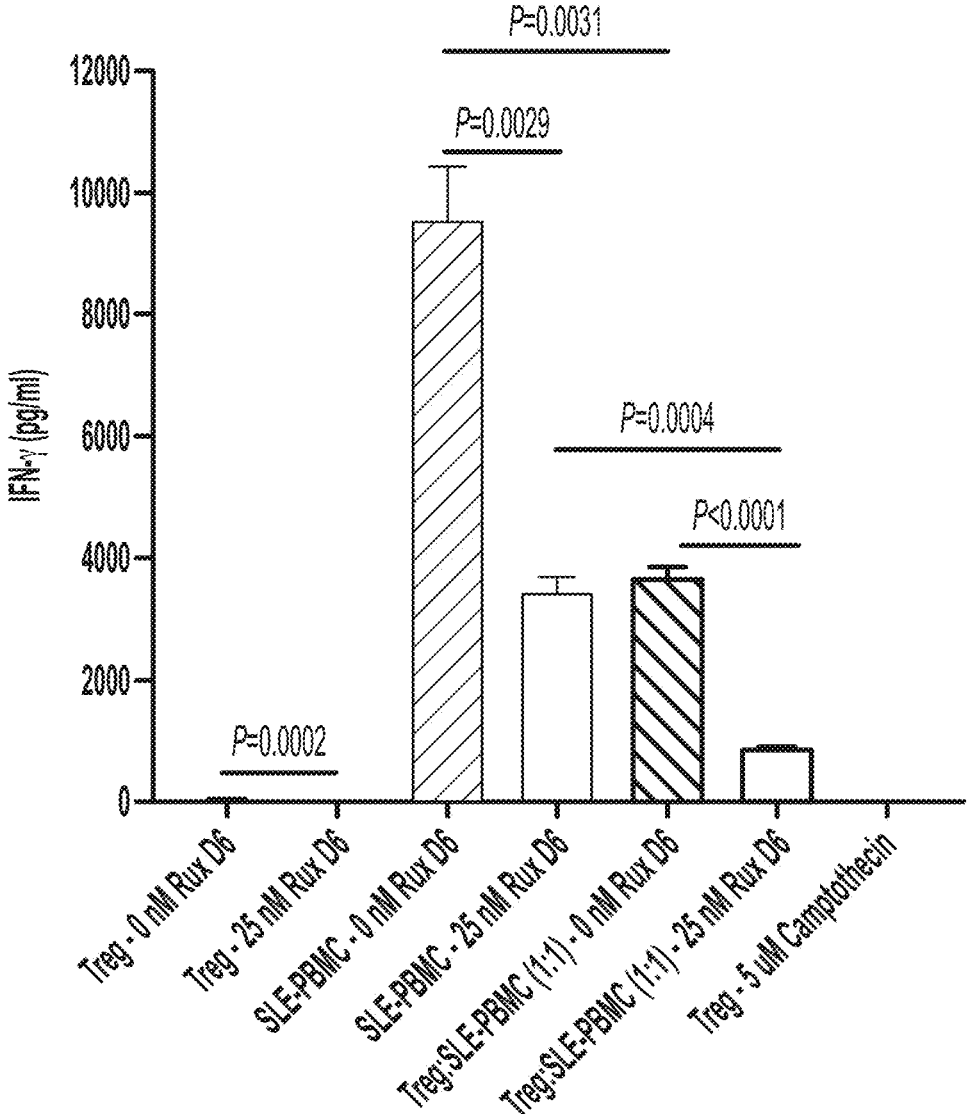
FIG. 32 is a bar graph depicting the amount of interferon (IFN)—gamma released by pathogenic lupus cells in the presence or absence of combinations of (1) activated Treg cells; (2) ruxolitinib; and/or (3) camptothecin. Rux=ruxolitinib. SLE-PBMC=peripheral blood mononuclear cells derived from subjects with systemic lupus erythematosus. D6=Day 6.

Ruxolitinib and CB Treg cells exhibit synergy in suppressing release of interferon-gamma (IFNγ) from pathogenic lupus cells. Peripheral blood mononuclear cells derived from subjects with systemic lupus erythematosus (SLE-PBMC) secrete a high level of the inflammatory cytokine IFNγ. The level of IFN-γ is decreased by the addition of ruxolitinib or CB Treg cells. However, when added together, the combination of CB Treg cells and ruxolitinib exert synergistic suppression of the release of IFNγ from SLE-PBMCs (FIG. 32). Camptothecin is used as a control to demonstrate that a non-specific inflammatory stimulus does not increase IFNγ secretion from CB Treg cells.

TABLE 35

| SOFA SCORE | 1 | 2 | 3 | 4 |
|---|---|---|---|---|
| Respiration PaO2/FiO2, mmHg | <400 | <300 | <200 with respiratory support | <100 |
| Coagulation Platelets ×10³/mm³ | <150 | <100 | <50 | <20 |
| Liver Bilirubin, mg/dl (μmol/l) | 1.2-1.9 (20-32) | 2.0-5.9 (33-101) | 6.0-11.9 (102-204) | >12.0 (<204) |
| Cardiovascular Hypotension | MAP <70 mmHg | Dopamine ≤5 or dobutamine (any dose)[a] | Dopamine >5 Or epinephrine ≤0.1 Or norepinephrine ≤0.1 | Dopamine >15 Or epinephrine >0.1 Or norepinephrine >0.1 |
| Central Nervous System Glasgow Coma Score | 13-14 | 10-12 | 6-9 | <6 |
| Renal Creatinine, mg/dl (μmol/l) or urine output | 1.2-1.9 (110-170) | 2.0-3.4 (171-299) | 3.5-4.9 (300-440) Or <500 ml/day | >5.0 (>440) Or <200 ml/day |

[a]Adrenergic agents administered for at least 1 h (doses given are in μg/kg-min)

Figures 5A, 5B, 5C, 5D:
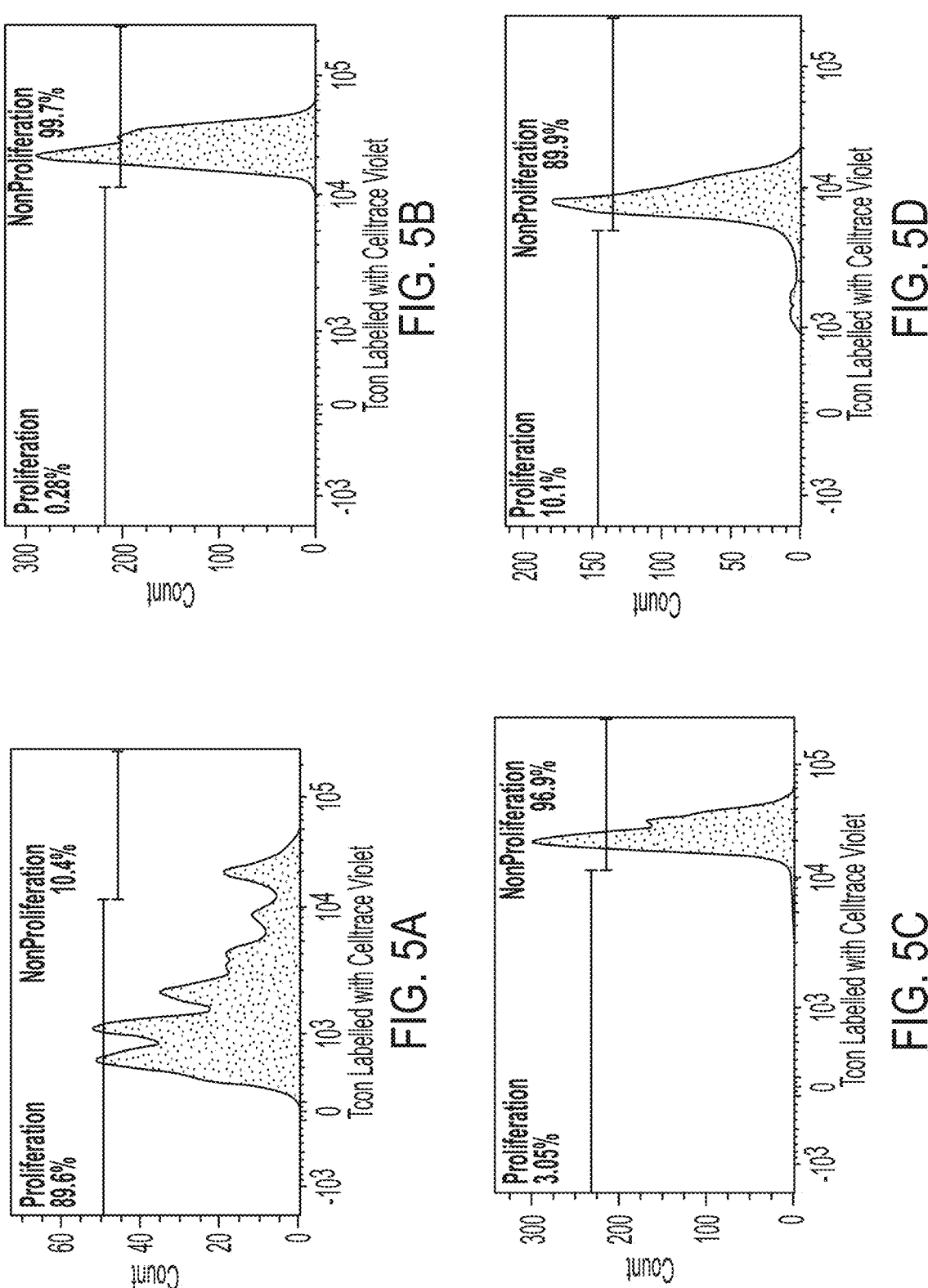
FIG. 5A-FIG. 5D depict graphs showing that cryopreserved cord blood (CB) Treg cells have comparable suppressor function compared to fresh CB Treg cells.
Figure 33:
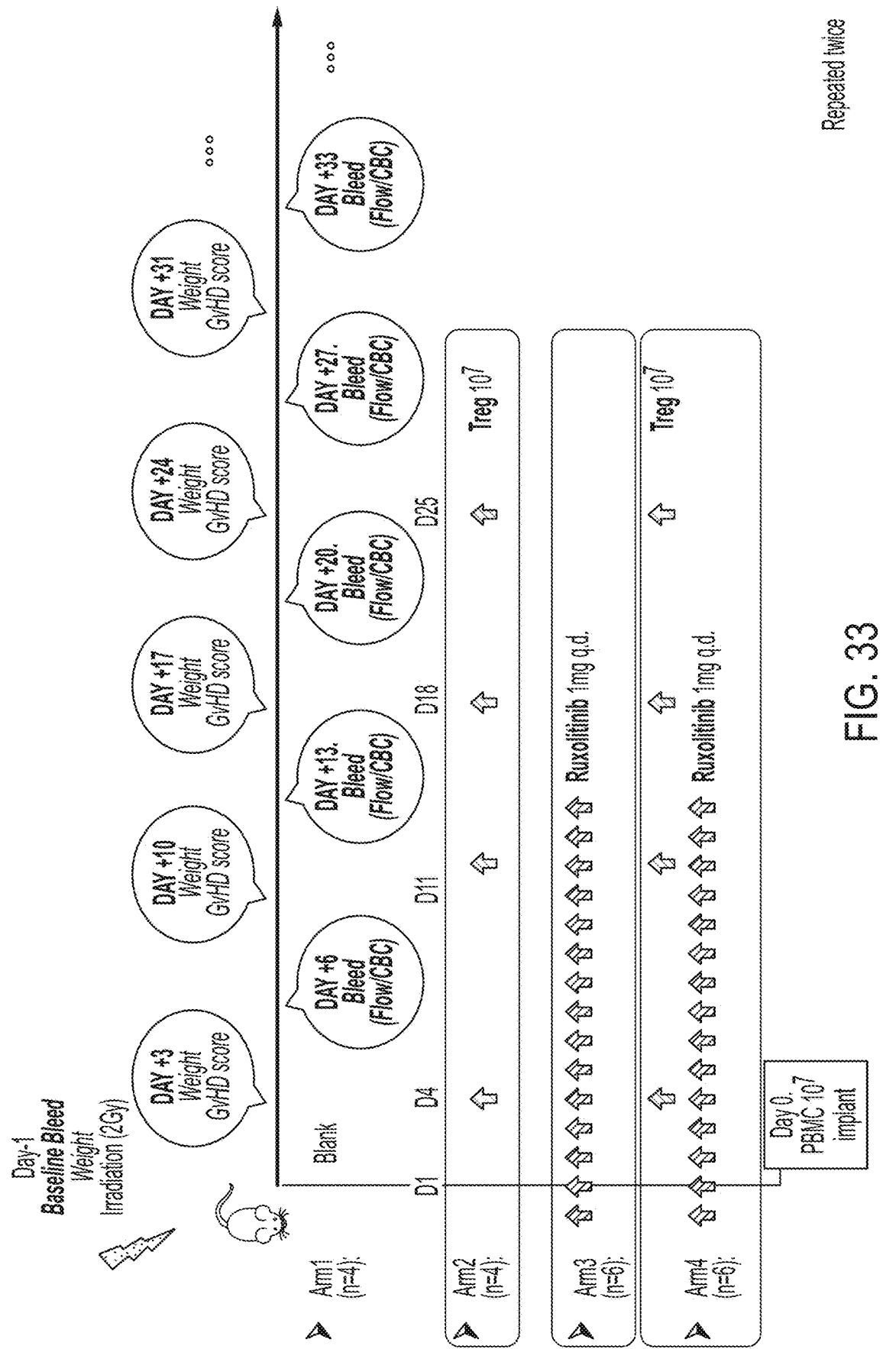
FIG. 33 depicts a schematic for treatment of a xenogeneic mouse graft versus host disease (GVHD) model with a ruxolitinib and activated Treg cells regimen. PBMC=peripheral blood mononuclear cells.

Example 11: Effects of Cryopreservation on Cell Suppression Activity of Cord Blood-Derived T Regulatory Cells Cryopreserved cord blood (CB) Treg cells (CK0802) were shown to have comparable suppressor function compared to fresh CB Treg cells. Tcon cells showed a high rate of proliferation in the presence of the costimulatory CD3/28 beads as evident by the serial dilution of the CellTrace™ Violet dye in the positive control arm (FIG. 5A), whereas no such proliferation was captured in the negative control arm in the absence of the CD3/28 beads (FIG. 5B). Whether the expanded CB Treg cells were derived from fresh cultures (FIG. 5C) or thawed from cryopreserved aliquots (FIG. 5D), A xenogeneic mouse graft versus host disease (GVHD) model was treated with a ruxolitinib and activated CB Treg cells regimen, as depicted in FIG. 33. NSG mice underwent sublethal irradiation on day −1 followed by injection of 1×10⁷ donor peripheral blood (PB) mononuclear cells (MNCs) on day 0. Oral ruxolitinib at 1 mg daily was fed continuously to the mice in the presence or absence of 1×10⁷ CB Treg cells, tagged with CellTrace™ Violet dye (ThermoFisher), administered on days +4, +7, +11, +18. Mice were followed every other day for weight, GVHD score and survival. Serial blood draws were performed to analyze for cell compartment and cytokine assays.

Figure 34B:
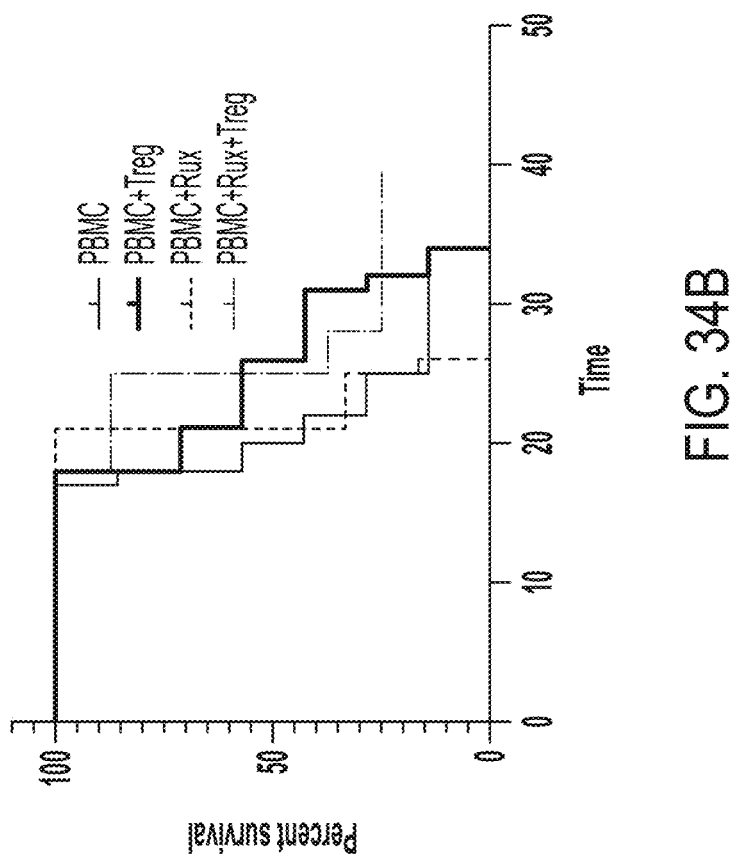
FIG. 34A-FIG. 34B depict graphs showing the effect of treatment with (1) activated Treg cells; (2) ruxolitinib; or (3) activated Treg cells and ruxolitinib on the GVHD score (FIG. 34A) or percent survival (FIG. 34B) in a xenogeneic mouse GVHD model. Rux or R=ruxolitinib. PBMC=peripheral blood mononuclear cells.
Figure 34A:
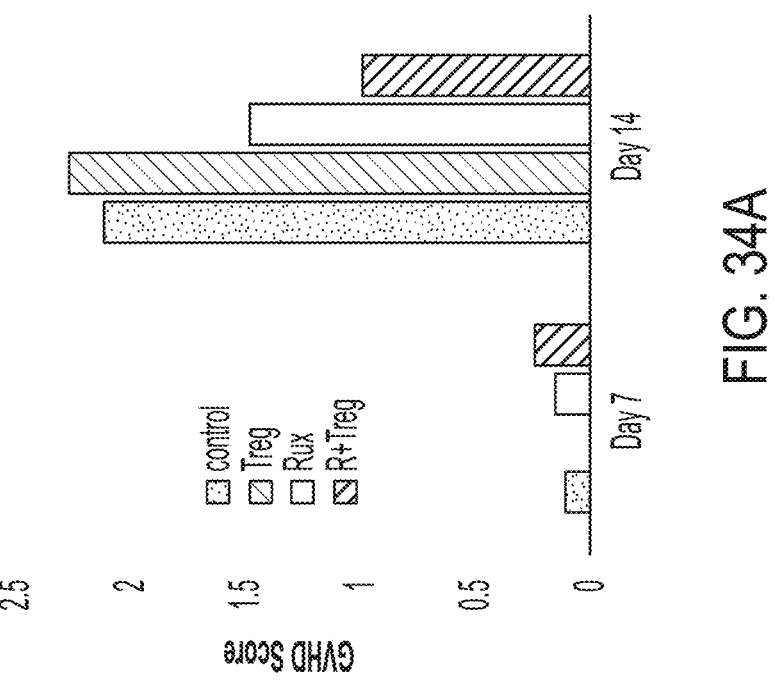
Figure 35C:
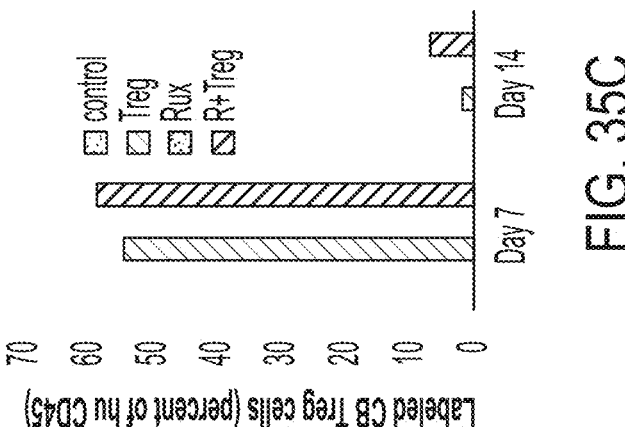
FIG. 35A-FIG. 35C depict a series of bar graphs showing the effect of treatment with (1) activated Treg cells; (2) ruxolitinib; or (3) activated Treg cells and ruxolitinib on activated Treg cell persistence in a xenogeneic mouse GVHD model.
Figure 35B:
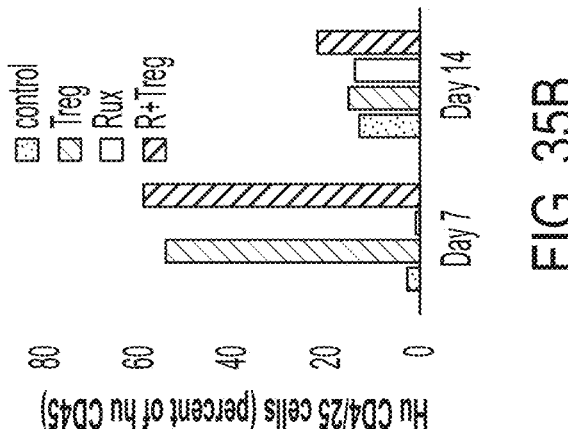
Figure 35A:
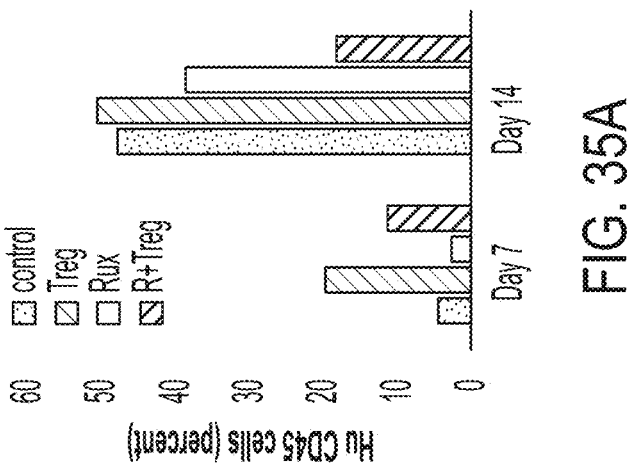

The combination treatment decreased the GVHD score (FIG. 34A) and improved survival (FIG. 34B) in the mouse model. Ruxolitinib improved CB Treg persistence in the mouse model (FIG. 35A-FIG. 35C). Ruxolitinib decreased the number of human cells as a single agent as well as in combination with CB Treg cells (FIG. 35A). Ruxolitinib increased the percentage of CD4 and CD25 co-expressing cells when administered in combination with CB Treg cells (FIG. 35B). Ruxolitinib increased the percentage of circulating CB Treg cells when given in combination with CB Treg cells as compared to CB Treg cells administered alone (FIG. 35C).

Figure 36C:
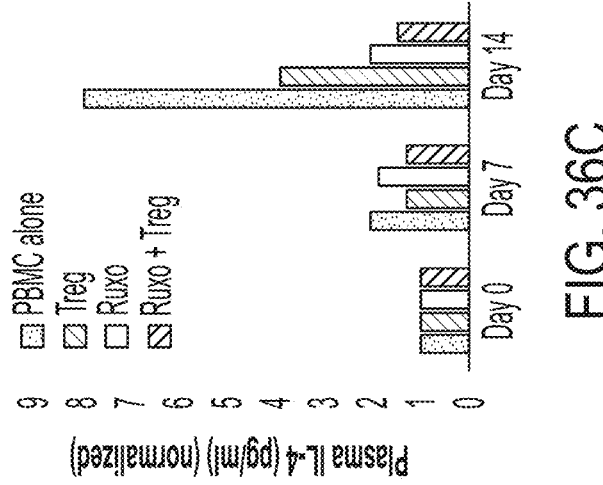
FIG. 36A-FIG. 36C depict a series of bar graphs showing the effect of treatment with (1) activated Treg cells; (2) ruxolitinib; or (3) activated Treg cells and ruxolitinib on cytokine secretion in a xenogeneic mouse GVHD model.
Figure 36B:
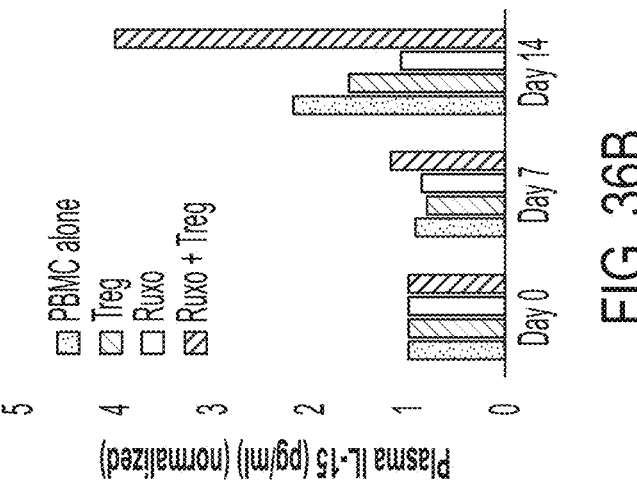
Figure 36A:
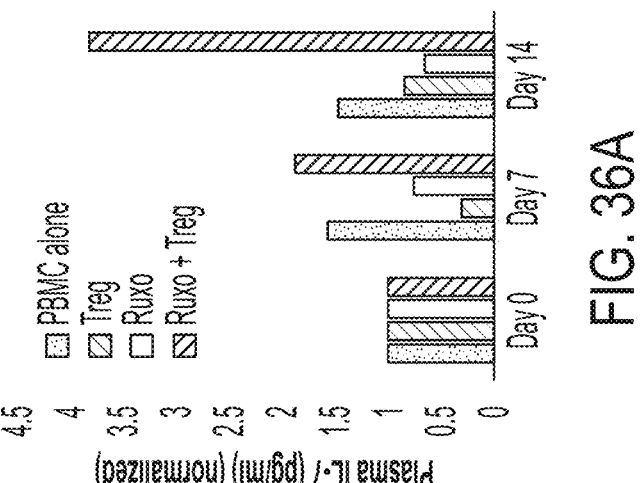

Ruxolitinib enhanced the survival signal pathways of IL-7 and IL-15 and dampened the inhibitory signal pathway of IL-4 for CB Treg cells in the xenogeneic mouse GVHD model. Levels of plasma IL-7 (FIG. 36A) and plasma IL-15 (FIG. 36B) were increased when ruxolitinib was administered in combination with CB Treg cells. Increased IL-7 availability enhances Treg survival, stabilizes the Treg molecular signature, enhances surface IL-2Ra expression, and improves IL-2 binding of Treg cells (Schmaler et al. Proc Natl Acad Sci USA. 112(43):13330-5, 2015). IL-15 impairs upregulation of RORγt and IL-17 expression and improves Treg proliferation (Tosiek et al. (2016) Nat Commun 7:10888). Plasma IL-4 levels were decreased when ruxolitinib was administered in combination with CB Treg cells (FIG. 36C). IL-4 production by Th2 cells is inhibited by Tregs (Pace et al. J Immunol 2005; 174:7645-7653).

Figure 37C:
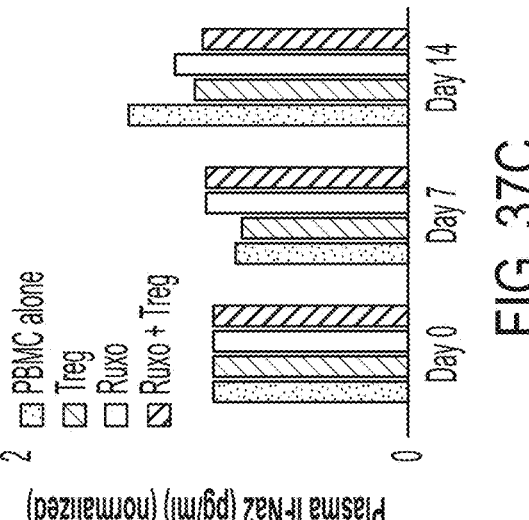
FIG. 37A-FIG. 37E depict a series of bar graphs showing the effect of treatment with (1) activated Treg cells; (2) ruxolitinib; or (3) activated Treg cells and ruxolitinib on inflammatory cytokine secretion in a xenogeneic mouse GVHD model.
Figure 37B:
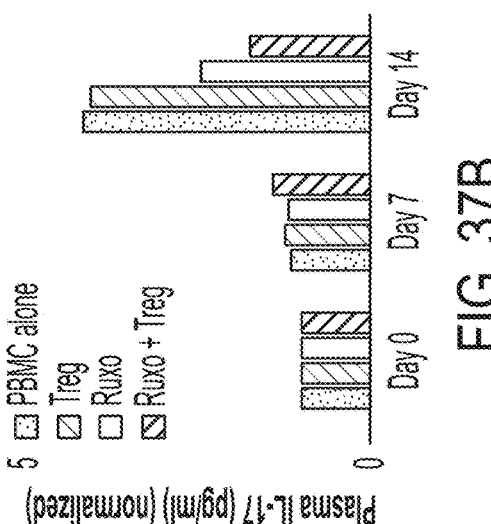
Figure 37A:
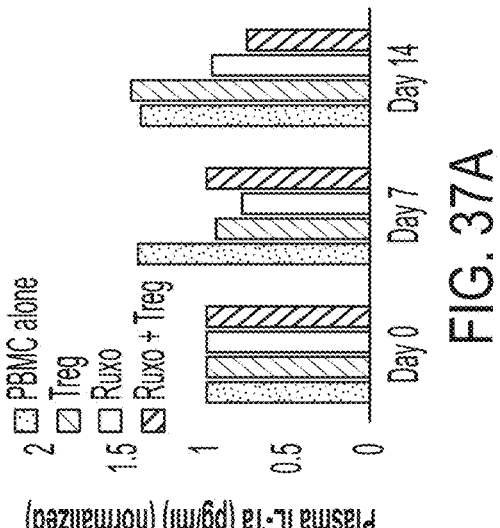
Figure 37E:
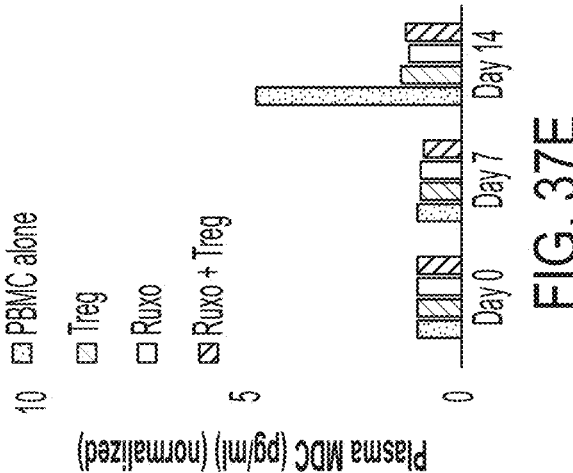
Figure 37D:
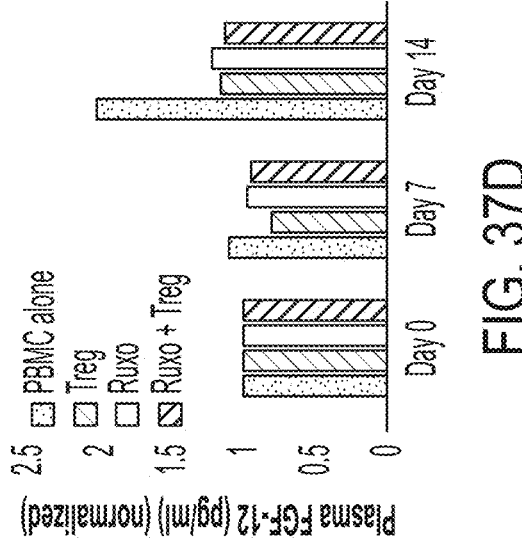

The combination of ruxolitinib and CB Treg cells decreased the secretion of inflammatory cytokines in the xenogeneic mouse GVHD model. The plasma levels of IL-1a (FIG. 37A), IL-17 (FIG. 37B) and IFNa2 (FIG. 37C) were reduced by addition of ruxolitinib to CB Treg cells. The levels of FGF-12 (FIG. 37D) and Macrophage-Derived Chemokine (MDC) (FIG. 37E) were reduced equally by administration of CB Treg cells alone, ruxolitinib alone, and the combination of ruxolitinib and CB Treg cells.

Figure 38C:
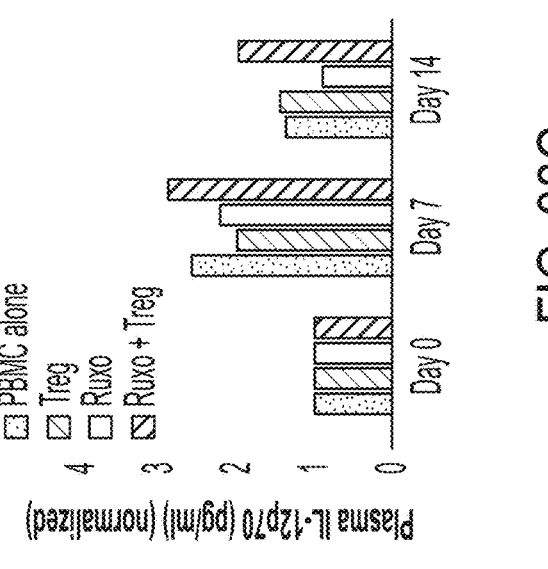
FIG. 38A-FIG. 38C depict a series of bar graphs showing the effect of treatment with (1) activated Treg cells; (2) ruxolitinib; or (3) activated Treg cells and ruxolitinib on anti-inflammatory cytokine secretion in a xenogeneic mouse GVHD model.
Figure 38B:
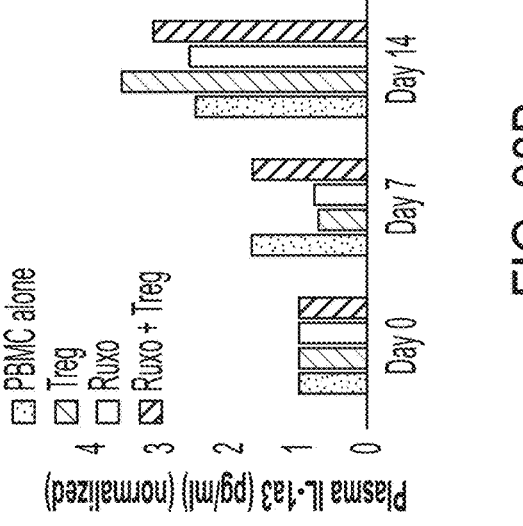
Figure 38A:
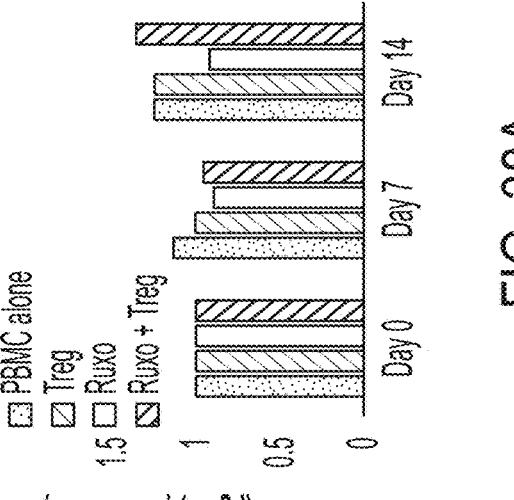
Figure 39B:
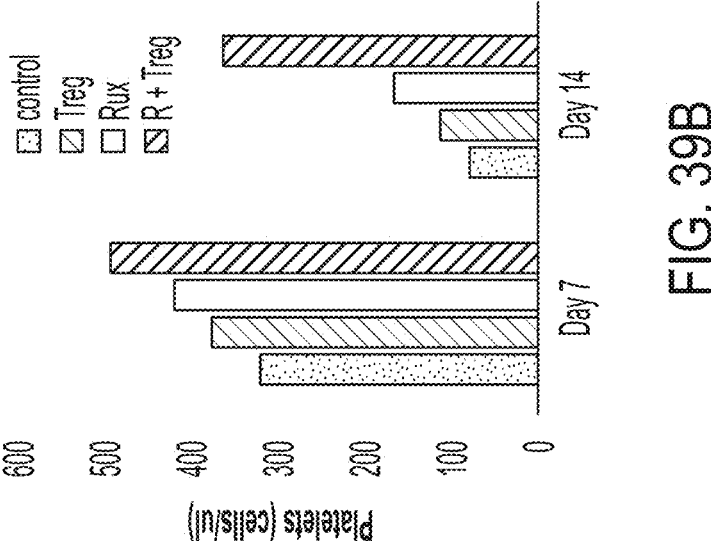
FIG. 39A-FIG. 39B depict a series of bar graphs showing the effect of treatment with (1) activated Treg cells; (2) ruxolitinib; or (3) activated Treg cells and ruxolitinib on hematologic parameters in a xenogeneic mouse GVHD model.
Figure 39A:
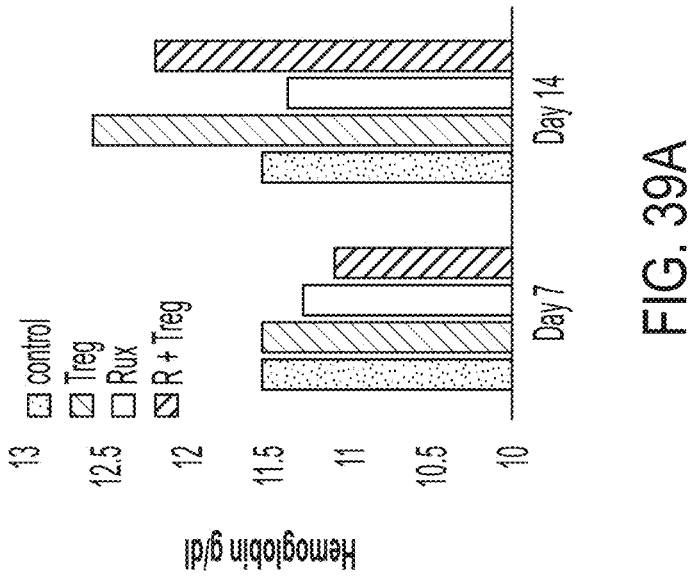

The combination of ruxolitinib and CB Treg cells increased the secretion of anti-inflammatory cytokines in the xenogeneic mouse GVHD model. The plasma levels of IL-1RA (FIG. 38A), IL-1a3 (FIG. 38B) and IL-12p70 (FIG. 38C) were increased. The combination of ruxolitinib and CB Treg cells improved hematologic parameters in the xenogeneic mouse GVHD model. The level of platelets was increased when ruxolitinib and CB Treg cells were both administered (FIG. 39B). At day 14, a significant decrease in hemoglobin level is evident in the ruxolitinib alone arm compared to increased hemoglobin level in the CB Treg cells+ruxolitinib arm (FIG. 39A).

Example 13: Effects of Cord Blood-Derived T Regulatory Cells on Chimeric Antigen Receptor T Cells A xenogeneic lymphoma model was created using NSG mice where $0.3\times10^6$ GFP-labeled Raji cells were injected on day 0 in all mice followed by $0.3\times10^6$ cells of i) mock-CAR T, ii) no CART, or iii) CD19-CAR T cells on day +5. Additional injections of $1\times10^7$ CB Treg cells on day +11, +18, +25 were added to the no CAR T arm and the CD19-CAR T arm such that there were 3 mice per arm. Mice were followed for weight, GVHD score and survival. Noninvasive bioluminescence was used to perform serial imaging to evaluate the tumor burden. Serial blood was drawn for cell analysis and cytokine assay.

Figure 59A:
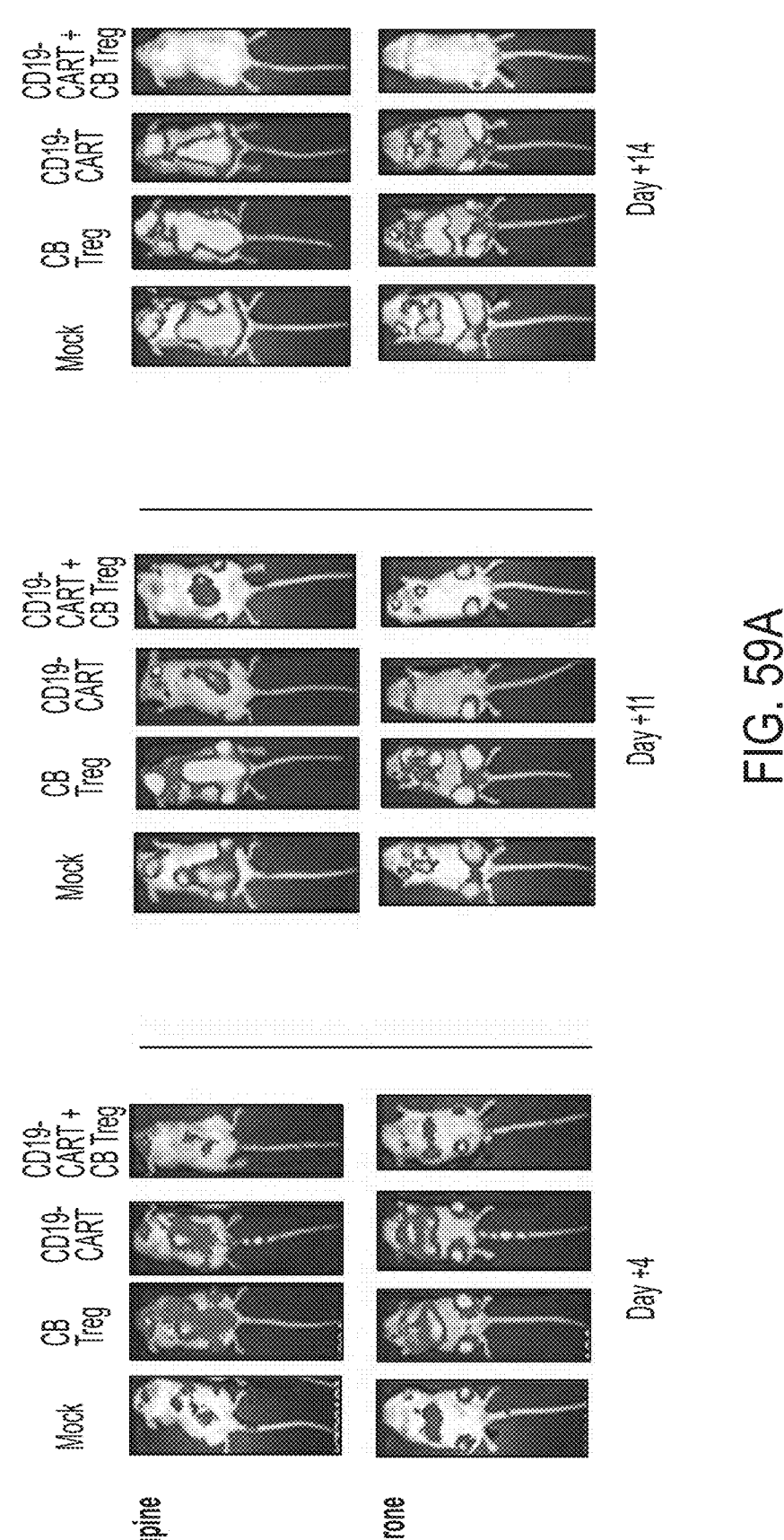
FIG. 59A-FIG. 59D depict data from a study of a xenogeneic lymphoma mouse model treated with i) mock-chimeric antigen receptor (CAR) T cells, ii) cord blood-derived Treg cells, iii) CD19-CAR T cells, or (iv) cord blood-derived Treg cells+CD19-CAR T cells.
Figure 59D:
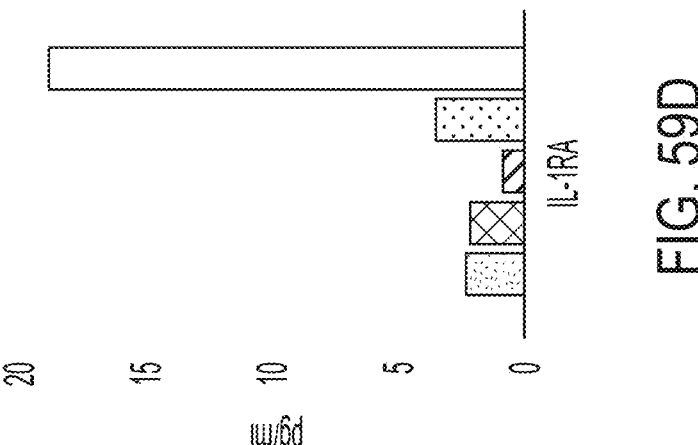
Figure 59C:
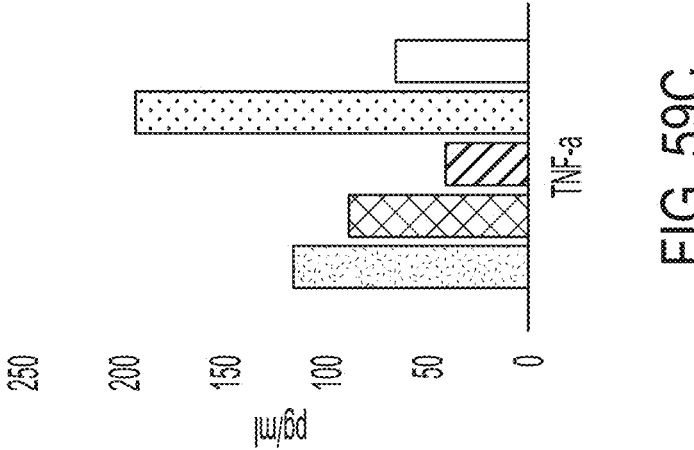
Figure 59B:
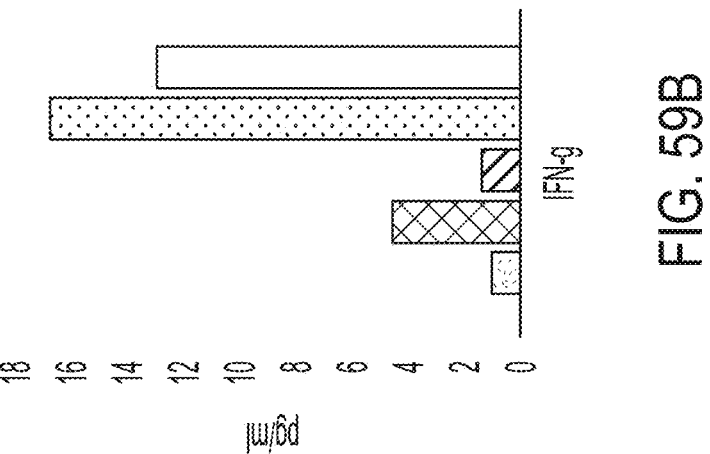

As shown in FIG. 59A, in vivo proliferation of GFP-labeled Raji cells was evident in all mice day by day +4. CD19-CAR T but not the mock-CAR T cells decreased the tumor burden at day +11. However, at day +14 all mice including CD19-CAR T cell recipients showed progression whereas CD19-CAR T+CB Treg cell recipient showed no evidence of bioluminescence. A superior survival in the CD19-CAR T+CB Treg cells recipients was evident when compared to other treatment arms (FIG. 60A). At the time of euthanasia, different organs were evaluated for the detection of the CD19-CART cells and were recovered only in the CD19-CART+CB Treg cells recipients (FIG. 60B). The CD19-CAR T recipients showed an increase in the inflammatory cytokines on day +16 PB samples including IFN-gamma (FIG. 59B) and TNF-alpha (FIG. 59C) which were decreased in the CD19-CAR T+CB Treg arm. Furthermore, a reciprocal increase of the anti-inflammatory cytokine IL-1RA was observed in the CD19-CAR T +CB Treg arm compared to the CD19-CAR T alone (FIG. 59D).

The addition of CB Treg cells to CD19-CAR T cells in a xenogeneic lymphoma model led to dampening of the cytokine storm and improved on target efficacy of CAR T cells.

Figure 62:
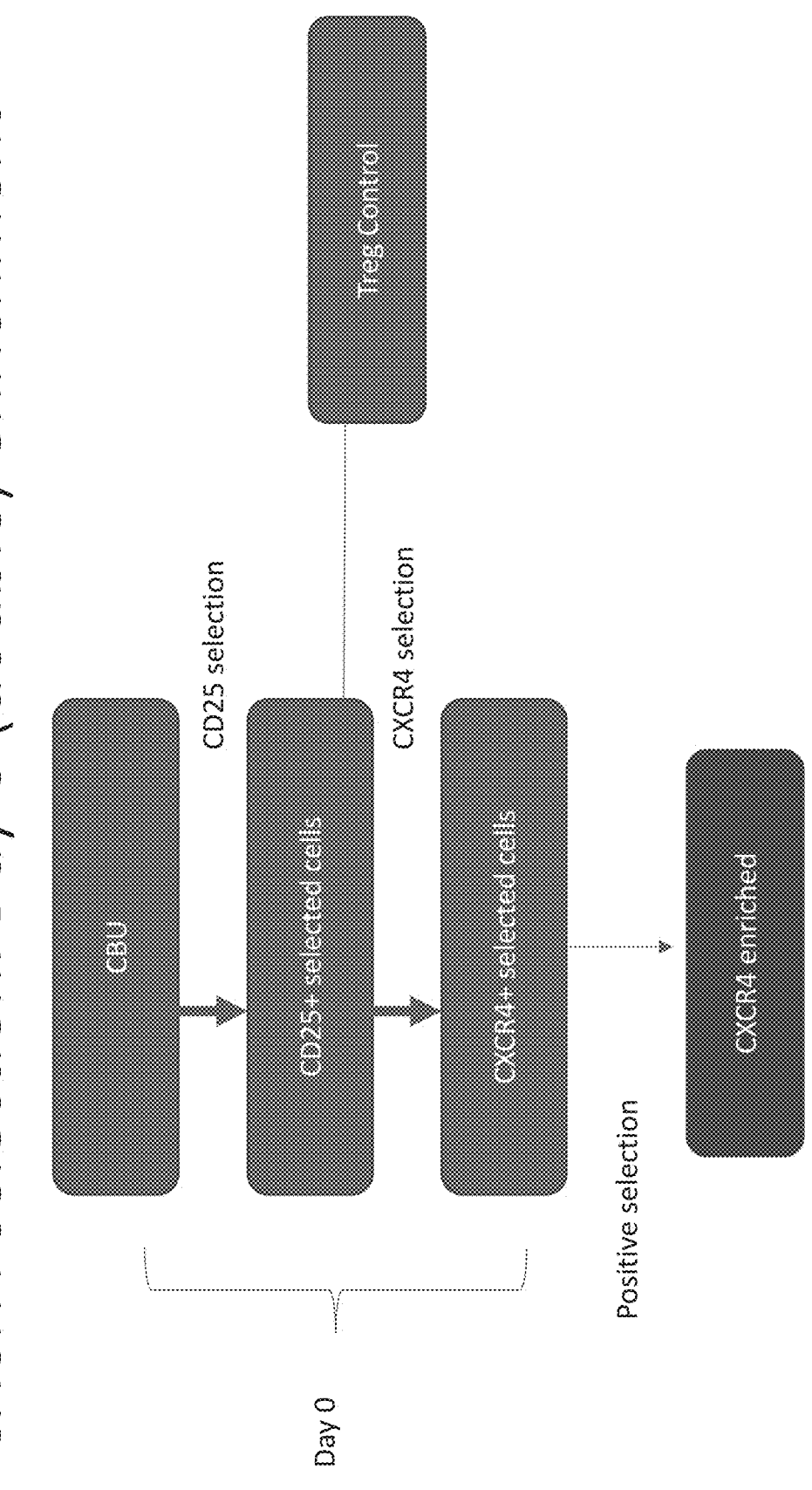
FIG. 62 is a flow chart depicting the "Day 0 (double) enrichment" method for selecting CXCR4-expressing cord blood-derived Treg cells to produce an enriched CXCR4+ Treg cell culture.
Figure 63:
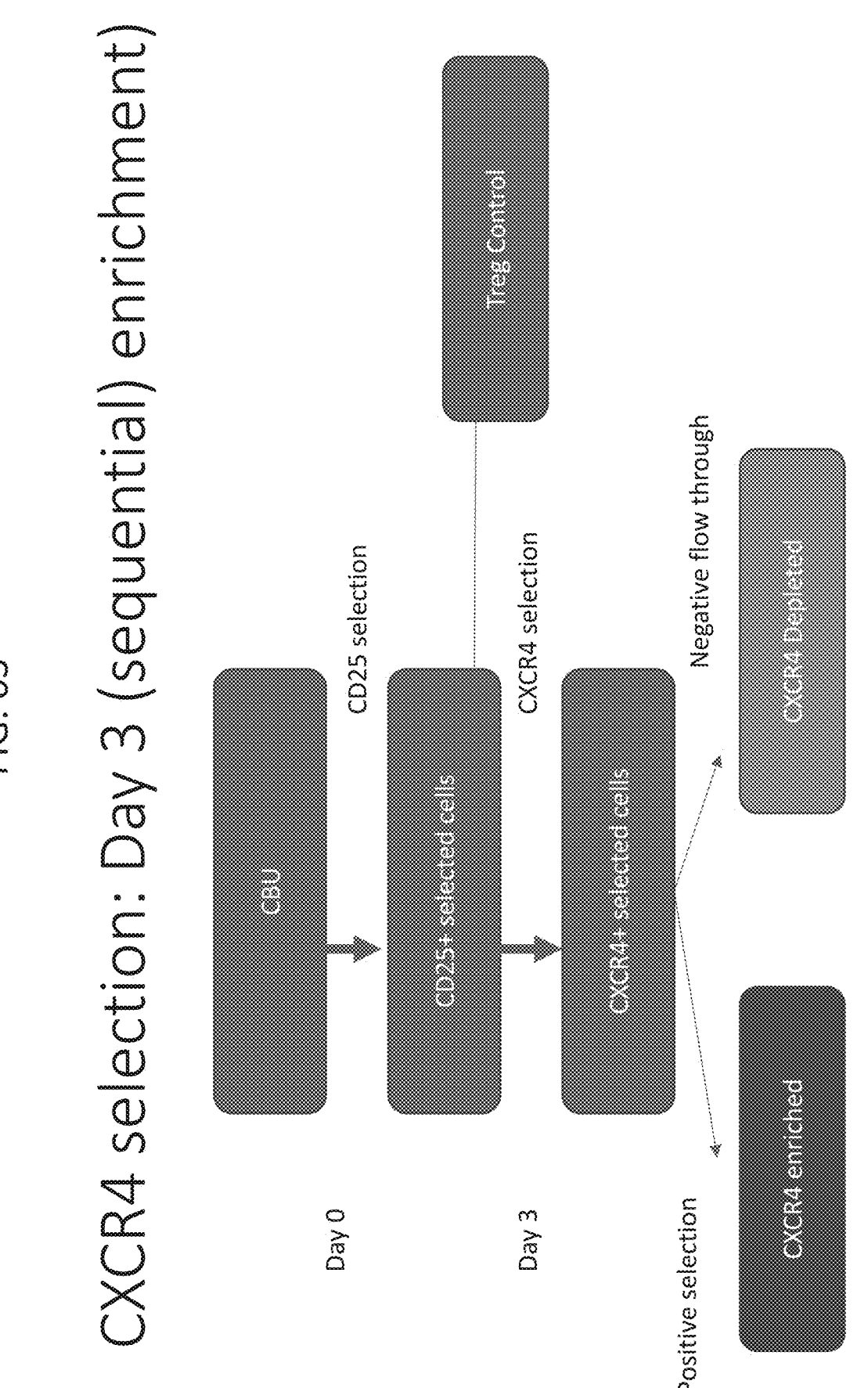
FIG. 63 is a flow chart depicting the "Day 3 (sequential) enrichment" method for selecting CXCR4-expressing cord blood-derived Treg cells to produce an enriched CXCR4+ Treg cell culture.

Example 14: Analysis of Alternative Selection Methods for CXCR4-Expressing Cord Blood-Derived T Regulatory Cells Two methods for selecting CXCR4-expressing cord blood-derived Treg cells to produce an enriched CXCR4$^+$ Treg cell culture were analyzed. The first method is referred to as "Day 0 (double) enrichment" (FIG. 62). This method involves CD25$^+$ cell selection on day 0, followed by cell washing, followed by incubation with CXCR4 microbeads and then a second positive enrichment. The second method is referred to as "Day 3 (sequential) enrichment" (FIG. 63). This method involves CD25$^+$ cell selection on day 0, followed by cell culture, followed by cell washing to uncouple CD3/28 microbeads, followed by incubation with CXCR4 microbeads and then a second positive enrichment.

Three cultures of Treg cells were produced by the method described in FIG. 63 on different dates and from different cord blood units. The characteristics of these cells on day of CXCR4 enrichment step are shown in Table 36.

TABLE 36

| | Culture 1 | Culture 2 | Culture 3 |
|---|---|---|---|
| Day 0 | | | |
| CD25 (×10^6) | 22.00 | 16 | 24 |
| Day 3 | | | |
| Cell count (×10^6/ml) | 0.66 | 0.763 | 0.217 |
| Tot vol (ml) | 42 | 30.4 | 29.7 |
| Flask #1 (ml) | 21.5 | 14.9 | 29.7 |
| Flask #2 (ml) | 20.5 | 15.5 | |
| Cell count (×10^6) | 27.76 | 23.2 | 6.44 |
| Viability (%) | 89.4 | 88.1 | 88.4 |
| Viable cells (×10^6) | 24.82 | 20.44 | 5.69 |
| CXCR4 enriched cells cultured (×10^6) | 1.89 | 3.4 | 1.07 |
| CXCR4 negative total cell count (×10^6) | 0.0085 | 0.158 | 0.0688 |
| Treg control cell no. (×10^6) | 0.66 | 0.763 | 0.217 |

Figures 64A, 64B, 64C:
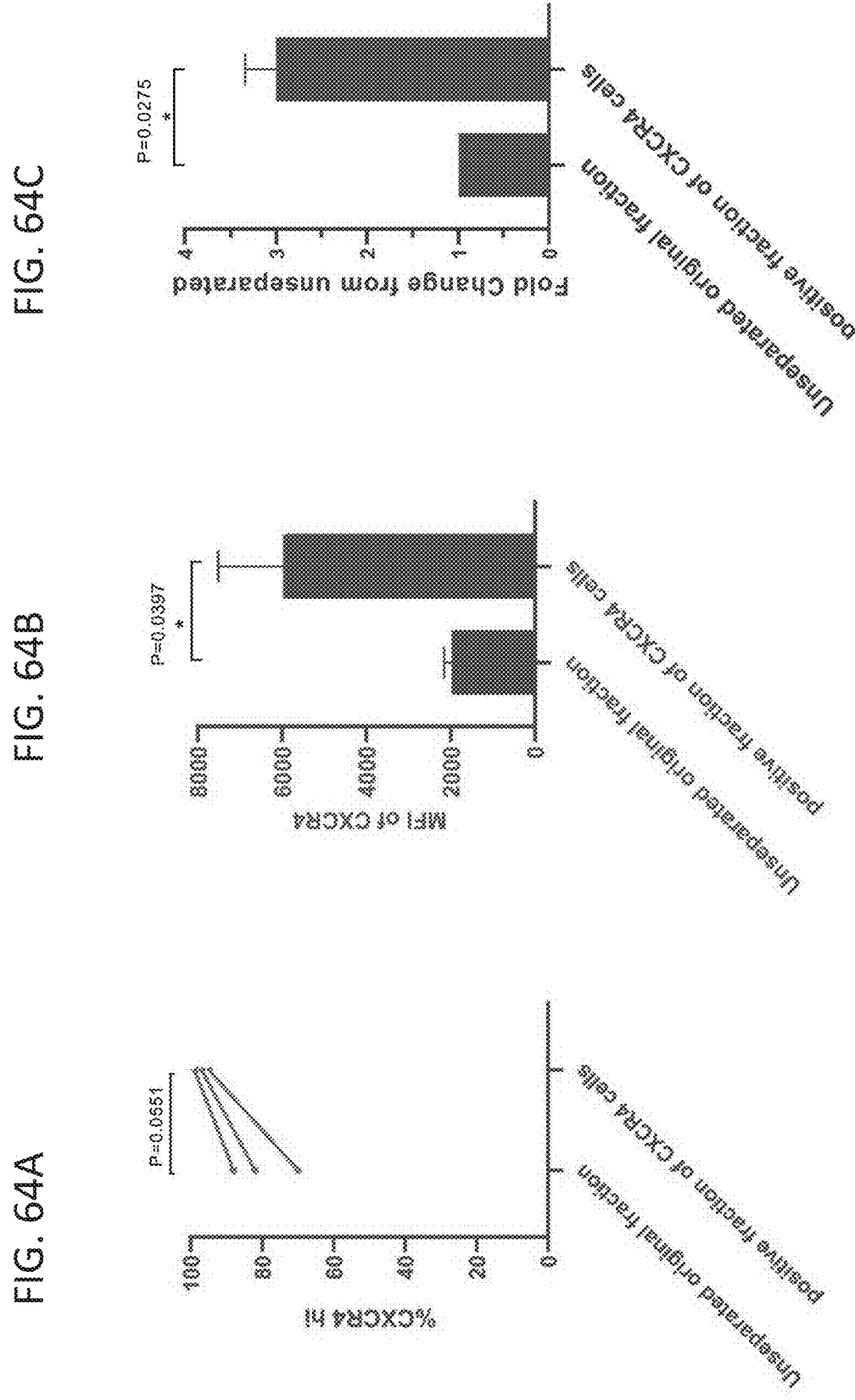
FIG. 64A-FIG. 64C depict data from flow cytometry analyses of CXCR4 unseparated fraction and positive fraction Treg cells produced by the "Day 3 (sequential) enrichment" method.

FIG. 64A, FIG. 64B and FIG. 64C depict summary data from Culture 1, Culture 2 and Culture 3 cultures showing that day 3 (D3) Treg cells can be efficiently enriched by magnetic separation for CXCR4. FIG. 64A shows frequency of CXCR4$^{hi}$ in D3 CXCR4 unseparated fraction and positive fraction Treg cells (see also Table 37). Paired t test showed a difference between the two groups (17±7.211, P=0.0551). FIG. 64B shows summary data showing mean/median fluorescence for CXCR4 in D3 CXCR4 unseparated fraction and positive fraction Treg cells (see also Table 38). Paired t test showed a statistically significant difference between the two groups (4000±1424, P=0.0397). FIG. 64C shows summary data showing fold change for CXCR4 in D3 CXCR4 unseparated fraction and positive fraction Treg cells (see also Table 39). Paired t test showed a statistically significant difference between the two groups (2.007±0.5886, P=0.0275).

TABLE 37

|  | Unseparated original fraction | positive fraction of CXCR4 cells |
|---|---|---|
| culture 1 | 88 | 99 |
| culture 2 | 82 | 97 |
| culture 3 | 70 | 95 |

TABLE 38

|  | Unseparated original fraction | positive fraction of CXCR4 cells |
|---|---|---|
| culture 1 | 1754 | 4831 |
| culture 2 | 2064 | 5347 |
| culture 3 | 2098 | 7738 |

TABLE 39

|  | Unseparated original fraction | positive fraction of CXCR4 cells |
|---|---|---|
| culture 1 | 1 | 2.75 |
| culture 2 | 1 | 2.59 |
| culture 3 | 1 | 3.68 |

FIG. 65 shows the effect of the CXCR4 enrichment step on the Treg CXCR4 enriched cells and compared with the CXCR4 negative cells as well as the pre-selection population from a representative culture. FIG. 65A shows the comparison of the mean flourescent intensity of CXCR4 expression of day 3 pre-selection population (median MFI=2064) vs. the mean flourescent intensity of CXCR4 expression of day 3 CXCR4 negative population (median MFI=54) vs. the mean fluorescent intensity of CXCR4 expression of day 3 positive-selection population (median MFI=5347). FIG. 65B shows the histogram representation of the mean fluorescent intensity of CXCR4 expression of day 3 cell populations including pre-selection Treg cells vs. CXCR4 negative Treg cell population vs. CXCR4 enriched Treg cells in one graph. FIG. 65C shows the contour plot of the mean fluorescent intensity of CXCR4 expression of day 3 cell populations including pre-selection Treg cells vs. CXCR4 negative Treg cell population vs. CXCR4 enriched Treg cells in one graph.

Figures 66A, 66B, 66C:
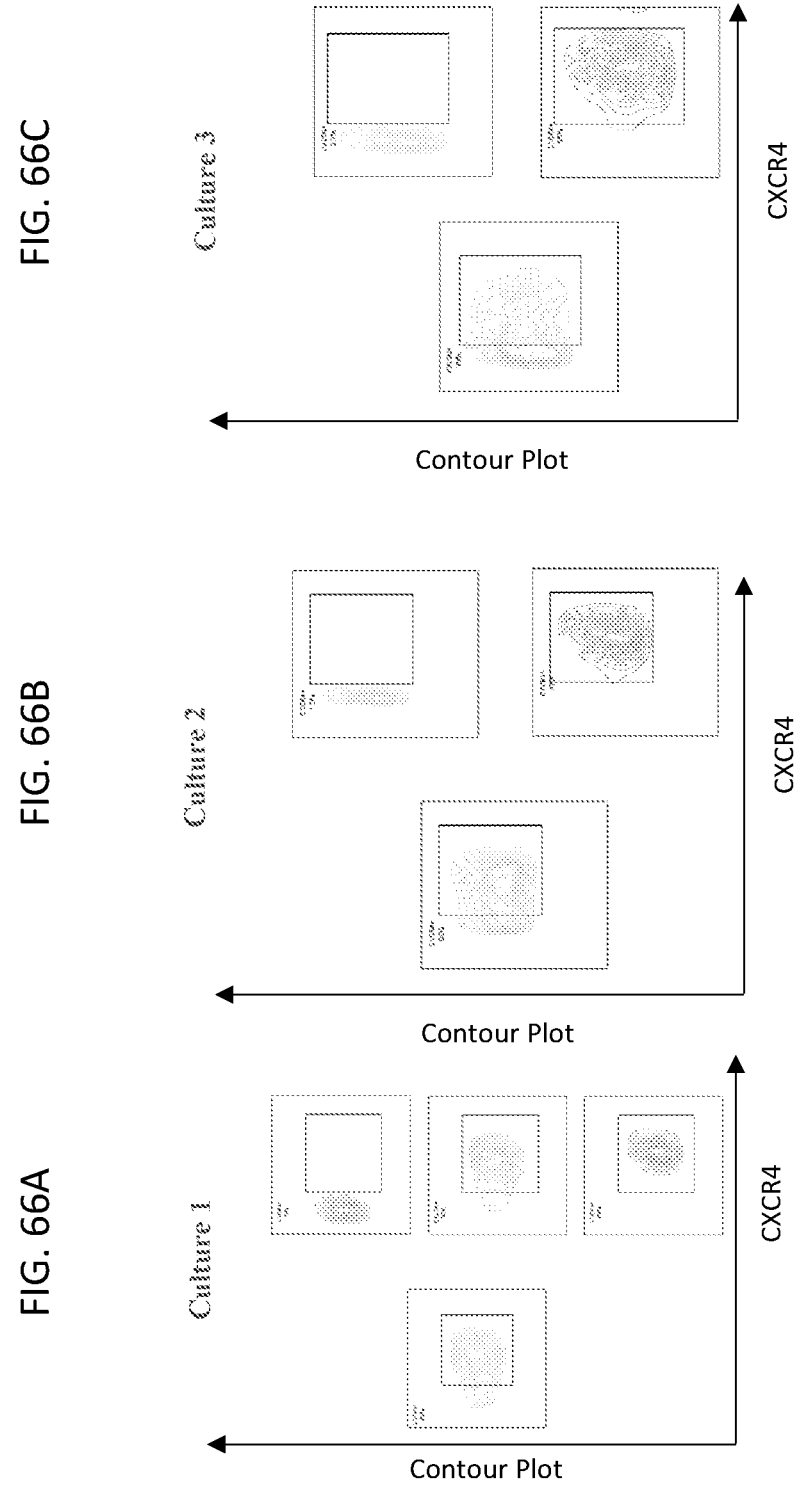
FIG. 66A-FIG. 66C depict contour plots for CXCR4 expression on D3 (day 3) CB Treg cells.

FIG. 66A-FIG. 66C show the effect of CXCR4 magnetic enrichment for CXCR4 expression on D3 CB Treg cells. FIG. 66A shows that in Culture 1, compared with unseparated D3 CB Treg, D3 CB Treg$^{CXCR4}$ showed 2.75-fold increase in CXCR4 expression. FIG. 66B shows that in Culture 2, compared with unseparated D3 CB Treg, D3 CB Treg$^{CXCR4}$ showed 2.59-fold increase in CXCR4 expression. FIG. 66C shows that in Culture 3, compared with unseparated D3 CB Treg, D3 CB Treg$^{CXCR4}$ showed 3.68-fold increase in CXCR4 expression.

Figure 67:
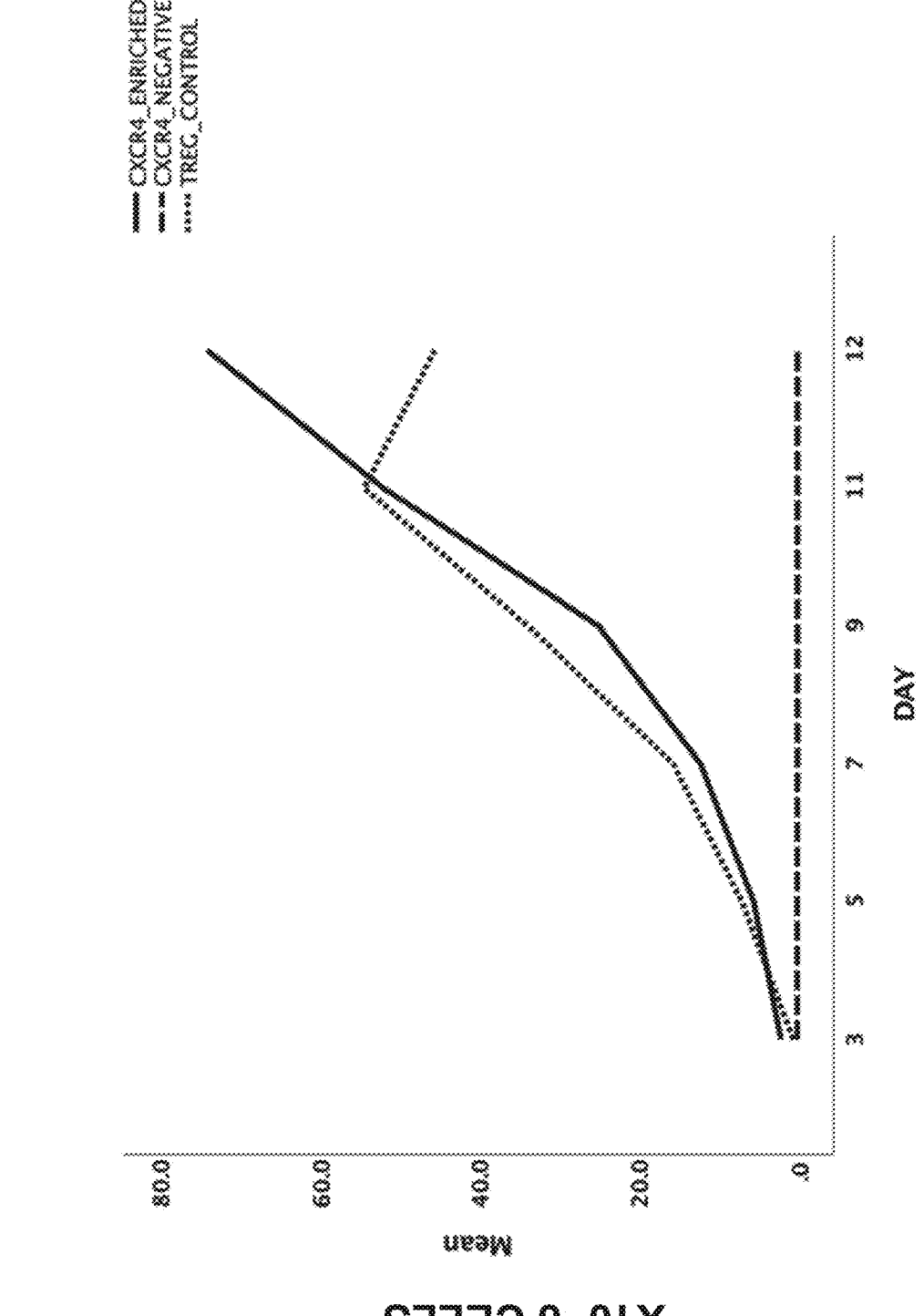
FIG. 67 depict line graphs showing cell numbers in the categories "CXCR4 enriched", "CXCR4 negative", and "Treg Control" at various culture days. This graph depicts combined data from all three cultures (Culture 1, Culture 2 and Culture 3).

FIG. 67 shows graphs showing cell numbers in the categories "CXCR4 enriched", "CXCR4 negative", and "Treg Control" at various culture days are shown in FIG. 67 (combined data from all three cultures (Culture 1, Culture 2 and Culture 3).

Figure 68B:
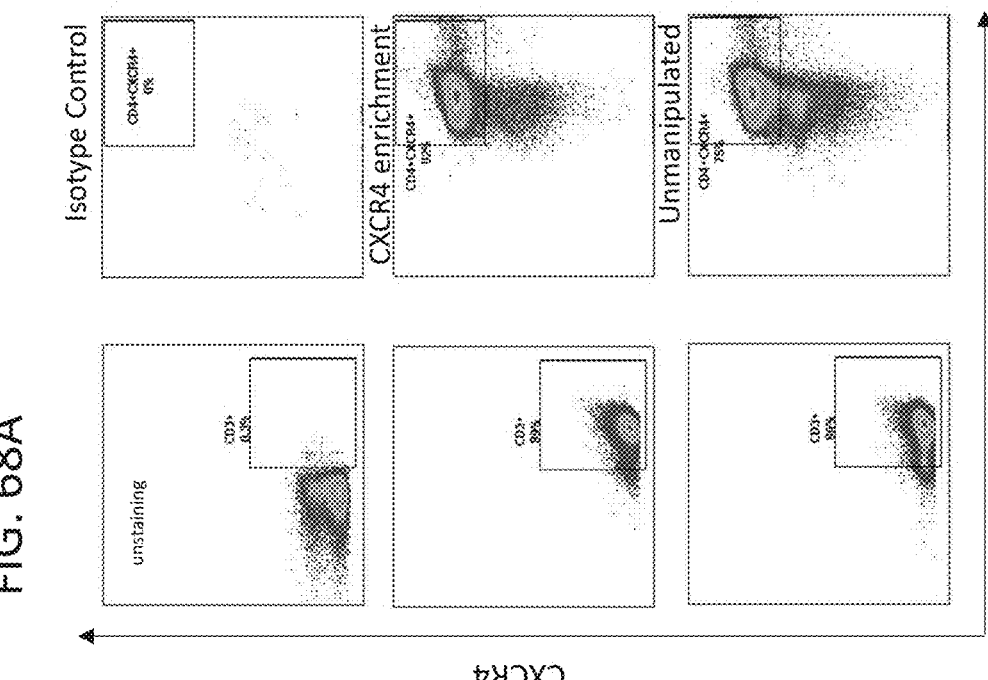
FIG. 68A—FIG. 68B depicts flow cytometry analysis of the Day 12 cell populations.
Figure 68A:
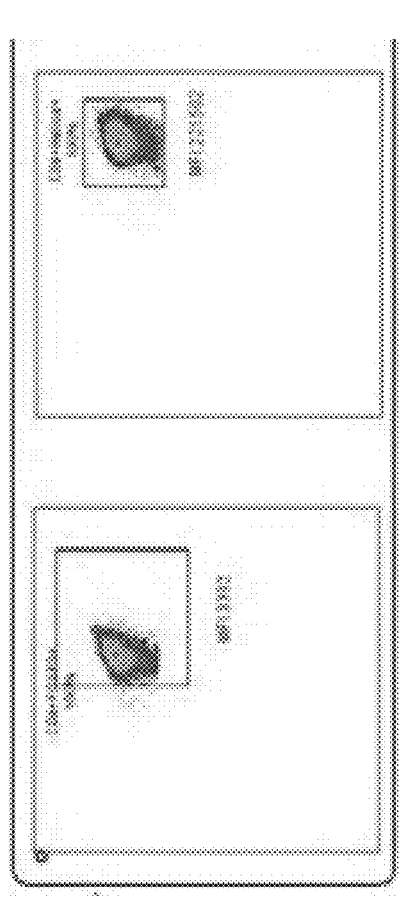

FIG. 68A and FIG. 68B show data related to the phenotype of day 12 culture product. FIG. 68A depicts dot plots showing results from CXCR4 magnetic enrichment for D12 (day 12) CB Treg cells from a representative culture. FIG. 68B depicts dot plot of the intracellular staining of FOXP3 and Helios in the CXCR4 enriched Treg cells at day 12.

Figure 69:
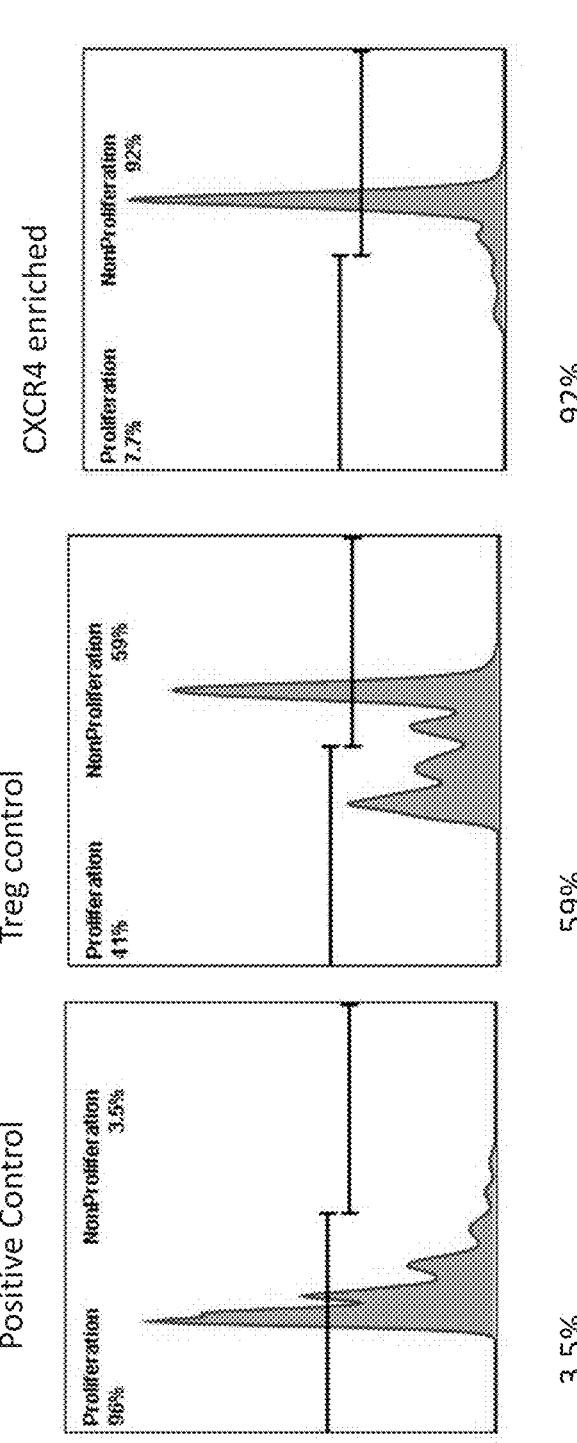
FIG. 69 depicts graphs showing results from a cell suppression assay from various fractions of a representative CXCR4 enrichment cell culture.
Figures 70A, 70B:
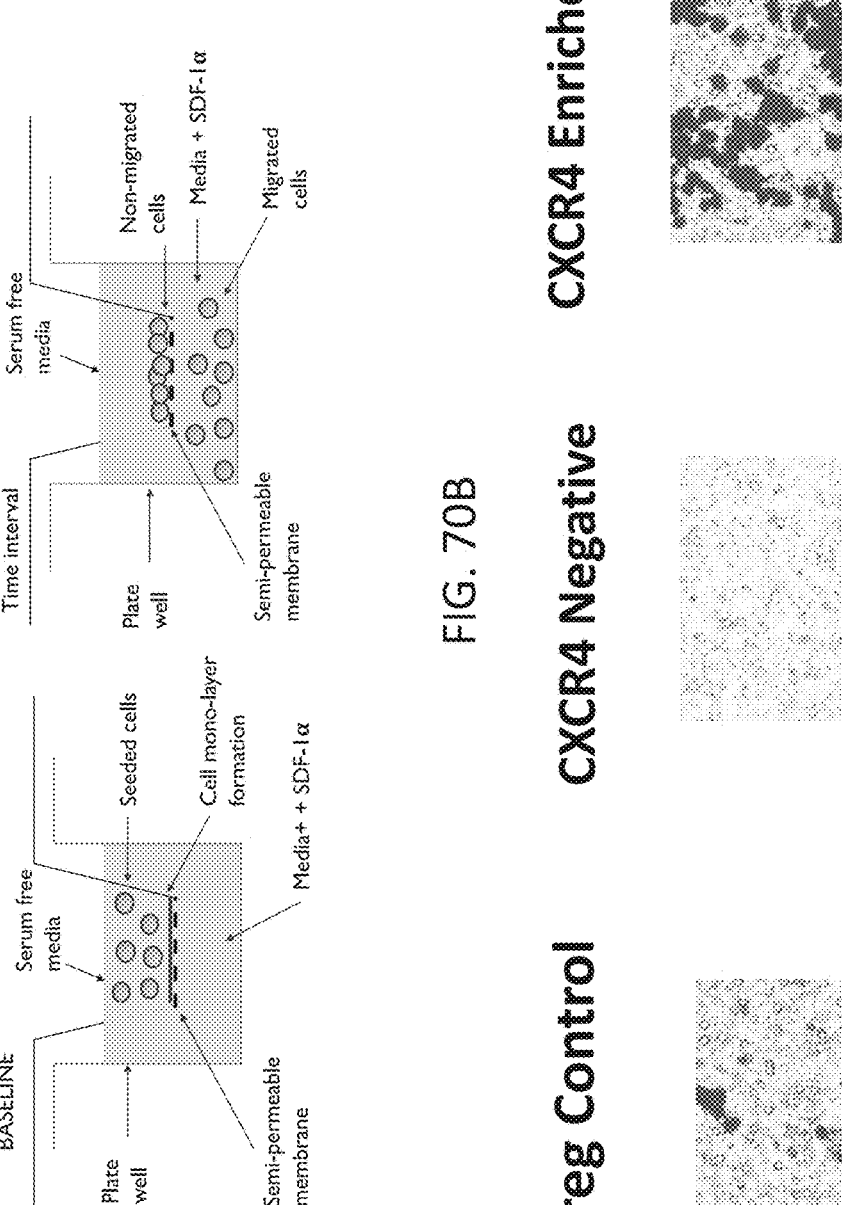
FIG. 70A-FIG. 70B shows the transwell migration of the D12 (day 12) CXCR4-enriched CB Treg cell population.

FIG. 69 depicts graphs showing results from cell suppression assay performed with the day 12 of a representative culture where the CXCR4 enriched Tregs exert superior suppression as compared to Treg control cell population. Donor CD4$^+$ T responder cells stained with CellTrace™ Violet dye were cultured with CD3/28 beads in 1:1 ratio for 96 hours under following conditions: i) no added cells—where 96% of the responder cells are actively proliferating; ii) Treg control cells added at 1:1 ratio to the Donor CD4$^+$ T responder cells—where 41% of the responder cells are actively proliferating and iii) Treg enriched in CXCR4 cells added at 1:1 ratio to the Donor CD4$^+$ T responder cells—where 7.7% of the responder cells are actively proliferating FIG. 70B depicts photomicrographs of the number of cells in the lower chamber in a transwell migration assay that show superior migration ability of the CXCR4-enriched Treg cells in response to the bone marrow stromal chemoattractant SDF1alpha. FIG. 70A shows the diagrammatic representation of the experiment design of the transwell migration assay. FIG. 70B shows that when layered at 1×10$^6$ cells in the top chamber of a 0.5 micron transwell, the CXCR4-enriched Treg cells migrate faster in response to SDF1 alpha at a concentration of 500 ng/ml when compared to the Treg control population and to the CXCR4-negative Treg cell population.

Example 15: Phase Ib, Safety Open-Label Study of Add-on Therapy with CK0804 in Patients with Myelofibrosis, with Suboptimal Response to Ruxolitinib This is a single arm study consisting of a safety run-in part of 9 patients followed by the expansion cohort of additional 15 patients for a total of 24 patients. Each patient will receive a single infusion of CK0804 (cryopreserved, allogeneic, cord blood derived, Treg cells, enriched for CXCR4-expressing Treg cells) at a fixed dose of 100 million cells to be administered every 28 days for up to 6 doses. Table 40 presents the objectives and endpoints. Table 41 presents the key study design elements.

TABLE 40

Primary and Secondary Objectives and Endpoints

| Objectives | Endpoints |
|---|---|
| Primary | |
| To determine the safety and tolerability, of CK0804 as an add-on therapy in subjects suffering from myelofibrosis, with suboptimal response to ruxolitinib | Safety, tolerability and treatment limiting toxicities of CK0804 as assessed by the incidence and severity of AE and SAEs determined by the NCI-CTCAE Version 5.0. |
| Major/Key Secondary | |
| To determine the efficacy of CKO804 as add-on therapy in subjects suffering from myelofibrosis, with suboptimal response to ruxolitinib | Assessment of treatment response, and its duration, using modified International Working Group-Myeloproliferative Neoplasm Research and Treatment (IWG-MRT). Disease response (ORR) will be defined as per modified IWG criteria (measured as CR, PR, SD, PD). |
| Exploratory | |
| To assess peripheral blood (PB) and bone marrow (BM) immune reconstitution, serum biomarkers and inflammatory cytokines at different time intervals | |

TABLE 41

Key Study Design Elements

| | |
|---|---|
| Study Phase | Phase 1B |
| Clinical Indication | Treatment of patients with myelofibrosis |
| Population | Male and female participants at least 18 years of age who have histologically-confirmed diagnosis of primary MF, post-PV, or post-ET MF according to the 2016 WHO criteria who fulfill the diagnostic criteria of myelofibrosis. Participant has been receiving ruxolitinib therapy, is unlikely to benefit from further ruxolitinib monotherapy in the opinion of the investigator and meeting the following criteria: receiving ruxolitinib >3 month prior to enrollment, AND stable dose for 8 weeks before starting therapy with CK0804 Participant with evidence of evaluable residual burden of disease following ruxolitinib monotherapy treatment, consisting of: presence of grade ≥2 anemia or thrombocytopenia or neutropenia, OR presence of disease-related symptoms, as determined by a Myeloproliferative Neoplasm Symptom Assessment Form Total Symptom Score (MPN SAF TSS) score of ≥10 points, OR documented splenomegaly of at least 5 cm below the costal margin as measured by physical examination |
| Investigational Product Route and Dosage | CK0804 is cryopreserved, allogeneic, cord blood-derived T-regulatory cell product enriched in CXCR4. CK0804 will be administered intravenously at a fixed dose of 100 million cells every 28 days for up to 6 infusions. |
| Number of Participants | Approximately 24 participants will be enrolled. Safety run part in will include up to 9 participants. Expansion part will include up to 15 additional participants. |
| Study Design | This is a single-arm, Open-label, safety Phase Ib study of CK0804 cells, for treatment of myelofibrosis composed of two parts. Safety run-in Part Safety and tolerability of add on treatment with CK0804 administered as IV infusion to subjects with myelofibrosis, with suboptimal response to ruxolitinib, who continue to receive stable dose of ruxolitinib. Initially 3 subjects will be treated, each at least 48 hours apart. Tolerability of the treatment will be assessed based on treatment limiting toxicities (TLTs) occurring up to 28 days after the first infusion. Additional 3 or 6 subjects will be tested in 3 + 3 + 3 design. The lowest treatment limiting toxicity (TLT) rate deemed overly toxic is 33%. Expansion Part Once total of 9 subjects are evaluated for tolerability in safety run-in phase and the treatment is deemed tolerable, additional participants may be included in the expansion stage in order to have approximately 24 evaluable MF participants treated overall in the study. The decision for expansion will be determined by the Sponsor in consultation with investigators. |
| Estimated Duration of Study Participation | Treatment: Subjects will receive six 28-day cycle treatment. Each treatment cycle consist of single infusion of CK0804 at a dose of 100 million cells on day 1 per cycle. End of Treatment: Once patients discontinue study drug (due to lack of benefit, adverse events, or study defined criteria) and will be performed at 1 month after the last dose of CK0804 |

TABLE 41-continued

Key Study Design Elements

| Study Phase | Phase 1B |
| --- | --- |
| Safety Assessment | Follow Up Period: Followed every 3 months for a total of 6 months after the last dose of CK0804 or until the start of a new therapy (whichever is earlier). End of Study. Date of last follow up visit of the last patient in the study. Safety and tolerability of CK0804 will be assessed by the incidence and severity of adverse events to be determined by the NCI-CTCAE Version 5.0. Treatment related toxicity is defined as; severe (grade 3 or 4) infusion-related toxicity within 24 hours (NCI-CTCAE V5.0) of exposure that does not resolve with standard of care treatment within 72 hours. regimen related death within 28 days |
| Efficacy Assessment | Assessment of treatment response, and its duration, using modified International Working Group-Myeloproliferative Neoplasm Research and Treatment (IWG-MRT). Disease response (ORR) will be defined as per modified IWG criteria (measured as CR, PR, SD, PD). |
| DMC | Yes |

What is claimed is:

1. A method for producing an expanded population of human T regulatory (Treg) cells enriched for CXCR4$^+$ Treg cells from a cryopreserved human umbilical cord blood unit, the method comprising:
(a) thawing the cryopreserved human umbilical cord blood unit;
(b) diluting and washing the thawed umbilical cord blood unit;
(c) isolating CD25+ Treg cells using double selection for CD25$^+$ cell surface expression with a reagent that specifically binds to CD25;
(d) ex vivo expanding the isolated CD25$^+$ Treg cells in a culture medium, in a gas permeable cultureware, in the presence of:
(1) an effective amount of interleukin-2 (IL-2);
(2) a reagent that specifically binds to CD3 and CD28; and
(3) magnetic microbeads coated with anti-CXCR4 antibody,
for up to 10 days or up to 12 days, wherein the culture medium is replaced about every 48 hours, to produce a CXCR4-enriched culture of CD25$^+$ Treg cells; and
(e) harvesting the CD25$^+$ CXCR4$^+$ cells from the culture medium to produce an expanded population of human Treg cells enriched for CXCR4$^+$ Treg cells.

2. The method of claim 1, wherein in step (d),
(1) the ex vivo expansion is initiated at day 0;
(2) the effective amount of IL-2 is added to the isolated CD25$^+$ Treg cells at day 0; and
(3) the reagent that specifically binds to CD3 and CD28 is added to the isolated CD25$^+$ Treg cells at day 0.

3. The method of claim 1, wherein the reagent that specifically binds to CD3 and CD28 is removed from the culture medium before the magnetic microbeads coated with anti-CXCR4 antibody are added to the culture medium.

4. The method of claim 1, wherein in step (d), the magnetic microbeads coated with anti-CXCR4 antibody are added to the culture medium 3 or 4 days after the ex vivo expansion is initiated.

5. The method of claim 1, wherein in step (d), the magnetic microbeads coated with anti-CXCR4 antibody are added to the culture medium for about 30 minutes before a double ferromagnetic column is used to harvest the CD25+ CXCR4$^+$ Treg cells.

6. The method of claim 1, wherein step (d) takes place over 4 or 5 days.

7. The method of claim 1, wherein the reagent that specifically binds to CD25 is an anti-CD25 antibody or an antigen-binding fragment thereof.

8. The method of claim 7, wherein the CD25$^+$ cells and the beads coated with anti-CD3 antibody and beads coated with anti-CD28 antibody are at a 1:1 ratio.

9. The method of claim 1, wherein the reagent that specifically binds to CD25 is conjugated to a solid support.

10. The method of claim 9, wherein the solid support is a magnetic microbead.

11. The method of claim 1, wherein the reagent that specifically binds to CD3 and CD28 comprises an anti-CD3 antibody or an antigen-binding fragment thereof and an anti-CD28 antibody or an antigen-binding fragment thereof.

12. The method of claim 1, wherein the reagent that specifically binds to CD3 and CD28 comprises beads coated with an anti-CD3 beads antibody or an antigen-binding fragment thereof and beads coated with anti-CD28 antibody or an antigen-binding fragment thereof.

13. The method of claim 12, wherein the beads coated with an anti-CD3 antibody and the beads coated with an anti-CD28 antibody are at a 1:1 ratio.

14. The method of claim 1, wherein the effective amount of IL-2 is about 1000 IU/ml.

15. The method of claim 1, wherein in step (d), IL-2 is added to the culture medium about every 48 hours.

16. The method of claim 1, wherein in step (e), about 1×10$^6$ CD25$^+$ cells/ml are cultured.

17. The method of claim 1, wherein in step (e), the cells are initially cultured in gas-permeable cultureware that has a membrane surface area of 10 cm$^2$.

18. The method of claim 17, wherein the culture is subsequently transferred to gas-permeable cultureware that has a membrane surface area of 100 cm$^2$.

19. The method of claim 1, wherein in step (d), the culture is not rocked or agitated when the IL-2 is added.

20. The method of claim 1, wherein in step (a), the cryopreserved human umbilical cord blood unit is thawed in a single step in a water bath.

21. The method of claim 1, wherein step (b) does not comprise manual washing.

22. The method of claim 1, wherein step (b) takes place in a solution comprising PBS, EDTA, and about 0.5% human serum albumin.

23. The method of claim 1, wherein a double ferromagnetic column method is used in step (c) to isolate CD25$^+$ Treg cells.

24. The method of claim 1, the method further comprising cryopreserving the expanded population of human Treg cells enriched for CXCR4$^+$ Treg cells.

25. The method of claim 1, wherein the expanded population of human Treg cells enriched for CXCR4" Treg cells is:

(i) ≥60% CD4$^+$CD25+;

(ii) ≥60% CD4$^+$CD25$^+$CXCR4$^+$; and (iii) ≤10% CD4 CD8$^+$, as measured by flow cytometry.

26. An expanded population of human Treg cells enriched for CXCR4+Treg cells produced by the method of claim 1, wherein the expanded population of human Treg cells comprises at least 60% CD4$^+$CD25$^+$ cells and less than 10% CD4$^-$CD8$^+$ cells.

27. A method for producing an expanded population of human Treg cells enriched for CXCR4$^+$ Treg cells from a cryopreserved human umbilical cord blood unit, the method comprising:

(a) thawing the cryopreserved human umbilical cord blood unit;

(b) diluting and washing the thawed umbilical cord blood unit;

(c) isolating Treg cells using double selection for CD25$^+$ cell surface expression with a reagent that specifically binds to CD25;

(d) ex vivo expanding the isolated CD25$^+$ Treg cells in a culture medium, in a gas permeable cultureware, wherein the ex vivo expansion step comprises:

(1) at day 0, adding beads coated with an anti-CD3antibody and beads coated with an anti-CD28 antibody to the culture medium;

(2) at day 2, adding about 1000 IU/ml IL-2 to the culture medium;

(3) at day 3 or 4, removing the beads coated with an anti-CD3 antibody and the beads coated with an anti-CD28 antibody from the culture medium and adding anti CXCR4 magnetic microbeads coated with anti-CXCR4 antibody to the culture medium; and (4) at day 3 or 4, removing the magnetic microbeads coated with anti-CXCR4 antibody attached to CXCR4$^+$ Treg cells from the culture medium, and adding fresh beads coated with an anti-CD3 antibody and beads coated with an anti-CD28 antibody to the CXCR4$^+$ Treg cells, wherein the ex vivo expansion takes place for up to 10 days or up to 12 days, wherein the culture medium is replaced about every 48 hours, to produce a CXCR4-enriched culture of CD25$^+$ Treg cells; and (e) harvesting the CD25$^+$ CXCR4$^+$ cells from the culture medium to produce an expanded population of human Treg cells enriched for CXCR4$^+$ Treg cells.

28. An expanded population of human Treg cells enriched for CXCR4$^+$ Treg cells produced by the method of claim 27, wherein the expanded population of human Treg cells comprises at least 60% CD4$^+$CD25$^+$ cells and less than 10% CD4$^-$CD8$^+$ cells.

* * * * *